US007910326B2

(12) United States Patent
Bloksberg et al.

(10) Patent No.: US 7,910,326 B2
(45) Date of Patent: Mar. 22, 2011

(54) MATERIALS AND METHODS FOR THE MODIFICATION OF PLANT LIGNIN CONTENT

(75) Inventors: Leonard N. Bloksberg, Auckland (NZ); Iikka Havukkala, Auckland (NZ)

(73) Assignees: Arborgen, Inc., Summerville, SC (US); Rubicon Forests Holdings Limited (NZ)

( * ) Notice: Subject to any disclaimer, the term of this patent is extended or adjusted under 35 U.S.C. 154(b) by 405 days.

(21) Appl. No.: 11/397,533

(22) Filed: Apr. 3, 2006

(65) Prior Publication Data

US 2006/0183895 A1 Aug. 17, 2006

Related U.S. Application Data

(63) Continuation of application No. 10/174,693, filed on Jun. 18, 2002, now Pat. No. 7,087,426, which is a continuation-in-part of application No. 09/615,192, filed on Jul. 12, 2000, now Pat. No. 6,410,718, which is a continuation-in-part of application No. 09/169,789, filed on Oct. 9, 1998, now Pat. No. 6,653,528, which is a continuation-in-part of application No. 08/975,316, filed on Nov. 21, 1997, now Pat. No. 5,952,486, which is a continuation-in-part of application No. 08/713,000, filed on Sep. 11, 1996, now Pat. No. 5,580,020.

(60) Provisional application No. 60/143,833, filed on Jul. 14, 1999.

(51) Int. Cl.
*C12P 21/02* (2006.01)

(52) U.S. Cl. ....... 435/69.1; 435/414; 435/419; 435/422; 435/430; 800/317.3; 800/319

(58) Field of Classification Search ........................ None
See application file for complete search history.

(56) References Cited

U.S. PATENT DOCUMENTS

| | | | |
|---|---|---|---|
| 5,122,466 | A | 6/1992 | Stomp et al. |
| 5,348,616 | A | 9/1994 | Hartman et al. |
| 5,451,514 | A | 9/1995 | Boudet et al. |
| 5,527,586 | A | 6/1996 | Schuler et al. |
| 5,597,613 | A | 1/1997 | Galarneau et al. |
| 5,658,575 | A | 8/1997 | Ribier et al. |
| 5,735,985 | A | 4/1998 | Ghosh et al. |
| 5,850,020 | A | 12/1998 | Bloksberg et al. |
| 5,952,486 | A | 9/1999 | Bloksberg et al. |
| 6,110,401 | A | 8/2000 | Lee et al. |
| 6,190,929 | B1 | 2/2001 | Wang et al. |
| 6,204,434 | B1 | 3/2001 | Bloksberg et al. |
| 6,225,143 | B1 | 5/2001 | Rao et al. |
| 6,309,580 | B1 | 10/2001 | Chou |
| 6,410,718 | B1 | 6/2002 | Bloksberg et al. |
| 6,482,742 | B1 | 11/2002 | Chou |
| 6,517,995 | B1 | 2/2003 | Jacobson et al. |
| 6,580,172 | B2 | 6/2003 | Mancini et al. |
| 6,653,528 | B1 | 11/2003 | Bloksberg et al. |
| 6,716,754 | B2 | 4/2004 | Hofmann |
| 7,067,426 | B2 | 6/2006 | Hofmann |

FOREIGN PATENT DOCUMENTS

| | | |
|---|---|---|
| AU | 733388 | 4/1998 |
| AU | 756359 | 9/2003 |
| BR | 9205894-9 | 9/1994 |
| EP | 0513884 | 11/1992 |
| EP | 0516958 | 12/1992 |
| EP | 0632128 | 1/1995 |
| EP | 0716147 | 6/1996 |
| JP | 04-330285 | 11/1992 |
| JP | 09-173069 | 7/1997 |
| NZ | 328434 | 5/1998 |
| NZ | 334565 | 12/2000 |
| NZ | 510940 | 1/2004 |
| NZ | 529839 | 12/2004 |
| WO | WO 90/08828 | 8/1990 |
| WO | WO 93/05159 | 3/1993 |
| WO | WO 93/05160 | 3/1993 |
| WO | WO 93/15599 | 8/1993 |
| WO | WO 93/24638 | 12/1993 |
| WO | WO 94/08036 | 4/1994 |
| WO | WO 94/21794 | 9/1994 |
| WO | WO 94/23044 | 10/1994 |
| WO | WO 95/07993 | 3/1995 |
| WO | WO 95/27790 | 10/1995 |
| WO | WO 96/20595 | 7/1996 |
| WO | WO 97/23599 | 7/1997 |
| WO | WO 97/30162 | 8/1997 |
| WO | WO 97/32023 | 9/1997 |
| WO | WO 97/45549 | 12/1997 |
| WO | WO 98/03535 | 1/1998 |
| WO | WO 98/11205 | 3/1998 |
| WO | WO 98/13503 | 4/1998 |
| WO | WO 98/39454 | 9/1998 |
| WO | WO 99/10498 | 3/1999 |
| WO | WO 00/22099 | 4/2000 |
| WO | WO 00/36081 | 6/2000 |
| ZA | 97/10451 | 7/1999 |
| ZA | 2001/2534 | 9/2001 |

OTHER PUBLICATIONS

Branch, TIBS, vol. 23,(1998), pp. 45-50.* "Information About HS II RTV High Strength Moldmaking Silicone Rubber Product Line" Down Corning: 1992.

(Continued)

*Primary Examiner* — James S Ketter
(74) *Attorney, Agent, or Firm* — Cooley LLP

(57) ABSTRACT

Novel isolated polynucleotides and polypeptides associated with the lignin biosynthetic pathway are provided, together with genetic constructs including such sequences. Methods for the modulation of lignin content, lignin structure and lignin composition in target organisms are also disclosed, the methods comprising incorporating one or more of the polynucleotides of the present invention into the genome of a target organism.

17 Claims, 3 Drawing Sheets

OTHER PUBLICATIONS

"New polymer materials for nanoimprinting"; H. Schulz et al.; J. Vac. Sci, Techol. B18(4) Jul./Aug. 2000; pp. 1861-1865.
Allina et al., "4-coumarate coenzyme A ligase in hybrid poplar," Plant Physiol. 116:743-754 (1998).
Atanassova, R. et al. Altered lignin composition in transgenic tobacco expressing O-methyltransferase sequence in sense and antisense orientation, Plant Jnl. 8:465-477, 1995.
Bachem, C.W.B., et al. Antisense expression of polyphenol oxidase genes inhibits enzymatic browning in potato tubers, Biotechnology 12:1101-1105, 1994.
Bao W. et al. A laccase associated with lignification in loblolly pine xylem Science 260:672-674, 1993.
Bate, N.J. et al., Quantitative relationship between phenylalanine ammonia-lyase levels and phenylpropanoid accumulation in transgenic tobacco identifies a rate-determining step in natural product biosynthesis, Proc. Natl. Acad. Sci. USA 91:7608-7612, 1994.
Baucher, M. et al., Higher extractability of lignin in poplar by reducing cinnamyl alcohol dehydrogenase activity, Somatic Cell Genetics and Molecular Genetics of Trees, ISBN 0-7923-4179-1, pp. 153-158, 1996.
Bloksberg, Studies on the Biology of Phenylalanine Ammonia Lyase and Plant Pathogen Interaction, Genetics, Abstract iii, Dec. 1991.
Boudet et al., "La lignification domestiquee," Biofutur 158:27-31 (1996).
Boudet, "Genes involved in monolignol biosynthesis and their manipulation for tailoring ne ligning," American Chemical Society, Abstracts of paper at the National Meeting (1996).
Boudet et al., "Tansley Review No. 80: Biochemistry and Molecular Biology of Lignification," New Phytol. 129:203-236 (1995).
Boudet, A.M. et al., Lignin genetic engineering, Molecular Breeding 2: 25-39, 1996.
Bowie et al., Deiphering the Message in Protein Sequences: Tolerance to Amino Acid Substitutions, Mar. 16, Science, 1990, vol. 247, pp. 1306-1310.
Bugos et al., cDNA cloning, sequence analysis and seasonal expression of lignin-bispecific caffeic acid/5-hydroxyferulic acid O-methyltransferase of aspen, Plant Mol Biol 17: 1203-1215, 1991.
Bugos, et al., Characterization of bispecific caffeic acid/5-hydroxyferulic acid O-methyltransferase from aspen, Phytochemistry 31:1495-1498, 1992.
Burgess et al., Possible Dissociation of the Heparin-binding and Mitogenic Activities of Heparin-binding ( Acidic Fibroblast) Growth Factor-1 . . . , 1990, The Journal of Cell Biology, pp. 2129-2138.
Chabbert et al., Manipulation of lignin quality in transgenic poplar, Biotechnol. Pulp. Pap. Ind. Proc. Int. Conf. 6.sup.th, pp. 319-322, 1995.
Collazo et al., Structure and expression of the lignin O-methyltransferase gene from *Zea mays* L., Plant Mol Biol 20: 857-867, 1992.
Covitz et al., "Expressed sequence tags from a root-hair-enriched *Medicago truncula*ta cDNA library," Database EM_EST, online, AA660330 (1997).
Database Dissabs, AN97:45741 Dissabs Order No. AARNN14739, Dharmawardhana, D.P. et al. A biochemical and molecular study of lignin biosynthesis (*Pinus contorta*, glucosidase, conferin, xylem).
Davies, K.M. et al. *Malus sp.* mRNA for anthocyanin hydroxylase, EMBL Accession No. X71360, Apr. 27, 1993.
de Carvalho et al., Suppression of beta-1,3-glucanase transgene expression in homozygous plants. EMBO J. Jul. 1992;11(7):2595-2602.
Dharmawardhana et al., A .beta.-Glucosidase from Lodgepole Pine Xylem Specific for the Lignin Precursor Coniferin, Plant Physiol, 107:331-339, 1995.
Dixon, R. A. et al., Metabolic engineering: prospects for crop improvement through genetic manipulation of phenylpropanoid biosynthesis and defense responses—a review, Gene Papers 179:61-71, 1996.
Dwivedi et al., Modification of lignin biosynthesis in transgenic *Nicotiana* through expression of an antisense O-methyltransferase gene from Populus, Plant Molecular Biology 26:61-71, 1994.
Ehlting, Jurgen et al., "Three 4-cournarate:coenzyme A ligases in *Arabidopsis thaliana* represent two evolutionarily divergent classes in angiosperms," The Plant Journal, vol. 19, No. 1, pp. 9-20 (1999).
Elkind Y. et al., Abnormal plant development and down-regulation of phenylpropanoid biosynthesis in transgenic tobacco containing a heterologous phenylalanine ammonia-lyase gene Proc. Nati Acad. Sci. USA 87:9057-9061, 1990.
EMBL Accession No. D87520 (Sep. 8, 1996).
EMBL Accession No. L07634 (Jan. 7, 1993).
EMBL Accession No. U29243 (Jul. 9, 1995).
EMBL Accession No. X52623 (Jul. 9, 1990).
EMBL Accession No. GED520, Akashi et al. (1996).
EMBL Accession No. GMCYP73, Schopfer and Ebel (1998).
EMBL Accession No. OS4CL, Dube (1990).
EMBL Accession No. PAC4HYDRO, Mitzuni et al. (1993).
EMBL Accession No. PS29243, Frank (1995).
EMBL Accession No. PSCYTP450, Van Meir and Wittek (1997).
EMBL Accession No. U62392 (1996).
Eriksson et al., Laccase as a target for decreasing the lignin content in transgenic trees through antisense genetic engineering, Biotechnol. Pulp Pap. Ind. Proc. 6$^{th}$ Intl. Conf. pp. 310-314, 1996.
Feuillet et al. Tissue- and cell-specific expression of cinnamyl alcohol dehydrogenase promoter in transgenic poplar plants, Plant Mol Biol 27:651-67, 1995.
Franke et al., Modified lignin in tobacco and poplar plant over-expressiing the *Arabidopsis* gene encoding ferulate 5-hydroxlase, 2000, The Plant Journal, vol. 22, pp. 223-234.
Galaud et al., "*Aribidopsis* ESTs," Database EM_EST, online, A1138417 (1998).
GenBank Accession No. AF008183 (Feb. 26, 1998).
GenBank Accession No. AF041049; Hu, W.J., et al.; submitted Jan. 6, 1998.
GenBank Accession No. AF052223; Heath, R.L., et al.; submitted Mar. 5, 1998.
GenBank Accession No. AF239686; Kumar, A., et al.; submitted Feb. 28, 2000.
GenBank Accession No. AJ244010; Rech, P., et al.; submitted Jul. 21, 1999.
GenBank Accession No. ATU38416, Meyer et al. (1996).
GenBank Accession No. AW191302; Bossinger, G.; submitted Nov. 23, 1999.
GenBank Accession No. AW244908; Walbot, V., et al.; submitted Feb. 28, 2000.
GenBank Accession No. BE454671; Wing, R. A.; submitted Jul, 26, 2000.
GenBank Accession No. L43362 (Jul. 7, 1995).
GenBank Accession No. PTU12012 (Mar. 23, 1996).
GenBank Accession No. RIC4CL2R, Zhao et al. (1995).
GenBank Accession No. U12012 (Mar. 23, 1996).
GenBank Accession No. U12013 (Mar. 23, 1996).
GenBank Accession No. U38416 (Aug. 12, 1996).
GenBank Accession No. U39404 (Feb. 7, 1997).
GenBank Accession No. U39405 (Feb. 7, 1997).
GenBank Accession No. X92437 (Jul. 17, 1998).
GenBank Accession No. Z49263 (Sep. 25, 1997).
GenPep Accession No. AAA62426, Zou and Taylor (1994).
GenPep Accession No. AAA92669, Voo et al. (1995).
GenPep Accession No. AAB18637, Lee and Douglas (1996).
GenPep Accession No. AAB18638 (Mar. 7, 1996).
GenPep Accession No. AAC39365 (Jun. 12, 1997).
GenPep Accession No. AAC39366 (Jun. 12, 1997).
GenPep Accession No. AAD40664, Becker-Andre et al. (1991).
GenPep Accession No. BAA07828 (Dec. 8, 1994).
Goffner D. et al., E. gunnii mRNA for cinnamyl alcohol dehydrogenase, EMBL Accession No. X88797, Dec. 31, 1995.
Grima-Pettenati, J. et al., E. gunnii OMT mRNA for O-methyltransferase, EMBL Accession No. X74814, Dec. 31, 1993.
Halpin, C. et al., Manipulation of lignin quality by clownregulation of cinnamyl alcohol dehydrogenase, Plant Journal 6:3, 339-350, 1994.
Hauffe, Karl D. et al., "A Parsley 4CL-1 Promoter Fragment Specifies Complex Expression Patterns in Transgenic Tobacco," The Plant Cell, vol. 3., No. 2, pp. 435-443 (May 1991).

Hauffe, Karl D. et al., "Combinatorial interactions between positive and negative cis-acting elements control spatial patterns of 4CL-1 expression in transgenic tobacco," The Plant Journal, vol. 4., No. 2, pp. 235-253 (Aug. 1993).
Heidari, et al., "Large scale nanolithography using nanoimprint lithography" J.Vac.Sci. Techol. B17(6), Nov./Dec. 1999: 1999 American Vacuum Society: pp. 2961-2964.
Hermann et al., Enzymatic synthesis of lignin: purification to homogeneity of the three O-methyltransferases of tobacco and production of specific antibodies, Arch Biochem Biophys 253: 367-376, 1987.
Hill et al., Functional Analysis of Conserved Histdines in ADP-Glucose Phyrophosphorylase from *Escherichia coli*, 1998, Biochemical and Biophysical, vol. 244, pp. 573-577.
Hosel et al., Characterization of beta-glucosidase isoenzymes possibly involved in lignification from chick pea (*Cicer arietinum* L.) cell suspension cultures, Eur J Biochem 84: 487-492, 1978.
Hotze, M. et al., Cinnamate 4-hydroxylase from *Catharanthus roseus*, and a strategy for the functional expression of plant cytochrome P.sub.450 proteins as translational fusions with P.sub. 450 reductase in *Escherichia coli*, FEBS letters 374:345-350, 1995.
Hotze, M., et al., *C. roseus* mRNA for cinnamate 4-hydroxylase (CYP73), EMBL Sequence Database, Rel. 39, Apr. 15, 1994, Accession No. Z32563, (XP-002054206).
Hrmova M. et al., *Hordeum vulgare* beta-d-glucan exohydrolase, isoenzyme exoII, mRNA, complete cds, EMBL Accession No. U46003, Feb. 29, 1996.
Hu et al. Compartmentalized expression of two structurally and functionally distinct 4-coumarate: CoA ligase genes in aspen (*populus tremuloides*) Proc. Natl. Acad. Sci. U.S.A. 95 (9), 5407-5412 1998.
Hu, Wen-Jing et al., "Repression of lignin biosynthesis promotes cellulose accumulation and growth in transgenic trees," Nature Biotechnology, vol. 17, No. 8, pp. 808-812 (Aug. 1999).
In re Bloksberg, et al., Materials and Methods for the Modification of Plant Lignin Content, U.S. Appl. No. 09/211,710; Filed Dec. 14, 1998; Allowed Claims.
In re Genesis Research & Development Corp. and Fletcher Challenge Forests Ltd; PCT International Search Report; Int'l No. PCT/NZ99/00168 filed Oct. 6, 1999 (7 sheets).
Kajita et al., Immunological characterization of transgenic tobacco plants with a chimeric gene for 4-coumarate:CoA ligase that have altered lignin in their xylem tissue, 1997, Plant Science, pp. 109-118.
Kajita, Shinya et al., "Alterations in the Biosynthesis of Lignin in Transgenic Plants with Chimeric Genes for 4-Coumarate:Coenzyme A Ligase," Plant Cell Physiol. vol. 37, No. 7, pp. 957-965 (Oct. 1996).
Kawai, S., et al., *Populus kitakamiensis* cyp 73a gene for cinnamic acid 4-hydroxylase complete cds. EMBL Sequence Database, Rel. 46, Dec. 30, 1995, Accession No. D82812 (XP002054135).
Lagrimini, L M., Wound-induced deposition of polyphenols in transgenic plants overexpressing peroxidase Plant Physiol. 96:577-583, 1991.
Lazar et al., Transforming Growth Factor x: Mutation of Aspartic Acid 47 and Leucine 48 Results in Different Biological Activities, Mar. 1988, Molecular and Cellular Biology, pp. 1247-1252.
Lee et al., "Two divergrent members of a tobacco 4-coumarate coenzyme A ligase (4CL) gene family," Plant Physiol. 112:193-205 (1996).
Lee, Diane et al., "Antisense Suppression of 4-Coumarate:Coenzyme A Ligase Activity in *Arabidopsis* Leads to Altered Lignin Subunit Composition," The Plant Cell, vol. 9, No. 11, pp. 1985-1998 (Nov. 1997).
Liu, T.Y. et al. Lignin contect and composition in tobacco plants with over and under expressed peroxidase, Supplement to Plant Physiol. 102:103, 1993.
Ludertiz et al., Enzymatic synthesis of lignin precursors. Comparison of cinnamoyl-CoA reductase and cinnamyl alcohol: NADP+ dehydrogenase from spruce S(*Picea abies* L.) and soybean )Glycine max L.), Eur. J. Biochem 119: 115-124, 1981.
MacKay et al. Genetic analysis of cinnamyl alcohol dehydrogenase in loblolly pine: single gene inheritance, molecular characterization and evolution. Mol. Gen. Genet. (1995) 247: 537-545, Jul. 1995.
Mason, M.E., et al., *Pinus elliotti* PEC18 mRNA partial sequence, EMBL Sequence Database, Rel. 47 May 31, 1996, Accession No. U55006 (XP 002054138).
McIntyre, C.L. et al. Strategies for the suppression of peroxidase gene expression in tobacco. II. In vivo suppression of peroxidase activity in transgenic tobacco using ribozyme and antisense constructs Transgenic Research 5:263-270, 1996.
Meyer K. et al., *Arabidopsis thaliana* ferulate-5-hydroxylase (FAH1) mRNA, completed cds, EMBL Accession No. U38416, Aug. 13, 1996.
Meyer K. et al., Ferulate-5-hydroxylase from *Arabidopsis thaliana* defines a new family of cytochrome P450-dependent monooxygenases Proc. Natl. Acad. Sci. USA 93:6869-6874, 1996.
Mizutani, M. et al., Molecular Cloning and Sequencing of a cDNA Encoding Mung Bean Cytochrome P450 Possessing Cinnamate 4-Hydroxylase Activity, Biochemical and Biophysical Research Communications 190:3, 875-880, 1993.
Napoli et al., Introduction of a Chimeric Chalcone Synthase Gene into Petunia Results in Reversible Co-Suppression of Homologous Genes in trans, The Plant Cell 2: 279-289, Apr. 1990.
Neustaedter, David A. et al., "A novel parsley 4CLI cis-element is required for developmentqally regulated expression and protein-DNA complex formation," The Plant Journal, vol. 18, No. 1, pp. 77-88 (Apr. 1999).
Newman T., et al., 10030 *Arabidopsis thaliana* cDNA clone 143C13T7, EMBL Accession No. T46767, Feb. 11, 1995.
Ni et al., "Reduced lignin in transgenic plants containing a caffeic acid O-methyltransferase antisense gene," Transgenic Res. 3:120-126 (1994).
Piquemal et al., Down-relgulation of Cinnamoyl-CoA Reductase induces significant changes of lignin profiles in transgenic tobacco plants, 1998, The Plant Journal, vol. 13, No. 1, pp. 71-83.
PIR; Accession No. PQ0773 (Jul. 14, 1994).
Plant Physiol. 105:749-750 (1994).
Poedomenge et al., A cDNA Encoding S-Adenosyl-L-Methionine:Caffeic Acid 3-O-Methyltransferase from Eucalyptus, 1994, Plant Physiol, vol. 105, pp. 749-750.
Prima-Pettenati et al., Molecular cloning and expression of a Eucalyptus gunnii cDNA clone encoding cinnamyl alcohol dehydrogenase, Plant Mol Biol 21: 1085-95, 1993.
Raynal et al. *A. thaliana* transcribed sequence; clone PAP790; 5' end similar to cinnamyl alcohol dehydrogenase: *Stylosanthes hmilis*, EMBL Accession No. 246703, Nov. 18, 1994.
Rech, P. et al., E. gunii mRNA for caffeoyl-CoA O-methyltransferase, EMBL Accession No. Y12228, Apr. 8, 1997.
Ritter D. et al., *Gossypium hirsutum* peroxidase mRNA, complete cds, EMBL Accession No. L08199, Dec. 24, 1992.
Rounsley et al., "A BAC end sequence database for identifying minimal overlaps in *Arabidopsis* Genomic Sequencing," Database EM_GSS, online, B97241 (1998).
Sarni et al., Purification and properties of cinnamoyl-CoA reductase and cinnamyl alcohol dehydrogenase from poplar stems (*Populus X euramericana*) Eur J. Biochem 139: 259-265, 1984.
Schmid et al., Enzymic synthesis of lignin precursors. Purification and properties of UDP glucose: coniferyl-alcohol glucosyltransferase from cambial sap of spruce (*Picea abies* L), Eur J. Biochem 123: 363-70, 1982.
Sewait et al., Reduced Lignin Content and Altered Lignin Composition in Transgenic Tobacco Down-Regulated in Expression of L-Phenylalanine Ammonia-Lyase or Cinnamate 4-Hydroxylase, Plant Physiol, 115:41-50, 1997.
Shiokawa, T. et al., Expression analysis of a cinnamic acid 4-hydroxylase gene from a hybrid aspen, *Populus kitakamiensis*, Chem. Abstracts, vol. 125, No. 13, abstract No. 163462, Sep. 23, 1996.
Sikorski, R.S. et al., Yeast centromere vector pRS415 with LEU2 marker, complete sequence, EMBL Accession No. U03449, Jan. 8. 1984.
Smith et al. Nature. 1988. vol. 334: 724-726, 1988.
Southerton et al., "Eucaluypt MADS-box genes expressed in developing flowers," Plant Physiol. 118:365-372 (1998).
Swiss Prot 4CL_PINTA, Voos (1995).
Swiss Prot 4CL1_SOLTU (1991).
Swiss Prot 4CL2_SOLTU (1991).
Swiss Prot 4CL2_SOYBN (1993).
Swiss Prot CAMT-POPKI, Kwai and Mauyama (1998).

Swiss-Prot: Accession No. P14912 (Apr. 1, 1990).
Swiss-Prot: Accession No. P14913 (Apr. 1, 1990).
Swiss-Prot: Accession No. P93711 (Jul. 15, 1998).
Swiss-Prot; Accession No. P13687 (Jul. 1, 1993).
Swiss-Prot; Accession No. P14912 (Apr. 1, 1990).
Tsai, C-J et al. Plant Physiol. (1998) 117:101-112.
Udagama-Randeniya, P.V. et al., Coniferyl alcohol oxidase: A catechol oxidase? Trees 10:102-108, 1995.
Uhlmann, A, Ebel J., "Molecular doing and expression of 4-cournarate:coenzyme A ligase, an enzyme involved in the resistance response of soybean (*Glyrine max.* L.) against pathogen attack," Plant Physiol., vol. 102, No. 4, pp. 1147-1156 (Aug. 1993).
Van Doorsselaere et al., "A novel lignin in poplar trees with a reduced caffeic acic/5-hydroxyferulic acid O-methyltransferase activity," Plant J. 8:855-864 (1995).
Van Doorsselaere et al., One-step purification and characterization of a lignin-specific O-methyltransferase from poplar, Gene 133: 213-317, 1993.
Voo, K.S. et al. *Pinus taeda* PT4CL2 4-coumarate-CoA ligase enzyme, mRNA complete cds, EMBL Accession No. U12013, Jul. 27, 1994.
Voo, Kui Shin, Whetten, Ross W., O'Malley, David M., and Sederoff, Ronald R., 4-Coumarate:Coenzyme A Ligase from Loblolly Pine Xylem, Plant Physiology, 1995, pp. 85-97, vol. 108.
Wagner, A. et al., "Direct Submission", Genbank Sequence Database, (Sep. 29, 1996).
Wagner et al.. "Isolation and Characterisation of a Cinnamyl-Alcohol Dehydrogenase Gene from *Pinus radiata*", Queenstown Molecular Biology Meeting, New Zealand Forest Research Institute (Aug. 1996).
Wagner, A., et al., *Pinus radiata* cinnamyl alcohol dehydrogenase (CAD) mRNA, complete cds, EMBL Sequence Database, Rel. 48 Jul. 28, 1996, Accession No. U62394 (XP002054137).
Website: http://www.dow.com/cyclotene/apps/app11.htm: Cyclotene: Bumping/Redistribution/Wafer Level Packaging (WLP): May 14, 2001.
Website: http://www.dow.com/cyclotene/over.htm; Cyclotene: BCB Properties; May 14, 2001.
Website: http://www.dow.com/cyclotene/over/tg.htm; Tg vs Cure; May 14, 2001.
Website: http://www.dow.com/cyclotene/prods/prod1.htm: Cyclotene: Photosensitive Resins: May 14, 2001.
Website: http://www.dow.com/cycotene/apps/app13.htm: Cyclotene: Multilayer Interconnects: May 14, 2001.
Wengenmayer et al., "Enzymic synthesis of lignin precursors. Purification and properties of a cinnamoyl-CoA:NADPH reductase from cell suspension cultures of soybean (Glycinemax)," Eur J. Biochem 65: 529-536 (1976).
Whetten et al., "The pine gene discovery project," Database EM_EST, online, AW043205 (1999).
Whetten et al., Lignin Biosynthesis, The Plant Cell 7: 1001-1013, Jul. 1995.
Willekens, H.D. *N. plumbaginifolia* mRNA for catalase (cat3 gene), EMBL Accession No. Z36977, Sep. 7, 1994.
Yahiaoui et al. Comparative Efficiency of Different Constructs for Down Regulation of Tobacco Cinnamyl Alcohol Dehydrogenase vol. 49, No. 2 pp. 295-306 1998.
Yu, L.X. et al. *Lycopersicon chilense* unknown protein (LC15) mRNA, complete cds; EMBL Accession No. U19099, Oct. 3, 1995.
Zhang X.H. et al., *Pinus taeda* xylem 4-coumarate:CoA ligase (1p4CL-1) gene, complete cds, EMBL Accession No. U39405, Jan. 1, 1996.
Zhang, X.H. et al., *Pinus taedae* phenylalanine ammonia-lyase (1pPAL) gene complete cds, EMBL Accession No. U39792, Jan. 1, 1996.
Zhang, X.H., Chang, V.L., "Molecular cloing of 4-cournarate:coenzyme A ligase, in loblolly pine and the roles of this enzyme in the biosynthesis of lignin in compression wood," Plant Physiol., vol. 113, No. 1, pp. 65-74 (Jan. 1997).
Zhao et al., "Nucleotide sequence of rice 4 coumarate coenzyme A ligase gene 4-CL.1," Nucl. Acids Res. 18:6144 (1990).

* cited by examiner

MATERIALS AND METHODS FOR THE MODIFICATION OF PLANT LIGNIN CONTENT

CROSS-REFERENCE TO RELATED APPLICATIONS

This application is a continuation of U.S. patent application Ser. No. 10/174,693, filed Jun. 18, 2002, which is a continuation-in-part of U.S. application Ser. No. 09/615,192, filed Jul. 12, 2000, now U.S. Pat. No. 6,410,718, which claims priority from U.S. Application No. 60/143,833, filed Jul. 14, 1999 and is a continuation-in-part of U.S. application Ser. No. 09/169,789, filed Oct. 9, 1998, now U.S. Pat. No. 6,653,528, which is a continuation-in-part of U.S. patent application Ser. No. 08/975,316, filed Nov. 21, 1997, now U.S. Pat. No. 5,952, 486, which is a continuation-in-part of U.S. patent application Ser. No. 08/713,000, filed Sep. 11, 1996, now U.S. Pat. No. 5,850,020.

Reference to Sequence Listing Submitted Electronically

The contents of the text file submitted electronically are incorporated herein by reference in their entirety: A computer readable format copy of the Sequence Listing (filename: ARBG_001_06US_SubSeqList_ST25.txt, date recorded: Aug. 28, 2009, file size 451 kilobytes).

TECHNICAL FIELD OF THE INVENTION

This invention relates to polynucleotides, including partial and extended sequences as well as probes and primers, constructs comprising the polynucleotides, biological materials (including plants, microorganisms and multicellular organisms) incorporating the polynucleotides, polypeptides encoded by the polynucleotides, and methods for using the polynucleotides and polypeptides. The invention relates, more particularly, to the modification of lignin content and composition in biological materials including plants, to polypeptides involved in the lignin biosynthetic pathway, and to polynucleotides encoding such enzymes.

BACKGROUND OF THE INVENTION

Lignin is an insoluble polymer that is primarily responsible for the rigidity of plant stems. Specifically, lignin serves as a matrix around the polysaccharide components of some plant cell walls. The higher the lignin content, the more rigid the plant. For example, tree species synthesize large quantities of lignin, with lignin constituting between 20% to 30% of the dry weight of wood. In addition to providing rigidity, lignin aids in water transport within plants by rendering cell walls hydrophobic and water impermeable. Lignin also plays a role in disease resistance of plants by impeding the penetration and propagation of pathogenic agents.

The high concentration of lignin in trees presents a significant problem in the paper industry wherein considerable resources must be employed to separate lignin from the cellulose fiber needed for the production of paper. Methods typically employed for the removal of lignin are highly energy- and chemical-intensive, resulting in increased costs and increased levels of undesirable waste products. In the U.S. alone, about 20 million tons of lignin are removed from wood per year.

Lignin is largely responsible for the digestibility, or lack thereof, of forage crops, with small increases in plant lignin content resulting in relatively high decreases in digestibility. For example, crops with reduced lignin content provide more efficient forage for cattle, with the yield of milk and meat being higher relative to the amount of forage crop consumed. During normal plant growth, the increase in dry matter content is accompanied by a corresponding decrease in digestibility. When deciding on the optimum time to harvest forage crops, farmers must therefore chose between a high yield of less digestible material and a lower yield of more digestible material.

For some applications, an increase in lignin content is desirable since increasing the lignin content of a plant would lead to increased mechanical strength of wood, changes in its color and increased resistance to rot. Mycorrhizal species composition and abundance may also be favorably manipulated by modifying lignin content and structural composition.

As discussed in detail below, lignin is formed by polymerization of at least three different monolignols that are synthesized in a multistep pathway, each step in the pathway being catalyzed by a different enzyme. It has been shown that manipulation of the number of copies of genes encoding certain enzymes, such as cinnamyl alcohol dehydrogenase (CAD) and caffeic acid 3-O-methyltransferase (COMT) results in modification of the amount of lignin produced; see, for example, U.S. Pat. No. 5,451,514 and PCT Publication No. WO 94/23044. Furthermore, it has been shown that antisense expression of sequences encoding CAD in poplar leads to the production of lignin having a modified composition (Grand C et al., *Planta* (*Berl.*) 163:232-237, 1985).

While polynucleotides encoding some of the enzymes involved in the lignin biosynthetic pathway have been isolated for certain species of plants, genes encoding many of the enzymes in a wide range of plant species have not yet been identified. Thus there remains a need in the art for materials useful in the modification of lignin content and composition in plants and for methods for their use.

SUMMARY OF THE INVENTION

Briefly, the present invention provides isolated polynucleotides identified in the attached Sequence Listing as SEQ ID NO: 1-266, 350-375, 404 and 406, variants of those sequences, genetic constructs comprising such sequences, extended sequences comprising the sequences of SEQ ID NO: 1-266, 350-375, 404 and 406, and their variants, probes and primers corresponding to the sequences set out in SEQ ID NO: 1-266, 350-375, 404, 406 and their variants, and polynucleotides comprising at least a specified number of contiguous residues of any of the polynucleotides identified as SEQ ID NO: 1-266, 350-375, 404 and 406 (x-mers), all of which are referred to herein, collectively, as "polynucleotides of the present invention." Polynucleotides of the present invention are preferably obtainable from eucalyptus and pine species, and preferably comprise open reading frames or partial open reading frames encoding enzymes, or functional portions of enzymes, involved in the lignin biosynthetic pathway. Genetic constructs incorporating such polynucleotides, methods for using such polynucleotides and genetic constructs, and biological materials, including plant cells and plants having an altered genomic and/or lignin content and composition are provided. The present invention also provides isolated polypeptide sequences identified in the attached Sequence Listing as SEQ ID NO: 267-349, 376-401, 405 and 407; polypeptide variants of those sequences; and polypeptides comprising the inventive polypeptide sequences and variants of those sequences.

In one aspect, the present invention provides isolated polynucleotides encoding the following enzymes, or portions of the following enzymes: cinnamate 4-hydroxylase (C4H), coumarate 3-hydroxylase (C3H), phenolase (PNL), O-methyl transferase (OMT), cinnamyl alcohol dehydrogenase (CAD), cinnamoyl-CoA reductase (CCR), phenylalanine ammonia-lyase (PAL), 4-coumarate: CoA ligase (4CL), coniferol glucosyl transferase (CGT), coniferin beta-glucosidase (CBG), laccase (LAC), peroxidase (POX), ferulate-5-hydroxylase (F5H), alpha amylase, caffeic acid methyl transferase, caffeoyl CoA methyl transferase, coumerate 6A ligase, cytochrome P450 LXX1A, diphenol oxidase, flavonol glucosyl transferase, flavonoid hydroxylase, and isoflavone reductase.

In one embodiment, polynucleotides of the present invention encompass polynucleotides comprising a nucleotide sequence selected from the group consisting of: (a) polynucleotides recited in SEQ ID NO: 1-266, 350-375, 404 and 406; (b) complements of the polynucleotides recited in SEQ ID NO: 1-266, 350-375, 404 and 406; (c) reverse complements of the sequences recited in SEQ ID NO: 1-266, 350-375, 404 and 406; (d) reverse sequences of the sequences recited in SEQ ID NO: 1-266, 350-375, 404 and 406; and (e) variants of the polynucleotides recited in SEQ ID NO: 1-266, 350-375, 404 and 406. In another embodiment of the present invention, the inventive polynucleotides comprise at least a specified number of contiguous residues (x-mers) of any of the polynucleotides of SEQ ID NO: 1-266, 350-375, 404 and 406. In yet another aspect, the inventive polynucleotides comprise probes and primers corresponding to any of the polynucleotides of SEQ ID NO: 1-266, 350-375, 404 and 406.

In a further aspect, the present invention provides genetic constructs comprising a polynucleotide of the present invention, either alone or in combination with one or more of the inventive sequences, or in combination with one or more known polynucleotides; together with host cells and transgenic cells comprising such constructs.

In a related aspect, the present invention provides genetic constructs comprising, in the 5'-3' direction, a gene promoter sequence; an open reading frame coding for at least a functional portion of an enzyme encoded by a polynucleotide of the present invention; and a gene termination sequence. An open reading frame may be orientated in either a sense or antisense direction. Genetic constructs comprising a non-coding region of a gene coding for an enzyme encoded by the above polynucleotides or a polynucleotide complementary to a non-coding region, together with a gene promoter sequence and a gene termination sequence, are also provided. Preferably, the gene promoter and termination sequences are functional in a host cell, such as a plant cell. Most preferably, the gene promoter and termination sequences are those of the original enzyme genes but others generally used in the art, such as the Cauliflower Mosaic Virus (CMV) promoter, with or without enhancers, such as the Kozak sequence or Omega enhancer, and *Agrobacterium tumefaciens* nopalin synthase terminator may be usefully employed in the present invention. Tissue-specific promoters may be employed in order to target expression to one or more desired tissues. In a preferred embodiment, the gene promoter sequence provides for transcription in xylem. The construct may further include a marker for the identification of transformed cells.

In a further aspect, transgenic cells, such as transgenic plant cells, comprising the genetic constructs of the present invention are provided, together with plants comprising such transgenic cells, and fruits and seeds of such plants.

In yet another aspect, methods for modulating the lignin content and composition of a target organism such as a plant are provided, such methods including stably incorporating into the genome of the target plant a genetic construct comprising a polynucleotide of the present invention. In a preferred embodiment, the target plant is a woody plant, preferably selected from the group consisting of eucalyptus and pine species, most preferably from the group consisting of *Eucalyptus grandis* and *Pinus radiata*. In a related aspect, a method for producing a plant having altered lignin content is provided, the method comprising transforming a plant cell with a genetic construct comprising a polynucleotide of the present invention to provide a transgenic cell, and cultivating the transgenic cell under conditions conducive to regeneration and mature plant growth.

In yet a further aspect, the present invention provides methods for modifying the activity of an enzyme in a target organism such as a plant, comprising stably incorporating into the genome of the target organism a genetic construct of the present invention. In a preferred embodiment, the target plant is a woody plant, preferably selected from the group consisting of eucalyptus and pine species, most preferably from the group consisting of *Eucalyptus grandis* and *Pinus radiata*.

The present invention also provides polypeptides encoded by the inventive polynucleotides. In certain specific embodiments, such polypeptides comprise a sequence selected from the group consisting of: SEQ ID NO: 267-349, 376-401, 405 and 407, and variants of those sequences.

BRIEF DESCRIPTION OF THE FIGURES

The above-mentioned and additional features of the present invention and the manner of obtaining them will become apparent, and the invention will be best understood by reference to the following more detailed description, read in conjunction with the accompanying drawing.

DETAILED DESCRIPTION

Lignin is formed by polymerization of at least three different monolignols, primarily para-coumaryl alcohol, coniferyl alcohol and sinapyl alcohol. While these three types of lignin subunits are well known, it is possible that slightly different variants of these subunits may be involved in the lignin biosynthetic pathway in various plants. The relative concentration of these residues in lignin varies among different plant species and within species. In addition, the composition of lignin may also vary among different tissues within a specific plant. The three monolignols are derived from phenylalanine in a multistep process and are believed to be polymerized into lignin by a free radical mechanism.

Figure 1:
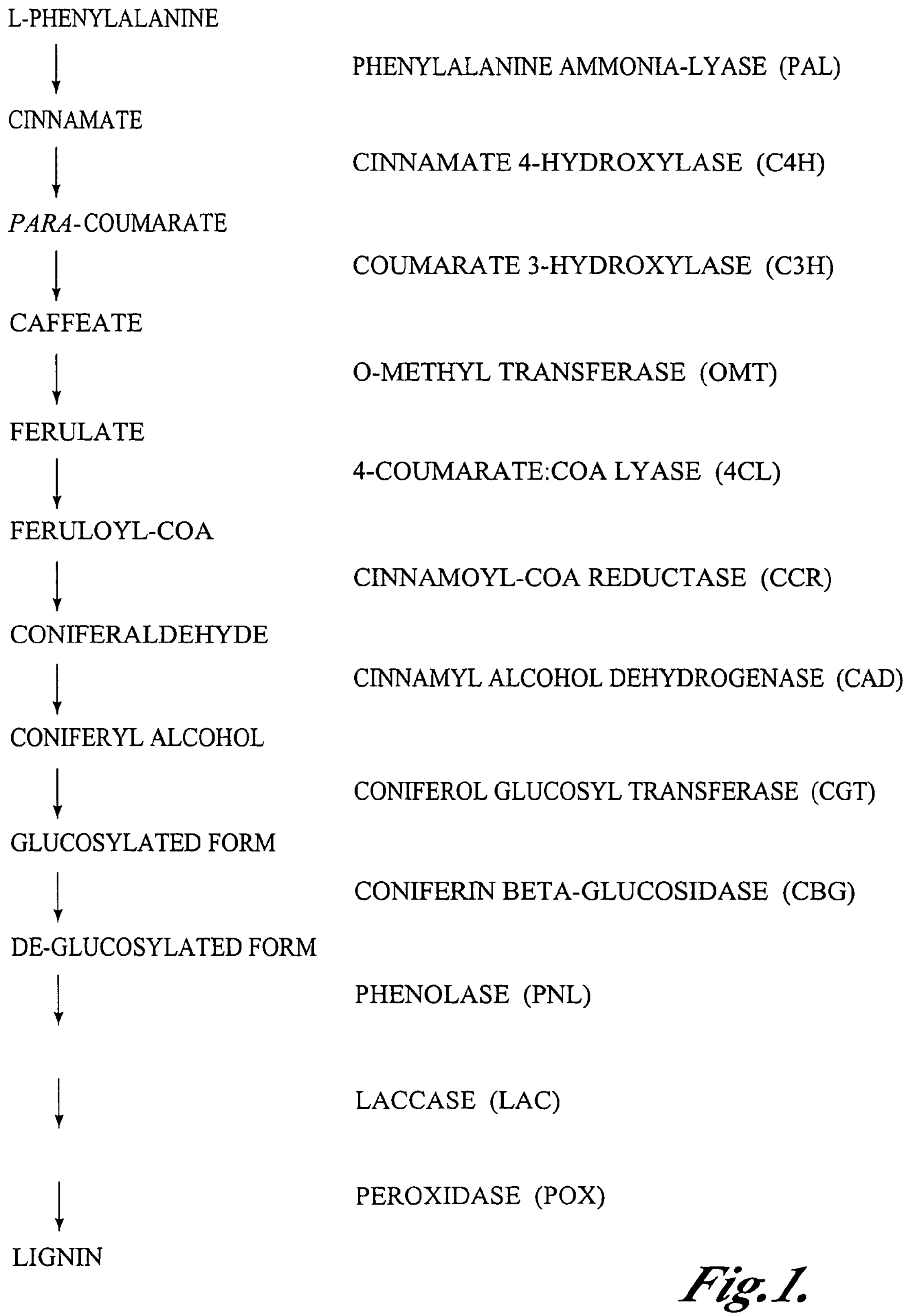
FIG. 1 is a schematic overview of the lignin biosynthetic pathway.

FIG. 1 shows different steps in the biosynthetic pathway for coniferyl alcohol together with the enzymes responsible for catalyzing each step. para-Coumaryl alcohol and sinapyl alcohol are synthesized by similar pathways. Phenylalanine is first deaminated by phenylalanine ammonia-lyase (PAL) to give cinnamate which is then hydroxylated by cinnamate 4-hydroxylase (C4H) to form p-coumarate. p-Coumarate is hydroxylated by coumarate 3-hydroxylase to give caffeate. The newly added hydroxyl group is then methylated by O-methyl transferase (OMT) to give ferulate which is conjugated to coenzyme A by 4-coumarate:CoA ligase (4CL) to form feruloyl-CoA. Reduction of feruloyl-CoA to coniferaldehyde is catalyzed by cinnamoyl-CoA reductase (CCR). Coniferaldehyde is further reduced by the action of cinnamyl alcohol dehydrogenase (CAD) to give coniferyl alcohol which is then converted into its glucosylated form for export from the cytoplasm to the cell wall by coniferol glucosyl transferase (CGT). Following export, the de-glucosylated form of coniferyl alcohol is obtained by the action of coniferin beta-glucosidase (CBG). Finally, polymerization of the three monolignols to provide lignin is catalyzed by phenolase (PNL), laccase (LAC) and peroxidase (POX).

The formation of sinapyl alcohol involves an additional enzyme, ferulate-5-hydroxylase (F5H). For a more detailed review of the lignin biosynthetic pathway, see Whetton R and Sederoff R, *The Plant Cell,* 7:1001-1013, 1995.

Quantitative and qualitative modifications in plant lignin content are known to be induced by external factors such as light stimulation, low calcium levels and mechanical stress. Synthesis of new types of lignins, sometimes in tissues not normally lignified, can also be induced by infection with pathogens. In addition to lignin, several other classes of plant products are derived from phenylalanine, including flavonoids, coumarins, stilbenes and benzoic acid derivatives, with the initial steps in the synthesis of all these compounds being the same. Thus modification of the action of PAL, C4H, 4CL and other enzymes involved in the lignin biosynthetic pathway may affect the synthesis of other plant products in addition to lignin.

Using the methods and materials of the present invention, the lignin content of a plant may be modulated by modulating expression of polynucleotides of the present invention, or by modifying the polypeptides encoded by polynucleotides or the polynucleotides. The lignin content of a target organism, such as a plant, may be modified, for example, by incorporating additional copies of genes encoding enzymes involved in the lignin biosynthetic pathway into the genome of the target plant. Similarly, a modified lignin content can be obtained by transforming the target plant with antisense copies of such genes. In addition, the number of copies of genes encoding for different enzymes in the lignin biosynthetic pathway can be manipulated to modify the relative amount of each monolignol synthesized, thereby leading to the formation of lignin having altered composition. The alteration of lignin composition would be advantageous, for example, in applications of wood processing for paper, and may also be effective in altering the palatability of wood materials to rotting fungi.

In a first aspect, the present invention provides isolated polynucleotide sequences identified in the attached Sequence Listing as SEQ ID NO: 1-266, 350-375, 404 and 406, variants of those sequences, extended sequences comprising the sequences set out in SEQ ID NO: 1-266, 350-375, 404 and 406, and their variants, probes and primers corresponding to the sequences set out in SEQ ID NO: 1-266, 350-375, 404 and 406, and their variants, polynucleotides comprising at least a specified number of contiguous residues of any of the polynucleotides identified as SEQ ID NO: 1-266, 350-375, 404 and 406 (x -mers), and extended sequences comprising portions of the sequences set out in SEQ ID NO: 1-266, 350-375, 404 and 406, all of which are referred to herein, collectively, as "polynucleotides of the present invention." The present invention also provides isolated polypeptide sequences identified in the attached Sequence Listing as SEQ ID NO: 267-349, 376-401, 405 and 407, polypeptide variants of those sequences, and polypeptides comprising the isolated polypeptide sequences and variants of those sequences.

The polynucleotides disclosed herein were derived from forestry plant sources, namely from *Eucalyptus grandis* and *Pinus radiata*. Some of the polynucleotides of the present invention are "partial" sequences, in that they do not represent a full length gene encoding a full length polypeptide. Such partial sequences may be extended by analyzing and sequencing various DNA libraries using primers and/or probes and well known hybridization and/or PCR techniques. Partial sequences may be extended until an open reading frame encoding a polypeptide, a full length polynucleotide and/or gene capable of expressing a polypeptide, or another useful portion of the genome is identified. Such extended sequences, including full length polynucleotides and genes, are described as "corresponding to" a sequence identified as one of the sequences of SEQ ID NO: 1-266, 350-375, 404 and 406, or a variant thereof, or a portion of one of the sequences of SEQ ID NO: 1-266, 350-375, 404 and 406, or a variant thereof, when the extended polynucleotide comprises an identified sequence or its variant, or an identified contiguous portion (x-mer) of one of the sequences of SEQ ID NO: 1-266, 350-375, 404 and 406, or a variant thereof. Similarly, RNA sequences, reverse sequences, complementary sequences, antisense sequences, and the like, corresponding to the polynucleotides of the present invention, may be routinely ascertained and obtained using the cDNA sequences identified as SEQ ID NO: 1-266, 350-375, 404 and 406.

The polynucleotides identified as SEQ ID NO: 1-266, 350-375, 404 and 406 contain open reading frames ("ORFs") or partial open reading frames encoding polypeptides and functional portions of polypeptides. Additionally, open reading frames encoding polypeptides may be identified in extended or full length sequences corresponding to the sequences set out as SEQ ID NO: 1-266, 350-375, 404 and 406. Open reading frames may be identified using techniques that are well known in the art. These techniques include, for example, analysis for the location of known start and stop codons, most likely reading frame identification based on codon frequencies, etc. . Tools and software for ORF analysis, include, for example, GeneWise, available from The Sanger Center, Wellcome Trust Genome Campus, Hinxton, Cambridge, CB10 1SA, United Kingdom; Diogenes, available from Computational Biology Centers, University of Minnesota, Academic Health Center, UMHG Box 43 Minneapolis Minn. 55455; and GRAIL, available from the Informatics Group, Oak Ridge National Laboratories, Oak Ridge, Tenn. Open reading frames and portions of open reading frames are present and may be identified in the polynucleotides of the present invention. Once a partial open reading frame is identified, the polynucleotide may be extended in the area of the partial open reading frame using techniques that are well known in the art until the polynucleotide for the full open reading frame is identified. Thus, open reading frames encoding polypeptides may be identified using the polynucleotides of the present invention.

Once open reading frames are identified in the polynucleotides of the present invention, the open reading frames may be isolated and/or synthesized. Expressible genetic constructs comprising the open reading frames and suitable promoters, initiators, terminators, etc., which are well known in the art, may then be constructed. Such genetic constructs may be introduced into a host cell to express the polypeptide encoded by the open reading frame. Suitable host cells may include various prokaryotic and eukaryotic cells, including plant cells, mammalian cells, bacterial cells, algae and the like.

Polypeptides encoded by the polynucleotides of the present invention may be expressed and used in various assays to determine their biological activity. Such polypeptides may be used to raise antibodies, to isolate corresponding interacting proteins or other compounds, and to quantitatively determine levels of interacting proteins or other compounds.

The present invention also contemplates methods for modulating the polynucleotide and/or polypeptide content and composition of a forestry species, such methods involving stably incorporating into the genome of the organism a genetic construct comprising one or more polynucleotides of the present invention. In one embodiment, the target organism is a forestry species, preferably a woody plant, more preferably a woody plant of the *Pinus* or *Eucalyptus* species, and most preferably *Eucalyptus grandis* or *Pinus radiata*. In a related aspect, a method for producing a forestry plant having an altered genotype or phenotype is provided, the method comprising transforming a plant cell with a genetic construct of the present invention to provide a transgenic cell, and cultivating the transgenic cell under conditions conducive to regeneration and mature plant growth. Forestry plants having an altered genotype or phenotype as a consequence of modulation of the level or content of a polynucleotide or polypeptide of the present invention compared to a wild-type organism, as well as components (seeds, etc.) of such forestry plants, and the progeny of such forestry plants, are contemplated by and encompassed within the present invention.

The isolated polynucleotides of the present invention also have utility in genome mapping, in physical mapping, and in positional cloning of genes. Additionally, the polynucleotide sequences identified as SEQ ID NO: 1-266, 350-375, 404 and 406, and their variants, may be used to design oligonucleotide probes and primers. Oligonucleotide probes and primers have sequences that are substantially complementary to the polynucleotide of interest over a certain portion of the polynucleotide. Oligonucleotide probes designed using the polynucleotides of the present invention may be used to detect the presence and examine the expression patterns of genes in any organism having sufficiently similar DNA and RNA sequences in their cells using techniques that are well known in the art, such as slot blot DNA hybridization techniques. Oligonucleotide primers designed using the polynucleotides of the present invention may be used for PCR amplifications. Oligonucleotide probes and primers designed using the polynucleotides of the present invention may also be used in connection with various microarray technologies, including the microarray technology used by Synteni (Palo Alto, Calif.).

The polynucleotides of the present invention may also be used to tag or identify an organism or reproductive material therefrom. Such tagging may be accomplished, for example, by stably introducing a non-disruptive non-functional heterologous polynucleotide identifier into an organism, the polynucleotide comprising one of the polynucleotides of the present invention.

The polypeptides of the present invention and the polynucleotides encoding the polypeptides have activity in lignin biosynthetic pathways in plants. The polynucleotides were identified by DNA and polypeptide similarity searches. The polynucleotides and polypeptides of the present invention have demonstrated similarity to the following polypeptides that are known to be involved in lignin biosynthetic processes:

TABLE 1

| POLYPEPTIDE IDENTITY | POLYNUCLEOTIDE SEQ ID NO. | POLYPEPTIDE SEQ ID NO. |
|---|---|---|
| Cinnamate 4-hydroxylase (C4H) | 2, 3, 17, 48, 49, 92, 124, 125, 153-163 | |
| Coumarate 3-hydroxylase (C3H) | 4, 18, 50-52, 93, 101, 126, 127, 149-152 | |
| Phenolase (PNL) | 5, 35, 36, 81, 116, 183 | |
| O-methyl transferase (OMT) | 6, 22-25, 53-55, 94, 104-107, 173-175 | |
| Cinnamyl alcohol dehydrogenase (CAD) | 1, 7, 30, 71, 95, 112, 164 | |
| Cinnamoyl-CoA reductase (CCR) | 8, 26-29, 58-70, 96, 108-111, 128-134, 167 | |
| Phenylalanine ammonia-lyase (PAL) | 9-11, 16, 45-47, 97, 98, 100, 122, 123, 176 242-248 | 325-331 |
| 4-coumarate:CoA ligase (4CL) | 2, 56-57, 90, 147, 158, 196-200, 265, 266, 406 | 279-283, 348, 349, 407 |
| Coniferol glucosyl transferase (CGT) | 31-33, 72, 113-115, 135, 168 | |
| Coniferin beta-glucosidase (CBG) | 34, 73-80, 136-141, 165, 166 | |
| Laccase (LAC) | 37-41, 82-84, 117, 118, 142-144, 172 | |
| Peroxidase (POX) | 13, 42-44, 85-89, 91, 119-121, 145, 146, 177-182, 249-250, 264, 350-375 | 332-333 347, 376-401 |
| Ferulate-5-hydroxylase (F5H) | 19-21, 102, 103, 169-171, 404 | 405 |
| Alpha amylase | 184-186 | 267-269 |
| Caffeic acid methyl transferase | 187-192 | 270-275 |
| Caffeoyl CoA methyl transferase | 193-195 | 276-278 |

TABLE 1-continued

| POLYPEPTIDE IDENTITY | POLYNUCLEOTIDE SEQ ID NO. | POLYPEPTIDE SEQ ID NO. |
|---|---|---|
| Cytochrome P450 LXXIA | 201-206 | 284-289 |
| Diphenol oxidase | 207-217<br>251-263 | 290-300<br>334-346 |
| Flavonol glucosyl transferase | 218 | 301 |
| Flavonoid hydroxylase | 219-233 | 302-316 |
| Isoflavone reductase | 234-241 | 317-324 |

In one embodiment, isolated polynucleotides of the present invention comprise a sequence selected from the group consisting of: (a) sequences recited in SEQ ID NO: 1-266, 350-375, 404 and 406; (b) complements of the sequences recited in SEQ ID NO: 1-266, 350-375, 404 and 406; (c) reverse complements of the sequences recited in SEQ ID NO: 1-266, 350-375, 404 and 406; (d) reverse sequences of the sequences recited in SEQ ID NO: 1-266, 350-375, 404 and 406; and (e) sequences having at least 50%, 75%, 90%, 95% or 98% identity, as defined herein, to a sequence of (a)-(d) or a specified region of a sequence of (a)-(d).

In a further aspect, isolated polypeptides encoded by the polynucleotides of the present invention are provided. In one embodiment, such polypeptides comprise an amino acid sequence recited in SEQ ID NO: 267-349, 376-401, 405 and 407, and variants thereof, as well as polypeptides expressed by polynucleotides of the present invention, including polynucleotides comprising a sequence of SEQ ID NO: 1-266, 350-375, 404 and 406.

In another aspect, the invention provides genetic constructs comprising a polynucleotide of the present invention, either alone, in combination with one or more additional polynucleotides of the present invention, or in combination with one or more known polynucleotides, together with cells and target organisms comprising such constructs.

In a related aspect, the present invention provides genetic constructs comprising, in the 5'-3' direction, a gene promoter sequence, an open reading frame coding for at least a functional portion of a polypeptide encoded by a polynucleotide of the present invention, and a gene termination sequence. The open reading frame may be oriented in either a sense or antisense direction. Genetic constructs comprising a gene promoter sequence, a polynucleotide of the present invention, and a gene termination sequence are also contemplated, as are genetic constructs comprising a gene promoter sequence, an Lintranslated region of a polynucleotide of the present invention, or a nucleotide sequence complementary to an untranslated region, and a gene termination sequence. The genetic construct may further include a marker for the identification of transformed cells.

The gene promoter and termination sequences are preferably functional in a host plant and, most preferably, are those native to the host plant. Promoter and termination sequences that are generally used in the art, such as the Cauliflower Mosaic Virus (CMV) promoter, with or without enhancers such as the Kozak sequence or Omega enhancer, and *Agrobacterium tumefaciens* nopaline synthase terminator, are useful. Tissue-specific promoters may be employed in order to target expression to one or more desired tissues.

In a further aspect, methods for producing forestry plants having a modified content of a polynucleotide or polypeptide of the present invention compared to a native organism are provided. The methods involve transforming a target forestry plant with a genetic construct of the present invention to provide a transgenic cell, and cultivating the transgenic cell under conditions conducive to regeneration and mature plant growth. Cells comprising the genetic constructs of the present invention are provided, together with tissues and forestry plants comprising such transgenic cells, and fruits, seeds and other products, derivatives, or progeny of such forestry plants.

The word "polynucleotide(s)," as used herein, means a polymeric collection of nucleotides and includes DNA and corresponding RNA molecules and both single and double stranded molecules, including HnRNA and mRNA molecules, sense and anti-sense strands of DNA and RNA molecules, and cDNA, genomic DNA, and wholly or partially synthesized polynucleotides. An HnRNA molecule contains introns and "corresponds to" a DNA molecule in a generally one-to-one manner. An mRNA molecule "corresponds to" an HnRNA and DNA molecule from which the introns have been excised. A polynucleotide of the present invention may be an entire gene, or any portion thereof. A gene is a DNA sequence which codes for a functional protein or RNA molecule. Operable anti-sense polynucleotides may comprise a fragment of the corresponding polynucleotide, and the definition of "polynucleotide" therefore includes all operable anti-sense fragments. Anti-sense polynucleotides and techniques involving anti-sense polynucleotides are well known in the art and are described, for example, in Robinson-Benion et al., "Antisense techniques," *Methods in Enzymol.* 254(23): 363-375, 1995; and Kawasaki et al., *Artific. Organs* 20(8): 836-848, 1996.

Complements of such isolated polynucleotides, reverse complements of such isolated polynucleotides, and reverse sequences of such isolated polynucleotides, together with variants of such sequences, are also provided. The definition of the terms "complement", "reverse complement" and "reverse sequence", as used herein, is best illustrated by the following example. For the sequence 5' AGGACC 3', the complement, reverse complement and reverse sequence are as follows:

```
complement              3' TCCTGG 5'
reverse complement      3' GGTCCT 5'
reverse sequence        5' CCAGGA 3'.
```

As used herein, the term "oligonucleotide" refers to a relatively short segment of a polynucleotide sequence, generally comprising between 6 and 60 nucleotides, and comprehends both probes for use in hybridization assays and primers for use in the amplification of DNA by polymerase chain reaction.

Identification of genomic DNA and heterologous species DNAs can be accomplished by standard DNA/DNA hybridization techniques, under appropriately stringent conditions, using all or part of a cDNA sequence as a probe to screen an appropriate library. Alternatively, PCR techniques using oligonucleotide primers that are designed based on known genomic DNA, cDNA and protein sequences can be used to amplify and identify genomic and cDNA sequences. Synthetic DNAs corresponding to the identified sequences and variants may be produced by conventional synthesis methods. All of the polynucleotides described herein are isolated and purified, as those terms are commonly used in the art.

In another aspect, the present invention provides isolated polypeptides encoded, or partially encoded, by the above polynucleotides. As used herein, the term "polypeptide"

encompasses amino acid chains of any length, including full length proteins, wherein the amino acid residues are linked by covalent peptide bonds. The term "polypeptide encoded by a polynucleotide" as used herein, includes polypeptides encoded by a polynucleotide which comprises an isolated DNA sequence or variant provided herein. In specific embodiments, the inventive polypeptides comprise an amino acid sequence selected from the group consisting of sequences provided in SEQ ID NO: 267-349, 376-401, 405 and 407, as well as variants of such sequences.

Polypeptides of the present invention may be produced recombinantly by inserting a DNA sequence that encodes the polypeptide into an expression vector and expressing the polypeptide in an appropriate host. Any of a variety of expression vectors known to those of ordinary skill in the art may be employed. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. coli*, insect, yeast or a mammalian cell line such as COS or CHO. The DNA sequences expressed in this manner may encode naturally occurring polypeptides, portions of naturally occurring polypeptides, or other variants thereof.

In a related aspect, polypeptides are provided that comprise at least a functional portion of a polypeptide having an amino acid sequence selected from the group consisting of sequences provided in SEQ ID NO:267-349, 376-401, 405 and 407, and variants thereof. As used herein, the "functional portion" of a polypeptide is that portion which contains the active site essential for affecting the function of the polypeptide, for example, the portion of the molecule that is capable of binding one or more reactants. The active site may be made up of separate portions present on one or more polypeptide chains and will generally exhibit high binding affinity.

Functional portions of a polypeptide may be identified by first preparing fragments of the polypeptide by either chemical or enzymatic digestion of the polypeptide, or by mutation analysis of the polynucleotide that encodes the polypeptide and subsequent expression of the resulting mutant polypeptides. The polypeptide fragments or mutant polypeptides are then tested to determine which portions retain biological activity, using, for example, the representative assays provided below.

A functional portion comprising an active site may be made up of separate portions present on one or more polypeptide chains and generally exhibits high substrate specificity. The term "polypeptide encoded by a polynucleotide" as used herein, includes polypeptides encoded by a polynucleotide comprising a partial isolated polynucleotide of the present invention.

Portions and other variants of the inventive polypeptides may also be generated by synthetic or recombinant means. Synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85: 2149-2146, 1963. Equipment for automated synthesis of polypeptides is commercially available from suppliers such as Perkin Elmer/Applied Biosystems, Inc. (Foster City, Calif.), and may be operated according to the manufacturer's instructions. Variants of a native polypeptide may be prepared using standard mutagenesis techniques, such as oligonucleotide-directed site-specific mutagensis (Kunkel, T., *Proc. Natl. Acad. Sci. USA* 82: 488-492, 1985). Sections of DNA sequences may also be removed using standard techniques to permit preparation of truncated polypeptides.

In general, the polypeptides disclosed herein are prepared in an isolated, substantially pure form. Preferably, the polypeptides are at least about 80% pure; more preferably at least about 90% pure; and most preferably, at least about 99% pure.

As used herein, the term "variant" comprehends nucleotide or amino acid sequences different from the specifically identified sequences, wherein one or more nucleotides or amino acid residues is deleted, substituted, or added. Variants may be naturally occurring allelic variants, or non-naturally occurring variants. Variant sequences (polynucleotide or polypeptide) preferably exhibit at least 50%, more preferably at least 75%, and most preferably at least 90%, 95% or 98% identity to a sequence of the present invention. The percentage identity is determined by aligning the two sequences to be compared as described below, determining the number of identical residues in the aligned portion, dividing that number by the total number of residues in the inventive (queried) sequence, and multiplying the result by 100.

Polynucleotide and polypeptide sequences may be aligned, and percentage of identical nucleotides in a specified region may be determined against another polynucleotide, using computer algorithms that are publicly available. Two exemplary algorithms for aligning and identifying the similarity of polynucleotide sequences are the BLASTN and FASTA algorithms. Polynucleotides may also be analyzed using the BLASTX algorithm, which compares the six-frame conceptual translation products of a nucleotide query sequence (both strands) against a protein sequence database. The similarity of polypeptide sequences may be examined using the BLASTP algorithm. The BLASTN, BLASTX and BLASTP programs are available on the NCBI anonymous FTP server and from the National Center for Biotechnology Information (NCBI) National Library of Medicine, Building 38A, Room 8N805, Bethesda, Md. 20894 USA. The BLASTN algorithm Version 2.0.4 [Feb. 24, 1998] and Version 2.0.6 [Sep. 16, 1998], set to the default parameters described in the documentation and distributed with the algorithm, are preferred for use in the determination of polynucleotide variants according to the present invention. The BLASTP algorithm, set to the default parameters described in the documentation and distributed with the program, is preferred for use in the determination of polypeptide variants according to the present invention. The use of the BLAST family of algorithms, including BLASTN, BLASTP, and BLASTX, is described at NCBI's website and in the publication of Altschul Stephen F, et al., "Gapped BLAST and PSI-BLAST: a new generation of protein database search programs," *Nucleic Acids Res.* 25: 3389-3402, 1997.

The computer algorithm FASTA is available on the Internet and from the University of Virginia by contacting David Hudson, Assistant Provost for Research, University of Virginia, PO Box 9025, Charlottesville, Va. 22906-9025 USA. FASTA Version 2.0.4, February 1996, set to the default parameters described in the documentation and distributed with the algorithm, may be used in the determination of variants according to the present invention. The use of the FASTA algorithm is described in Pearson W R and Lipman D J, "Improved Tools for Biological Sequence Analysis," *Proc. Natl. Acad. Sci. USA* 85: 2444-2448, 1988; and Pearson W R, "Rapid and Sensitive Sequence Comparison with FASTP and FASTA," *Methods in Enzymology* 183: 63-98, 1990.

The following running parameters are preferred for determination of alignments and similarities using BLASTN that contribute to the E values and percentage identity for polynucleotide sequences: Unix running command: blastall -p blastn -d embldb -e 10 -GO -E0 -r 1 -v 30 -b 30 -i queryseq -o results; the parameters are: -p Program Name [String]; -d Database [String]; -e Expectation value (E) [Real]; -G Cost to open a gap (zero invokes default behavior) [Integer]; -E Cost to extend a gap (zero invokes default behavior) [Integer]; -r Reward for a nucleotide match (blastn only) [Integer]; -v Number of one-line descriptions (V) [Integer]; -b Number of alignments to show (B) [Integer]; -i Query File [File In]; and -o BLAST report Output File [File Out] Optional. The following running parameters are preferred for determination of alignments and similarities using BLASTP that contribute to the E values and percentage identity of polypeptide sequences: blastall -p blastp -d swissprotdb -e 10 -G 0 -E 0 -v 30 -b 30 -i queryseq -o results; the parameters are: -p Program Name [String]; -d Database [String]; -e Expectation value (E) [Real]; -G Cost to open a gap (zero invokes default behavior) [Integer]; -E Cost to extend a gap (zero invokes default behavior) [Integer]; -v Number of one-line descriptions (v) [Integer]; -b Number of alignments to show (b) [Integer]; -I Query File [File In]; -o BLAST report Output File [File Out] Optional. The "hits" to one or more database sequences by a queried sequence produced by BLASTN, FASTA, BLASTP or a similar algorithm, align and identify similar portions of sequences. The hits are arranged in order of the degree of similarity and the length of sequence overlap. Hits to a database sequence generally represent an overlap over only a fraction of the sequence length of the queried sequence.

The BLASTN, FASTA, and BLASTP algorithms also produce "Expect" (E) values for alignments. The Expect value (E) indicates the number of hits one can "expect" to see over a certain number of contiguous sequences by chance when searching a database of a certain size. The Expect value is used as a significance threshold for determining whether the hit to a database, such as the preferred EMBL database, indicates true similarity. For example, an E value of 0.1 assigned to a polynucleotide hit is interpreted as meaning that in a database of the size of the EMBL database, one might expect to see 0.1 matches over the aligned portion of the sequence with a similar score simply by chance. By this criterion, the aligned and matched portions of the polynucleotide sequences then have a probability of 90% of being the same. For sequences having an E value of 0.01 or less over aligned and matched portions, the probability of finding a match by chance in the EMBL database is 1% or less using the BLASTN or FASTA algorithm.

According to one embodiment, "variant" polynucleotides and polypeptides, with reference to each of the polynucleotides and polypeptides of the present invention, preferably comprise sequences having the same number or fewer nucleic or amino acids than each of the polynucleotides or polypeptides of the present invention and producing an E value of 0.01 or less when compared to the polynucleotide or polypeptide of the present invention. That is, a variant polynucleotide or polypeptide is any sequence that has at least a 99% probability of being the same as the polynucleotide or polypeptide of the present invention, measured as having an E value of 0.01 or less using the BLASTN, FASTA, or BLASTP algorithms set at parameters described above. According to a preferred embodiment, a variant polynucleotide is a sequence having the same number or fewer nucleic acids than a polynucleotide of the present invention that has at least a 99% probability of being the same as the polynucleotide of the present invention, measured as having an E value of 0.01 or less using the BLASTN or FASTA algorithms set at parameters described above. Similarly, according to a preferred embodiment, a variant polypeptide is a sequence having the same number or fewer amino acids than a polypeptide of the present invention that has at least a 99% probability of being the same as a polypeptide of the present invention, measured as having an E value of 0.01 or less using the BLASTP algorithm set at the parameters described above.

Alternatively, variant polynucleotides or polypeptides of the present invention comprise a sequence exhibiting at least 50%; more preferably at least 75%; more preferably yet at least 90%; and most preferably at least 98% similarity to a polynucleotide or polypeptide of the present invention, determined as described below. Polynucleotides and polypeptides having a specified percentage similarity to a polynucleotide or polypeptide specified in one of the SEQ ID NOS. thus share a high degree of similarity in their primary structure. In addition to a specified percentage similarity to a polynucleotide of the present invention, variant polynucleotides and polypeptides preferably have additional structural and/or functional features in common with a polynucleotide of the present invention.

Polynucleotides having a specified degree of identity to, or capable of hybridizing to, a polynucleotide of the present invention preferably additionally have at least one of the following features: (1) they contain an open reading frame or partial open reading frame encoding a polypeptide, or a functional portion of a polypeptide, having substantially the same functional properties as the polypeptide, or functional portion thereof, encoded by a polynucleotide in a recited SEQ ID NO.; or (2) they contain identifiable domains in common. Similarly, polypeptides, or functional portions of polypeptides, having a specified degree of identity to a polypeptide of the present invention shares a high degree of identity in their primary structure and have substantially similar functional properties.

As noted above, the percentage identity is determined by aligning sequences using one of the BLASTN, FASTA, or BLASTP algorithms, set at the running parameters described above, and identifying the number of identical nucleic or amino acids over the aligned portions; dividing the number of identical nucleic or amino acids by the total number of nucleic or amino acids of the polynucleotide or polypeptide of the present invention; and then multiplying by 100 to determine the percentage identity. For example, a polynucleotide of the present invention having 220 nucleic acids has a hit to a polynucleotide sequence in the EMBL database having 520 nucleic acids over a stretch of 23 nucleotides in the alignment produced by the BLASTN algorithm using the parameters described above. The 23 nucleotide hit includes 21 identical nucleotides, one gap and one different nucleotide. The percentage identity of the polynucleotide of the present invention to the hit in the EMBL library is thus $^{21}/_{220}$ times 100, or 9.5%. The polynucleotide sequence in the EMBL database is thus not a variant of a polynucleotide of the present invention.

Alternatively, variant polynucleotides of the present invention hybridize to the polynucleotide sequences recited in SEQ ID NO: 1-266, 350-375, 404 and 406, or complements, reverse sequences, or reverse complements of those sequences, under stringent conditions. As used herein, "stringent conditions" refers to prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

The present invention also encompasses polynucleotides that differ from the disclosed sequences but that, as a consequence of the discrepancy of the genetic code, encode a polypeptide having similar enzymatic activity as a polypeptide encoded by a polynucleotide of the present invention. Thus, polynucleotides comprising sequences that differ from the polynucleotide sequences recited in SEQ ID NO: 1-266, 350-375, 404 and 406, or complements, reverse sequences, or reverse complements of those sequences as a result of conservative substitutions are contemplated by and encompassed within the present invention. Additionally, polynucleotides comprising sequences that differ from the polynucleotide sequences recited in SEQ ID NO: 1-266, 350-375, 404 and 406, or complements, reverse complements, or reverse sequences as a result of deletions and/or insertions totaling less than 10% of the total sequence length are also contemplated by and encompassed within the present invention. Similarly, polypeptides comprising sequences that differ from the polypeptide sequences recited in SEQ ID NO: 267-349, 376-401, 405 and 407 as a result of amino acid substitutions, insertions, and/or deletions totaling less than 10% of the total sequence length are contemplated by and encompassed within the present invention, provided the variant polypeptide has activity in a lignin biosynthetic pathway.

The polynucleotides of the present invention, including variants, may be isolated from various libraries assembled from plant or non-plant organisms, or may be synthesized using techniques that are well known in the art. Polynucleotides of the present invention may be isolated by high throughput sequencing of cDNA libraries prepared from *Eucalyptus grandis* and *Pinus radiata* as described below in Examples 1 and 2. Alternatively, oligonucleotide probes based on the sequences provided in SEQ ID NO: 1-266, 350-375, 404 and 406 may be synthesized and used to identify positive clones in either cDNA or genomic DNA libraries from *Eucalyptus grandis* and *Pinus radiata* by means of hybridization or PCR techniques. Probes may be shorter than the sequences provided herein but should be at least about 10, preferably at least about 15 and most preferably at least about 20 nucleotides in length. Hybridization and PCR techniques suitable for use with such oligonucleotide probes are well known in the art. Positive clones may be analyzed by restriction enzyme digestion, DNA sequencing or the like.

Variants of the polynucleotides of the present invention derived from other eucalyptus and pine species, as well as from other commercially important species utilized by the lumber industry, are contemplated. These include the following gymnosperms, by way of example: loblolly pine *Pinus taeda*, slash pine *Pinus elliotti*, sand pine *Pinus clausa*, longleaf pine *Pinus palustrus*, shortleaf pine *Pinus echinata*, ponderosa pine *Pinus ponderosa*, Jeffrey pine *Pinus jeffrey*, red pine *Pinus resinosa*, pitch pine *Pinus rigida*, jack pine *Pinus banksiana*, pond pine *Pinus serotina*, Eastern white pine *Pinus strobus*, Western white pine *Pinus monticola*, sugar pine *Pinus lambertiana*, Virginia pine *Pinus virginiana*, lodgepole pine *Pinus contorta*, Caribbean pine *Pinus caribaea, P. pinaster*, Calabrian pine *P. brutia*, Afghan pine *P. eldarica*, Coulter pine *P. coulteri*, European pine *P. nigra* and *P. sylvestris*; Douglas-fir *Pseudotsuga menziesii*; the hemlocks which include Western hemlock *Tsuga heterophylla*, Eastern hemlock *Tsuga canadensis*, Mountain hemlock *Tsuga mertensiana*; the spruces which include the Norway spruce *Picea abies*, red spruce *Picea rubens*, white spruce *Picea glauca*, black spruce *Picea mariana*, Sitka spruce *Picea sitchensis*, Englemann spruce *Picea engelmanni*, and blue spruce *Picea pungens*; redwood *Sequoia sempervirens*; the true firs include the Alpine fir *Abies lasiocarpa*, silver fir *Abies amabilis*, grand fir *Abies grandis*, nobel fir *Abies procera*, white fir *Abies concolor*, California red fir *Abies magnifica*, and balsam fir *Abies balsamea*, the cedars which include the Western red cedar *Thuja plicata*, incense cedar *libocedrus decurrens*, Northern white cedar *Thuja occidentalis*, Port Orford cedar *Chamaecyparis lawsoniona*, Atlantic white cedar *Chamaecyparis thyoides*, Alaska yellow-cedar *Chamaecyparis nootkatensis*, and Eastern red cedar *Huniperus virginiana*; the larches which include Eastern larch *Larix laricina*, Western larch *Larix occidentalis*, European larch *Larix decidua*, Japanese larch *Larix leptolepis*, and Siberian larch *Larix siberica*; bold cypress *Taxodium distichum* and Giant sequoia *Sequoia gigantea*; and the following angiosperms, by way of example: *Eucalyptus alba, E. bancroftii, E. botyroides, E. bridgesiana, E. calophylla, E. camaldulensis, E. citriodora, E. cladocalyx, E. coccifera, E. curtisii, E. dalrympleana, E. deglupta, E. delagatensis, E. diversicolor, E. dunnii, E. ficifolia, E. globulus, E. gomphocephala, E. gunnii, E. henryi, E. laevopinea, E. macarthurii, E. macrorhyncha, E. maculata, E. marginata, E. megacarpa, E. melliodora, E. nicholii, E. nitens, E. nova-angelica, E. obliqua, E. obtusiflora, E. oreades, E. pauciflora, E. polybractea, E. regnans, E. resinifera, E. robusta, E. rudis, E. saligna, E. sideroxylon, E. stuartiana, E. tereticornis, E. torelliana, E. urnigera, E. urophylla, E. viminalis, E. viridis, E. wandoo* and *E. youmanni.*

The polynucleotides of the present invention may alternatively be synthesized, for example, using automated oligonucleotide synthesizers (e.g., Beckman Oligo 1000M DNA Synthesizer) to obtain polynucleotide segments of up to 50 or more nucleic acids. A plurality of such polynucleotide segments may then be ligated using standard DNA manipulation techniques that are well known in the art of molecular biology. One conventional and exemplary polynucleotide synthesis technique involves synthesis of a single stranded polynucleotide segment having, for example, 80 nucleic acids, and hybridizing that segment to a synthesized complementary 85 nucleic acid segment to produce a 5 nucleotide overhang. The next segment may then be synthesized in a similar fashion, with a 5 nucleotide overhang on the opposite strand. The "sticky" ends ensure proper ligation when the two portions are hybridized. In this way, a complete polynucleotide of the present invention may be synthesized entirely in vitro.

The polynucleotides identified as SEQ ID NO: 1-266, 350-375, 404 and 406 represent both "partial" and full length sequences. Partial sequences do not represent the full coding portion of a gene encoding a naturally occurring polypeptide. The partial polynucleotide sequences disclosed herein may be employed to obtain the corresponding full length genes for various species and organisms by, for example, screening DNA expression libraries using hybridization probes based on the polynucleotides of the present invention, or using PCR amplification with primers based upon the polynucleotides of the present invention. In this way one can, using methods well known in the art, extend a polynucleotide of the present invention upstream and downstream of the corresponding mRNA, as well as identify the corresponding genomic DNA, including the promoter and enhancer regions, of the complete gene.

The present invention thus comprehends isolated polynucleotides comprising a sequence identified in SEQ ID NO: 1-266, 350-375, 404 and 406, or a variant of one of the specified sequences, that encode a functional polypeptide, including full length genes. Such extended polynucleotides may have a length of from about 50 to about 4,000 nucleic acids or base pairs, and preferably have a length of less than about 4,000 nucleic acids or base pairs, more preferably a length of less than about 3,000 nucleic acids or base pairs, more preferably yet a length of less than about 2,000 nucleic acids or base pairs. Under some circumstances, extended polynucleotides of the present invention may have a length of less than about 1,800 nucleic acids or base pairs, preferably less than about 1,600 nucleic acids or base pairs, more preferably less than about 1,400 nucleic acids or base pairs, more preferably yet less than about 1,200 nucleic acids or base pairs, and most preferably less than about 1,000 nucleic acids or base pairs.

Polynucleotides of the present invention also comprehend polynucleotides comprising at least a specified number of contiguous residues (x-mers) of any of the polynucleotides identified as SEQ ID NO: 1-266, 350-375, 404 and 406 or their variants. According to preferred embodiments, the value of x is preferably at least 20, more preferably at least 40, more preferably yet at least 60, and most preferably at least 80. Thus, polynucleotides of the present invention include polynucleotides comprising a 20-mer, a 40-mer, a 60-mer, an 80-mer, a 100-mer, a 120-mer, a 150-mer, a 180-mer, a 220-mer a 250-mer, or a 300-mer, 400-mer, 500-mer or 600-mer of a polynucleotide identified as SEQ ID NO: 1-266, 350-375, 404 and 406, or a variant of any x-mer. That is, the definitions for variants described above in terms of E values, % similarity and hybridization, apply also to any x-mer of any polynucleotide of the present invention.

Polynucleotide probes and primers complementary to and/or corresponding to SEQ ID NO: 1-266, 350-375, 404 and 406, and variants of those sequences, are also comprehended by the present invention. Such oligonucleotide probes and primers are substantially complementary to the polynucleotide of interest. An oligonucleotide probe or primer is described as “corresponding to” a polynucleotide of the present invention, including one of the sequences set out as SEQ ID NO: 1-266, 350-375, 404 and 406 or a variant, if the oligonucleotide probe or primer, or its complement, is contained within one of the sequences set out as SEQ ID NO: 1-266, 350-375, 404 and 406 or a variant of one of the specified sequences.

Two single stranded sequences are said to be substantially complementary when the nucleotides of one strand, optimally aligned and compared, with the appropriate nucleotide insertions and/or deletions, pair with at least 80%, preferably at least 90% to 95%, and more preferably at least 98% to 100%, of the nucleotides of the other strand. Alternatively, substantial complementarity exists when a first DNA strand will selectively hybridize to a second DNA strand under stringent hybridization conditions. Stringent hybridization conditions for determining complementarity include salt conditions of less than about 1 M, more usually less than about 500 mM and preferably less than about 200 mM. Hybridization temperatures can be as low as 5° C., but are generally greater than about 22° C., more preferably greater than about 30° C. and most preferably greater than about 37° C. Longer DNA fragments may require higher hybridization temperatures for specific hybridization. Since the stringency of hybridization may be affected by other factors such as probe composition, presence of organic solvents and extent of base mismatching, the combination of parameters is more important than the absolute measure of any one alone. The DNAs from plants or samples or products containing plant material can be either genomic DNA or DNAs derived by preparing cDNA from the RNAs present in the sample.

In addition to DNA-DNA hybridization, DNA-RNA or RNA-RNA hybridization assays are also possible. In the first case, the mRNAs from expressed genes would then be detected instead of genomic DNA or cDNA derived from mRNA of the sample. In the second case, RNA probes could be used. In addition, artificial analogs of DNA hybridizing specifically to target sequences could also be used.

In specific embodiments, the oligonucleotide probes and/or primers comprise at least about 6 contiguous residues, more preferably at least about 10 contiguous residues, and most preferably at least about 20 contiguous residues complementary to a polynucleotide sequence of the present invention. Probes and primers of the present invention may be from about 8 to 100 base pairs in length or, preferably, from about 10 to 50 base pairs in length or, more preferably, from about 15 to 40 base pairs in length. The probes can be easily selected using procedures well known in the art, taking into account DNA-DNA hybridization stringencies, annealing and melting temperatures, potential for formation of loops and other factors, which are well known in the art. Tools and software suitable for designing probes and PCT primers are well known in the art. Preferred techniques for designing PCR primers are disclosed in Dieffenbach C W and Dvksler G S, *PCR primer: a laboratory manual*, CSHL Press: Cold Spring Harbor, N.Y., 1995. A software program suitable for designing probes, and especially for designing PCR primers, is available from Premier Biosoft International, 3786 Corina Way, Palo Alto, Calif. 94303-4504.

A plurality of oligonucleotide probes or primers corresponding to polynucleotides of the present invention may be provided in a kit form. Such kits generally comprise multiple DNA or oligonucleotide probes, each probe being specific for a polynucleotide sequence. Kits of the present invention may comprise one or more probes or primers corresponding to a polynucleotide of the present invention, including a polynucleotide sequence identified in SEQ ID NO: 1-266, 350-375, 404 and 406.

In one embodiment useful for high-throughput assays, the oligonucleotide probe kits of the present invention comprise multiple probes in an array fonnat, wherein each probe is immobilized in a predefined, spatially addressable location on the surface of a solid substrate. Array formats which may be usefully employed in the present invention are disclosed, for example, in U.S. Pat. Nos. 5,412,087, 5,545,531, and PCT Publication No. WO 95/00530, the disclosures of which are hereby incorporated by reference.

The significance of high-throughput screening systems is apparent for applications such as plant breeding and quality control operations in which there is a need to identify large numbers of seed lots and plant seedlings, to examine samples or products for unwanted plant materials, to identify plants or samples or products containing plant material for quarantine purposes etc. or to ascertain the true origin of plants or samples or products containing plant material. Screening for the presence or absence of polynucleotides of the present invention used as identifiers for tagging plants is valuable for later detecting the amount of gene flow in plant breeding, introgression of genes via dispersed pollen, etc.

In this manner, oligonucleotide probe kits of the present invention may be employed to examine the presence/absence (or relative amounts in case of mixtures) of polynucleotides of the present invention in different samples or products containing different materials rapidly and in a cost-effective manner. Examples of plant species that may be examined using the present invention, include forestry species, such as pine and eucalyptus species, other tree species, agricultural plants including crop and forage plants, and horticultural plants.

Another aspect of the present invention involves collections of polynucleotides of the present invention. A collection of polynucleotides of the present invention, particularly the polynucleotides identified as SEQ ID NO: 1-266, 350-375, 404 and 406, and variants and x-mers thereof, may be recorded and/or stored on a storage medium and subsequently accessed for purposes of analysis, comparison, etc. Suitable storage media include magnetic media such as magnetic diskettes, magnetic tapes, CD-ROM storage media, optical storage media, and the like. Suitable storage media and methods for recording and storing information, as well as accessing information such as polynucleotide sequences recorded on such media, are well known in the art. The polynucleotide information stored on the storage medium is preferably computer-readable and may be used for analysis and comparison of the polynucleotide information.

Another aspect of the present invention thus involves storage medium on which are recorded a collection of the polynucleotides of the present invention, particularly a collection of the polynucleotides identified as SEQ ID NO: 1-266, 350-375, 404 and 406, and variants thereof, as well as x-mers of the polynucleotides of SEQ ID NO: 1-266, 350-375, 404 and 406, and extended sequences, probes and primers comprising or correspond to a polynucleotide of SEQ ID NO: 1-266, 350-375, 404 and 406. According to one embodiment, the storage medium includes a collection of at least 20, preferably at least 50, more preferably at least 100, and most preferably at least 200 of the polynucleotides of the present invention, preferably the polynucleotides identified as SEQ ID NO: 1-266, 350-375, 404 and 406, or variants of those polynucleotides.

In another aspect, the present invention provides genetic constructs comprising, in the 5'-3' direction, a gene promoter sequence; an open reading frame coding for at least a functional portion of a polypeptide encoded by a polynucleotide of the present invention; and a gene termination sequence. As used herein, the "functional portion" of an enzyme is a portion that contains an active site essential for affecting a metabolic step, i.e. a portion of the molecule that is capable of binding one or more reactants or is capable of improving or regulating the rate of reaction. An active site may be made up of separate portions present on one or more polypeptide chains and will generally exhibit high substrate specificity. The term "enzyme encoded by a nucleotide sequence" as used herein, includes enzymes encoded by a nucleotide sequence which includes the partial isolated polynucleotides of the present invention.

The open reading frame may be orientated in either a sense or antisense direction. For applications where amplification of lignin synthesis is desired, the open reading frame may be inserted in the construct in a sense orientation, such that transformation of a target organism with the construct will lead to an increase in the number of copies of the gene and therefore an increase in the amount of enzyme. When down-regulation of lignin synthesis is desired, the open reading frame may be inserted in the construct in an antisense orientation, such that the RNA produced by transcription of the polynucleotide is complementary to the endogenous mRNA sequence. This, in turn, will result in a decrease in the number of copies of the gene and therefore a decrease in the amount of enzyme. Alternatively, regulation may be achieved by inserting appropriate sequences or subsequences (e.g., DNA or RNA) in ribozyrne constructs.

Genetic constructs comprising a non-coding region of a gene coding for an enzyme encoded by the above DNA sequences or a nucleotide sequence complementary to a non-coding region, together with a gene promoter sequence and a gene termination sequence, are also provided. As used herein the term "non-coding region" includes both transcribed sequences which are not translated, and non-transcribed sequences within about 2000 base pairs 5' or 3' of the translated sequences or open reading frames. Examples of non-coding regions which may be usefully employed in the inventive constructs include introns and 5'- non-coding leader sequences. Transformation of a target plant with such a DNA construct may lead to a reduction in the amount of lignin synthesized by the plant by the process of cosuppression, in a manner similar to that discussed, for example, by Napoli et al., *Plant Cell* 2:279-290, 1990; and de Carvalho Niebel et al., *Plant Cell* 7:347-358, 1995.

The genetic constructs of the present invention further comprise a gene promoter sequence and a gene termination sequence, operably linked to the polynucleotide to be transcribed, which control expression of the gene. The gene promoter sequence is generally positioned at the 5' end of the polynucleotide to be transcribed, and is employed to initiate transcription of the polynucleotide. Gene promoter sequences are generally found in the 5' non-coding region of a gene but they may exist in introns (Luehrsen K R, *Mol. Gen. Genet.* 225:81-93, 1991, or in the coding region, as for example in PAL of tomato (Bloksberg, *Studies on the Biology of Phenylalanine Ammonia Lyase and Plant Pathogen Interaction*, Ph.D. Thesis, University of California, Davis, 1991, University Microfilms International Order No. 9217564). When the construct includes an open reading frame in a sense orientation, the gene promoter sequence also initiates translation of the open reading frame. For genetic constructs comprising either an open reading frame in an antisense orientation or a non-coding region, the gene promoter sequence consists only of a transcription initiation site having a RNA polymerase binding site.

A variety of gene promoter sequences which may be usefully employed in the genetic constructs of the present invention are well known in the art. The promoter gene sequence, and also the gene termination sequence, may be endogenous to the target plant host or may be exogenous, provided the promoter is functional in the target host. For example, the promoter and termination sequences may be from other plant species, plant viruses, bacterial plasmids and the like. Preferably, gene promoter and termination sequences are from the inventive sequences themselves.

Factors influencing the choice of promoter include the desired tissue specificity of the construct, and the timing of transcription and translation. For example, constitutive promoters, such as the 35S Cauliflower Mosaic Virus (CaMV 35S) promoter, will affect the activity of the enzyme in all parts of the plant. Use of a tissue specific promoter will result in production of the desired sense or antisense RNA only in the tissue of interest. With genetic constructs employing inducible gene promoter sequences, the rate of RNA polymerase binding and initiation can be modulated by external stimuli, such as light, heat, anaerobic stress, alteration in nutrient conditions and the like. Temporally regulated promoters can be employed to effect modulation of the rate of RNA polymerase binding and initiation at a specific time during development of a transformed cell. Preferably, the original promoters from the enzyme gene in question, or promoters from a specific tissue-targeted gene in the organism to be transformed, such as eucalyptus or pine are used. Other examples of gene promoters which may be usefully employed in the present invention include, mannopine synthase (mas), octopine synthase (ocs) and those reviewed by Chua et al., *Science* 244:174-181, 1989.

The gene termination sequence, which is located 3' to the polynucleotide to be transcribed, may come from the same gene as the gene promoter sequence or may be from a different gene. Many gene termination sequences known in the art may be usefully employed in the present invention, such as the 3' end of the *Agrobacterium tumefaciens* nopaline synthase gene. However, preferred gene terminator sequences are those from the original enzyme gene or from the target species to be transformed.

The genetic constructs of the present invention may also contain a selection marker that is effective in plant cells, to allow for the detection of transformed cells containing the inventive construct. Such markers, which are well known in the art, typically confer resistance to one or more toxins. One example of such a marker is the NPTII gene whose expression results in resistance to kanamycin or hygromycin, antibiotics which are usually toxic to plant cells at a moderate concentration (Rogers et al., in Weissbach A and H, eds., *Methods for Plant Molecular Biology*, Academic Press Inc.: San Diego, Calif., 1988). Alternatively, the presence of the desired construct in transformed cells can be determined by means of other techniques well known in the art, such as Southern and Western blots.

Techniques for operatively linking the components of the inventive genetic constructs are well known in the art and include the use of synthetic linkers containing one or more restriction endonuclease sites as described, for example, by Maniatis et al., (*Molecular cloning: a laboratory manual*, CSHL Press: Cold Spring Harbor, N.Y., 1989). The genetic construct of the present invention may be linked to a vector having at least one replication system, for example, *E. coli*, whereby after each manipulation, the resulting construct can be cloned and sequenced and the correctness of the manipulation determined.

The genetic constructs of the present invention may be used to transform a variety of plants, both monocotyledonous (e.g., grasses, corn, grains, oat, wheat and barley), dicotyledonous (e.g., *Arabidopsis*, tobacco, legumes, alfalfa, oaks, eucalyptus, maple), and Gymnosperms (e.g., Scots pine; see Aronen, *Finnish Forest Res. Papers*, Vol. 595, 1996), white spruce (Ellis et al., *Biotechnology* 11:94-92, 1993), and larch (Huang et al., *In Vitro Cell* 27:201-207, 1991). In a preferred embodiment, the inventive genetic constructs are employed to transform woody plants, herein defined as a tree or shrub whose stem lives for a number of years and increases in diameter each year by the addition of woody tissue. Preferably the target plant is selected from the group consisting of eucalyptus and pine species, most preferably from the group consisting of *Eucalyptus grandis* and *Pinus radiata*. As discussed above, transformation of a plant with a genetic construct including an open reading frame coding for an enzyme encoded by an inventive polynucleotide wherein the open reading frame is orientated in a sense direction will produce a modified lignin content in the plant. Transformation of a plant with a genetic construct comprising an open reading frame in an antisense orientation or a non-coding (untranslated) region of a gene will also produced a modification in the lignin content of the transformed plant.

Polynucleotides of the present invention may also be used to specifically suppress gene expression by methods that operate post-transcriptionally to block the synthesis of products of targeted genes, such as RNA interference (RNAi) and quelling. Briefly, traditional methods of gene suppression, employing anti-sense RNA or DNA, operate by binding to the reverse sequence of a gene of interest such that binding interferes with subsequent cellular processes and therefore blocks synthesis of the corresponding protein. RNAi also operates on a post-translational level and is sequence specific, but suppresses gene expression far more efficiently. Exemplary methods for controlling or modifying gene expression using RNAi are provided in WO 99/49029 and WO 99/53050. In these methods, post-transcriptional gene silencing is brought about by a sequence-specific RNA degradation process which results in the rapid degradation of transcripts of sequence-related genes. Studies have shown that double-stranded RNA may act as a mediator of sequence-specific gene silencing (see, for example, Montgomery and Fire, *Trends in Genetics*, 14:255-258, 1998). Gene constructs that produce transcripts with self-complementary regions are particularly efficient at gene silencing. A unique feature of this post-transcriptional gene silencing pathway is that silencing is not limited to the cells where it is initiated. The gene-silencing effects may be disseminated to other parts of an organism and even transmitted through the germ line to several generations.

The polynucleotides of the present invention may thus be employed to generate gene silencing constructs and/or gene-specific self-complementary RNA sequences that can be delivered by conventional art-known methods to plant tissues, such as forage grass tissues. Within genetic constructs, sense and antisense sequences can be placed in regions flanking an intron sequence in proper splicing orientation with donor and acceptor splicing sites, such that intron sequences are removed during processing of the transcript and sense and antisense sequences, as well as splice junction sequences, bind together to form double-stranded RNA. Alternatively, spacer sequences of various lengths may be employed to separate self-complementary regions of sequence in the construct. During processing of the gene construct transcript, intron sequences are spliced-out, allowing sense and antisense sequences, as well as splice junction sequences, to bind forming double-stranded RNA. Select ribonucleases then bind to and cleave the double-stranded RNA, thereby initiating the cascade of events leading to degradation of specific mRNA gene sequences, and silencing specific genes. Alternatively, rather than using a gene construct to express the self-complementary RNA sequences, the gene-specific double-stranded RNA segments are delivered to one or more targeted areas to be internalized into the cell cytoplasm to exert a gene silencing effect. The double-stranded RNA must have sufficient homology to the targeted gene to mediate RNAi and is preferably at least 25 nucleotides in length. Preferably, the double-stranded RNA corresponds specifically to a polynucleotide of the present invention. Gene silencing RNA sequences comprising the polynucleotides of the present invention are useful for creating genetically modified plants with desired phenotypes as well as for characterizing genes (for example, in high-throughput screening of sequences), and studying their functions in intact organisms.

The production of RNA in target cells may be controlled by choice of the promoter sequence, or by selecting the number of functional copies or the site of integration of the polynucleotides incorporated into the genome of the target organism. A target plant may be transformed with more than one construct of the present invention, thereby modulating the lignin biosynthetic pathway for the activity of more than one enzyme, affecting enzyme activity in more than one tissue or affecting enzyme activity at more than one expression time. Similarly, a construct may be assembled containing more than one open reading frame coding for an enzyme encoded by a polynucleotide of the present invention or more than one non-coding region of a gene coding for such an enzyme. The polynucleotides of the present invention may also be employed in combination with other known sequences encoding enzymes involved in the lignin biosynthetic pathway. In this manner, it may be possible to add a lignin biosynthetic pathway to a non-woody plant to produce a new woody plant.

Techniques for stably incorporating genetic constructs into the genome of target plants are well known in the art and include *Agrobacterium tumefaciens* mediated introduction, electroporation, protoplast fusion, injection into reproductive organs, injection into immature embryos, high velocity projectile introduction and the like. The choice of technique will depend upon the target plant to be transformed. For example, dicotyledonous plants and certain monocots and gymnosperms may be transformed by *Agrobacterium* Ti plasmid technology, as described, for example by Bevan (*Nucl. Acid Res.* 12:8711-8721, 1984). Targets for the introduction of the genetic constructs of the present invention include tissues, such as leaf tissue, disseminated cells, protoplasts, seeds, embryos, meristematic regions; cotyledons, hypocotyls, and the like. One preferred method for transforming eucalyptus and pine is a biolistic method using pollen (see, for example, Aronen, *Finnish Forest Res. Papers*, Vol. 595:53, 1996) or easily regenerable embryonic tissues. Other transformation techniques which may be usefully employed in the inventive methods include those taught by Ellis et al. (*Plant Cell Reports,* 8:16-20, 1989), Wilson et al. (*Plant Cell Reports* 7:704-707, 1989) and Tautorus et al. (*Theor. Appl. Genet.* 78:531-536, 1989).

Once the cells are transformed, cells having the inventive genetic construct incorporated in their genome may be selected by means of a marker, such as the kanamycin resistance marker discussed above. Transgenic cells may then be cultured in an appropriate medium to regenerate whole plants, using techniques well known in the art. In the case of protoplasts, the cell wall is allowed to reform under appropriate osmotic conditions. In the case of seeds or embryos, an appropriate germination or callus initiation medium is employed. For explants, an appropriate regeneration medium is used. Regeneration of plants is well established for many species. For a review of regeneration of forest trees, see Dunstan et al., "Somatic embryogenesis in woody plants," in Thorpe T A, ed., *In vitro embryogenesis of plants*, Current Plant Science and Biotechnology in Agriculture 20(12):471-540, 1995. Specific protocols for the regeneration of spruce are discussed by Roberts et al., ("Somatic embryogenesis of spruce," in Redenbaugh K, ed., *Synseed: applications of synthetic seed to crop improvement*, CRC Press: Chapter 23, pp. 427-449, 1993). The resulting transformed plants may be reproduced sexually or asexually, using methods well known in the art, to give successive generations of transgenic plants.

In yet a further aspect, the present invention provides methods for modifying the level (concentration) or activity of a polypeptide in a host organism, comprising stably incorporating into the genome of the plant a construct comprising a polynucleotide of the present invention. The genetic constructs of the present invention may be used to transform a variety of organisms. Such organisms include plants, such as monocotyledonous angiosperms (e.g., grasses, corn, grains, oat, wheat and barley), and dicotyledonous angiosperms (e.g., *Arabidopsis*, tobacco, legumes, alfalfa, oaks, eucalyptus, maple), and gymnosperms (e.g., Scots pine; see Aronen, *Finnish Forest Res. Papers*, Vol. 595, 1996), white spruce (Ellis et al., *Biotechnology* 11:94-92, 1993), and larch (Huang et al., *In Vitro Cell* 27:201-207, 1991).

In preferred embodiments, the genetic constructs of the present invention are employed to transform woody plants, herein defined as a tree or shrub having a stem that lives for a number of years and increases in diameter each year as a consequence of the addition of woody tissue. The target plant is preferably selected from the group consisting of eucalyptus and pine species, most preferably from the group consisting of *Eucalyptus grandis* and *Pinus radiata*, but also including any of the species in the following list:

Pines: *Pinus banksiana, Pinus bnitia, Pinus caribaea, Pinus clausa, Pinus contorta, Pinus coulteri, Pinus echinata, Pinus eldarica, Pinus ellioti, Pinus jeffreyi, Pinus lambertiana, Pinus monticola, Pinus nigra, Pinus palustrus, Pinus pinaster, Pinus ponderosa, Pinus resinosa, Pinus rigida, Pinus serotina, Pinus strobus, Pinus sylvestris, Pinus taeda, Pinus virginiana.*

Other gymnosperms: *Abies amabilis, Abies balsamea, Abies concolor, Abies grandis, Abies lasiocarpa, Abies magnifica, Abies procera, Chamaecyparis lawsoniona, Chamaecyparis nootkatensis, Chamaecyparis thyoides, Huniperus virginiana, Larix decidua, Larix laricina, Larix leptolepis, Larix occidentalis, Larix siberica, Libocedrus decurrens, Picea abies, Picea engelmanni, Picea glauca, Picea mariana, Picea pungens, Picea rubens, Picea sitchensis, Pseudotsuga menziesii, Sequoia gigantea, Sequoia sempervirens, Taxodium distichum, Tsuga canadensis, Tsuga heterophylla, Tsuga mertensiana, Thuja occidentalis, Thuja plicata.*

Eucalypts: *Eucalyptus alba, Eucalyptus bancroftii, Eucalyptus botyroides, Eucalyptus bridgesiana, Eucalyptus calophylla, Eucalyptus camaldulensis, Eucalyptus citriodora, Eucalyptus cladocalyx, Eucalyptus coccifera, Eucalyptus curtisii, Eucalyptus dalrympleana, Eucalyptus deglupta, Eucalyptus delagatensis, Eucalyptus diversicolor, Eucalyptus dunnii, Eucalyptus ficifolia, Eucalyptus globulus, Eucalyptus gomphocephala, Eucalyptus gunnii, Eucalyptus henryi, Eucalyptus laevopinea, Eucalyptus macarthurii, Eucalyptus macrorhyncha, Eucalyptus maculata, Eucalyptus marginata, Eucalyptus megacarpa, Eucalyptus melliodora, Eucalyptus nicholii, Eucalyptus nitens, Eucalyptus nova-anglica, Eucalyptus obliqua, Eucalyptus obtusiflora, Eucalyptus oreades, Eucalyptus pauciflora, Eucalyptus polybractea, Eucalyptus regnans, Eucalyptus resinifera, Eucalyptus robusta, Eucalyptus rudis, Eucalyptus saligna, Eucalyptus sideroxylon, Eucalyptits stuartiana, Eucalyptus tereticornis, Eucalyptus torelliana, Eucalyptus urnigera, Eucalyptus urophylla, Eucalyptus viminalis, Eucalyptus viridis, Eucalyptus wandoo, Eucalyptus youmanni*; and hybrids of any of the above species.

Further, the polynucleotides of the present invention have particular application for use as non-disruptive tags for marking organisms, particularly plants. Other organisms may, however, be tagged with the polynucleotides of the present invention, including commercially valuable animals, fish, bacteria and yeasts. Constructs comprising polynucleotides of the present invention may be stably introduced into an organism as heterologous, non-functional, non-disruptive tags. It is then possible to identify the origin or source of the organism at a later date by determining the presence or absence of the tag(s) in a sample of material.

Detection of the tag(s) may be accomplished using a variety of conventional techniques, and will generally involve the use of nucleic acid probes. Sensitivity in assaying the presence of probe can be usefully increased by using branched oligonucleotides, as described in Horn T, Chang C A and Urdea M S, "Chemical synthesis and characterization of branched oligodeoxyribonucleotides (bDNA) for use as signal amplifiers in nucleic acid quantification assays," *Nucleic Acids Research* 25(23):4842-4849, 1997), enabling detection of as few as 50 DNA molecules in the sample.

The following examples are offered by way of illustration and not by way of limitation.

EXAMPLE 1

Isolation and Characterization of cDNA Clones from *Eucalyptus grandis*

Two *Eucalyptus grandis* cDNA expression libraries (one from a mixture of various tissues from a single tree and one from leaves of a single tree) were constructed and screened as follows.

mRNA was extracted from the plant tissue using the protocol of Chang et al. (*Plant Molecular Biology Reporter* 11:113-116, 1993) with minor modifications. Specifically, samples were dissolved in CPC-RNAXB (100 mM Tris-Cl, pH 8.0; 25 mM EDTA; 2.0 M NaCl; 2% CTAB; 2% PVP and 0.05% Spermidine*3 HCl) and extracted with chloroform: isoamyl alcohol, 24:1. mRNA was precipitated with ethanol and the total RNA preparate was purified using a Poly(A) Quik mRNA Isolation Kit (Stratagene, La Jolla, Calif.). A cDNA expression library was constructed from the purified mRNA by reverse transcriptase synthesis followed by insertion of the resulting cDNA clones in Lambda ZAP using a ZAP Express cDNA Synthesis Kit (Stratagene), according to the manufacturer's protocol. The resulting cDNAs were packaged using a Gigapack II Packaging Extract (Stratagene) employing 1 μl of sample DNA from the 5 μl ligation mix. Mass excision of the library was done using XL1-Blue MRF' cells and XLOLR cells (Stratagene) with ExAssist helper phage (Stratagene). The excised phagemids were diluted with NZY broth (Gibco BRL, Gaithersburg, Md.) and plated out onto LB-kanamycin agar plates containing X-gal and isopropylthio-beta-galactoside (IPTG).

Of the colonies plated and picked for DNA miniprep, 99% contained an insert suitable for sequencing. Positive colonies were cultured in NZY broth with kanamycin and cDNA was purified by means of alkaline lysis and polyethylene glycol (PEG) precipitation. Agarose gel at 1% was used to screen sequencing templates for chromosomal contamination. Dye primer sequences were prepared using a Turbo Catalyst 800 machine (Perkin Elmer/Applied Biosystems, Foster City, Calif.) according to the manufacturer's protocol.

DNA sequences for positive clones were obtained using a Perkin Elmer/Applied Biosystems Prism 377 sequencer. cDNA clones were sequenced first from the 5' end and, in some cases, also from the 3' end. For some clones, internal sequence was obtained using subcloned fragments. Subcloning was performed using standard procedures of restriction mapping and subcloning to pBluescript II SK+ vector.

The determined cDNA sequences were compared to known sequences in the EMBL database (release 46, March 1996) using the FASTA algorithm of February 1996 (Version 2.0.4) or the BLASTN algorithm Version 2.0.4 [Feb. 24, 1998], or Version 2.0.6 [Sep. 16, 1998], set to the preferred parameters described above. Multiple alignments of redundant sequences were used to build up reliable consensus sequences. Based on similarity to known sequences from other plant species, the isolated polynucleotides of the present invention were identified as encoding a specified enzyme.

Using the procedures described above, cDNA sequences derived from the *Eucalyptus graitdis* library encoding the following polypeptides were isolated: PAL (SEQ ID NO: 16, 100, 242-246); C4H (SEQ ID NO: 17, 153, 154, and 161); C3H (SEQ ID NO: 18, 101, 149 and 150); F5H (SEQ ID NO: 19-21, 102, 103, 169-171 and 404); OMT (SEQ ID NO: 22-25, 104-107, 173 and 174); CCR (SEQ ID NO: 26-29 and 108-111); CAD (SEQ ID NO: 1, 30 and 112); CGT (SEQ ID NO: 31-33 and 113-115); CBG (SEQ ID NO: 34, 165 and 166); PNL (SEQ ID NO: 35,36 and 116); LAC (SEQ ID NO: 37-41, 117 and 118); POX (SEQ ID NO: 42-44, 119-121, 179, 249-250 and 350-358); 4CL (SEQ ID NO: 266); caffeic acid methyl transferase (SEQ ID NO: 187-192); caffeoyl CoA methyl transferase (SEQ ID NO: 193-195); coumarate Co-A ligase (SEQ ID NO: 196-198); cytochrome P450 LXX1A (SEQ ID NO: 201-206); diphenol oxidase (SEQ ID NO: 207-217); flavonol glucosyl transferase (SEQ ID NO: 218); flavonoid hydroxylase (SEQ ID NO: 219-223); and isoflavone reductase (SEQ ID NO: 234-240).

As shown in Table 1, above, the amino acid sequences encoded by SEQ ID NO: 187-191, 193-198, 201-217, 219-223, 234-239, 242-246, 249, 250, 266 and 350-358 are provided in SEQ ID NO: 270-274, 276-281, 284-300, 302-306, 317-322, 325-329, 332, 333, 349 and 376-384, respectively. SEQ ID NO: 107 is a full-length version of SEQ ID NO: 24 and 106; SEQ ID NO: 108 is a full-length version of SEQ ID NO: 26; SEQ ID NO: 266 is a full-length version of SEQ ID NO: 196 and 197; and SEQ ID NO: 404 is a full-length version of SEQ ID NO: 20 and 103.

EXAMPLE 2

Isolation and Characterization of cDNA Clones from *Pinus radiata* a) Isolation of cDNA Clones by High Through-Put Screening

A *Pinus radiata* cDNA expression library was constructed from xylem and screened as described above in Example 1. DNA sequences for positive clones were obtained using forward and reverse primers on a Perkin Elmer/Applied Biosystems Prism 377 sequencer and the determined sequences were compared to known sequences in the EMBL database as described above.

Based on similarity to known sequences from other plant species, the isolated DNA sequences were identified as encoding the enzymes C4H (SEQ ID NO: 2, 3, 48, 49, 92, 124, 125, 155-160, 162 and 163); C3H (SEQ ID NO: 4, 50-52, 93, 126, 127, 151 and 152); PNL (SEQ ID NO: 5, 81 and 183 ); OMT (SEQ ID NO: 6, 53-55, 94 and 175); CAD (SEQ ID NO: 7, 71, 95 and 164); CCR (SEQ ID NO: 8, 58-70, 96, 128-134 and 167); PAL (SEQ ID NO: 9-11, 45-47, 97, 98, 122, 123 and 176, 247 and 248); 4CL (SEQ ID NO: 12, 56, 57, 90, 99, 147, 148, 199, 200, 265 and 406); CGT (SEQ ID NO: 72, 135 and 168); CBG (SEQ ID NO: 73-80 and 136-141); LAC (SEQ ID NO: 82-84, 142-144 and 172); POX (SEQ ID NO: 85-89, 91, 145, 146, 177, 178, 180-182, 264, 359-375); alpha amylase (SEQ ID NO: 184-186); flavonoid hydroxylase (SEQ ID NO: 224-233); isoflavone reductase (SEQ ID NO: 241); and diphenol oxidase (SEQ ID NO: 251-263).

As shown in Table 1, above, the amino acid sequences encoded by SEQ ID NO: 184-186, 192, 199-200, 218, 224-233, 240-241, 247-248, 251-265, 359-375 and 406 are provided in SEQ ID NO: 267-269, 275, 282-283, 301, 307-316, 323-324, 330-331, 334-348, 385-401 and 407, respectively. SEQ ID NO: 90 is a full-length version of SEQ ID NO: 12 and 56; SEQ ID NO: 94 is a full-length version of SEQ ID NO: 53; SEQ ID NO: 265 is a full-length version of SEQ ID NO: 57; SEQ ID NO: 363 is a full-length version of SEQ ID NO: 372; and SEQ ID NO: 406 is a full-length version of SEQ ID NO: 200.

b) Isolation of cDNA Clones by PCR

Two PCR probes, hereinafter referred to as LNB010 and LNB011 (SEQ ID NO: 14 and 15, respectively) were designed based on conserved domains in the following peroxidase sequences previously identified in other species: vanpox, hvupox6, taepox, hvupox1, osapox, ntopox2, ntopox1, lespox, pokpox, luspox, athpox, hrpox, spopox, and tvepox (Genbank Accession Nos. D11337, M83671, X56011, X58396, X66125, J02979, D11396, X71593, D 1102, L07554, M58381, X57564, Z22920, and Z31011, respectively).

RNA was isolated from pine xylem and first strand cDNA was synthesized as described above. This cDNA was subjected to PCR using 4 μM LNB010, 4 μM LNB011, 1× Kogen's buffer, 0.1 mg/ml BSA, 200 mM dNTP, 2 mM $Mg^{2+}$, and 0.1 U/μl of Taq polymerase (Gibco BRL). Conditions were 2 cycles of 2 min at 94° C., 1 min at 55° C. and 1 min at 72° C.; 25 cycles of 1 min at 94° C., 1 min at 55° C., and 1 min at 72° C.; and 18 cycles of 1 min at 94° C., 1 min at 55° C., and 3 min at 72° C. in a Stratagene Robocycler. The gene was re-amplified in the same manner. A band of about 200 bp was purified from a TAE agarose gel using a Schleicher & Schuell Elu-Quik DNA purification kit and clones into a T-tailed pBluescript vector (Marchuk D et al., *Nucleic Acids Res.* 19:1154, 1991). Based on similarity to known sequences, the isolated gene (SEQ ID NO: 13) was identified as encoding pine peroxidase (POX).

EXAMPLE 3

Use of an O-Methyltransferase (OMT) Gene to Modify Lignin Biosynthesis a) Transformation of Tobacco Plants with a *Pinus radiata* OMT Gene Sense and anti-sense constructs containing a polynucleotide including the coding region of OMT (SEQ ID NO: 53) from Pinus radiata were inserted into *Agrobacterium tumefaciens* LBA4301 (provided as a gift by Dr. C. Kado, University of California, Davis, Calif.) by direct transformation using published methods (see, An G, Ebert P R, Mitra A, Ha S B, "Binary Vectors," in Gelvin S B, Schilperoort R A, eds., *Plant Molecular Biology Manual*, Kluwer Academic Publishers: Dordrecht, 1988). The presence and integrity of the transgenic constructs were verified by restriction digestion and DNA sequencing.

Tobacco (*Nicotiana tabacum* cv. Samsun) leaf sections were transformed using the method of Horsch et al. (*Science,* 227:1229-1231, 1985). Five independent transformed plant lines were established for the sense construct and eight independent transformed plant lines were established for the anti-sense construct for OMT. Transformed plants containing the appropriate lignin gene construct were verified using Southern blot experiments. A "+" in the column labeled "Southern" in Table 2 below indicates that the transformed plant lines were confirmed as independent transformed lines.

b) Expression of *Pinus* OMT in Transformed Plants

Total RNA was isolated from each independent transformed plant line created with the OMT sense and anti-sense constructs. The RNA samples were analysed in Northern blot experiments to determine the level of expression of the transgene in each transformed line. The data shown in the column labeled "Northern" in Table 2 shows that the transformed plant lines containing the sense and anti-sense constructs for OMT all exhibited high levels of expression, relative to the background on the Northern blots. OMT expression in sense plant line number 2 was not measured because the RNA sample showed signs of degradation. There was no detectable hybridisation to RNA samples from empty vector-transformed control plants.

c) Modulation of OMT Enzyme Activity in Transformed Plants

The total activity of OMT enzyme, encoded by the *Pinus* OMT gene and by the endogenous tobacco OMT gene, in transformed tobacco plants was analysed for each transformed plant line created with the OMT sense and anti-sense constructs. Crude protein extracts were prepared from each transformed plant and assayed using the method of Zhang et al. (*Plant Physiol.,* 113:65-74, 1997). The data contained in the column labeled "Enzyme" in Table 1 shows that the transformed plant lines containing the OMT sense construct generally had elevated OMT enzyme activity, with a maximum of 199%, whereas the transformed plant lines containing the OMT anti-sense construct generally had reduced OMT enzyme activity, with a minimum of 35%, relative to empty vector-transformed control plants. OMT enzyme activity was not estimated in sense plant line number 3.

d) Effects of *Pinus* OMT on Lignin Concentration in Transformed Plants

The concentration of lignin in the transformed tobacco plants was determined using the well-established procedure of thioglycolic acid extraction (see, Freudenberg et al., *Constitution and Biosynthesis of Lignin*, Springer-Verlag: Berlin, 1968). Briefly, whole tobacco plants, of an average age of 38 days, were frozen in liquid nitrogen and ground to a fine powder in a mortar and pestle. 100 mg of frozen powder from one empty vector-transformed control plant line, the five independent transformed plant lines containing the sense construct for OMT and the eight independent transformed plant lines containing the anti-sense construct for OMT were extracted individually with methanol, followed by 10% thioglycolic acid and finally dissolved in 1 M NaOH. The final extracts were assayed for absorbance at 280 nm. The data shown in the column labelled "TGA" in Table 2 shows that the transformed plant lines containing the sense and the anti-sense OMT gene constructs all exhibited significantly decreased levels of lignin, relative to the empty vector-transformed control plant lines.

TABLE 2

| plant line | transgene | orientation | Southern | Northern | Enzyme | TGA |
|---|---|---|---|---|---|---|
| 1 | control | na | + | blank | 100 | 104 |
| 1 | OMT | sense | + | 2.9E+6 | 86 | 55 |
| 2 | OMT | sense | + | na | 162 | 58 |
| 3 | OMT | sense | + | 4.1E+6 | na | 63 |
| 4 | OMT | sense | + | 2.3E+6 | 142 | 66 |
| 5 | OMT | sense | + | 3.6E+5 | 199 | 75 |
| 1 | OMT | anti-sense | + | 1.6E+4 | 189 | 66 |
| 2 | OMT | anti-sense | + | 5.7E+3 | 35 | 70 |
| 3 | OMT | anti-sense | + | 8.0E+3 | 105 | 73 |
| 4 | OMT | anti-sense | + | 1.4E+4 | 109 | 74 |
| 5 | OMT | anti-sense | + | 2.5E+4 | 87 | 78 |
| 6 | OMT | anti-sense | + | 2.5E+4 | 58 | 84 |
| 7 | OMT | anti-sense | + | 2.5E+4 | 97 | 92 |
| 8 | OMT | anti-sense | + | 1.1E+4 | 151 | 94 |

These data clearly indicate that lignin concentration, as measured by the TGA assay, can be directly manipulated by either sense or anti-sense expression of a lignin biosynthetic gene such as OMT.

EXAMPLE 4

Use of a 4-Coumarate:CoA Ligase (4CL) Gene to Modify Lignin Biosynthesis a) Transformation of Tobacco Plants with a *Pinus radiata* 4CL Gene Sense and anti-sense constructs containing a polynucleotide including the coding region of 4CL (SEQ ID NO: 56) from *Pinus radiata* were inserted into *Agrobacterium tumefaciens LBA*4301 by direct transformation as described above. The presence and integrity of the transgenic constructs were verified by restriction digestion and DNA sequencing.

Tobacco (*Nicotiana tabacum* cv. Samsun) leaf sections were transformed as described above. Five independent transformed plant lines were established for the sense construct and eight independent transformed plant lines were established for the anti-sense construct for 4CL. Transformed plants containing the appropriate lignin gene construct were verified using Southern blot experiments. A "+" in the column labeled "Southern" in Table 3 indicates that the transformed plant lines listed were confirmed as independent transformed lines.

b) Expression of *Pinus* 4CL in Transformed Plants

Total RNA was isolated from each independent transformed plant line created with the 4CL sense and anti-sense constructs. The RNA samples were analysed in Northern blot experiments to determine the level of expression of the transgene in each transformed line. The data shown in the column labelled "Northern" in Table 3 below shows that the transformed plant lines containing the sense and anti-sense constructs for 4CL all exhibit high levels of expression, relative to the background on the Northern blots. 4CL expression in anti-sense plant line number 1 was not measured because the RNA was not available at the time of the experiment. There was no detectable hybridisation to RNA samples from empty vector-transformed control plants.

c) Modulation of 4CL Enzyme Activity in Transformed Plants

The total activity of 4CL enzyme, encoded by the *Pinus* 4CL gene and by the endogenous tobacco 4CL gene, in transformed tobacco plants was analysed for each transformed plant line created with the 4CL sense and anti-sense constructs. Crude protein extracts were prepared from each transformed plant and assayed using the method of Zhang et al. (*Plant Physiol.,* 113:65-74, 1997). The data contained in the column labeled "Enzyme" in Table 3 shows that the transformed plant lines containing the 4CL sense construct had elevated 4CL enzyme activity, with a maximum of 258%, and the transformed plant lines containing the 4CL anti-sense construct had reduced 4CL enzyme activity, with a minimum of 59%, relative to empty vector-transformed control plants.

d) Effects of *Pinus* 4CL on Lignin Concentration in Transformed Plants

The concentration of lignin in samples of transformed plant material was determined as described in Example 3. The data shown in the column labelled "TGA" in Table 3 shows that the transformed plant lines containing the sense and the anti-sense 4CL gene constructs all exhibited significantly decreased levels of lignin, relative to the empty vector-transformed control plant lines. These data clearly indicate that lignin concentration, as measured by the TGA assay, can be directly manipulated by either sense or anti-sense expression of a lignin biosynthetic gene such as 4CL.

TABLE 3

| plant line | transgene | orientation | Southern | Northern | Enzyme | TGA |
|---|---|---|---|---|---|---|
| 1 | control | na | + | blank | 100 | 92 |
| 2 | control | na | + | blank | 100 | 104 |
| 1 | 4CL | sense | + | 2.3E+4 | 169 | 64 |
| 2 | 4CL | sense | + | 4.5E+4 | 258 | 73 |
| 3 | 4CL | sense | + | 3.1E+4 | 174 | 77 |
| 4 | 4CL | sense | + | 1.7E+4 | 164 | 80 |
| 5 | 4CL | sense | + | 1.6E+4 | 184 | 92 |
| 1 | 4CL | anti-sense | + | na | 59 | 75 |
| 2 | 4CL | anti-sense | + | 1.0E+4 | 70 | 75 |
| 3 | 4CL | anti-sense | + | 9.6E+3 | 81 | 80 |
| 4 | 4CL | anti-sense | + | 1.2E+4 | 90 | 83 |
| 5 | 4CL | anti-sense | + | 4.7E+3 | 101 | 88 |
| 6 | 4CL | anti-sense | + | 3.9E+3 | 116 | 89 |
| 7 | 4CL | anti-sense | + | 1.8E+3 | 125 | 94 |
| 8 | 4CL | anti-sense | + | 1.7E+4 | 106 | 97 |

EXAMPLE 5

Transformation of Tobacco Using the Inventive Lignin Biosynthetic Genes

Sense and anti-sense constructs containing polynucleotides including the coding regions of C3H (SEQ ID NO: 18), F5H (SEQ ID NO: 19), CCR (SEQ ID NO: 26) and CGT (SEQ ID NO: 31) from *Eucalyptus grandis*, and OMT (SEQ ID NO: 6), PAL (SEQ ID NO: 45 and 47), C4H (SEQ ID NO: 48 and 49), PNL (SEQ ID NO: 81) and LAC (SEQ ID NO: 83) from *Pinus radiata* were inserted into *Agrobacterium tumefaciens* LBA4301 by direct transformation as described above. The presence and integrity of the transgenic constructs were verified by restriction digestion and DNA sequencing.

Tobacco (*Nicotiana tabacum* cv. Samsun) leaf sections were transformed as described in Example 3. Up to twelve independent transformed plant lines were established for each sense construct and each anti-sense construct listed in the preceding paragraph. Transformed plants containing the appropriate lignin gene construct were verified using Southern blot experiments. All of the transformed plant lines analysed were confirmed as independent transformed lines.

EXAMPLE 6

Manipulation of Lignin Content in Transformed Plants a) Determination of Transgene Expression by Northern Blot Experiments Total RNA was isolated from each independent transformed plant line described in Example 5. The RNA samples were analysed in Northern blot experiments to determine the level of expression of the transgene in each transformed line. The column labelled "Northern" in Table 4 shows the level of transgene expression for all plant lines assayed, relative to the background on the Northern blots. There was no detectable hybridisation to RNA samples from empty vector-transforned control plants.

b) Determination of Lignin Concentration in Transformed Plants

The concentration of lignin in empty vector-transforned control plant lines and in up to twelve independent transformed lines for each sense construct and each anti-sense construct described in Example 5 was determined as described in Example 3. The column labelled "TGA" in Table 4 shows the thioglycolic acid extractable lignins for plant lines transformed with C3H, F5H, CCR, PAL, C4H, PNL and LAC, expressed as the average percentage of TGA extractable lignins in transformed plants versus control plants. The range of variation is shown in parentheses.

TABLE 4

| transgene | orientation | no. of lines | Northern | TGA |
|---|---|---|---|---|
| control | na | 3 | blank | 100 (92-104) |
| C3H | sense | 5 | 3.7E+4 | 74 (67-85) |
| F5H | sense | 10 | 5.8E+4 | 70 (63-79) |
| F5H | anti-sense | 9 | 5.8E+4 | 73 (35-93) |
| CCR | sense | 1 | na | 74 |
| CCR | anti-sense | 2 | na | 74 (62-86) |
| PAL | sense | 5 | 1.9E+5 | 77 (71-86) |
| PAL | anti-sense | 4 | 1.5E+4 | 62 (37-77) |
| C4H | anti-sense | 10 | 5.8E+4 | 86 (52-113) |
| PNL | anti-sense | 6 | 1.2E+4 | 88 (70-114) |
| LAC | sense | 5 | 1.7E+5 | na |
| LAC | anti-sense | 12 | 1.7E+5 | 88 (73-114) |

Figure 5:
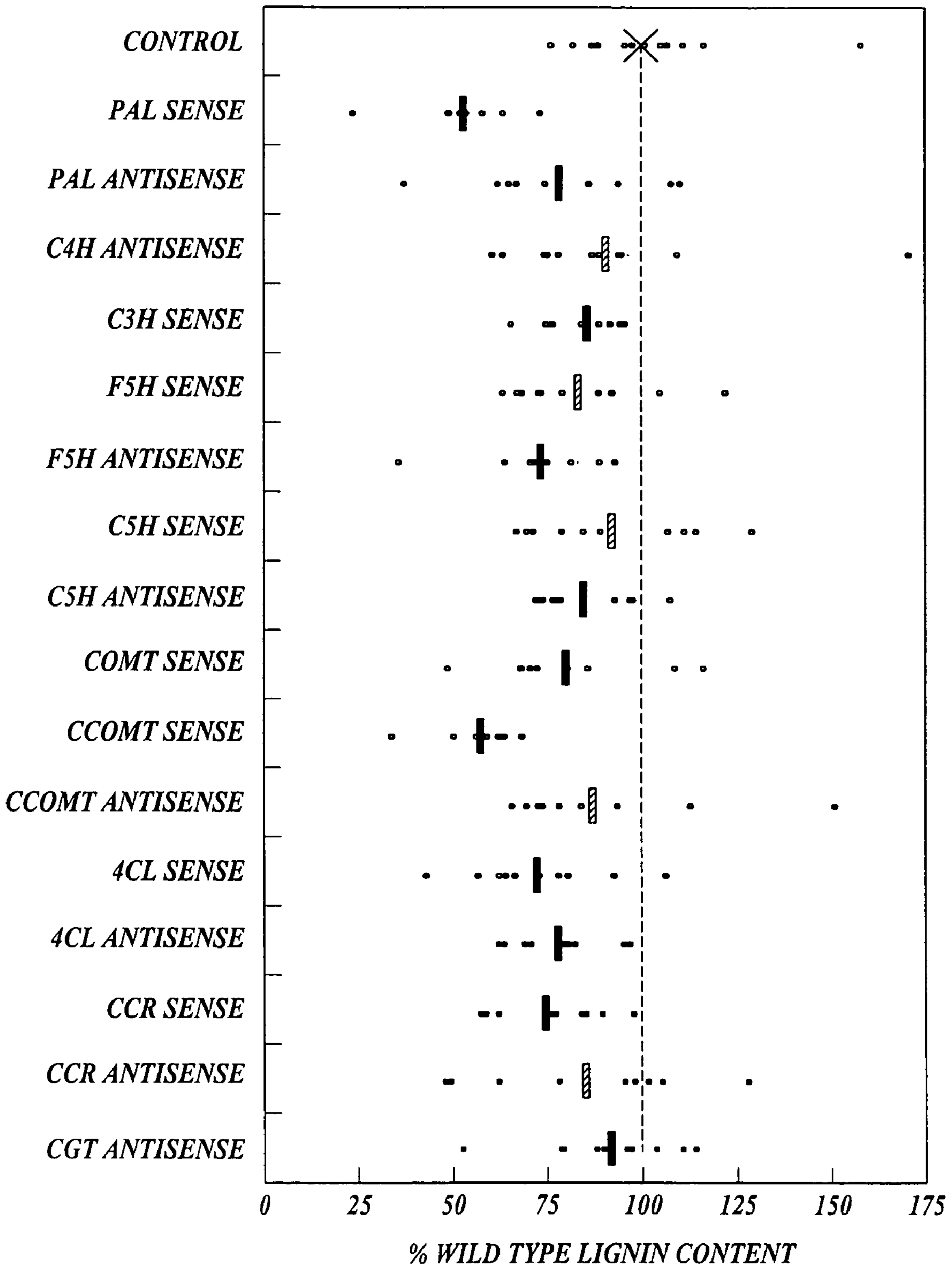
FIG. 5 shows the amount of extractable lignin, as a percentage of wild type lignin content, present in tobacco plants transformed with sense and anti-sense genetic constructs of the present invention.

FIG. 5 illustrates the quantity of extractable lignin, as a percentage of wild type lignin content, in tobacco plants transformed with PAL (sense and anti-sense), C4H (anti-sense), C3H (sense), F5H (sense and antisense), C5H (sense and antisense) C3H (sense; referred to as COMT in FIG. 5), OMT (sense and antisense; referred to as CCOMT in FIG. 5), 4CL (sense and antisense), CCR (sense and antisense) and CGT (antisense) constructs as described in Example 5. Thioglycolic acid-extractable lignin quantities were measured in transgenic plants, normalized to empty-vector control plants. Three extracts were independently derived from each of approximately 10 independently derived transgenic plants. The average of the three extracts is shown by a black dot, as the lignin value for that plant. The average of ten independent transgenic plants transformed with a given cDNA construct is shown as a bar. The average of empty vector transformed control plants is shown as an X. The value for the controls is extrapolated across the field to facilitate comparison. Black bars indicate means which are significantly reduced ($p<0.05$) in lignin content with respect to control plants. Grey bars indicate means which are not significantly changed from control plants.

Transformed plant lines containing the sense and the anti-sense lignin biosynthetic gene constructs exhibited a mean level of lignin content that was significantly lower than that of empty vector-transformed control plant lines. The most dramatic effects on lignin concentration were seen in the OMT sense plants, and in the PAL sense plants. These data clearly indicate that lignin concentration, as measured by the TGA assay, can be directly manipulated by conventional anti-sense methodology and also by sense over-expression using the inventive lignin biosynthetic genes.

EXAMPLE 7

Modulation of Lignin Enzyme Activity in Transformed Plants

The activities and substrate specificities of selected lignin biosynthetic enzymes were assayed in crude extracts from transformed tobacco plants containing sense and anti-sense constructs for PAL (SEQ ID NO: 45), PNL (SEQ ID NO: 81) and LAC (SEQ ID NO: 83) from *Pinus radiata*, and CGT (SEQ ID NO: 31) from *Eucalyptus grandis.*

Enzyme assays were performed using published methods for PAL (Southerton S G and Deverall B J, *Plant Path.* 39:223-230, 1990), CGT (Vellekoop P et al., *FEBS,* 330:36-40, 1993), PNL (Espin C J et al., *Phytochemistry* 44:17-22, 1997) and LAC (Bao W et al., *Science,* 260:672-674, 1993). The data shown in the column labelled "Enzyme" in Table 5 shows the average enzyme activity from replicate measures for all plant lines assayed, expressed as a percent of enzyme activity in empty vector-transformed control plants. The range of variation is shown in parentheses.

TABLE 5

| Transgene | orientation | no. of lines | enzyme |
|---|---|---|---|
| control | na | 3 | 100 |
| PAL | sense | 5 | 87 (60-124) |
| PAL | anti-sense | 3 | 53 (38-80) |
| CGT | anti-sense | 1 | 89 |
| PNL | anti-sense | 6 | 144 (41-279) |
| LAC | sense | 5 | 78 (16-240) |
| LAC | anti-sense | 11 | 64 (14-106) |

All of the transformed plant lines, except the PNL anti-sense transformed plant lines, showed average lignin enzyme activities which were significantly lower than the activities observed in empty vector-transformed control plants. The most dramatic effects on lignin enzyme activities were seen in the PAL anti-sense transformed plant lines in which all of the lines showed reduced PAL activity and in the LAC anti-sense transformed plant lines which showed as little as 14% of the LAC activity in empty vector-transformed control plant lines.

EXAMPLE 8

Functional Identification of Lignin Biosynthetic Genes

Sense constructs containing polynucleotides including the coding regions for PAL (SEQ ID NO: 47), OMT (SEQ ID NO: 53), 4CL (SEQ ID NO: 56 and 57) and POX (SEQ ID NO: 86) from *Pinus radiata*, and OMT (SEQ ID NO: 23 and 24), CCR (SEQ ID NO: 26-28), CGT (SEQ ID NO: 31 and 33) and POX (SEQ ID NO: 42 and 44) from *Eucalyptus grandis* were inserted into the commercially available protein expression vector, pProEX-1 (Gibco BRL). The resultant constructs were transformed into *E. coli* XL1-Blue (Stratagene), which were then induced to produce recombinant protein by the addition of IPTG. Purified proteins were produced for the *Pinus* OMT and 4CL constructs and the *Eucalyptus* OMT and POX constructs using Ni column chromatography (Janknecht R et al., *Proc. Natl. Acad. Sci.,* 88:8972-8976, 1991). Enzyme assays for each of the purified proteins conclusively demonstrated the expected substrate specificity and enzymatic activity for the genes tested.

The data for two representative enzyme assay experiments, demonstrating the verification of the enzymatic activity of a *Pinus radiata* 4CL gene (SEQ ID NO: 56) and a *Pinus radiata* OMT gene (SEQ ID NO: 53), are shown in Table 6. For the 4CL enzyme, one unit equals the quantity of protein required to convert the substrate into product at the rate of 0.1 absorbance units per minute. For the OMT enzyme, one unit equals the quantity of protein required to convert 1 pmole of substrate to product per minute.

TABLE 6

| trans-gene | purifi-cation step | total ml extract | total mg protein | total units activity | % yield activ-ity | fold purifi-cation |
|---|---|---|---|---|---|---|
| 4CL | crude | 10 ml | 51 mg | 4200 | 100 | 1 |
| | Ni column | 4 ml | 0.84 mg | 3680 | 88 | 53 |
| OMT | crude | 10 ml | 74 mg | 4600 | 100 | 1 |
| | Ni column | 4 ml | 1.2 mg | 4487 | 98 | 60 |

The data shown in Table 6 indicate that both the purified 4CL enzyme and the purified OMT enzyme show high activity in enzyme assays, confirming the identification of the 4CL and OMT genes described in this application. Crude protein preparations from *E. coli* transformed with empty vector show no activity in either the 4CL or the OMT enzyme assay.

EXAMPLE 9

Demonstration of the Presence/Absence of Unique Sequence Identifiers in Plants Transgenic tobacco plants were created using unique identifier sequences which are not found in tobacco. The unique identifier sequences inserted were isolated from *Pinus*

*radiata*, SEQ ID NO: 402, and *Eucalyptus grandis*, SEQ ID NO: 403. The unique identifier sequences were inserted into *Agrobacterium tumefaciens* LBA4301 (provided as a gift by Dr. C. Kado, University of California, Davis, Calif.) by direct transformation using published methods (see, An G, Ebert P R, Mitra A, Ha S B, "Binary Vectors," in Gelvin S B, Schilperoort R A, eds., *Plant Molecular Biology Manual, Kluwer Academic Publishers: Dordrecht,* 1988). The presence and integrity of the unique identifier sequences in the *Agrobacterium* transgenic constructs were verified by restriction digestion and DNA sequencing.

Tobacco (*Nicotiana tabacum* cv. Samsun) leaf sections were transformed using the method of Horsch et al. (*Science,* 227:1229-1231, 1985). Three independent transformed plant lines were established for each unique sequence identifier used. Two empty-vector control plant lines were established using an empty gene transfer vector which lacked a unique sequence identifier.

The uniqueness of the sequence identifiers was assayed using Southern blot analyses to test for the presence of the sequence identifier in the genome of the plants. If the sequence identifier is unique and therefore useful as a tag, then the sequence identifier should be clearly absent in plants which have not been tagged and it should be clearly present in plants which have been tagged. In the present example, the unique identifiers would be expected to be absent in the empty-vector transformed control plants. The unique identifier would be expected to be present in the transgenic plants transformed with the unique sequence identifiers.

Figure 2:
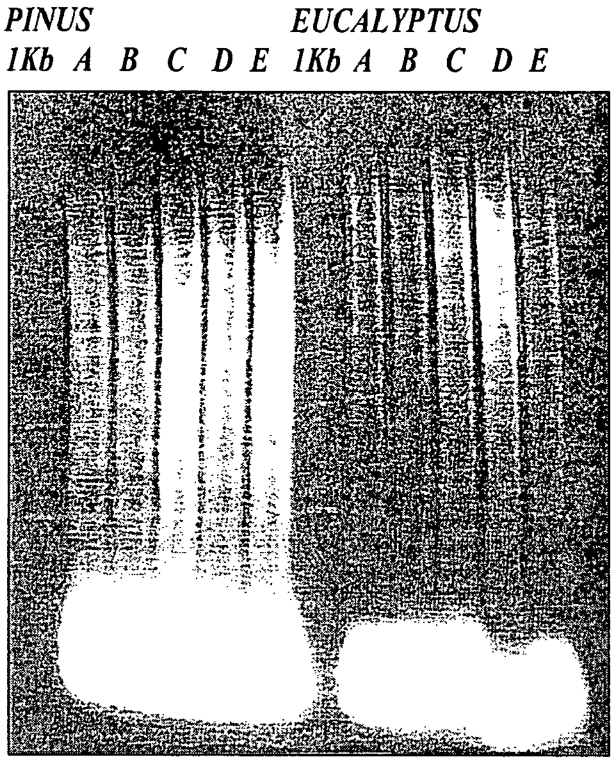
FIG. 2 illustrates genomic DNA samples from tobacco plants created in a tagging experiment using a unique sequence identifier from *Pinus* (left panel) and a unique sequence identifier from *Eucalyptus* (right panel). In both panels, lanes A and B contain DNA samples from empty-vector transformed control plants and lanes C-E contain DNA samples from plants transformed with a unique sequence identifier.

Genomic DNA was prepared from empty-vector transformed control plants and plants transformed with unique sequence identifiers using the cetyltrimethyl-ammonium bromide (CTAB) extraction method of Murray and Thompson (*Nucleic Acids Research* 8:4321-4325, 1980). The DNA samples were digested with the restriction enzyme EcoRi in the case of the plants transformed with the *Pinus* unique sequence identifier (SEQ ID NO: 402) and the restriction enzyme XbaI in the case of the plants transformed with the *Eucalyptus* unique sequence identifier (SEQ ID NO: 403). The DNA fragments produced in the restriction digests were resolved on a 1% agarose gel; the left panel of FIG. 2 and the right panel of FIG. 2 show the DNA fragment patterns of the DNA samples from the *Pinus* and *Eucalyptus* experiments, respectively.

After the agarose gel electrophoresis step, the DNA samples were transferred to Hybond-N+ brand nylon membranes (Amersham Life Science, Little Chalfont, Buckinghamshire, England) using methods established by Southern (*J. Mol. Bio.* 98:503-517). The nylon membranes were probed with radioactively-labeled probes for the unique sequence identifiers identified above and washed at high stringency (final wash: 0.5× salt sodium citrate buffer (SSC) plus 0.1% sodium dodecyl sulfate (SDS), 15 minutes at 65° C.). The hybridisation of the probes to complementary sequences in the genomic DNA samples was detected using auto-radiography. The results are shown in FIGS. 3 and 4.

Figure 3:
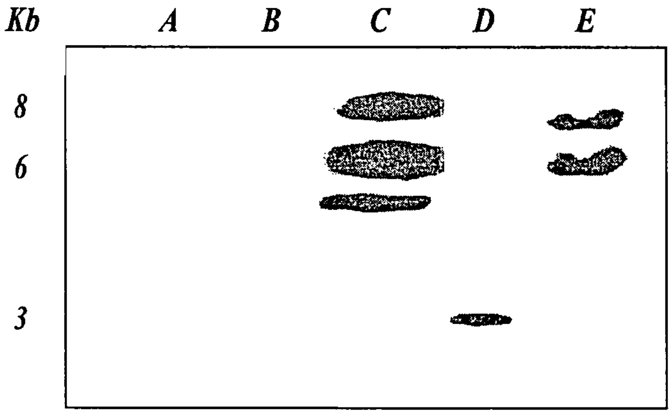
FIG. 3 demonstrates detection of a Pinus unique sequence identifier in transformed tobacco plants. Lanes A and B show the hybridization of a probe from SEQ ID NO: 402 to the genomic DNA of tobacco plants which lack the *Pinus* unique sequence identifier (empty-vector transformed control plants). Lanes C-E show the hybridization of the probe to the genomic DNA of tobacco plants containing one to three copies of the *Pinus* unique sequence identifier.

FIG. 3 (corresponding to the left panel of FIG. 2) shows the hybridisation pattern detected in the Southern blot analysis using a probe derived from the Pinus sequence identifier (SEQ ID NO: 402). Lanes A-B contain DNA samples from empty-vector transformed control plants and lanes C-E contain DNA from plants transformed with SEQ ID NO: 402. There is no hybridization in lanes A-B indicating that SEQ ID NO: 402 is not present in empty-vector transformed tobacco plants; that is, SEQ ID NO: 402 is a unique tag suitable for unambiguous marking of tobacco plants. There is strong hybridisation in lanes C-E indicating that the plants which received SEQ ID NO: 402 via transformation have been clearly and unambiguously tagged with the unique sequence contained in SEQ ID NO: 402.

Figure 4:
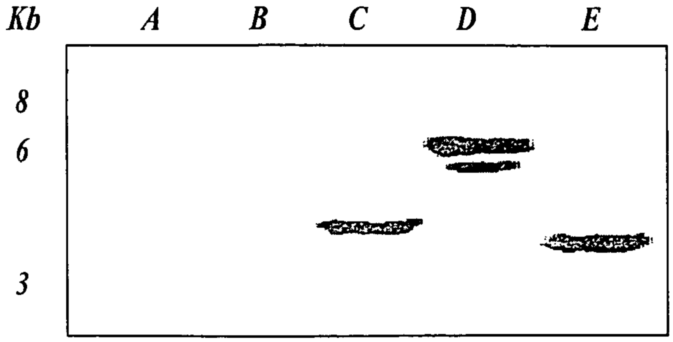
FIG. 4 demonstrates detection of a *Eucalyptus* unique sequence identifier in transformed tobacco plants. Lanes A and B show the hybridization of a probe from SEQ ID NO: 403 to the genomic DNA of tobacco plants which lack the *Eucalyptus* unique sequence identifier (empty-vector transformed control plants). Lanes C-E show the hybridization of the probe to the genomic DNA of tobacco plants containing one to two copies of the *Eucalyptus* unique sequence identifier.

FIG. 4 (corresponding to the right panel of FIG. 2) shows the hybridization pattern detected in the Southern blot analysis using a probe derived from the Eucalyptus sequence identifier (SEQ ID NO: 403). Lanes A-B contain DNA samples from empty-vector transformed control plants and lanes C-E contain DNA from plants transformed with SEQ ID NO: 403. There is no hybridisation in lanes A-B indicating that SEQ ID NO: 403 is not present in empty-vector transformed tobacco plants; that is, SEQ ID NO: 403 is a unique tag suitable for unambiguous marking of tobacco plants. There is strong hybridisation in lanes C-E indicating that the plants which received SEQ ID NO: 403 via transformation have been clearly and unambiguously tagged with the unique sequence contained in SEQ ID NO: 403.

The present example clearly demonstrates the utility of the sequences disclosed in this specification for the purposes of unambiguously tagging transgenic materials. A unique sequence was selected from a large number of potential tags and shown to be absent in the genome of the organism to be tagged. The tag was inserted into the genome of the organism to be tagged and a well-established DNA detection method was used to clearly detect the unique sequence identifier used as the tag.

Because of the sequence-specific detection methods used in the example, a user of the invention disclosed in this specification has both a high likelihood of finding a sequence identifier, among the list which has been disclosed, which will be useful for tagging any given organism and an unequivocal method for demonstrating that a tagged organism could only have acquired a given tag through the deliberate addition of the unique sequence to the genome of the organism to be tagged. If the user of this invention maintains the precise sequence of the tag used in a given organism as a secret, then any disputes as to the origin and history of the organism can be unambiguously resolved using the tag detection techniques demonstrated in the present example.

SEQ ID NO: 1-407 are set out in the attached Sequence Listing. The codes for nucleotide sequences used in the attached Sequence Listing, including the symbol "n," conform to WIPO Standard ST.25 (1998), Appendix 2, Table 1.

All references cited herein, including patent references and non-patent publications, are hereby incorporated by reference in their entireties.

While in the foregoing specification this invention has been described in relation to certain preferred embodiments, and many details have been set forth for purposes of illustration, it will be apparent to those skilled in the art that the invention is susceptible to additional embodiments and that certain of the details described herein may be varied considerably without departing from the basic principles of the invention.

We claim:

1. A transgenic plant cell comprising a genetic construct, said genetic construct comprising a polynucleotide comprising a nucleotide sequence selected from the group consisting of:

(1) the nucleotide sequence of SEQ ID NO: 266;

(2) complements of the nucleotide sequence of SEQ ID NO: 266;

(3) a portion of a nucleotide sequence comprising at least 180 contiguous nucleotides of a nucleotide sequence selected from the group consisting of a nucleotide sequence recited in (1)-(2);

(4) a nucleotide sequence comprising a non-coding region of SEQ ID NO: 266 or complements of a non-coding region of SEQ ID: 266; and (5) a nucleotide sequence having at least 95% identity or at least 98% identity to a nucleotide sequence recited in (1)-(4).

2. The transgenic plant cell of claim 1, wherein said genetic construct further comprises, in the 5'-3' direction:

(a) a gene promoter sequence;

(b) the polynucleotide; and (c) a gene termination sequence.

3. The transgenic plant cell of claim 2, wherein the gene promoter sequence is functional in a plant host to provide for transcription in xylem.

4. The transgenic plant cell of claim 1, wherein said portions of the nucleotide sequence comprises at least 220 contiguous nucleotides; at least 250 contiguous nucleotides; at least 300 contiguous nucleotides; at least 400 contiguous nucleotides; at least 500 contiguous nucleotides or at least 600 contiguous nucleotides.

5. A plant comprising the transgenic plant cell of claim 1, or fruit or seeds or progeny thereof

6. A plant comprising the transgenic plant cell of claim 2, or fruit or seeds or progeny thereof

7. The plant of claim 6, wherein the plant contains one or more of altered lignin content, altered lignin composition, and altered lignin structure.

8. The plant of claim 7, wherein the plant is a eucalyptus or a pine species.

9. A method for modulating one or more of the lignin content, the lignin composition, and the lignin structure of a plant, wherein said method comprises incorporating into the genome of the plant a polynucleotide comprising a nucleotide sequence selected from the group consisting of:

(1) the nucleotide sequence of SEQ ID NO: 266;

(2) complements of the nucleotide sequence of SEQ ID NO: 266;

(3) a portion of a nucleotide sequence comprising at least 180 contiguous nucleotides of a nucleotide sequence selected from the group consisting of a nucleotide sequence recited in (1)-(2);

(4) a nucleotide sequence comprising a non-coding region of SEQ ID NO: 266 or complements of a non-coding region of SEQ ID: 266; and (5) a nucleotide sequence having at least 95% identity or at least 98% identity to a nucleotide sequence recited in (1)-(4);

wherein a 4-coumarate CoA ligase having activity in a lignin biosynthetic pathway of the plant is modulated following incorporation of said polynucleotide.

10. The method of claim 9, wherein the plant is a eucalyptus or a pine species.

11. The method of claim 9, wherein said portion of the nucleotide sequence comprises at least 220 contiguous nucleotides; at least 250 contiguous nucleotides; at least 300 contiguous nucleotides; at least 400 contiguous nucleotides; at least 500 contiguous nucleotides or at least 600 contiguous nucleotides.

12. A method for producing a plant having one or more of altered lignin content, altered lignin composition, and altered lignin structure, comprising cultivating the transgenic plant cell of claim 2, under conditions conducive to regeneration and mature plant growth to produce a plant.

13. The method of claim 12, wherein the gene promoter sequence is functional in a plant host to provide for transcription in xylem.

14. A method for modifying the activity of a polypeptide involved in a lignin biosynthetic pathway in a plant, comprising introducing into cells of the plant a single or double stranded polynucleotide corresponding to a polynucleotide comprising a nucleotide sequence selected from the group consisting of:

(1) the nucleotide sequence recited of SEQ ID NO: 266;

(2) complements of the nucleotide sequence of SEQ ID NO: 266, (3) a portion of a nucleotide sequence comprising at least 180 contiguous nucleotides of a nucleotide sequence selected from the group consisting of a nucleotide sequence recited in (1)-(2);

(4) a nucleotide sequence comprising a non-coding region of SEQ ID NO: 266 or complements of a non-coding region of SEQ ID: 266; and (5) a nucleotide sequence having at least 95% identity or at least 98% identity to a nucleotide sequence recited in (1)-(4);

wherein said introduction results in the inhibition of expression of a 4-coumarate CoA ligase having activity in a lignin biosynthetic pathway of the plant.

15. The method of claim 14, wherein the polynucleotide is contained in a genetic construct, wherein said genetic construct comprises, in the 5'-3' direction:

(a) a gene promoter sequence;

(b) the polynucleotide; and (c) a gene termination sequence.

16. The method of claim 15, wherein said portion of the nucleotide sequence comprises at least 220 contiguous nucleotides; at least 250 contiguous nucleotides; at least 300 contiguous nucleotides; at least 400 contiguous nucleotides; at least 500 contiguous nucleotides or at least 600 contiguous nucleotides.

17. The method of claim 15, wherein the gene promoter sequence is functional in a plant host to provide for transcription in xylem.

* * * * *

SEQUENCE LISTING

<160> NUMBER OF SEQ ID NOS: 407

<210> SEQ ID NO 1
<211> LENGTH: 535
<212> TYPE: DNA
<213> ORGANISM: Eucalyptus grandis
<220> FEATURE:
<221> NAME/KEY: misc_feature
<222> LOCATION: (110)..(110)
<223> OTHER INFORMATION: n is a, c, g, or t

<400> SEQUENCE: 1
cttcgcgcta ccgcatactc caccaccgcg tgcagaagat gagctcggag ggtgggaagg 60
aggattgcct cggttgggct gcccgggacc cttctgggtt cctctccccn tacaaattca 120
cccgcaggcc gtgggaagcg aagacgtctc gattaagatc acgcactgtg gagtgtgcta 180
cgcagatgtg gcttggacta ggaatgtgca gggacactcc aagtatcctc tggtgccggg 240
gcacgagata gttggaattg tgaaacaggt tggctccagt gtccaacgct tcaaagttgg 300
cgatcatgtg ggggtgggaa cttatgtcaa ttcatgcaga gagtgcgagt attgcaatga 360
caggctagaa gtccaatgtg aaaagtcggt tatgactttt gatggaattg atgcagatgg 420
tacagtgaca aagggaggat attctagtca cattgtcgtc catgaaaggt attgcgtcag 480
gattccagaa aactacccga tggatctagc agcgcattgc tctgtgctgg atcac 535

<210> SEQ ID NO 2
<211> LENGTH: 671
<212> TYPE: DNA
<213> ORGANISM: Pinus radiata

<400> SEQUENCE: 2
gcgcctgcag gtcgacacta gtggatccaa agaattcggc acgaggttgc aggtcgggga 60
tgatttgaat cacagaaacc tcagcgattt tgccaagaaa tatggcaaaa tctttctgct 120
caagatgggc cagaggaatc ttgtggtagt ttcatctccc gatctcgcca aggaggtcct 180
gcacacccag ggcgtcgagt ttgggtctcg aacccggaac gtggtgttcg atatcttcac 240
gggcaagggg caggacatgg tgttcaccgt ctatggagat cactggagaa agatgcgcag 300
gatcatgact gtgcctttct ttacgaataa agttgtccag cactacagat tcgcgtggga 360
agacgagatc agccgcgtgg tcgcggatgt gaaatcccgc gccgagtctt ccacctcggg 420
cattgtcatc cgtagcgcct ccagctcatg atgtataata ttatgtatag gatgatgttc 480
gacaggagat tcgaatccga ggacgacccg cttttcctca agctcaaggc cctcaacgga 540
gagcgaagtc gattggccca gagctttgag tacaattatg gggatttcat tcccagtctt 600
aggcccttcc tcagaggtta tcacagaatc tgcaatgaga ttaaagagaa acggctctct 660
cttttcaagg a 671

<210> SEQ ID NO 3
<211> LENGTH: 940
<212> TYPE: DNA
<213> ORGANISM: Pinus radiata
<220> FEATURE:
<221> NAME/KEY: misc_feature
<222> LOCATION: (463)..(463)
<223> OTHER INFORMATION: n is a, c, g, or t

<400> SEQUENCE: 3
cttcaggaca agggagagat caatgaggat aatgttttgt acatcgttga gaacatcaac 60

-continued

```
gttgcagcaa ttgagacaac gctgtggtcg atggaatggg gaatagcgga gctggtgaac    120

caccaggaca ttcagagcaa ggtgcgcgca gagctggacg ctgttcttgg accaggcgtg    180

cagataacgg aaccagacac gacaaggttg ccctaccttc aggcggttgt gaaggaaacc    240

cttcgtctcc gcatggcgat cccgttgctc gtcccccaca tgaatctcca cgacgccaag    300

ctcgggggct acgatattcc ggcagagagc aagatcctgg tgaacgcctg gtggttggcc    360

aacaaccccg ccaactggaa gaaccccgag gagttccgcc ccgagcggtt cttcgaggag    420

gagaagcaca ccgaagccaa tggcaacgac ttcaaattcc tgnccttcgg tgtggggagg    480

aggagctgcc cgggaatcat tctggcgctg ctctcctcgc actctccatc ggaagacttg    540

ttcagaactt ccaccttctg ccgccgcccg ggcagagcaa agtggatgtc actgagaagg    600

gcgggcaatt cagccttcac attctcaacc attctctcat cgtcgccaag cccatagctt    660

ctgcttaatc ccaacttgtc agtgactggt atataaatgc gcgcacctga acaaaaaaca    720

ctccatctat catgactgtg tgtgcgtgtc cactgtcgag tctactaaga gctcatagca    780

cttcaaaagt ttgctaggat ttcaataaca gacaccgtca attatgtcat gtttcaataa    840

aagtttgcat aaattaaatg atatttcaat atactatttt gactctccac caattgggga    900

attttactgc taaaaaaaaa aaaaaaaaaa aaaaaaaaaa                          940
```

```
<210> SEQ ID NO 4
<211> LENGTH: 949
<212> TYPE: DNA
<213> ORGANISM: Pinus radiata
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (805)..(806)
<223> OTHER INFORMATION: n is a, c, g, or t
<220> FEATURE:
<221> NAME/KEY: misc_feature
<222> LOCATION: (808)..(808)
<223> OTHER INFORMATION: n is a, c, g, or t
<220> FEATURE:
<221> NAME/KEY: misc_feature
<222> LOCATION: (828)..(828)
<223> OTHER INFORMATION: n is a, c, g, or t
<220> FEATURE:
<221> NAME/KEY: misc_feature
<222> LOCATION: (843)..(843)
<223> OTHER INFORMATION: n is a, c, g, or t
<220> FEATURE:
<221> NAME/KEY: misc_feature
<222> LOCATION: (851)..(851)
<223> OTHER INFORMATION: n is a, c, g, or t
<220> FEATURE:
<221> NAME/KEY: misc_feature
<222> LOCATION: (867)..(867)
<223> OTHER INFORMATION: n is a, c, g, or t
<220> FEATURE:
<221> NAME/KEY: misc_feature
<222> LOCATION: (872)..(872)
<223> OTHER INFORMATION: n is a, c, g, or t
<220> FEATURE:
<221> NAME/KEY: misc_feature
<222> LOCATION: (874)..(874)
<223> OTHER INFORMATION: n is a, c, g, or t
<220> FEATURE:
<221> NAME/KEY: misc_feature
<222> LOCATION: (876)..(876)
<223> OTHER INFORMATION: n is a, c, g, or t
<220> FEATURE:
```

-continued

<221> NAME/KEY: misc_feature
<222> LOCATION: (879)..(879)
<223> OTHER INFORMATION: n is a, c, g, or t
<220> FEATURE:
<221> NAME/KEY: misc_feature
<222> LOCATION: (884)..(884)
<223> OTHER INFORMATION: n is a, c, g, or t
<220> FEATURE:
<221> NAME/KEY: misc_feature
<222> LOCATION: (888)..(888)
<223> OTHER INFORMATION: n is a, c, g, or t
<220> FEATURE:
<221> NAME/KEY: misc_feature
<222> LOCATION: (896)..(896)
<223> OTHER INFORMATION: n is a, c, g, or t
<220> FEATURE:
<221> NAME/KEY: misc_feature
<222> LOCATION: (902)..(902)
<223> OTHER INFORMATION: n is a, c, g, or t
<220> FEATURE:
<221> NAME/KEY: misc_feature
<222> LOCATION: (912)..(912)
<223> OTHER INFORMATION: n is a, c, g, or t
<220> FEATURE:
<221> NAME/KEY: misc_feature
<222> LOCATION: (919)..(919)
<223> OTHER INFORMATION: n is a, c, g, or t
<220> FEATURE:
<221> NAME/KEY: misc_feature
<222> LOCATION: (922)..(923)
<223> OTHER INFORMATION: n is a, c, g, or t
<220> FEATURE:
<221> NAME/KEY: misc_feature
<222> LOCATION: (925)..(925)
<223> OTHER INFORMATION: n is a, c, g, or t
<220> FEATURE:
<221> NAME/KEY: misc_feature
<222> LOCATION: (930)..(930)
<223> OTHER INFORMATION: n is a, c, g, or t
<220> FEATURE:
<221> NAME/KEY: misc_feature
<222> LOCATION: (936)..(936)
<223> OTHER INFORMATION: n is a, c, g, or t

<400> SEQUENCE: 4
nngctcnacc gacggtggac ggtccgctac tcagtaactg agtgggatcc cccgggctga 60
caggcaattc gatttagctc actcattagg caccccaggc tttacacttt atgcttccgg 120
ctcgtatgtt gtgtggaatt gtgagcggat aacaatttca cacaggaaac agctatgacc 180
atgattacgc caagcgcgca attaaccctc actaaaggga acaaaagctg gagctccacc 240
gcggtggcgg ccgctctaga actagtggat ccaaagaatt cggcacgaga cccagtgacc 300
ttcaggcctg agagatttct tgaggaagat gttgatatta agggccatga ttacaggcta 360
ctgccattgg tgcagggcgc aggatctgcc ctggtgcaca attgggtatt aatttagttc 420
agtctatgtt gggacacctg cttcatcatt tcgtatgggc acctcctgag ggaatgaagg 480
cagaagacat agatctcaca gagaatccag ggcttgttac tttcatggcc aagcctgtgc 540
aggccattgc tattcctcga ttgcctgatc atctctacaa gcgacagcca ctcaattgat 600
caattgatct gatagtaagt ttgaattttg ttttgataca aaacgaaata acgtgcagtt 660
tctccttttc catagtcaac atgcagcttt ctttctctga agcgcatgca gctttctttc 720
tctgaagccc aacttctagc aagcaataac tgtatatttt agaacaaata cctattcctc 780
aaattgagwa tttctctgta ggggnngnta attgtgcaat ttgcaagnaa tagtaaagtt 840
tantttaggg nattttaata gtcctangta anangnggna atgntagngg gcattnagaa 900
anccctaata gntgttggng gnngntaggn tttttnacca aaaaaaaaa 949

<210> SEQ ID NO 5

-continued

<211> LENGTH: 959
<212> TYPE: DNA
<213> ORGANISM: Pinus radiata
<220> FEATURE:
<221> NAME/KEY: misc_feature
<222> LOCATION: (697)..(697)
<223> OTHER INFORMATION: n is a, c, g, or t

<400> SEQUENCE: 5

```
gaattcggca cgagaaagcc ctagaatttt ttcagcatgc tatcacagcc ccagcgacaa     60

ctttaactgc aataactgtg gaagcgtaca aaaagtttgt cctagtttct ctcattcaga    120

ctggtcaggt tccagcattt ccaaaataca cacctgctgt tgtccaaaga aatttgaaat    180

cttgcactca gccctacatt gatttagcaa acaactacag tagtgggaaa atttctgtat    240

tggaagcttg tgtcaacacg aacacagaga agttcaagaa tgatagtaat ttggggttag    300

tcaagcaagt tttgtcatct ctttataaac ggaatattca gagattgaca cagacatatc    360

tgaccctctc tcttcaagac atagcaagta cggtacagtt ggagactgct aagcaggctg    420

aactccatgt tctgcagatg attcaagatg gtgagatttt tgcaaccata aatcagaaag    480

atgggatggt gagcttcaat gaggatcctg aacagtacaa aacatgtcag atgactgaat    540

atatagatac tgcaattcgg agaatcatgg cactatcaaa gaagctcacc acagtagatg    600

agcagatttc gtgtgatcat tcctacctga gtaaggtggg gagagagcgt tcaagatttg    660

acatagatga ttttgatact gttccccaga agttcanaaa tatgtaacaa atgatgtaaa    720

tcatcttcaa gactcgctta tattcattac tttctatgtg aattgatagt ctgttaacaa    780

tagtactgtg gctgagtcca gaaaggatct ctcggtatta tcacttgaca tgccatcaaa    840

aaaatctcaa atttctcgat gtctagtctt gattttgatt atgaatgcga cttttagttg    900

tgacatttga gcacctcgag tgaactacaa agttgcatgt taaaaaaaaa aaaaaaaaa     959
```

<210> SEQ ID NO 6
<211> LENGTH: 1026
<212> TYPE: DNA
<213> ORGANISM: Pinus radiata

<400> SEQUENCE: 6

```
gaattcggca cgagctttga ggcaacctac attcattgaa tcccaggatt tcttcttgtc     60

caaacaggtt taaggaaatg gcaggcacaa gtgttgctgc agcagaggtg aaggctcaga    120

caacccaagc agaggagccg gttaaggttg tccgccatca agaagtggga cacaaaagtc    180

ttttgcagag cgatgccctc tatcagtata tattggaaac gagcgtgtac cctcgtgagc    240

ccgagccaat gaaggagctc cgcgaagtga ctgccaagca tccctggaac ctcatgacta    300

cttctgccga tgagggtcaa tttctgggcc tcctgctgaa gctcattaac gccaagaaca    360

ccatggagat tggggtgtac actggttact cgcttctcag cacagccctt gcattgcccg    420

atgatggaaa gattctagcc atggacatca acagagagaa ctatgatatc ggattgccta    480

ttattgagaa agcaggagtt gcccacaaga ttgacttcag agagggccct gctctgccag    540

ttctggacga actgcttaag aatgaggaca tgcatggatc gttcgatttt gtgttcgtgg    600

atgcggacaa agacaactat ctaaactacc acaagcgtct gatcgatctg gtgaaggttg    660

gaggtctgat tgcatatgac aacaccctgt ggaacggatc tgtggtggct ccacccgatg    720

ctcccctgag gaaatatgtg agatattaca gagatttcgt gatggagcta aacaaggccc    780

ttgctgtcga tccccgcatt gagatcagcc aaatcccagt cggtgacggc gtcacccttt    840

gcaggcgtgt ctattgaaaa caatccttgt ttctgctcgt ctattgcaag cataaaggct    900
```

ctctgattat aaggagaacg ctataatata tggggttgaa gccatttgtt ttgtttagtg 960
tattgataat aaagtagtac agcatatgca aagtttgtat caaaaaaaaa aaaaaaaaaa 1020
aaaaaa 1026

<210> SEQ ID NO 7
<211> LENGTH: 1454
<212> TYPE: DNA
<213> ORGANISM: Pinus radiata

<400> SEQUENCE: 7
gaattcggca cgaggccaac tgcaagcaat acagtacaag agccagacga tcgaatcctg 60
tgaagtggtt ctgaagtgat gggaagcttg gaatctgaaa aaactgttac aggatatgca 120
gctcgggact ccagtggcca cttgtcccct tacacttaca atctcagaaa gaaaggacct 180
gaggatgtaa ttgtaaaggt catttactgc ggaatctgcc actctgattt agttcaaatg 240
cgtaatgaaa tggacatgtc tcattaccca atggtccctg gcatgaagt ggtggggatt 300 gtaacagaga ttggcagcga ggtgaagaaa ttcaaagtgg gagagcatgt aggggttggt 360
tgcattgttg ggtcctgtcg cagttgcggt aattgcaatc agagcatgga acaatactgc 420
agcaagagga tttggaccta caatgatgtg aaccatgacg gcacacctac tcagggcgga 480
tttgcaagca gtatggtggt tgatcagatg twtgtggttc gaatcccgga gaatcttcct 540
ctggaacaag cggcccctct gttatgtgca ggggttacag ttttcagccc aatgaagcat 600
ttcgccatga cagagcccgg gaagaaatgt gggattttgg gtttaggagg cgtggggcac 660
atgggtgtca agattgccaa agcctttgga ctccacgtga cggttatcag ttcgtctgat 720
aaaaagaaag aagaagccat ggaagtcctc ggcgccgatg cttatcttgt tagcaaggat 780
actgaaaaga tgatggaagc agcagagagc ctagattaca taatggacac cattccagtt 840
gctcatcctc tggaaccata tcttgccctt ctgaagacaa atggaaagct agtgatgctg 900
ggcgttgttc cagagtcgtt gcacttcgtg actcctctct taatacttgg gagaaggagc 960
atagctggaa gtttcattgg cagcatggag gaaacacagg aaactctaga tttctgtgca 1020
gagaagaagg tatcatcgat gattgaggtt gtgggcctgg actacatcaa cacggccatg 1080
gaaaggttgg agaagaacga tgtccgttac agatttgtgg tggatgttgc tagaagcaag 1140
ttggataatt agtctgcaat caatcaatca gatcaatgcc tgcatgcaag atgaatagat 1200
ctggactagt agcttaacat gaaagggaaa ttaaattttt atttaggaac tcgatactgg 1260
tttttgttac tttagtttag cttttgtgag gttgaaacaa ttcagatgtt tttttaactt 1320
gtatatgtaa agatcaattt ctcgtgacag taaataataa tccaatgtct tctgccaaat 1380
taatatatgt attcgtattt ttatatgaaa aaaaaaaaaa aaaaaaaaaa aaaaaaaaaa 1440
aaaaaaaaaa aaaa 1454

<210> SEQ ID NO 8
<211> LENGTH: 740
<212> TYPE: DNA
<213> ORGANISM: Pinus radiata

<400> SEQUENCE: 8
gaattcggca cgagaccatt tccagctaat attggcatag caattggtca ttctatcttt 60
gtcaaaggag atcaaacaaa ttttgaaatt ggacctaatg gtgtggaggc tagtcagcta 120
tacccagatg tgaaatatac cactgtcgat gagtacctca gcaaatttgt gtgaagtatg 180
cgagattctc ttccacatgc ttcagagata cataacagtt tcaatcaatg tttgtcctag 240

-continued gcatttgcca aattgtgggt tataatcctt cgtaggtgtt tggcagaaca gaacctcctg 300
tttagtatag tatgacgagc taggcactgc agatccttca cacttttctc ttccataaga 360
aacaaatact cacctgtggt ttgttttctt tctttctgga actttggtat ggcaataatg 420
tctttggaaa ccgcttagtg tggaatgcta agtactagtg tccagagttc taagggagtt 480
ccaaaatcat ggctgatgtg aactggttgt tccagagggt gtttacaacc aacagttgtt 540
cagtgaataa ttttgttaga gtgtttagat ccatctttac aaggctattg agtaaggttg 600
gtgttagtga acggaatgat gtcaaatctt gatgggctga ctgactctct tgtgatgtca 660
aatcttgatg gattgtgtct ttttcaatgg taaaaaaaaa aaaaaaaaaa aaaaaaaaaa 720
aaaaaaaaaa aaaaaaaaaa 740

<210> SEQ ID NO 9
<211> LENGTH: 624
<212> TYPE: DNA
<213> ORGANISM: Pinus radiata

<400> SEQUENCE: 9
gaattcctgc agcccggggg atccactagt tctagagcgg ccgccaccgc ggtggagctc 60
gcgcgcctgc aggtcgacac tagtggatcc aaagaattcg gcacgaggcc cgacggccac 120
ttgttggacg ccatggaagc tctccggaaa gccgggattc tggaaccgtt taaactgcag 180
cccaaggaag gactggctct cgtcaacggc acagcggtgg gatccgccgt ggccgcgtcc 240
gtctgtgttg acgccaacgt gctgggcgtg ctggctgaga ttctgtctgc gctcttctgc 300
gaggtgatgc aagggaaacc ggagttcgta gatccgttaa cccaccagtt gaagcaccac 360
ccagggcaga tcgaagccgc ggccgtcatg gagttcctcc tcgacggtag cgactacgtg 420
aaagaagcag cgcggcttca cgagaaagac ccgttgagca aaccgaaaca agaccgctac 480
gctctgcgaa catcgccaca gtggttgggg cctccgatcg aagtcatccg cgctgcyact 540
cactccatcg agcgggagat caattccgtc aacgacaatc cgttaatcga tgtctccagg 600
gacatggctg tccacggcgg caac 624

<210> SEQ ID NO 10
<211> LENGTH: 278
<212> TYPE: DNA
<213> ORGANISM: Pinus radiata

<400> SEQUENCE: 10
gaattcctgc agcccggggg atccactagt tctagagcgg ccgccaccgc ggtggagctc 60
cagtacctgg ccaaccccgt cacgactcac gtccagagcg ccgaacaaca caaccaggat 120
gtcaattccc tcggcttgat ctccgccaga aagactgccg aggccgttga gattttaaag 180
ctgatgttcg ctacatatct ggtggcctta tgccaggcga tcgatctccg gcacctggaa 240
gaaaacatgc gatccgttgt gaagcacgta gtcttgca 278

<210> SEQ ID NO 11
<211> LENGTH: 765
<212> TYPE: DNA
<213> ORGANISM: Pinus radiata

<400> SEQUENCE: 11
gagctcctgc aagtcatcga tcatcagccc gttttctcgt acatcgacga tcccacaaat 60
ccatcatacg cgcttatgct ccaactcaga gaagtgctcg tagatgaggc tctcaaatca 120
tcttgcccag acgggaatga cgaatccgat cacaatttgc agcccgctga gagcgctgga 180

-continued

```
gctgctggaa tattacccaa ttgggtgttt agcaggatcc ccatatttca agaggagttg    240

aaggcccgtt tagaggaaga ggttccgaag gcgagggaac gattcgataa tggggacttc    300

ccaattgcaa acagaataaa caagtgcagg acatatccca tttacagatt cgtgagatca    360

gagttgggaa ccgatttgct aacagggccc aagtggagaa gccccggcga agatatagaa    420

aaggtatttg agggcatttg ccaagggaaa attggaaacg tgatcctcaa atgtctggac    480

gcttggggtg ggtgcgctgg accattcact ccacgtgcat atcctgcgtc tcctgcagcg    540

ttcaatgcct catattgggc atggtttgat agcaccaaat caccctctgc aacgagcggc    600

agaggtttct ggagcgccca acaacaacaa gttctttgat ttaactgact cttaagcatt    660

cctaaacagc ttgttcttcg caataacgaa tctttcatct tcgttacttt gtaaaagatg    720

gggttccaac aaaatagaag aaatattttc gatccaaaaa aaaaa                    765
```

<210> SEQ ID NO 12
<211> LENGTH: 453
<212> TYPE: DNA
<213> ORGANISM: Pinus radiata

<400> SEQUENCE: 12

```
tgattatgcg gatccttggg cagggatacg gcatgacaga agcaggcccg gtgctggcaa     60

tgaacctagc cttcgcaaag aatcctttcc ccgccaaatc tggctcctgc ggaacagtcg    120

tccggaacgc tcaaataaag atcctcgatt acaggaactg gcgagtctct cccgcacaat    180

caagccggcg aaatctgcat ccgcggaccc gaaataatga aaggatatat taacgacccg    240

gaatccacgg ccgctacaat cgatgaagaa ggctggctcc acacaggcga cgtcgggtac    300

attgacgatg acgaagaaat cttcatagtc gacagagtaa aggagattat caatataaag    360

gcttccaggt ggatcctgct aatcgaattc ctgcagcccg ggggtccact agttctagag    420

cggccgccac cgcggtggag ctccagcttt tgt                                 453
```

<210> SEQ ID NO 13
<211> LENGTH: 278
<212> TYPE: DNA
<213> ORGANISM: Pinus radiata

<400> SEQUENCE: 13

```
tcttcgaatt ctctttcacg actgcttcgt taatggctgc gatggctcga tattgttaga     60

tgataactca acgttcaccg gagaaaagac tgcaggccca aatgttaatt ctgcgagagg    120

attcgacgta atagacacca tcaaaactca agttgaggca gcctgcagtg gtgtcgtgtc    180

agttgccgac attctcgcca ttgctgcacg cgattcagtc gtccaactgg ggggcccaac    240

atggacggta cttctgggag aaaagacgga tccgatca                            278
```

<210> SEQ ID NO 14
<211> LENGTH: 23
<212> TYPE: DNA
<213> ORGANISM: Pinus radiata

<400> SEQUENCE: 14

```
cttcgaattc wyttycayga ytg                                             23
```

<210> SEQ ID NO 15
<211> LENGTH: 22
<212> TYPE: DNA
<213> ORGANISM: Pinus radiata

<400> SEQUENCE: 15

-continued

```
gatcggatcc rtcyykycty cc                                            22


<210> SEQ ID NO 16
<211> LENGTH: 472
<212> TYPE: DNA
<213> ORGANISM: Eucalyptus grandis

<400> SEQUENCE: 16

aattcggcac gagacgacct cttgtatcgg acccggatcc gctatcgtta acgtacacac     60

gttctagtgc tgaatggaga tggagagcac caccggcacc ggcaacggcc ttcacagcct    120

ctgcgccgcc gggagccacc atgccgaccc actgaactgg ggggcggcgg cagcagccct    180

cacagggagc cacctcgacg aggtgaagcg gatggtcgag gagtaccgga ggccggcggt    240

gcgcctcggc ggggagtccc tcacgatagc ccaggtggcg gcggtggcga gtcaggaggg    300

ggtaggggtc gagctctcgg aggcggcccg tcccagggtc aaggccagca gcgactgggt    360

catggagagc atgaacaagg gaactgacag ctacggggtc accaccgggt tcggcggcaa    420

cttctcaaac cggaggccga agcaaggcgg tccttttcag aaggaactta ta            472


<210> SEQ ID NO 17
<211> LENGTH: 622
<212> TYPE: DNA
<213> ORGANISM: Eucalyptus grandis

<400> SEQUENCE: 17

ccaaagctcc tagtgcctca tgagtctgct gaggattgca caattggcgg gttcgacgtg     60

ccccgaggca ccatgatcct ggttaatgcg tgggcaattc aaagagaccc aaaagtgtgg    120

gacgatccca caaattttaa accggagagg tacgagggat tggaaggtga tcatgcctac    180

cgactattgc cgtttgggat ggggaggaga agttgtcctg gtgctggcct tgccaataga    240

gtggtgagct tggtcctggc ggcgcttatt cagtgcttcg aatgggaacg agttggcgaa    300

gaattggtgg acttgtccga ggggacggga ctcacaatgc caaagagaga gccattggag    360

gccttgtgca aagcgcgtga atgcatgata gctaatgttc ttgcgcacct ttaagaaggt    420

cgttgtctaa tgaatttaca ttggtgatgt atctccaatg tttttgaata atcaaataga    480

ctgaaaatag gccagtgcag ctttaggaat gatcgtgagc atcaatagca tcctgaggag    540

gccaatgcag ctttaggcct ttctcttagg agaaaaatga tggtttatat aggtactggc    600

aacattgttc aaaaaaaaaa aa                                            622


<210> SEQ ID NO 18
<211> LENGTH: 414
<212> TYPE: DNA
<213> ORGANISM: Eucalyptus grandis

<400> SEQUENCE: 18

cacgctcgac gaattcggta ccccgggttc gaaatcgata agcttggatc caaagcaaca     60

cattgaactc tctctctctc tctctctctc tctctctctc tcccccaccc cccccttccca   120

accccaccca catacagaca agtagatacg cgcacacaga agaagaaaag atgggggttt    180

caatgcagtc aatcgcacta gcgacggttc tggccgtcct aacgacatgg gcgtggaggg    240

cggtgaactg ggtgtggctg aggccgaaga ggctcgagag gcttctgaga cagcaaggtc    300

tctccggcaa gtcctacacc ttcctggtcg gcgacctcaa ggagaacctg cggatgctca    360

aggaagccaa gtccaagccc atcgccgtct ccgatgacat caagcctcgt ctct          414


<210> SEQ ID NO 19
```

<211> LENGTH: 469
<212> TYPE: DNA
<213> ORGANISM: Eucalyptus grandis

<400> SEQUENCE: 19
gaattcggca cgagtgtctc tctctctctc tctctctgta aaccaccatg ctcttcctca 60
ctcatctcct agcagttcta ggggttgtgt tgctcctgct aattctatgg agggcaagat 120
cttctccgaa caaacccaaa ggtactgcct tacccccgga gctgccgggc gcatggccga 180
tcataggcca catccacttg ctgggcggcg agaccccgct ggccaggacc ctggccgcca 240
tggcggacaa gcagggcccg atgtttcgga tccgtctcgg agtccacccg gcgaccatca 300
taagcagccg tgaggcggtc cgggagtgct tcaccaccca cgacaaggac ctcgcttctc 360
gccccaaatc caaggcggga atccacttgg gctacgggta tgccggtttt ggcttcgtag 420
aatacgggga cttttggcgc gagatgagga agatcaccat gctcgagct 469

<210> SEQ ID NO 20
<211> LENGTH: 341
<212> TYPE: DNA
<213> ORGANISM: Eucalyptus grandis

<400> SEQUENCE: 20
cgggctcgtg gctcggctcc ggcgcaacgc ccttcccacc gggcccgagg ggcctcccgg 60
tcatcgggaa catgctcatg atgggcgagc tcacccaccg cggcctcgcg agtctggcga 120
agaagtatgg cgggatcttc cacctccgca tgggcttcct gcacatggtt gccgtgtcgt 180
cccccgacgt ggcccgccag gtcctccagg tccacgacgg gatcttctcg aaccggcctg 240
ccaccatcgc gatcagctac ctcacgtatg accgggccga catggccttc gcgcactacg 300
gcccgttctg gcggcagatg cggaagctgt gcgtgatgaa a 341

<210> SEQ ID NO 21
<211> LENGTH: 387
<212> TYPE: DNA
<213> ORGANISM: Eucalyptus grandis

<400> SEQUENCE: 21
gaattcggca cgagcgggct cgtggctcgg ctccggcgca acgcccttcc caccgggccc 60
gaggggcctc ccggtcatcg ggaacatgct catgatgggc gagctcaccc accgcggcct 120
cgcgagtctg gcgaagaagt atggcgggat cttccacctc cgcatgggct tcctgcacat 180
ggttgccgtg tcgtcccccg acgtggcccg ccaggtcctc caggtccacg acgggatctt 240
ctcgaaccgg cctgccacca tcgcgatcag ctacctcacg tatgaccggg ccgacatggc 300
cttcgcgcac tacggcccgt tctggcggca gatgcggaag ctgtgcgtga tgaaagctct 360
tcagcggaag cgggctgagt cgtggga 387

<210> SEQ ID NO 22
<211> LENGTH: 443
<212> TYPE: DNA
<213> ORGANISM: Eucalyptus grandis

<400> SEQUENCE: 22
cacgagctcg tgagccttcc cggagacaag gccatcttac ttcgcaacaa attgcgtccg 60
cactcctttc tcaagaaacc tagtcatcca agaagcagag cattgcaact gcaaacagcc 120
aaagcccaaa ctcgtacaga aggagagaga gagagagaat agaagcatga gtgcatgcac 180
gaaccaagca atcacgacgg ccagtgaaga tgaagagttc ttgttcgcca tggaaatgaa 240

```
tgctctgata gcactcccct tggtcttgaa ggccaccatc gaactgggga tcctcgaaat    300

actggccgag tgcgggccta tggctccact ttcgcctgct cagattgcct cccgtctctc    360

cgcaaagaac ccggaagccc ccgtaaccct tgaccggatc ctccggtttc tcgccagcta    420

ctccatcctc tcttgcactc tcg                                            443


<210> SEQ ID NO 23
<211> LENGTH: 607
<212> TYPE: DNA
<213> ORGANISM: Eucalyptus grandis

<400> SEQUENCE: 23

gaattcggca cgagccaacc ctggaccagg tacttttggc aggcggtcca ttgcccttca     60

aaccggtcca aaccggacca tcactgtcct tatatacgtt gcatcatgcc tgctcataga    120

acttaggtca actgcaacat ttcttgatca caacatatta caatattcct aagcagagag    180

agagagagag agagagagag agagagagag agagtttgaa tcaatggcca ccgccggaga    240

ggagagccag acccaagccg ggaggcacca ggaggttggc cacaagtctc tccttcagag    300

tgatgctctt taccaatata ttttggagac cagcgtgtac ccaagagagc ctgagcccat    360

gaaggagctc agggaaataa cagcaaaaca tccatggaac ataatgacaa catcagcaga    420

cgaagggcag ttcttgaaca tgcttctcaa gctcatcaaa gccaagaaca ccatggagat    480

tggtgtcttc actggctact ctctcctcgc caccgctctt gctcttcctg atgacggaaa    540

gattttggct atggacatta acagagagag ctatgaactt ggcctgccgg catccaaaaa    600

gccggtg                                                              607


<210> SEQ ID NO 24
<211> LENGTH: 421
<212> TYPE: DNA
<213> ORGANISM: Eucalyptus grandis

<400> SEQUENCE: 24

gaattcggca cgagccgttt tatttcctct gatttccttt gctcgagtct cgcggaagag     60

agagaagaga ggagaggaga gaatgggttc gaccggatcc gagacccaga tgaccccgac    120

ccaagtctcg gacgaggagg cgaacctctt cgccatgcag ctggcgagcg cctccgtgct    180

ccccatggtc ctcaaggccg ccatcgagct cgacctcctc gagatcatgg ccaaggccgg    240

gccgggcgcg ttcctctccc cgggggaagt cgcggcccag ctcccgaccc agaaccccga    300

ggcacccgta atgctcgacc ggatcttccg gctgctggcc agctactccg tgctcacgtg    360

caccctccgc gacctccccg atggcaaggt cgagcggctc tacggcttag cgccggtgtg    420

c                                                                    421


<210> SEQ ID NO 25
<211> LENGTH: 760
<212> TYPE: DNA
<213> ORGANISM: Eucalyptus grandis

<400> SEQUENCE: 25

ggaagaagcc gagcaaacga attgcagacg ccattgaaaa aagacacgaa agagatcaag     60

aaggagctta agaagcatca tcaatggcag ccaacgcaga gcctcagcag acccaaccag    120

cgaagcattc ggaagtcggc cacaagagcc tcttgcagag cgatgctctc taccagtata    180

tattggagac cagcgtctac ccaagagagc cagagcccat gaaggagctc agggaaataa    240

cagccaaaca tccatggaac ctgatgacca catcggcgga tgaagggcag ttcctgaaca    300
```

-continued

```
tgctcctcaa gctcatcaac gccaagaaca ccatggagat cggcgtctac accggctact    360

ctctcctcgc aaccgccctt gctcttcccg atgacggaaa gatcttggcc atggccatca    420

atagggagaa cttcgagatc gggctgcccg tcatccagaa ggccggcctt gcccacaaga    480

tcgatttcag agaaggccct gccctgccgc tccttgatca gctcgtgcaa gatgagaaga    540

accatggaac gtacgacttc ttctcaatcc ttaatcgttc atttgaatac aaatacatgc    600

tcaatggttc aaagacaaca taagacagaa gatggaaaaa atagaaagga aggaaagtat    660

taagggtagt ttctcatttc atcaatgctt gattttgaga tctcctttct ggtgcgatca    720

gctgacccgg cggcacaggt gatgccatcc ccgacgggaa                          760
```

<210> SEQ ID NO 26
<211> LENGTH: 508
<212> TYPE: DNA
<213> ORGANISM: Eucalyptus grandis

<400> SEQUENCE: 26

```
gaattcggta cccgggttcg aaatcgataa gcttggatcc aaagaattcg gcacgagatc     60

actaaccatc tgcctttctt catcttcttt cttctgcttc tcctccgttt cctcgtttcg    120

atatcgtgaa aggagtccgt cgacgacaat ggccgagaag agcaaggtcc tgatcatcgg    180

agggacgggc tacgtcggca agttcatcgt ggaagcgagt gcaaaagcag ggcatcccac    240

gttcgcgctg gttaggcaga gcacggtctc cgaccccgtc aagggccagc tcgtcgagag    300

cttcaagaac ttgggcgtca ctctgctcat cggtgatctg tacgatcatg agagcttggt    360

gaaggcaatc aagcaagccg acgtggtgat atcgacagtg ggcacatgc aaatggcgga     420

tcagaccaaa gaatcgtcga cgccattaaa ggaagctggc aacgttaagg tttgttggtt    480

ggttcatttg atctggtttg ggggggtc                                       508
```

<210> SEQ ID NO 27
<211> LENGTH: 495
<212> TYPE: DNA
<213> ORGANISM: Eucalyptus grandis

<400> SEQUENCE: 27

```
gaattcggca cgaggttaat ggcagtgcag cctcaacacc acccaccttc ctccatctct     60

ctcctccctt cttctttctc tgacttcaat ggcagccgac tccatgcttg cgttcagtat    120

aagaggaagg tggggcagcc taaaggggca ctgcgggtca ctgcatcaag caataagaag    180

atcctcatca tgggaggcac ccgtttcatc ggtgtgtttt tgtcgagact acttgtcaaa    240

gaaggtcatc aggtcacttt gtttaccaga ggaaaagcac ccatcactca acaattgcct    300

ggtgagtcgg acaaggactt cgctgatttt tcatccaaga tcctgcattt gaaaggagac    360

agaaaggatt ttgattttgt taaatctagt cttgctgcag aaggctttga cgttgtttat    420

gacattaacg gcgagaggcg gatgaagtcg caccaatttt ggatgcctgc caaaccttga    480

accagtcaac tactg                                                     495
```

<210> SEQ ID NO 28
<211> LENGTH: 472
<212> TYPE: DNA
<213> ORGANISM: Eucalyptus grandis

<400> SEQUENCE: 28

```
gaattcggca cgagcataag ctctcccgta atcctcacat cacatggcga agagcaaggt     60

cctcgtcgtt ggcggcactg gctacctcgg gcggaggttc gtgagggcga gcctggacca    120
```

gggccacccc acgtacgtcc tccagcgtcc ggagaccggc ctcgacattg agaagctcca 180
gacgctactg cgcttcaaga ggcgtggcgc ccaactcgtc gaggcctcgt tctcagacct 240
gaggagcctc gtcgacgctg tgaggcgggt cgatgtcgtc gtctgtgcca tgtcgggggt 300
ccacttccgg agccacaaca tcctgatgca gctcaagctc gtggaggcta tcaaagaagc 360
tggaaatgtc aagcggtttt tgccgtcaga gttcggaatg gacccggccc tcatgggtca 420
tgcaattgag ccgggaaggg tcacgttcga tgagaaatgg aggtgagaaa ag 472

<210> SEQ ID NO 29
<211> LENGTH: 396
<212> TYPE: DNA
<213> ORGANISM: Eucalyptus grandis

<400> SEQUENCE: 29
gaattcggca cgaggaggca cctcctcgaa acgaagaaga agaaggacga aggacgaagg 60
agacgaaggc gagaatgagc gcggcgggcg gtgccgggaa ggtcgtgtgc gtgaccgggg 120
cgtccggtta catcgcctcg tggctcgtca agctcctcct ccagcgcggc tacaccgtca 180
aggccaccgt ccgcgatccg aatgatccaa aaaagactga acatttgctt ggacttgatg 240
gagcgaaaga tagacttcaa ctgttcaaag caaacctgct ggaagagggt tcatttgatc 300
ctattgttga gggttgtgca ggcgtttttc aaactgcctc tcccttttat catgatgtca 360
aggatccgca ggcagaatta cttgatccgg ctgtaa 396

<210> SEQ ID NO 30
<211> LENGTH: 592
<212> TYPE: DNA
<213> ORGANISM: Eucalyptus grandis

<400> SEQUENCE: 30
gaattcggca cgaggttgaa cctcccgtcc tcggctctgc tcggctcgtc accctcttcg 60
cgctcccgca tactccacca ccgcgtacag aagatgagct cggagggtgg gaaggaggat 120
tgcctcggtt gggctgcccg ggacccttct gggttcctct cccccctacaa attcacccgc 180 agggccgtgg gaagcgaaga cgtctcgatt aagatcacgc actgtggagt gtgctacgca 240
gatgtggctt ggactaggaa tgtgcaggga cactccaagt atcctctggt gccagggcac 300
gagatagttg gaattgtgaa acaggttggc tccagtgtcc aacgcttcaa agttggcgat 360
catgtggggg tgggaactta tgtcaattca tgcagagagt gcgagtattg caatgacagg 420
ctagaagtcc aatgtgaaaa gtcggttatg acttttgatg gaattgatgc agatggtaca 480
gtgacaaagg gaggatattc tagtcacatt gtcgtccatg aaaggtattg cgtcaggatt 540
ccagaaaact acccgatgga tctagcagcg catttgctct gtgctggatc ac 592

<210> SEQ ID NO 31
<211> LENGTH: 468
<212> TYPE: DNA
<213> ORGANISM: Eucalyptus grandis

<400> SEQUENCE: 31
gaattcggca cgagaactca tcttgaaatg tcattggagt catcatcctc tagtgagaag 60
aaacaaatgg gttccgccgg attcgaatcg gccacaaagc cgcacgccgt ttgcattccc 120
taccctgcac aaagccacat tggcgccatg ctcaagctag caaagctcct ccatcacaag 180
ggcttccaca tctccttcgt caacaccgag ttcaaccacc ggcggctcgc cagggctcga 240
ggccccgagt tcacaaatgg aatgctgagc gactttcagt tcctgacaat ccccgatggt 300
cttcctcctt cggacttgga tgcgatccaa gacatcaaga tgctctgcga atcgtccagg 360
aactatatgg tcagccccat caacgatctt gtatcgagcc tgggctcgaa cccgagcgtc 420
cctccggtga cttgcatcaa tctcggatgg tttcatgaca ctcgtgac 468

<210> SEQ ID NO 32
<211> LENGTH: 405
<212> TYPE: DNA
<213> ORGANISM: Eucalyptus grandis

<400> SEQUENCE: 32
ctttactccg ccaagaagat ccaatcgcag ttttcgcaat tggcccatta cacaaatgcg 60
gtccatcttc atcgggaagt ctcttggcag aagaccggag ttgcatttcc tggctggaca 120
agcaagcccc taactcagtg gtctatgtga gtcttgggag catcgcctct gtgaacgagt 180
cggaattttc cgaaatagct ttaggtttag ccgatagcca gcagccattc ttgtgggtgg 240
ttcgacccgg gtcagtgagc ggctcggaac tcttagagaa tttgcccggt tgctttctgg 300
aggcattaca ggagaggggg aagattgtga aatgggcgcc tcaacatgaa gtgctggctc 360
atcgggctgt cggagcgttt tggactcaca atggatggaa ctcca 405

<210> SEQ ID NO 33
<211> LENGTH: 380
<212> TYPE: DNA
<213> ORGANISM: Eucalyptus grandis

<400> SEQUENCE: 33
ggcaaacacg cccgttttcg ttttactaag agaagatggt gagcgttgtg gctggtagag 60
tcgagagctt gtcgagcagt ggcattcagt cgatcccgca ggagtatgtg aggccgaagg 120
aggagctcac aagcattggc gacatcttcg aggaggagaa gaagcatgag ggccctcagg 180
tcccgaccat cgacctcgag gacatagcgt ctaaagaccc cgtggtgagg gagaggtgcc 240
acgaggagct caggaaggct gccaccgact ggggcgtcat gcacctcgtc aaccatggga 300
tccccaacga cctgattgag cgtgtaaaga aggctggcga ggtgttcttc aacctcccga 360
tcgaggagaa ggacaagcat 380

<210> SEQ ID NO 34
<211> LENGTH: 305
<212> TYPE: DNA
<213> ORGANISM: Eucalyptus grandis

<400> SEQUENCE: 34
ttgtacccga agatctccgg gaccgttcga cggcgacatc gccgtcggcc gggaacccgt 60
cgaggccgcc gccggaggcc ggggagaagc tggagtagcc gccgtagccg gagaaggcgc 120
cgtcgtggtc ggcggcggcg gcgtggtgga cctcatcgcc gtccatgctg aaggcgtcga 180
aggaagcgga catggctggg ggatcgatcg accgatccga tcggccggag gatttcgaga 240
tcggagatgg agagatggaa atgaaagaga gagagagaga gagatccggt ggactggtgg 300
tgttt 305

<210> SEQ ID NO 35
<211> LENGTH: 693
<212> TYPE: DNA
<213> ORGANISM: Eucalyptus grandis

<400> SEQUENCE: 35
gaattcggca cgagctaaga gaggagagga gaggagcaag atggcactag caggagctgc 60
actgtcagga accgtggtga gctccccctt tgtgaggatg cagcctgtga acagactcag 120
ggcattcccc aatgtgggtc aggccctgtt tggtgtcaac tctggccgtg gcagagtgac 180
tgccatggcc gcttacaagg tcaccctgct cacccctgaa ggcaaagtcg aactcgacgt 240
ccccgacgat gtttacatct tggactacgc cgaggagcaa ggcatcgact tgccctactc 300
ctgccgtgcc ggctcttgct cctcctgcgc gggcaaggtc gtggcgggga gcgtcgacca 360
gagcgacggc agcttcctgg atgatgatca gattgaggaa ggttgggtcc tcacttgtgt 420
cgcctaccct aagtctgagg tcaccattga gacccacaag gaagaggagc tcactgcttg 480
aagctctcct atatttgctt ttgcataaat cagtctcact ctacgcaact ttctccactc 540
tctcccccct tcactacatg tttgttagtt cctttagtct cttccttttt tactgtacga 600
gggatgattt gatgttattc tgagtctaat gtaatggctt ttctttttcc tatttctgta 660
tgaggaaata aaactcatgc tctaaaaaaa aaa 693

<210> SEQ ID NO 36
<211> LENGTH: 418
<212> TYPE: DNA
<213> ORGANISM: Eucalyptus grandis

<400> SEQUENCE: 36
aggactttat tataagcatt gtaaaaagag tcaaactaat acatcgcaag aattgggtta 60
tccaataatc tacaaaaaga aaaaagtttg atgcattgag atggtaactg cttaattcaa 120
atgccttagt ttgaaaaatt aaccaactat taaaattaat gatgatgaat atggattatg 180
tgtgaaaaac tatatagact taaaattgac tcagaagaca ttcttttctt cttattttat 240
gatatgatga attcggtcta aacaggcaaa tggtgtcaaa cgggaagtcg gcaaaactct 300
tcctcggcag tgactaccgg gcgggcgatg atgcggatcc gggggccggg tcgctggaga 360
acatcccgca cggaccggtc cacgtttggt gcggtgacaa caggcagccc aacctgga 418

<210> SEQ ID NO 37
<211> LENGTH: 777
<212> TYPE: DNA
<213> ORGANISM: Eucalyptus grandis

<400> SEQUENCE: 37
gaattcggca cgagcataca actacactgc gacgccgccg cagaacgcga gcgtgccgac 60
catgaacggc accaaggtct accggttgcc gtataacgct acggtccagc tcgttttaca 120
ggacaccggg ataatcgcgc cggagaccca ccccatccat ctgcacggat tcaacttctt 180
cggtgtgggc aaaggagtgg ggaattatga cccaaagaag gatcccaaga agttcaatct 240
ggttgaccca gtggagagga acaccattgg aatcccatct ggtggatgga tagccatcag 300
attcacagca gacaatccag gagtttggtt cctgcactgc catctggaag tgcacacaac 360
ttggggactg aagatggcat tcttggtgga caatgggaag gggcctaaag agaccctgct 420
tccacctcca agtgatcttc caaaatgttg atcatttgat catgaggacg acaagcgatt 480
actaatgaca ccaagttagt ggaatcttct ctttgaaaaa gaagaagaag agcaagaaga 540
ataagaaaga tgaggagaga agccatagaa gatttgacca agaagagaga gggcaataaa 600
ccaaagagac ccttgagatc acgacatccc gcaattgttt ctagagtaat agaaggattt 660
actccgacac tgctacaata aattaaggaa gacaaggaat ttggtttttt tcattggagg 720
agtgtaattt gttttttggc aagctcatca catgaatcac atggaaaaaa aaaaaaa 777

<210> SEQ ID NO 38

<211> LENGTH: 344
<212> TYPE: DNA
<213> ORGANISM: Eucalyptus grandis

<400> SEQUENCE: 38

```
atatgttcag aatttcaaat gtgggaatgt caacctcctt gaacttcaga attcagggcc    60
atacgttgaa gctagtcgag gttgaaggat ctcacaccgt ccagaacatg tatgattcaa   120
tcgatgttca cgtgggccaa tccatggctg tcttagtgac cttaaatcag cctccaaagg   180
actactacat tgtcgcatcc acccggttca ccaagacggt tctcaatgca actgcagtgc   240
tacactacac caactcgctt accccagttt ccgggccact accagctggt ccaacttacc   300
aaaaacattg gtccatgaag caagcaagaa caatcaggtg gaac                    344
```

<210> SEQ ID NO 39
<211> LENGTH: 341
<212> TYPE: DNA
<213> ORGANISM: Eucalyptus grandis

<400> SEQUENCE: 39

```
gccgcaactg caattctctt cgtaaaacat gacggctgtc ggcaaaacct ctttcctctt    60
gggagctctc ctcctcttct ctgtggcggt gacattggca gatgcaaaag tttactacca   120
tgattttgtc gttcaagcga ccaaggtgaa gaggctgtgc acgacccaca acaccatcac   180
ggtgaacggg caattcccgg gtccgacttt ggaagttaac gacggcgaca ccctcgttgt   240
caatgtcgtc aacaaagctc gctacaacgt caccattcac tggcacggcg tccggcaggt   300
gagatctggt tgggctgatg gggcggaatt tgtgactcaa t                       341
```

<210> SEQ ID NO 40
<211> LENGTH: 358
<212> TYPE: DNA
<213> ORGANISM: Eucalyptus grandis

<400> SEQUENCE: 40

```
gaattcggca cgagatatgt tcagaatttc aaatgtggga atgtcaacct ccttgaactt    60
cagaattcag ggccatacgt tgaagctagt cgaggttgaa ggatctcaca ccgtccagaa   120
catgtatgat tcaatcgatg ttcacgtggg ccaatccatg gctgtcttag tgaccttaaa   180
tcagcctcca aaggactact acattgtcgc atccacccgg ttcaccaaga cggttctcaa   240
tgcaactgca gtgctacact acaccaactc gcttacccca gtttccgggc cactaccagc   300
tggtccaact taccaaaaac attggtccat gaagcaagca agaacaatca ggtggaac     358
```

<210> SEQ ID NO 41
<211> LENGTH: 409
<212> TYPE: DNA
<213> ORGANISM: Eucalyptus grandis

<400> SEQUENCE: 41

```
atcaagagtt tgagtctaaa ccttgtctaa tcctctctcg catagtcatt tggagacgaa    60
tgctgatcgg ccgcagctgc attctcttcg taaaacatga cggctgtcgg caaaacctct   120
ttcctcttgg gagctctcct cctcttctct gtggcggtga cattggcaga tgcaaaagtt   180
tactaccatg attttgtcgt tcaagcgacc aaggtgaaga ggctgtgcac gacccacaac   240
accatcacgg tgaacgggca attcccgggt ccgactttgg aagttaacga cggcgacacc   300
ctcgttgtca atgtcgtcaa caaagctcgc tacaacgtca ccattcactg gcacggcgtc   360
cggcaggtga gatctggttg ggctgatggg gcggaatttg tgactcaat               409
```

<210> SEQ ID NO 42
<211> LENGTH: 515
<212> TYPE: DNA
<213> ORGANISM: Eucalyptus grandis

<400> SEQUENCE: 42
ctctctctct ctctctctct gtgtgttcat tctcgttgag ctcgtggtcg cctcccgcca 60
tggatccgca caagtaccgt ccatccagtg ctttcaacac ttctttctgg actacgaact 120
ctggtgctcc tgtctggaac aataactctt cgttgactgt tggaagcaga ggtccaattc 180
ttcttgagga ttatcacctc gtggagaaac ttgccaactt tgatagggag aggattccag 240
agcgtgtggt gcatgccaga ggagccagtg caaagggatt ctttgaggtc actcatgaca 300
tttcccagct tacctgtgct gatttccttc gggcaccagg agttcaaaca cccgtgattg 360
tccgtttctc cactgtcatc cacgaaaggg gcagccctga aaccctgagg gaccctcgag 420
gttttgctgt gaagttctac acaagagagg gtaactttga tctggtggga aacaatttcc 480
ctgtcttctt tgtccgtaat gggataaatt ccccg 515

<210> SEQ ID NO 43
<211> LENGTH: 471
<212> TYPE: DNA
<213> ORGANISM: Eucalyptus grandis

<400> SEQUENCE: 43
gaattcggca cgaggctccc tctcgtactg ccatactcct gggacgggat tcggataggg 60
atttgcggcg atccatttct cgattcaagg ggaagaatca tggggaagtc ctacccgacc 120
gtaagccagg agtacaagaa ggctgtcgag aaatgcaaga agaagttgag aggcctcatc 180
gctgagaaga gctgcgctcc gctcatgctc cgcatcgcgt ggcactccgc cggtaccttc 240
gatgtgaaga cgaagaccgg aggcccgttc gggaccatga agcacgccgc ggagctcagc 300
cacggggcca acagcgggct cgacgttgcc gatcaggtct tgcagccgat caaggatcag 360
ttccccgtca tcacttatgc tgatttctac cagctggctg gcgtcgttgc tgtggaagtt 420
actggtggac ctgaagttgc ttttcacccg gaagagaggc aaaccacaac c 471

<210> SEQ ID NO 44
<211> LENGTH: 487
<212> TYPE: DNA
<213> ORGANISM: Eucalyptus grandis

<400> SEQUENCE: 44
gaattcggca cgagctccca cttctgtctc gccaccatta ctagcttcaa agcccagatc 60
tcagtttcgt gctctcttcg tcatctctgc ctcttgccat ggatccgtac aagtatcgcc 120
cgtccagcgc ttacgattcc agcttttgga caaccaacta cggtgctccc gtctggaaca 180
atgactcatc gctgactgtt ggaactagag gtccgattct cctggaggac taccatctga 240
ttgagaaact tgccaacttc gagagagaga ggattcctga gcgggtggtc catgcacggg 300
gagccagcgc gaaagggttc ttcgaggtca cccacgacat ctctcacttg acctgtgctg 360
atttcctccg ggctcctgga gtccagacgc ccgtaatcgt ccgtttctcc accgtcatcc 420
acgagcgcgg cagcccgaac ctcagggacc ctcgtggttt tgcagtgaag ttctacacca 480
gagaggg 487

<210> SEQ ID NO 45
<211> LENGTH: 684
<212> TYPE: DNA

<213> ORGANISM: Pinus radiata

<400> SEQUENCE: 45
gaattcctgc agcccggggg atccactagt tctagagcgg ccgccaccgc ggtggagctc 60
gcgcgcctgc aggtcgacac tagtggatcc aaagaattcg gcacgaggcc cgacggccac 120
ttgttggacg ccatggaagc tctccggaaa gccgggattc tggaaccgtt taaactgcag 180
cccaaggaag gactggctct cgtcaacggc acagcggtgg gatccgccgt ggccgcgtcc 240
gtctgttttg acgccaacgt gctgggcgtg ctggctgaga ttctgtctgc gctcttctgc 300
gaggtgatgc aagggaaacc ggagttcgta gatccgttaa cccaccagtt gaagcaccac 360
ccagggcaga tcgaagccgc ggccgtcatg gagttcctcc tcgacggtag cgactacgtg 420
aaagaagcag cgcggcttca cgagaaagac ccgttgagca aaccgaaaca agaccgctac 480
gctctgcgaa catcgccaca gtggttgggg cctccgatcg aagtcatccg cgctgctact 540
cactccatcg agcgggagat caattccgtc aacgacaatc cgttaatcga tgtctccagg 600
gacatggctc tccacggcgg caacttccag ggaacaccca tcggagtttc catggacaac 660
atgcgaatct ctttggcagc cgtc 684

<210> SEQ ID NO 46
<211> LENGTH: 418
<212> TYPE: DNA
<213> ORGANISM: Pinus radiata

<400> SEQUENCE: 46
gaattcggca cgaggacaag gtcataggcc ctctcttcaa atgcttggat gggtggaaag 60
gaactcctgg cccattctga aataaataat cttccaagat cgcctttata caacgactgc 120
tatgatttga gtcctcggat ctttttgttg atgcagttgt ttaccgatct ggaatttgat 180
tggtcataaa gcttgatttt gtttttcttt cttttgtttt atactgctgg atttgcatcc 240
cattggattt gccagaaata tgtaagggtg gcagatcatt tgggtgatct gaaacatgta 300
aaagtggcgg atcatttggg tagcatgcag atcagttggg tgatcgtgta ctgctttcac 360
tattacttac atatttaaag atcgggaata aaaacatgat tttaattgaa aaaaaaaa 418

<210> SEQ ID NO 47
<211> LENGTH: 479
<212> TYPE: DNA
<213> ORGANISM: Pinus radiata

<400> SEQUENCE: 47
gatatcccaa cgaccgaaaa cctgtatttt cagggcgcca tggggatccg gaattcggca 60
cgagcaagga agaaaatatg gttgcagcag cagaaattac gcaggccaat gaagttcaag 120
ttaaaagcac tgggctgtgc acggacttcg gctcgtctgg cagcgatcca ctgaactggg 180
ttcgagcagc caaggccatg gaaggaagtc actttgaaga agtgaaagcg atggtggatt 240
cgtatttggg agccaaggag atttccattg aagggaaatc tctgacaatc tcagacgttg 300
ctgccgttgc tcgaagatcg caagtgaaag tgaaattgga tgctgcggct gccaaatcta 360
gggtcgagga gagttcaaac tgggttctca cccagatgac caaggggacg gatacctatg 420
gtgtcactac tggtttcgga gccacttctc acaggagaac gaaccaggga gccgagctt 479

<210> SEQ ID NO 48
<211> LENGTH: 1785
<212> TYPE: DNA
<213> ORGANISM: Pinus radiata

<400> SEQUENCE: 48

```
tatcgataag cttgatatcg aattcctgca gcccggggga tccactagtt ctagagcggc      60
cgccaccgcg gtggagctcg cgcgcctgca ggtcgacact agtggatcca aagaattcgg     120
cacgaggttg caggtcgggg atgatttgaa tcacagaaac ctcagcgatt ttgccaagaa     180
atatggcaaa atctttctgc tcaagatggg ccagaggaat cttgtggtag tttcatctcc     240
cgatctcgcc aaggaggtcc tgcacaccca gggcgtcgag tttgggtctc gaacccggaa     300
cgtggtgttc gatatcttca cgggcaaggg gcaggacatg gtgttcaccg tctatggaga     360
tcactggaga aagatgcgca ggatcatgac tgtgcctttc tttacgaata aagttgtcca     420
gcactacaga ttcgcgtggg aagacgagat cagccgcgtg gtcgcggatg tgaaatcccg     480
cgccgagtct tccacctcgg gcattgtcat ccgtaggcgc ctccagctca tgatgtataa     540
tattatgtat aggatgatgt tcgacaggag attcgaatcc gaggacgacc cgcttttcct     600
caagctcaag gccctcaacg gagagcgaag tcgattggcc cagagctttg agtacaatta     660
tggggatttc attcccattc ttaggccctt cctcagaggt tatctcagaa tctgcaatga     720
gattaaagag aaacggctct ctcttttcaa ggactacttc gtggaagagc gcaagaagct     780
caacagtacc aagactagta ccaacaccgg gggagctcaa gtgtgcaatg gaccatattt     840
tagatgctca ggacaaggga gagatcaatg aggataatgt tttgtacatc gttgagaaca     900
tcaacgttgc agcaattgag acaacgctgt ggtcgatgga atggggaata gcggagctgg     960
tgaaccacca ggacattcag agcaaggtgc gcgcagagct ggacgctgtt cttggaccag    1020
gcgtgcagat aacggaacca gacacgacaa ggttgcccta ccttcaggcg gttgtgaagg    1080
aaacccttcg tctccgcatg gcgatcccgt tgctcgtccc ccacatgaat ctccacgacg    1140
ccaagctcgg gggctacgat attccggcag agagcaagat cctggtgaac gcctggtggt    1200
tggccaacaa ccccgccaac tggaagaacc ccgaggagtt ccgcccccgag cggttcttcg    1260
aggaggagaa gcacaccgaa gccaatggca acgacttcaa attcctgcct tcggtgtggg    1320
gaggaggagc tgcccgggaa tcattctggc gctgcctctc ctcgcactct ccatcggaag    1380
acttgttcag aacttccacc ttctgccgcc gcccgggcag agcaaagtgg atgtcactga    1440
gaagggcggg cagttcagcc ttcacattct caaccattct ctcatcgtcg ccaagcccat    1500
agcttctgct taatcccaac ttgtcagtga ctggtatata aatgcgcgca cctgaacaaa    1560
aaacactcca tctatcatga ctgtgtgtgc gtgtccactg tcgagtctac taagagctca    1620
tagcacttca aaagtttgct aggatttcaa taacagacac cgtcaattat gtcatgtttc    1680
aataaaagtt tgcataaatt aaatgatatt tcaatatact attttgactc tccaccaatt    1740
ggggaatttt actgctaaaa aaaaaaaaaa aaaaaaaaaa aaaaa                    1785
```

<210> SEQ ID NO 49
<211> LENGTH: 475
<212> TYPE: DNA
<213> ORGANISM: Pinus radiata

<400> SEQUENCE: 49

```
gaattcggca cgagatttcc atggacgatt ccgtttggct tcaattcgtt tcctctggct      60
gtcctcgtcc tcgttttcct tgttcttcct ccgacttttt ctctggaagc tatggcgtaa     120
taggaacctg ccgccaggac ccccggcatg gccgatcgta gggaacgtcc ttcagattgg     180
attttccagc ggcgcgttcg agacctcagt gaagaaattc catgagagat acggtccaat     240
attcactgtg tggctcggtt cccgccctct gctgatgatc accgaccgcg agcttgccca     300
```

```
cgaggcgctc gtacagaagg gctccgtctt cgctgaccgc ccgcccgccc tcgggatgca    360

gaaaatcttc agtagcaacc agcacaacat cacttcggct gaatacggcc cgctgtggcg    420

gagccttcgc aggaatctgg ttaaagaagc cctgagactt cggcgatgaa ggctt         475


<210> SEQ ID NO 50
<211> LENGTH: 801
<212> TYPE: DNA
<213> ORGANISM: Pinus radiata

<400> SEQUENCE: 50

gctccaccga cggtggacgg tccgctactc agtaactgag tgggatcccc cgggctgaca     60

ggcaattcga tttagctcac tcattaggca ccccaggctt tacactttat gcttccggct    120

cgtatgttgt gtggaattgt gagcggataa caatttcaca caggaaacag ctatgaccat    180

gattacgcca agcgcgcaat taaccctcac taaagggaac aaaagctgga gctccaccgc    240

ggtggcggcc gctctagaac tagtggatcc aaagaattcg gcacgagacc cagtgacctt    300

caggcctgag agatttcttg aggaagatgt tgatattaag ggccatgatt acaggctact    360

gccattcggt gcagggcgca ggatctgccc tggtgcacaa ttgggtatta atttagttca    420

gtctatgttg ggacacctgc ttcatcattt cgtatgggca cctcctgagg gaatgaaggc    480

agaagacata gatctcacag agaatccagg gcttgttact ttcatggcca agcctgtgca    540

ggccattgct attcctcgat tgcctgatca tctctacaag cgacagccac tcaattgatc    600

aattgatctg atagtaagtt tgaattttgt tttgatacaa aacgaaataa cgtgcagttt    660

ctccttttcc atagtcaaca tgcagctttc tttctctgaa gcgcatgcag ctttctttct    720

ctgaagccca acttctagca agcaataact gtatatttta gaacaaatac ctattcctca    780

aattgagtat ttctctgtag g                                              801


<210> SEQ ID NO 51
<211> LENGTH: 744
<212> TYPE: DNA
<213> ORGANISM: Pinus radiata

<400> SEQUENCE: 51

gggcccccct tcgaggtgga cactagtgga tccaaagaat tcggcacgag gttttatctg     60

aaggacgctg tgcttgaagg ctcccagcca ttcaccaaag cccatggaat gaatgcgttc    120

gagtacccgg ccatcgatca gagattcaac aagattttca acagggctat gtctgagaat    180

tctaccatgt tgatgaacaa gattttggat acttacgagg gttttaagga ggttcaggag    240

ttggtggatg tgggaggagg tattgggtcg actctcaatc tcatagtgtc taggtatccc    300

cacatttcag gaatcaactt cgacttgtcc catgtgctgg ccgatgctcc tcactaccca    360

gctgtgaaac atgtgggtgg agacatgttt gatagtgtac caagtggcca agctattttt    420

atgaagtgga ttctgcatga ttggagcgat gatcattgca ggaagctttt gaagaattgt    480

cacaaggcgt tgccagagaa ggggaaggtg attgcggtgg acaccattct cccagtggct    540

gcagagacat ctccttatgc tcgtcaggga tttcatacag atttactgat gttggcatac    600

aacccagggg gcaaggaacg cacagagcaa gaatttcaag atttagctaa ggagacggga    660

tttgcaggtg gtgttgaacc tgtatgttgt gtcaatggaa tgtgggtaat ggaattcctg    720

cagcccgggg gatccactag ttct                                           744


<210> SEQ ID NO 52
<211> LENGTH: 426
<212> TYPE: DNA
```

<213> ORGANISM: Pinus radiata

<400> SEQUENCE: 52
gtggccctgg aagtagtgtg cgcgacatgg attccttgaa tttgaacgag tttatgttgt 60
ggtttctctc ttggcttgct ctctacattg gatttcgtta tgttttgaga tcgaacttga 120
agctcaagaa gaggcgcctc ccgccgggcc catcgggatg gccagtggtg ggaagtctgc 180
cattgctggg agcgatgcct cacgttactc tctacaacat gtataagaaa tatggccccg 240
ttgtctatct caaactgggg acgtccgaca tggttgtggc ctccacgccc gctgcagcta 300
aggcgtttct gaagactttg gatataaact tctccaaccg gccgggaaat gcaggagcca 360
cgtacatcgc ctacgattct caggacatgg tgtgggcagc gtatggagga cggtggaaga 420
tggagc 426

<210> SEQ ID NO 53
<211> LENGTH: 562
<212> TYPE: DNA
<213> ORGANISM: Pinus radiata

<400> SEQUENCE: 53
cagttcgaaa ttaacctcac taaagggaac aaaagctgga gttcgcgcgc ctgcaggtcg 60
acactagtgg atccaaagaa ttcggcacga gctttgaggc aacctacatt cattgaatcc 120
caggatttct tcttgtccaa acaggtttaa ggaaatggca ggcacaagtg ttgctgcagc 180
agaggtgaag gctcagacaa cccaagcaga ggagccggtt aaggttgtcc gccatcaaga 240
agtgggacac aaaagtcttt tgcagagcga tgccctctat cagtatatat tggaaacgag 300
cgtgtaccct cgtgagcccg agccaatgaa ggagctccgc gaagtgactg ccaagcatcc 360
ctggaacctc atgactactt ctgccgatga gggtcaattt ctgggcctcc tgctgaagct 420
cattaacgcc aagaacacca tggagattgg ggtgtacact ggttactcgc ttctcagcac 480
agcccttgca ttgcccgatg atggaaagat tctagccatg gacatcaaca gagagaacta 540
tgatatcgga ttgcctataa tt 562

<210> SEQ ID NO 54
<211> LENGTH: 1074
<212> TYPE: DNA
<213> ORGANISM: Pinus radiata

<400> SEQUENCE: 54
tcgtgccgct cgatcctcac aggccctttt tatttccctg gtgaacgata cgatgggctc 60
gcacgctgag aatggcaacg gggtggaggt tgttgatcca acggacttaa ctgacatcga 120
gaatgggaaa ccaggttatg acaagcgtac gctgcctgcg gactggaagt ttggagtgaa 180
gcttcaaaac gttatggaag aatccattta caagtacatg ctggaaacat tcacccgcca 240
tcgagaggac gaggcgtcca aggagctctg ggaacgaaca tggaacctga cacagagagg 300
ggagatgatg acattgccag atcaggtgca gttcctgcgc ttgatggtaa agatgtcagg 360
tgctaaaaag gcattggaga tcggagtttt cactggctat tcattgctca atatcgctct 420
cgctcttcct tctgatggca aggtggtagc tgtggatcca ggagatgacc ccaaatttgg 480
ctggccctgc ttcgttaagg ctggagttgc agacaaagtg gagatcaaga aaactacagg 540
gttggactat ttggattccc ttattcaaaa gggggagaag gattgcttcg actttgcatt 600
cgtggacgca gacaaagtga actacgtgaa ctatcatcca cggctgatga agttagtgcg 660 cgtgggggc gtcataattt acgacgacac cctctggttt ggtctggtgg gaggaaagga 720

```
tccccacaac ctgcttaaga atgattacat gaggacttct ctggagggta tcaaggccat     780

caactccatg gtagccaacg accccaactt ggaggtcgcc acagtcttta tgggatatgg     840

tgtcactgtt tgttaccgca ctgcttagtt agctagtcct ccgtcattct gctatgtatg     900

tatatgataa tggcgtcgat ttctgatata ggtggttttt caatgtttct atcgtcatgt     960

tttctgttta gccagaatgt ttcgatcgtc atggtttctg ttaaagccag aataaaatta    1020

gccgcttgca gttcaaaaaa aaaaaaaaaa aaaaactcga gactagttct cttc          1074
```

<210> SEQ ID NO 55
<211> LENGTH: 1075
<212> TYPE: DNA
<213> ORGANISM: Pinus radiata

<400> SEQUENCE: 55

```
tcggagctct cgaatcctca caggcccttt ttatttccct ggtgaacgat acgatgggct      60

cgcacgctga gaatggcaac ggggtggagg ttgttgatcc aacggactta actgacatcg     120

aagaatggga aaccaggtta tgacaagcgt cgctgcctgc ggactggaag tttggagtga     180

agcttcaaaa cgttatggaa gaatccattt acaagtacat gctggaaaca ttcacccgcc     240

atcgagagga cgaggcgtcc aaggagctct gggaacgaac atggaacctg acacagagag     300

gggagatgat gacattgcca gatcaggtgc agttcctgcg cttgatggta aagatgtcag     360

gtgctaaaaa ggcattggag atcggagttt tcactggcta ttcattgctc aatatcgctc     420

tcgctcttcc ttctgatggc aaggtggtag ctgtggatcc aggagatgac cccaaatttg     480

gctggccctg cttcgttaag gctggagttg cagacaaagt ggagatcaag aaaactacag     540

ggttggacta tttggattcc cttattcaaa agggggagaa ggattgcttc gactttgcat     600

tcgtggacgc agacaaagtg aactacgtga actatcatcc acggctgatg aagttagtgc     660

gcgtgggggg cgtcataatt tacgacgaca ccctctggtt tggtctggtg ggaggaaagg     720

atccccacaa cctgcttaag aatgattaca tgaggacttc tctggagggt atcaaggcca     780

tcaactccat ggtagccaac gaccccaact tggaggtcgc cacagtcttt atgggatatg     840

gtgtcactgt ttgttaccgc actgcttagt tagctagtcc tccgtcattc tgctatgtat     900

gtatatgata atggcgtcga tttctgatat aggtggtttt tcaatgtttc tatcgtcatg     960

ttttctgttt agccagaatg tttcgatcgt catggtttct gttaaagcca gaataaaatt    1020

agccgcttgc agttcaaaaa aaaaaaaaaa aaaaaactcg agactagttc tcttc         1075
```

<210> SEQ ID NO 56
<211> LENGTH: 1961
<212> TYPE: DNA
<213> ORGANISM: Pinus radiata

<400> SEQUENCE: 56

```
gttttccgcc atttttcgcc tgtttctgcg gagaatttga tcaggttcgg attgggattg      60

aatcaattga aaggttttta ttttcagtat ttcgatcgcc atggccaacg gaatcaagaa     120

ggtcgagcat ctgtacagat cgaagcttcc cgatatcgag atctccgacc atctgcctct     180

tcattcgtat tgctttgaga gagtagcgga attcgcagac agaccctgtc tgatcgatgg     240

ggcgacagac agaacttatt gcttttcaga ggtggaactg atttctcgca aggtcgctgc     300

cggtctggcg aagctcgggt tgcagcaggg gcaggttgtc atgcttctcc ttccgaattg     360

catcgaattt gcgtttgtgt tcatgggggc ctctgtccgg ggcgccattg tgaccacggc     420

caatcctttc tacaagccgg gcgagatcgc caaacaggcc aaggccgcgg gcgcgcgcga     480
```

```
tcatagttac cctggcagct tatgtggaga aactggccga tctgcagagc cacgatgtgc    540

tcgtcatcac aatcgatgat gctcccaagg aaggttgcca acatatttcc gttctgaccg    600

aagccgacga aacccaatgc ccggccgtga caatccaccc ggacgatgtc gtggcgttgc    660

cctattcttc cggaaccacg gggctcccca agggcgtgat gttaacgcac aaaggcctgg    720

tgtccagcgt tgcccagcag gtcgatggtg aaaatcccaa tctgtatttc cattccgatg    780

acgtgatact ctgtgtcttg cctcttttcc acatctattc tctcaattcg gttctcctct    840

gcgcgctcag agccggggct gcgaccctga ttatgcagaa attcaacctc acgacctgtc    900

tggagctgat tcagaaatac aaggttaccg ttgccccaat tgtgcctcca attgtcctgg    960

acatcacaaa gagccccatc gtttcccagt acgatgtctc ggccgtccgg ataatcatgt   1020

ccggcgctgc gcctctcggg aaggaactcg aagatgccct cagagagcgt tttcccaagg   1080

ccattttcgg gcagggctac ggcatgacag aagcaggccc ggtgctggca atgaacctag   1140

ccttcgcaaa gaatcctttc cccgtcaaat ctggctcctg cggaacagtc gtccggaacg   1200

ctcaaataaa gatcctcgat acagaaactg gcgagtctct cccgcacaat caagccggcg   1260

aaatctgcat ccgcggaccc gaaataatga aaggatatat taacgacccg gaatccacgg   1320

ccgctacaat cgatgaagaa ggctggctcc acacaggcga cgtcgggtac attgacgatg   1380

acgaagaaat cttcatagtc gacagagtaa aggagattat caaatataag ggcttccagg   1440

tggctcctgc tgagctggaa gctttacttg ttgctcatcc gtcaatcgct gacgcagcag   1500

tcgttcctca aaagcacgag gaggcgggcg aggttccggt ggcgttcgtg gtgaagtcgt   1560

cggaaatcag cgagcaggaa atcaaggaat tcgtggcaaa gcaggtgatt ttctacaaga   1620

aaatacacag agtttacttt gtggatgcga ttcctaagtc gccgtccggc aagattctga   1680

gaaaggattt gagaagcaga ctggcagcaa aatgaaaatg aatttccata tgattctaag   1740

attcctttgc cgataattat aggattcctt tctgttcact tctatttata taataaagtg   1800

gtgcagagta agcgccctat aaggagagag agagcttatc aattgtatca tatggattgt   1860

caacgcccta cactcttgcg atcgctttca atatgcatat tactataaac gatatatgtt   1920

tttttataa atttactgca cttctcgttc aaaaaaaaaa a                        1961
```

<210> SEQ ID NO 57
<211> LENGTH: 1010
<212> TYPE: DNA
<213> ORGANISM: Pinus radiata

<400> SEQUENCE: 57

```
gacaaacttg gtcgtttgtt taggttttgc tgcaggtgaa cactaatatg gaaggccaga     60

ttgcagcatt aagcaaagaa gatgagttca tttttcacag cccttttcct gcagtacctg    120

ttccagagaa tataagtctt ttccagtttg ttctggaagg tgctgagaaa taccgtgata    180

aggtggccct cgtggaggcc tccacaggga aggagtacaa ctatggtcag gtgatttcgc    240

tcacaaggaa tgttgcagct gggctcgtgg acaaaggcat tcaaaagggc gatgttgtat    300

ttgttctgct tccaaatatg gcagaatacc ccattattgt gctgggaata atgttggccg    360

gcgcagtgtt ttctggggca aatccttctg cacacatcaa tgaagttgaa aaacatatcc    420

aggattctgg agcaaagatt gttgtgacag ttgggtctgc ttatgagaag gtgaggcaag    480

tgaaactgcc tgttattatt gcagataacg agcatgtcat gaacacaatt ccattgcagg    540

aaatttttga gagaaactat gaggccgcag ggccttttgt acaaatttgt caggatgatc    600

tgtgtgcact cccttattcc tctggcacca caggggcctc taaaggtgtc atgctcactc    660
```

```
acagaaatct gattgcaaat ctgtgctcta gcttgtttga tgtccatgaa tctcttgtag    720

gaaatttcac cacgttgggg ctgatgccat tctttcacat atatggcatc acgggcatct    780

gttgcgccac tcttcgcaac ggaggcaagg tcgtggtcat gtccagattc gatctccgac    840

actttatcag ttctttgatt acttatgagg tcaacttcgc gcctattgtc ccgcctataa    900

tgctctccct ccggtttaaa aatcctatcg ttaacgagtt cgatctcagc cgcttgaaac    960

tccaaagctg ttcatgactg cggctgctcc actggcgccg gatctactgc              1010
```

<210> SEQ ID NO 58
<211> LENGTH: 741
<212> TYPE: DNA
<213> ORGANISM: Pinus radiata

<400> SEQUENCE: 58

```
gaattcggca cgagaccatt tccagctaat attggcatag caattggtca ttctatcttt     60

gtcaaaggag atcaaacaaa ttttgaaatt ggacctaatg gtgtggaggc tagtcagcta    120

tacccagatg tgaaatatac cactgtcgat gagtacctca gcaaatttgt gtgaagtatg    180

cgagattctc ttccacatgc ttcagagata cataacagtt tcaatcaatg tttgtcctag    240

gcatttgcca aattgtgggt tataatcctt cgtaggtgtt tggcagaaca gaacctcctg    300

tttagtatag tatgacgagc taggcactgc agatccttca cacttttctc ttccataaga    360

aacaaatact cacctgtggt ttgttttctt tctttctgga actttggtat ggcaataatg    420

tctttggaaa ccgcttagtg tggaatgcta agtactagtg tccagagttc taagggagtt    480

ccaaaatcat ggctgatgtg aactggttgt tccagagggt gtttacaacc aacagttgtt    540

cagtgaataa ttttgttaga gtgtttagat ccatctttac aaggctattg agtaaggttg    600

gtgttagtga acggaatgat gtcaaatctt gatgggctga ctgactctct tgtgatgtca    660

aatcttgatg gattgtgtct ttttcaatgg taaaaaaaaa aaaaaaaaaa aaaaaaaaaa    720

aaaaaaaaaa aaaaaaaaaa a                                              741
```

<210> SEQ ID NO 59
<211> LENGTH: 643
<212> TYPE: DNA
<213> ORGANISM: Pinus radiata

<400> SEQUENCE: 59

```
ctcatctcgg agttgcaggc tgcagctttt ggcccaaagc atgatatcag atcaaacgac     60

gcagatgaag caaacggatc aaacagtttg cgttactgga gcagcgggtt tcattgcctc    120

atggcttgtc aagatgctcc tcatcagagg ttacactgtc agagcagcag ttcggaccaa    180

cccagctgat gataggtgga agtatgagca tctgcgagag ttggaaggag caaaagagag    240

gcttgagctt gtgaaagctg atattctcca ttaccagagc ttactcacag tcatcagagg    300

ttgccacggt gtctttcaca tggcttcagt tctcaatgat gaccctgagc aagtgataga    360

accagcagtc gaagggacga ggaatgtgat ggaggcctgc gcagaaactg gggtgaagcg    420

cgttgttttt acttcttcca tcggcgcagt ttacatgaat cctcatagag acccgctcgc    480

gattgtccat gatgactgct ggagcgattt gactactgcg tacaaaccaa gaattggtat    540

tgctatgcaa aaaccttggc agagaaatct gcatgggata ttgctaaggg aaggaattta    600

gagcttgcag tgataaatcc aggcctggcc ttaggtccct tga                      643
```

<210> SEQ ID NO 60
<211> LENGTH: 441
<212> TYPE: DNA

<213> ORGANISM: Pinus radiata

<400> SEQUENCE: 60
gaattcggca cgagaatttt tctgtggtaa gcatatctat ggctcaaacc agagagaagg 60
acgatgtcag cataacaaac tccaaaggat tggtatgcgt gacaggagcg gctggttact 120
tggcatcttg gcttatcaag cgtctcctcc agtgtggtta ccaagtgaga ggaactgtgc 180
gggatcctgg caatgagaaa aagatggctc atttatggaa gttagatggg gcgaaagaga 240
gactgcaact aatgaaagct gatttaatgg acgagggcag cttcgatgag gtcatcagag 300
gctgccatgg tgtttttcac acagcgtctc cagtcgtggg tgtcaaatca gatcccaaga 360
tatggtatgc tctggccaag actttagcag aaaaagcagc atgggatttt gcccaagaaa 420
accatctgga catggttgca g 441

<210> SEQ ID NO 61
<211> LENGTH: 913
<212> TYPE: DNA
<213> ORGANISM: Pinus radiata

<400> SEQUENCE: 61
gaattcggca cgaggaaaac atcatccagg cattttggaa atttagctcg ccggttgatt 60
caggatcctg caatggcttt tggcgaagag cagactgcct tgccacaaga aacgcctttg 120
aatcctccgg tccatcgagg aacagtgtgc gttacaggag ctgctgggtt catagggtca 180
tggctcatca tgcgattgct tgagcgagga tatagtgtta gagcaactgt gcgagacact 240
ggtaatcctg taaagacaaa gcatctgttg gatctgccgg gggcaaatga gagattgact 300
ctctggaaag cagatttgga tgatgaagga agctttgatg ctgccattga tgggtgtgag 360
ggtgttttcc atgttgccac tcccatggat ttcgagtccg aggatcccga gaatgagata 420
attaagccaa caatcaacgg ggtcttgaat gttatgagat cgtgtgcaaa agccaagtcc 480
gtgaagcgag ttgttttcac gtcatctgct gggactgtga attttacaga tgatttccaa 540
acaccaggca aagtttttga cgaatcatgc tggaccaacg tggatctttg cagaaaagtt 600
aaaatgacag gatggatgta ctttgtatcg aagacattag cagagaaagc tgcttgggat 660
tttgcagagg agaacaagat cgatctcatt actgttatcc ccacattggt cgttggacca 720
ttcattatgc agaccatgcc accgagcatg atcacagcct tggcactgtt aacgcggaat 780
gaaccccact acatgatact gagacaggta cagctggttc acttggatga tctctgtatg 840
tcacatatct ttgtatatga acatcctgaa gcaaagggca gatacatctc ttccacatgt 900
gatgctaccc att 913

<210> SEQ ID NO 62
<211> LENGTH: 680
<212> TYPE: DNA
<213> ORGANISM: Pinus radiata

<400> SEQUENCE: 62
gaattcggca cgagatcaat ttttgcatat tattaaaaag taagtgtatt cgttctctat 60
attgatcagt cacagagtca tggccagttg tggttccgag aaagtaagag ggttgaatgg 120
agatgaagca tgcgaagaga acaagagagt ggtttgtgta actggggcaa atgggtacat 180
cggctcttgg ctggtcatga gattactgga acatggctat tatgttcatg gaactgttag 240
ggacccagaa gacacaggga aggttgggca tttgctgcgg ctcccagggg caagtgagaa 300
gctaaagctg ttcaaggcag agcttaacga cgaaatggcc tttgatgatg ctgtgagcgg 360

-continued ttgtcaaggg gttttccacg ttgccaagcc tgttaatctg gactcaaacg ctcttcaggg 420
ggaggttgtt ggtcctgcgg tgaggggaac agtaaatctg cttcgagcct gcgaacgatc 480
gggcactgtg aaacgagtga tacatacctc gtccgtttca gcagtgagat tcactgggaa 540
acctgacccc cctgatactg tgctggatga atctcattgg acttcggtcg agtattgcag 600
aaagacaaag atggtcggat ggatgtacta catcgccaac acttatgcag aagagggagc 660
ccataagttc ggatcagaga 680

<210> SEQ ID NO 63
<211> LENGTH: 492
<212> TYPE: DNA
<213> ORGANISM: Pinus radiata

<400> SEQUENCE: 63
gaattcggca cgaggctggt tcaagtgtca gcccaatggc ctcccctaca gagaatcccc 60
agatttcaga agagctgcta aatcatgaga tccatcaagg aagtacagta tgtgtgacag 120
gagctgctgg cttcatagga tcatggctcg tcatgcgttt gcttgagcga ggatatactg 180
ttagaggaac tgtgcgagac actggtaatc cggtgaagac gaagcatcta ttggatctgc 240
ctggggcgaa tgagaggtta actctctgga aagcagattt ggatgatgaa ggaagctttg 300
acgccgccat tgatggttgt gagggagttt tccatgttgc cactcccatg gattttgaat 360
ccgaggaccc cgagaacgag ataattaaac ccgctgtcaa tgggatgttg aatgttttga 420
gatcgtgtgg gaaaaccaag tctatgaagc gagttgtttt cacgtcgtct gctgggactc 480
tgctttttac gg 492

<210> SEQ ID NO 64
<211> LENGTH: 524
<212> TYPE: DNA
<213> ORGANISM: Pinus radiata

<400> SEQUENCE: 64
gaattcggca cgagcttgtt caaagtcaca tatcttattt tctttgtgat atctgcaatt 60
tccaagcttt tcgtctacct ccctgaaaag atgagcgagg tatgcgtgac aggaggcaca 120
ggcttcatag ctgcttatct cattcgtagt cttctccaga aaggttacag agttcgcact 180
acagttcgca acccagataa tgtggagaag tttagttatc tgtgggatct gcctggtgca 240
aacgaaagac tcaacatcgt gagagcagat ttgctagagg aaggcagttt tgatgcagca 300
gtagatggtg tagatggagt attccatact gcatcacctg tcttagtccc atataacgag 360
cgcttgaagg aaaccctaat agatccttgt gtgaagggca ctatcaatgt cctcaggtcc 420
tgttcaagat caccttcagt aaagcgggtg gtgcttacat cctcctgctc atcaataccg 480
atacgactat aatagcttag agcgttccct gctggactga gtca 524

<210> SEQ ID NO 65
<211> LENGTH: 417
<212> TYPE: DNA
<213> ORGANISM: Pinus radiata

<400> SEQUENCE: 65
tcctaattgt tcgatcctcc cttttaaagc ccttccctgg ccttcattcc aggtcacaga 60
gttgttcatg cagtgctagc aggaggagca gcgttgcaat tggggaaaat tccaaaatca 120
ataacgagag gacagaagta agtttgtgga aatagcaacc atgccggtgt ttccttctgg 180
tctggacccc tctgaggaca atggcaagct cgtttgtgtc atggatgcgt ccagttatgt 240

```
aggtttgtgg attgttcagg gccttcttca acgaggctat tcagtgcatg ccacggtgca    300

gagagacgct ggcgaggttg agtctctcag aaaattgcat ggggatcgat tgcagatctt    360

ctatgcagat gtcttggatt atcacagcat tactgatgcg ctcaagggct gttctgg       417


<210> SEQ ID NO 66
<211> LENGTH: 511
<212> TYPE: DNA
<213> ORGANISM: Pinus radiata

<400> SEQUENCE: 66

atgacacgaa tttgtgcctc tctctgacca gagcttgaag ctctgtcttc tctgatatcg     60

cttcattcca tcatccagga gcttctgtta tatccatttc ctcaaaatgg atgcctacct    120

tgaagaaaat ggatacggcg cttccaattc tcggaaatta atgtgcctta ccgggggctg    180

gagtttcctg ggattcata  tcgcaagaat gctgctcggc cggggttact cagtccgttt    240

cgcaattccg gtaacgccag aagaggcagg ctcacttatg gaatccgaag aagcattatc    300

ggggaagctg gagatatgcc aagccgatct cttggattat cgcagcgttt tcggcaacat    360

caatggttgc tccggagtct tccacgtccc tgcgccctgt gatcatctgg atggattaca    420

ggagtatccg gtatgattag tttaatagat tgacggggta tcctgtatga attagtttat    480

gaatttaagg ttttcttaga atttggatac t                                   511


<210> SEQ ID NO 67
<211> LENGTH: 609
<212> TYPE: DNA
<213> ORGANISM: Pinus radiata

<400> SEQUENCE: 67

cattgatagt tgatggaaga ccatcagtaa agcatgaaaa agaaattgtt ccaaggtgaa     60

gaagtcagtt gctccagcag aacctttttta gcaattgttt ttgtatcctt tttgcctttg  120

aatatgtaat ccataaactt atgcaggaag tgcctcgtgc cgaattcggc acgagaatca    180

ctgaccttca catatttatt ccaattctaa tatctctact cgctgtctac ctgatttttc    240

agtggcgaac caacttgaca gggttggaca tggccaacag cagcaagatt ctgattattg    300

gaggaacagg ctacattggt cgtcatataa ccaaagccag ccttgctctt ggtcatccca    360

cattccttct tgtcagagag acctccgctt ctaatcctga gaaggctaag cttctggaat    420

ccttcaaggc ctcaggtgct attatactcc atggatcttt ggaggaccat gcaagtcttg    480

tggaggcaat caagaaagtt gatgtagtta tctcggctgt caagggacca cagctgacgg    540

ttcaaacagg atatttatcc agggtattta aagggagggt tggaacccat caagaagggt    600

tttggccaa                                                            609


<210> SEQ ID NO 68
<211> LENGTH: 474
<212> TYPE: DNA
<213> ORGANISM: Pinus radiata

<400> SEQUENCE: 68

gcaagatagg ttttattctt ctggagttgg gtgaggcttg gaaatttaag taaaaagggt     60

gcatagcaat taagcagttg cagccatggc ggtctgtgga actgaagtag ctcatactgt    120

gctctatgta gctgcagaca tggtggaaaa caacacgtct attgtgacca cctctatggc    180

tgcagcaaat tgtgagatgg agaagcctct tctaaattcc tctgccacct caagaatact    240

ggtgatggga gccacaggtt acattggccg ttttgttgcc caagaagctg ttgctgctgg    300
```

tcatcctacc tatgctctta tacgcccgtt tgctgcttgt gacctggcca aagcacagcg 360
cgtccaacaa ttgaaggatg ccggggtcca tatcctttat gggtctttga gtgatcacaa 420
cctcttagta aatacattga aggacatggg ccgttgttat ctctaccatt ggag 474

<210> SEQ ID NO 69
<211> LENGTH: 474
<212> TYPE: DNA
<213> ORGANISM: Pinus radiata

<400> SEQUENCE: 69
gcaagatagg ttttattctt ctggagttgg gtgaggcttg gaaatttaag taaaaagggt 60
gcatagcaat taagcagttg cagccatggc ggtctgtgga actgaagtag ctcatactgt 120
gctctatgta gctgcagaca tggtggaaaa caacacgtct attgtgacca cctctatggc 180
tgcagcaaat tgtgagatgg agaagcctct tctaaattcc tctgccacct caagaatact 240
ggtgatggga gccacaggtt acattggccg ttttgttgcc caagaagctg ttgctgctgg 300
tcatcctacc tatgctctta tacgcccgtt tgctgcttgt gacctggcca aagcacagcg 360
cgtccaacaa ttgaaggatg ccggggtcca tatcctttat gggtctttga gtgatcacaa 420
cctcttagta aatacattga aggacatggg ccgttgttat ctctaccatt ggag 474

<210> SEQ ID NO 70
<211> LENGTH: 608
<212> TYPE: DNA
<213> ORGANISM: Pinus radiata

<400> SEQUENCE: 70
cattgatagt tgatggaaga ccatcagtaa agcatgaaaa agaaattgtt ccaaggtgaa 60
gaagtcagtt gctccagcag aaccttttta gcaattgttt ttgtatcctt tttgcctttg 120
aatatgtaat ccataaactt atgcaggaag tgcctcgtgc cgaattcggc acgagaatca 180
ctgaccttca aatatttatt ccaattctaa tatctctact cgctgtctac ctgatttttc 240
agtggcgaac caacttgaca gggttggaca tggccaacag cagcaagatt ctgattattg 300
gaggaacagg ctacattggt cgtcatataa ccaaagccag ccttgctctt ggtcatccca 360
cattccttct tgtcagagag acctccgctt ctaatcctga gaaggctaag cttctggaat 420
ccttcaaggc ctcaggtgct attatactcc atggatcttt ggaggaccat gcaagtcttg 480
tggaggcaat caagaaagtt gatgtagtta tctcggctgt caagggacca cagctgacgg 540
atcaaacagg atatttatcc agggtattta aagggaggtt ggaacccatc aagaagggtt 600
ttggccaa 608

<210> SEQ ID NO 71
<211> LENGTH: 1474
<212> TYPE: DNA
<213> ORGANISM: Pinus radiata

<400> SEQUENCE: 71
gaattcggca cgagaaaacg tccatagctt ccttgccaac tgcaagcaat acagtacaag 60
agccagacga tcgaatcctg tgaagtggtt ctgaagtgat gggaagcttg gaatctgaaa 120
aaactgttac aggatatgca gctcgggact ccagtggcca cttgtcccct tacacttaca 180
atctcagaaa gaaaggacct gaggatgtaa ttgtaaaggt catttactgc ggaatctgcc 240
actctgattt agttcaaatg cgtaatgaaa tggacatgtc tcattaccca atggtccctg 300
ggcatgaagt ggtggggatt gtaacagaga ttggcagcga ggtgaagaaa ttcaaagtgg 360
gagagcatgt aggggttggt tgcattgttg ggtcctgtcg cagttgcggt aattgcaatc 420
agagcatgga acaatactgc agcaagagga tttggaccta caatgatgtg aaccatgacg 480
gcacacctac tcagggcgga tttgcaagca gtatggtggt tgatcagatg tttgtggttc 540
gaatcccgga gaatcttcct ctggaacaag cggcccctct gttatgtgca ggggttacag 600
ttttcagccc aatgaagcat ttcgccatga cagagcccgg gaagaaatgt gggattttgg 660
gtttaggagg cgtggggcac atgggtgtca agattgccaa agcctttgga ctccacgtga 720
cggttatcag ttcgtctgat aaaaagaaag aagaagccat ggaagtcctc ggcgccgatg 780
cttatcttgt tagcaaggat actgaaaaga tgatggaagc agcagagagc ctagattaca 840
taatggacac cattccagtt gctcatcctc tggaaccata tcttgccctt ctgaagacaa 900
atggaaagct agtgatgctg ggcgttgttc cagagccgtt gcacttcgtg actcctctct 960
taatacttgg gagaaggagc atagctggaa gtttcattgg cagcatggag gaaacacagg 1020
aaactctaga tttctgtgca gagaagaagg tatcatcgat gattgaggtt gtgggcctgg 1080
actacatcaa cacggccatg gaaaggttgg agaagaacga tgtccgttac agatttgtgg 1140
tggatgttgc tagaagcaag ttggataatt agtctgcaat caatcaatca gatcaatgcc 1200
tgcatgcaag atgaatagat ctggactagt agcttaacat gaaagggaaa ttaaattttt 1260
atttaggaac tcgatactgg tttttgttac tttagtttag cttttgtgag gttgaaacaa 1320
ttcagatgtt tttttaactt gtatatgtaa agatcaattt ctcgtgacag taaataataa 1380
tccaatgtct tctgccaaat taatatatgt attcgtattt ttatatgaaa aaaaaaaaaa 1440
aaaaaaaaaa aaaaaaaaaa aaaaaaaaaa aaaa 1474

<210> SEQ ID NO 72
<211> LENGTH: 1038
<212> TYPE: DNA
<213> ORGANISM: Pinus radiata

<400> SEQUENCE: 72
gaattcggca cgagagaggg ttatatatct tgattctgac ctgattgtcg tcgacgacat 60
tgccaagctc tgggccacgg atttggaatc tcgtgtcctc ggggcaccag agtactgcaa 120
ggcgaatttc acaaagtatt tcaccgataa tttctggtgg gatcccgcat tatccaagac 180
ctttgaggga aaaaaaccct gctacttcaa cacaggcgta atggtgatcg atcttgaaaa 240
atggcgggca ggggaattca caagaaagat cgaaatctgg atggacatac agaaggaacg 300
ccgtatctat gagctcggat cattaccgcc atttttactg gtatttgctg gtttggttaa 360
gcaagtcgat catcgttgga atcagcacgg tttaggcgga gataatttgc aaggcctttg 420
ccgagatctt caccctggac ctgtcagttt gttgcattgg agtggtaagg gcaaaccttg 480
gctacgcctg gaatgccaag cggacttgcc ctctggatac tttatgggct ccttatgatc 540
tttatcgatc aacgtattac ctaaatgggt gagagagcct ctctcctcgg ggtgcttttt 600
atcgaattaa acctgatttg ataaaatgcc aaatagaact ttacgcctat gcatctttca 660
gttttgaatt tcaattctgg taacgaatag aagaaaacaa tagcacagcc acaggcagga 720
caaatccatc atgagggacc aatcgtttga atttagtatt aataaggttg ttccatataa 780
cgcctgtgaa gaatgatatt gtggactgat ctatttatat ttgtactgcc atgccatcct 840
cagccagcag agaggcaagc aatgccgctg caagtcatgt agggaaggcg ttgtgaactc 900
aattttcggc gactgtacag gatgtaaatt tttggaacat taatatcatt atgataagtt 960
cctgaaccaa caactgtata ataccttata aatgtatctg caactccatt tttgcataaa 1020
aaaaaaaaaa aaaaaaaa 1038

<210> SEQ ID NO 73
<211> LENGTH: 372
<212> TYPE: DNA
<213> ORGANISM: Pinus radiata

<400> SEQUENCE: 73
ctaggggtct tggggggttc ctgatgccca attgttgctg tgcttggcat gaacccaaaa 60
catgcaagag atctgtagtc agtagtcttg ttggatctat agcttttaga aaagagtcac 120
gtccttttag ggtaacatca ttccaaccat atccagttcc accaccggct acaccttcaa 180
cgggaggagg agcaagatat tcagcattgc tttgggcacc agatggatag gcattatttt 240
ccatcggaat tcagccgagc tcgccccctc agtccaatcg tcgtgaaaat ccctcaaaat 300
tgggcaattc tggctcgaaa tcgccaaatt atgggctaca acaggattaa aattgcacag 360
aaatctgcca gt 372

<210> SEQ ID NO 74
<211> LENGTH: 545
<212> TYPE: DNA
<213> ORGANISM: Pinus radiata

<400> SEQUENCE: 74
aaagaattcg gcacgagggc aatccgagcc tagccaacca acttggcagc aaggagcaca 60
gggagttggc gagagaagct gttaggaaat ctttggtatt gttgaaaaat gggaagtcag 120
ccaacaagcc tttgctccct ttggagaaga atgcttccaa ggttcttgtt gcaggaaccc 180
atcctgataa tctgggttat cagtgtggtg gatggacgat ggaatggcaa ggattaagtg 240
gaaacataac cgtaggaact acaattctgg aagctatcaa actagctgtc agcccctcta 300
ctgaagtggt ttatgagcaa aatccagatg ctaactatgt caaaggacaa gggttttcat 360
atgccattgt ggttgtgggt gaggcaccat acgcagaaac gtttggagac aatcttaatt 420
tgaccattcc cctaggcgga ggggacacga ttaagacggt ctgtggctcc ttgaaatgcc 480
ttgtaatctt gatatctgga aggccacttg ttattgaacc ttatcttcca ttggtggatc 540
gtttt 545

<210> SEQ ID NO 75
<211> LENGTH: 463
<212> TYPE: DNA
<213> ORGANISM: Pinus radiata

<400> SEQUENCE: 75
gcaggtcgac actagtggat ccaaagaatt cggcacgaga aaaaacaaat gttagctagc 60
ctagtgatga gctttacgta tacctggcct tttatacatg gatctgagtt tttatgcagg 120
tgtagagcct tttgttactc tgtatcactg ggacttgcca caagctctgg aggacgaata 180
cggtggattt cgtagcaaaa aagttgtgga tgactttggc atattctcag aagaatgctt 240
tcgtgctttt ggagaccgtg tgaagtactg ggtaactgtt aacgaaccgt tgatcttctc 300
atatttttct tacgatgtgg ggcttcacgc accgggccgc tgttcgcctg gatttggaaa 360
ctgcactgcg ggaaattcag cgacagagcc ttatattgta gcccataaca tgcttcttgc 420
acatagtacc gctgttaaaa atatatagca taaataccca ggg 463

<210> SEQ ID NO 76
<211> LENGTH: 435
<212> TYPE: DNA

<213> ORGANISM: Pinus radiata

<400> SEQUENCE: 76
acactagtgg atccaaagaa ttcggcacga ggctaccatc ttccctcata atattgggct 60
tggagctacc agggatcctg atctggctag aagaataggg gctgctacgg ctttggaagt 120
tcgagctact ggcattcaat acacatttgc tccatgtgtt gctgtttgca gagatcctcg 180
atggggccgc tgctatgaga gctacagtga ggatccaaaa attgtcaagg ccatgactga 240
gattatcgtt ggcctgcaag ggaatcctcc tgctaattct acaaaagggg ggccttttat 300
agctggacag tcaaatgttg cagcttgtgc taagcatttt gtgggttatg gtggaacaac 360
caaaggtatc gatgagaata atactgttat caactatcaa gggttatttc aacattccaa 420 attacccccca atttt 435

<210> SEQ ID NO 77
<211> LENGTH: 451
<212> TYPE: DNA
<213> ORGANISM: Pinus radiata

<400> SEQUENCE: 77
gaattcggca cgagcctaga attctatggt gaaaattgtt gggacaaggc tgcccaagtt 60
tacaaaggaa cagtcccaaa tggttaaagg ttcaatagac tatctaggcg ttaaccaata 120
cactgcttat tacatgtatg atcctaaaca acctaaacaa aatgtaacag attaccagac 180
tggactggaa tacaggcttt gcatatgctc gcaatggagt gcctattgga ccaagggcga 240
actccaattg gctttacatt gtgccttggg gtctatacaa ggccgtcaca tacgtaaaag 300
aacactatgg aaatccaact atgattctct ctgaaaatgg aatggacgac ctggaaacgt 360
gacacttcca gcaggactgc atgataccat caggggtaac tactataaaa gctatttgca 420
aaatttgatt aatgcacgtg aatgaccggg g 451

<210> SEQ ID NO 78
<211> LENGTH: 374
<212> TYPE: DNA
<213> ORGANISM: Pinus radiata

<400> SEQUENCE: 78
ctgctctgca agcagtacta tgcacagcaa ggcctgctta actgaaaaca gagcgctgag 60
cttgaggaaa cgctcaagca ttgctgaggc caccgtttat ctaaatagcg caacataggg 120
cttcagaaaa atggcaatgg cacaagcatt cagaggccgt gtcttgcaag ctgcccgttt 180
gctccgccgc aacattctgc cggaggataa aagctttgga tccgctgctt ctcctagacg 240
agctcttagc ctgctctcat caaaagcctt catctctttc tctgttgaac ggcatcggct 300
agctgctaca aattcaacaa ttgtgttgca atctcgaaac ttttctgcaa aaggtaaaaa 360
gacaggacaa tctg 374

<210> SEQ ID NO 79
<211> LENGTH: 457
<212> TYPE: DNA
<213> ORGANISM: Pinus radiata

<400> SEQUENCE: 79
gaagaatgga agagattaat ggtgataacg cagtaaggag gagctgcttt cctccaggtt 60
tcatgtttgg gatagcaact tctgcttatc agtgtgaagg agctgccaac gaaggtggaa 120
aaggcccaag catctgggac tcattttcac gaacaccagg caaaattctt gatggaagca 180

-continued

```
acggtgatgt agcagtggat cagtatcatc gttataaggc agatgtaaaa ctgatgaaag    240

atatgggcgt ggctacctac agattctcga tttcatggcc tcgtatattt ccaaagggaa    300

aaggagagat caatgaggaa ggagtagcct attacaataa cctcatcaat gaactcctcc    360

agaatggaat ccaagcgtct gtcaactttg tttcactggg atactcccca gtctctggag    420

gatgaatatg gcggatttct gaggccaacc attgtga                             457
```

<210> SEQ ID NO 80
<211> LENGTH: 346
<212> TYPE: DNA
<213> ORGANISM: Pinus radiata

<400> SEQUENCE: 80

```
ggtgtgatgg caggaattcc agtcctaagg ccattttgca tctgtttgct ttcagtctac     60

atgctgcaca ttgtagctgc agtagcttca ccaaggctag gtagaagcag cttcccaagg    120

ggtttcaaat ttggtgcagg gtcatctgct tatcaggcgg aaggagctgc tcatgagggt    180

ggcaaaggcc caagcatttg ggatacattc tcccacactc caggtaaaat cgctgatggg    240

aatattggga tgttgcagta gatcaatacc accgttataa ggaagatgtg cagcttctca    300

aatacatggg aatggacgtc tatcgtttct ctatctcctg gtcacg                   346
```

<210> SEQ ID NO 81
<211> LENGTH: 957
<212> TYPE: DNA
<213> ORGANISM: Pinus radiata

<400> SEQUENCE: 81

```
gaattcggca cgagaaagcc ctagaatttt ttcagcatgc tatcacagcc ccagcgacaa     60

ctttaactgc aataactgtg gaagcgtaca aaaagtttgt cctagtttct ctcattcaga    120

ctggtcaggt tccagcattt ccaaaataca cacctgctgt tgtccaaaga aatttgaaat    180

cttgcactca gccctacatt gatttagcaa acaactacag tagtgggaaa atttctgtat    240

tggaagcttg tgtcaacacg aacacagaga agttcaagaa tgatagtaat ttggggttag    300

tcaagcaagt tttgtcatct ctttataaac ggaatattca gagattgaca cagacatatc    360

tgaccctctc tcttcaagac atagcaagta cggtacagtt ggagactgct aagcaggctg    420

aactccatgt tctgcagatg attcaagatg gtgagatttt tgcaaccata aatcagaaag    480

atgggatggt gagcttcaat gaggatcctg aacagtacaa aacatgtcag atgactgaat    540

atatagatac tgcaattcgg agaatcatgg cactatcaaa gaagctcacc acagtagatg    600

agcagatttc gtgtgatcat tcctacctga gtaaggtggg gagagagcgt tcaagatttg    660

acatagatga ttttgatact gttccccaga agttcacaaa tatgtaacaa atgatgtaaa    720

tcatcttcaa gactcgctta tattcattac tttctatgtg aattgatagt ctgttaacaa    780

tagtactgtg gctgagtcca gaaaggatct ctcggtatta tcacttgaca tgccatcaaa    840

aaaatctcaa atttctcgat gtctagtctt gattttgatt atgaatgcga cttttagttg    900

tgacatttga gcacctcgag tgaactacaa agttgcatgt taaaaaaaaa aaaaaaa      957
```

<210> SEQ ID NO 82
<211> LENGTH: 489
<212> TYPE: DNA
<213> ORGANISM: Pinus radiata

<400> SEQUENCE: 82

```
gcaggtcgac actagtggat ccaaagaatt cggcacgaga taagactaat tttccagaca     60
```

```
atcctccatt cccattcaat tacactggta ctccacccaa taatacacag gctgtgaatg    120

ggactagagt aaaagtcctt ccctttaaca caactgttca attgattctt caagacacca    180

gcatcttcag cacagacagc caccctgtcc atctccatgg tttcaatttc tttgtggtgg    240

gccaaggtgt tggaaactac aatgaatcaa cagatgcacc aaattttaac ctcattgacc    300

ctgtcgagag aaacactgtg ggagttccca aaggaggttg ggctgctata agatttcgtg    360

cagacaatcc aggggtttgg ttcatgcact gtcatttgga ggttcacaca tcgtggggac    420

tgaaaatggc gtgggtagta aagaacggaa aagggcccat cgattttcca cccgggtggg    480

taccagtaa                                                            489


<210> SEQ ID NO 83
<211> LENGTH: 471
<212> TYPE: DNA
<213> ORGANISM: Pinus radiata

<400> SEQUENCE: 83

gaattcggca cgagaaaacc ttttcagacg aatgttctga tgctcggccc cggccagaca     60

acagacatac ttctcactgc caatcaggct acaggtagat actacatggc tgctcgagca    120

tattccaacg ggcaaggagt tcccttcgat aacaccacta ccactgccat tttagaatac    180

gagggaagct ctaagacttc aactccagtc atgcctaatc ttccattcta taacgacacc    240

aacagtgcta ctagcttcgc taatggtctt agaagcttgg gctcacacga ccacccagtc    300

ttcgttcctc agagtgtgga ggagaatctg ttctacacca tcggtttggg gttgatcaaa    360

tgtccggggc agtcttgtgg aggtccaacg gatcaagatt tgcagcaagt atgaatacat    420

atcatttgtc ccgcaaccac ttcttccaat ccttcaagct cagcattttg g             471


<210> SEQ ID NO 84
<211> LENGTH: 338
<212> TYPE: DNA
<213> ORGANISM: Pinus radiata

<400> SEQUENCE: 84

gttcggcact gagagatcca tttctttcaa tgttgagaca gtgagtagta ttagtttgat     60

atctctttca ggaatatatc gtgcttgcag gatctttagt ttctgcaaca atgtcgttgc    120

aatcagtgcg tctatcttct gctctccttg ttttgctact agcatttgtt gcttacttag    180

ttgctgtaac aaacgcagat gtccacaatt ataccttcat tattagaaag agacagttac    240

caggctatgc aataagcgta taatcgccac cgtcaatggc agctaccagg cccaactatt    300

catgtacgtg atggagacgt tgttaattat caaagctt                            338


<210> SEQ ID NO 85
<211> LENGTH: 1229
<212> TYPE: DNA
<213> ORGANISM: pinus radiata

<400> SEQUENCE: 85

agagaaataa ttatatttgt aaatttaagt ctacgtttat taaaaaacta caaccctaaa     60

tgcaggagaa aaaacaagca tgctgtctac tgaagcttac aaatcaaatc cctgcgatat    120

gtcttttctc gtgccgaatt cggcacgaga agatcttggt tcgagtctct cagctctctc    180

caaaggaatt ttgtgggtca tttgcaggtg aagacaccat ggtgaaggct tatcccaccg    240

taagcgagga gtacaaggct gccattgaca aatgcaagag gaagctccga gctctcattg    300

cagagaagaa ctgtgcgccg atcatggttc gaatcgcatg gcacagcgct gggacttacg    360
```

-continued

```
atgtcaagac caagaccgga gggcccttcg ggacgatgag atatggggcc gagcttgccc     420

acggtgctaa cagtggtctg gacatcgcag ttaggctcct ggagccaatc aaggaacagt     480

tccccataat cacctatgct gacctttatc agttggctgg tgtggtggct gttgaagtga     540

ccgggggacc tgacattccg ttccatcctg gaagagaaga caagcctgag cctccagaag     600

aaggccgcct tcctgatgct acaaaaggac ctgatcatct gagggatgtt tttggtcaca     660

tggggttgaa tgataaggaa attgtggcct tgtctggtgc ccacaccttg ggagatgcc      720

acaaggagag atctggtttt gaaggaccat ggacctctaa ccccccttatc tttgacaact     780

cttacttcac agagcttgtg actggagaga aggaaggcct gcttcagttg ccatctgata     840

aggcactgct tgctgatcct agttttgcag tttatgttca gaagtatgca caggacgaag     900

acgctttctt tgctgactat gcggaagctc acctgaagct ttctgaactt gggtttgctg     960

atgcgtagat tcataccttc tgcagagaca attccttgct agatagcttc gttttgtatt    1020

tcatctaatc ttttcgatta tatagtcaca tagaagttgg tgttatgcgc catagtgata    1080

cttgaaccta catgtttttg aaaagtatcg atgttcttta aaatgaacat tgaatacaac    1140

attttggaat ctggttgtgt tctatcaagc gcatatttta atcgaatgct tcgttcctgt    1200

taaaaaaaaa aataaaataa aaaaaaaaa                                      1229
```

<210> SEQ ID NO 86
<211> LENGTH: 1410
<212> TYPE: DNA
<213> ORGANISM: Pinus radiata

<400> SEQUENCE: 86

```
gaagatgggg ctgtgggtgg tgctggcttt ggcgctcagt gcgcactatt gcagtctcag      60

gcttacaatg tggtaagttc aagcaatgct actgggagtt acagtgagaa tggattggtg     120

atgaattact atggggactc ttgccctcag gctgaagaga tcattgctga acaagtacgc     180

ctgttgtaca aaagacacaa gaacactgca ttctcatggc ttagaaatat tttccatgac     240

tgtgctgtgg agtcatgtga tgcatcgctt ctgttggact caacaaggaa cagcatatca     300

gaaaaggaca ctgacaggag cttcggcctc cgcaacttta ggtatttgga taccatcaag     360

gaagccgtgg agagggagtg ccccggggtc gtttcctgtg cagatatact cgttctctct     420

gccagagatg gcgttgtatc gttgggagga ccatacattc ccctgaagac gggaagaaga     480

gatggacgga agagcagagc agatgtggtg gagaattacc tgcccgatca caatgagagc     540

atctccactg ttctgtctcg cttcaaagcc atgggaatcg acacccgtgg ggttgttgca     600

ctgctggggg ctcacagcgt ggggaggact cactgcgtga agctggtgca caggctgtac     660

ccggaagtag atccgacact ggaccctggg cacgtggagc acatgaagca caagtgcccg     720

gacgcgatcc ccaacccgaa ggcagtgcag tatgtgcgga acgaccgggg aacgcctatg     780

aagctggaca acaactacta cgtgaacctg atgaacaaca aggggctcct aatagtggac     840

cagcaactgt atgcagattc gaggaccagg ccgtatgtga agaagatggc aaaaagccag     900

gaatacttct tcaaatactt ctcccgggcg ctcaccatcc tctctgagaa caatcctctc     960

accggcgctc gaggagaaat ccgtcggcag tgctcgctca aaaacaaatt gcacacaaaa    1020

agcaagcgtt gagcgatagc tcaatgccgc agtggtggga gtgatagcgt gatgccacag    1080

tggtgggcat ttcatatata aattgcagtt tgcgttttta ttagataatc ataatggtgt    1140

ggtgtgacta tgccctgcga atcacatcga tgaaccacaa ccgaaccgtg gaacagtagg    1200

cttattccct tatgtaagca gaacctttta ttataagcaa aaaagacaat cctgtctgtt    1260
```

```
attctagtat aattttgtca tcagttaaag ttgctcatct gataataact ggaaacggta   1320

aaatatgaca actacgtatc ttctttggtc atctgataat aaccggaaac gataaaatat   1380

gacaactaca tatattcttt aaaaaaaaaa                                    1410


<210> SEQ ID NO 87
<211> LENGTH: 687
<212> TYPE: DNA
<213> ORGANISM: Pinus radiata

<400> SEQUENCE: 87

gtagtttcgt tttacaacaa tctcaggttt tgaatctcag aatagttgcg aaaggaagcg     60

atgacgaagt acgtgatcgt tagctccatt gtgtgtttct ttgtatttgt ttctgcgtgc    120

ataatttctg tcaatggatt agttgtccat gaagatgatc tgtcaaagcc tgtgcatggg    180

ctttcgtgga cattttataa ggacagttgc cccgacttgg aggccatagt gaaatcggta    240

cttgagccgg cgttggacga agatatcact caggccgcag gcttgctgag acttcatttc    300

catgactgtt ttgtgcaggg ttgcgatggg tccgtgttgc tgacaggaac taaaagaaac    360

cccagtgagc aacaggctca gccaaactta acactaagag cccgggcctt gcagctgatc    420

gacgaaatta aaaccgctgt agaagctagc tgcagtgggg ttgtaacttg tgcagacatt    480

ctggctttgg ctgctcgtga ctccgtccgc tcaggaggcc caaaatttcc agtaccactt    540

ggccgcagag atagcctaaa gtttgccagt caatccgtag ttctcgccaa tataccaact    600

ccaactttaa atttgacaca gctgatgaac atttttggct ccaaaggatt cagtttggcc    660

gaaatggttg ctcttcaggt ggcacac                                        687


<210> SEQ ID NO 88
<211> LENGTH: 688
<212> TYPE: DNA
<213> ORGANISM: Pinus radiata

<400> SEQUENCE: 88

gtagtttcgt tttacaacaa tctacaggtt ttgaatctca gaatagttgc gaaaggaagc     60

gatgacgaag tacgtgatcg ttagctccat tgtatgtttc tttgtatttg tttctgcgtg    120

cataatttct gtcaatggat tagttgtcca tgaagatgat ctgtcaaagc ctgtgcatgg    180

gctttcgtgg acattttata aggacagttg ccccgacttg gaggccatag tgaaatcggt    240

acttgagccg gcgttggacg aagatatcac tcaggccgca ggttgctgag acttcatttc    300

catgactgtt ttgtgcaggg ttgcgatggg tccgtgttgc tgacaggaac taaaagaaac    360

ccccgagtga gcaacaggct cagccaaact taacactaag agcccgggcc ttgcagctga    420

tcgacgaaat taaaaccgct gtagaagcta gctgcagtgg ggttgtaact tgtgcagaca    480

ttctggcttt ggctgctcgt gactccgtcg ctcaggaggc ccaaaatttc cagtaccact    540

tggccgcaga gatagcctaa agtttgccag tcaatccgta gttctcgcca atataccaac    600

tccaacttta aatttgacac agctgatgaa catttttggc tccaaaggat tcagtttggc    660

cgaaatggtt gctcttcagg tggcacac                                       688


<210> SEQ ID NO 89
<211> LENGTH: 278
<212> TYPE: DNA
<213> ORGANISM: Pinus radiata

<400> SEQUENCE: 89

tcttcgaatt ctctttcacg actgcttcgt taatggctgc gatggctcga tattgttaga     60
```

```
tgataactca acgttcaccg gagaaaagac tgcaggccca aatgttaatt ctgcgagagg    120

attcgacgta atagacacca tcaaaactca agttgaggca gcctgcagtg gtgtcgtgtc    180

atgtgccgac attctcgcca ttgctgcacg cgattcagtc gtccaactgg ggggcccaac    240

atggacggta cttctgggag aaaagacgga tccgatca                            278


<210> SEQ ID NO 90
<211> LENGTH: 1960
<212> TYPE: DNA
<213> ORGANISM: Pinus radiata

<400> SEQUENCE: 90

gttttccgcc atttttcgcc tgtttctgcg gagaatttga tcaggttcgg attgggattg     60

aatcaattga aaggttttta ttttcagtat ttcgatcgcc atggccaacg gaatcaagaa    120

ggtcgagcat ctgtacagat cgaagcttcc cgatatcgag atctccgacc atctgcctct    180

tcattcgtat tgctttgaga gagtagcgga attcgcagac agaccctgtc tgatcgatgg    240

ggcgacagac agaacttatt gcttttcaga ggtggaactg atttctcgca aggtcgctgc    300

cggtctggcg aagctcgggt tgcagcaggg gcaggttgtc atgcttctcc ttccgaattg    360

catcgaattt gcgtttgtgt tcatgggggc ctctgtccgg ggcgccattg tgaccacggc    420

caatcctttc tacaagccgg gcgagatcgc caaacaggcc aaggccgcgg gcgcgcgcat    480

catagttacc ctggcagctt atgtggagaa actggccgat ctgcagagcc acgatgtgct    540

cgtcatcaca atcgatgatg ctcccaagga aggttgccaa catatttccg ttctgaccga    600

agccgacgaa acccaatgcc cggccgtgac aatccacccg gacgatgtcg tggcgttgcc    660

ctattcttcc ggaaccacgg ggctccccaa gggcgtgatg ttaacgcaca aaggcctggt    720

gtccagcgtt gcccagcagg tcgatggtga aaatcccaat ctgtatttcc attccgatga    780

cgtgatactc tgtgtcttgc ctcttttcca catctattct ctcaattcgg ttctcctctg    840

cgcgctcaga gccggggctg cgaccctgat tatgcagaaa ttcaacctca cgacctgtct    900

ggagctgatt cagaaataca aggttaccgt tgccccaatt gtgcctccaa ttgtcctgga    960

catcacaaag agccccatcg tttcccagta cgatgtctcg gccgtccgga taatcatgtc   1020

cggcgctgcg cctctcggga aggaactcga agatgccctc agagagcgtt ttcccaaggc   1080

cattttcggg cagggctacg gcatgacaga agcaggcccg gtgctggcaa tgaacctagc   1140

cttcgcaaag aatcctttcc ccgtcaaatc tggctcctgc ggaacagtcg tccggaacgc   1200

tcaaataaag atcctcgata cagaaactgg cgagtctctc ccgcacaatc aagccggcga   1260

aatctgcatc cgcggacccg aaataatgaa aggatatatt aacgacccgg aatccacggc   1320

cgctacaatc gatgaagaag gctggctcca cacaggcgac gtcgggtaca ttgacgatga   1380

cgaagaaatc ttcatagtcg acagagtaaa ggagattatc aaatataagg gcttccaggt   1440

ggctcctgct gagctggaag ctttacttgt tgctcatccg tcaatcgctg acgcagcagt   1500

cgttcctcaa aagcacgagg aggcgggcga ggttccggtg gcgttcgtgg tgaagtcgtc   1560

ggaaatcagc gagcaggaaa tcaaggaatt cgtggcaaag caggtgattt tctacaagaa   1620

aatacacaga gtttactttg tggatgcgat tcctaagtcg ccgtccggca agattctgag   1680

aaaggatttg agaagcagac tggcagcaaa atgaaaatga atttccatat gattctaaga   1740

ttcctttgcc gataattata ggattccttt ctgttcactt ctatttatat aataaagtgg   1800

tgcagagtaa gcgccctata aggagagaga gagcttatca attgtatcat atggattgtc   1860

aacgccctac actcttgcga tcgctttcaa tatgcatatt actataaacg atatatgttt   1920
```

tttttataaa tttactgcac ttctcgttca aaaaaaaaaa 1960

<210> SEQ ID NO 91
<211> LENGTH: 701
<212> TYPE: DNA
<213> ORGANISM: Pinus radiata

<400> SEQUENCE: 91
gtagtttcgt tttacaacaa tctcaggttt tgaatctcag aatagttgcg aaaggaagcg 60
atgacgaagt acgtgatcgt tagctccatt gtatgtttct ttgtatttgt ttctgcgtgc 120
ataatttctg tcaatggatt agttgtccat gaagatgatc tgtcaaagcc tgtgcatggg 180
ctttcgtgga cattttataa ggacagttgc cccgacttgg aggccatagt gaaatcggta 240
cttgagccgg cgttggacga agatatcact caggccgcag gttgctgaga cttcatttcc 300
atgactgttt tgtgcagggt tgcgatgggt ccgtgttgct gacaggaact aaaagaaacc 360
ccgagtgagc aacaggctca gccaaactta acactaagag cccgggcctt gcagctgatc 420
gacgaaatta aaaccgctgt agaagctagc tgcagtgggg ttgtaacttg tgcagacatt 480
ctggctttgg ctgctcgtga ctccgtcgct caggaggccc aaaatttcca gtaccacttg 540
gccgcagaga tagcctaaag tttgccagtc aatccgtagt tctcgccaat ataccaactc 600
caactttaaa tttgacacag ctgatgaaca tttttggctc caaaggattc agtttggccg 660
aaatggttgc tctttcaggt ggacacacaa tcggcattgg t 701

<210> SEQ ID NO 92
<211> LENGTH: 626
<212> TYPE: DNA
<213> ORGANISM: Pinus radiata

<400> SEQUENCE: 92
gttgcaggtc ggggatgatt tgaatcacag aaacctcagc gattttgcca agaaatatgg 60
caaaatcttt ctgctcaaga tgggccagag gaatcttgtg gtagtttcat ctcccgatct 120
cgccaaggag gtcctgcaca cccagggcgt cgagtttggg tctcgaaccc ggaacgtggt 180
gttcgatatc ttcacgggca aggggcagga catggtgttc accgtctatg gagatcactg 240
gagaaagatg cgcaggatca tgactgtgcc tttctttacg aataaagttg tccagcacta 300
cagattcgcg tgggaagacg agatcagccg cgtggtcgcg gatgtgaaat cccgcgccga 360
gtcttccacc tcgggcattg tcatccgtag cgcctccagc tcatgatgta taatattatg 420
tataggatga tgttcgacag gagattcgaa tccgaggacg acccgctttt cctcaagctc 480
aaggccctca acggagagcg aagtcgattg gcccagagct ttgagtacaa ttatggggat 540
ttcattccca gtcttaggcc cttcctcaga ggttatcaca gaatctgcaa tgagattaaa 600
gagaaacggc tctctctttt caagga 626

<210> SEQ ID NO 93
<211> LENGTH: 660
<212> TYPE: DNA
<213> ORGANISM: Pinus radiata
<220> FEATURE:
<221> NAME/KEY: misc_feature
<222> LOCATION: (516)..(517)
<223> OTHER INFORMATION: n is a, c, g, or t
<220> FEATURE:
<221> NAME/KEY: misc_feature
<222> LOCATION: (519)..(519)
<223> OTHER INFORMATION: n is a, c, g, or t
<220> FEATURE:
<221> NAME/KEY: misc_feature
<222> LOCATION: (539)..(539)

<223> OTHER INFORMATION: n is a, c, g, or t
<220> FEATURE:
<221> NAME/KEY: misc_feature
<222> LOCATION: (554)..(554)
<223> OTHER INFORMATION: n is a, c, g, or t
<220> FEATURE:
<221> NAME/KEY: misc_feature
<222> LOCATION: (562)..(562)
<223> OTHER INFORMATION: n is a, c, g, or t
<220> FEATURE:
<221> NAME/KEY: misc_feature
<222> LOCATION: (578)..(578)
<223> OTHER INFORMATION: n is a, c, g, or t
<220> FEATURE:
<221> NAME/KEY: misc_feature
<222> LOCATION: (583)..(583)
<223> OTHER INFORMATION: n is a, c, g, or t
<220> FEATURE:
<221> NAME/KEY: misc_feature
<222> LOCATION: (585)..(585)
<223> OTHER INFORMATION: n is a, c, g, or t
<220> FEATURE:
<221> NAME/KEY: misc_feature
<222> LOCATION: (587)..(587)
<223> OTHER INFORMATION: n is a, c, g, or t
<220> FEATURE:
<221> NAME/KEY: misc_feature
<222> LOCATION: (590)..(590)
<223> OTHER INFORMATION: n is a, c, g, or t
<220> FEATURE:
<221> NAME/KEY: misc_feature
<222> LOCATION: (595)..(595)
<223> OTHER INFORMATION: n is a, c, g, or t
<220> FEATURE:
<221> NAME/KEY: misc_feature
<222> LOCATION: (599)..(599)
<223> OTHER INFORMATION: n is a, c, g, or t
<220> FEATURE:
<221> NAME/KEY: misc_feature
<222> LOCATION: (607)..(607)
<223> OTHER INFORMATION: n is a, c, g, or t
<220> FEATURE:
<221> NAME/KEY: misc_feature
<222> LOCATION: (613)..(613)
<223> OTHER INFORMATION: n is a, c, g, or t
<220> FEATURE:
<221> NAME/KEY: misc_feature
<222> LOCATION: (623)..(623)
<223> OTHER INFORMATION: n is a, c, g, or t
<220> FEATURE:
<221> NAME/KEY: misc_feature
<222> LOCATION: (630)..(630)
<223> OTHER INFORMATION: n is a, c, g, or t
<220> FEATURE:
<221> NAME/KEY: misc_feature
<222> LOCATION: (633)..(634)
<223> OTHER INFORMATION: n is a, c, g, or t
<220> FEATURE:
<221> NAME/KEY: misc_feature
<222> LOCATION: (636)..(636)
<223> OTHER INFORMATION: n is a, c, g, or t
<220> FEATURE:
<221> NAME/KEY: misc_feature
<222> LOCATION: (641)..(641)
<223> OTHER INFORMATION: n is a, c, g, or t
<220> FEATURE:
<221> NAME/KEY: misc_feature
<222> LOCATION: (647)..(647)
<223> OTHER INFORMATION: n is a, c, g, or t

<400> SEQUENCE: 93
acccagtgac cttcaggcct gagagatttc ttgaggaaga tgttgatatt aagggccatg 60
attacaggct actgccattg gtgcagggcg caggatctgc cctggtgcac aattgggtat 120
taatttagtt cagtctatgt tgggacacct gcttcatcat ttcgtatggg cacctcctga 180
gggaatgaag gcagaagaca tagatctcac agagaatcca gggcttgtta ctttcatggc 240

```
caagcctgtg caggccattg ctattcctcg attgcctgat catctctaca agcgacagcc    300

actcaattga tcaattgatc tgatagtaag tttgaatttt gttttgatac aaaacgaaat    360

aacgtgcagt ttctcctttt ccatagtcaa catgcagctt tctttctctg aagcgcatgc    420

agctttcttt ctctgaagcc caacttctag caagcaataa ctgtatattt tagaacaaat    480

acctattcct caaattgagw atttctctgt aggggnngnt aattgtgcaa tttgcaagna    540

atagtaaagt ttantttagg gnattttaat agtcctangt aanangnggn aatgntagng    600

ggcattnaga aanccctaat agntgttggn ggnngntagg ntttttnacc aaaaaaaaaa    660
```

<210> SEQ ID NO 94
<211> LENGTH: 1012
<212> TYPE: DNA
<213> ORGANISM: Pinus radiata

<400> SEQUENCE: 94

```
ctttgaggca acctacattc attgaatccc aggatttctt cttgtccaaa caggtttaag     60

gaaatggcag gcacaagtgt tgctgcagca gaggtgaagg ctcagacaac ccaagcagag    120

gagccggtta aggttgtccg ccatcaagaa gtgggacaca aaagtctttt gcagagcgat    180

gccctctatc agtatatatt ggaaacgagc gtgtaccctc gtgagcccga gccaatgaag    240

gagctccgcg aagtgactgc caagcatccc tggaacctca tgactacttc tgccgatgag    300

ggtcaatttc tgggcctcct gctgaagctc attaacgcca agaacaccat ggagattggg    360

gtgtacactg gttactcgct tctcagcaca gcccttgcat tgcccgatga tggaaagatt    420

ctagccatgg acatcaacag agagaactat gatatcggat tgcctattat tgagaaagca    480

ggagttgccc acaagattga cttcagagag ggccctgctc tgccagttct ggacgaactg    540

cttaagaatg aggacatgca tggatcgttc gatttttgtgt tcgtggatgc ggacaaagac    600

aactatctaa actaccacaa gcgtctgatc gatctggtga aggttggagg tctgattgca    660

tatgacaaca ccctgtggaa cggatctgtg gtggctccac ccgatgctcc cctgaggaaa    720

tatgtgagat attacagaga tttcgtgatg gagctaaaca aggcccttgc tgtcgatccc    780

cgcattgaga tcagccaaat cccagtcggt gacggcgtca ccctttgcag gcgtgtctat    840

tgaaaacaat ccttgtttct gctcgtctat tgcaagcata aaggctctct gattataagg    900

agaacgctat aatatatggg gttgaagcca tttgttttgt ttagtgtatt gataataaag    960

tagtacagca tatgcaaagt ttgtatcaaa aaaaaaaaaa aaaaaaaaaa aa           1012
```

<210> SEQ ID NO 95
<211> LENGTH: 1460
<212> TYPE: DNA
<213> ORGANISM: Pinus radiata

<400> SEQUENCE: 95

```
aaaacgtcca tagcttcctt gccaactgca agcaatacag tacaagagcc agacgatcga     60

atcctgtgaa gtggttctga agtgatggga agcttggaat ctgaaaaaac tgttacagga    120

tatgcagctc gggactccag tggccacttg tccccttaca cttacaatct cagaaagaaa    180

ggacctgagg atgtaattgt aaaggtcatt tactgcggaa tctgccactc tgatttagtt    240

caaatgcgta atgaaatgga catgtctcat tacccaatgg tccctgggca tgaagtggtg    300

gggattgtaa cagagattgg cagcgaggtg aagaaattca aagtgggaga gcatgtaggg    360

gttggttgca ttgttgggtc ctgtcgcagt tgcggtaatt gcaatcagag catggaacaa    420

tactgcagca agaggatttg gacctacaat gatgtgaacc atgacggcac acctactcag    480
```

```
ggcggatttg caagcagtat ggtggttgat cagatgtttg tggttcgaat cccggagaat    540
cttcctctgg aacaagcggc ccctctgtta tgtgcagggg ttacagtttt cagcccaatg    600
aagcatttcg ccatgacaga gcccgggaag aaatgtggga ttttgggttt aggaggcgtg    660
gggcacatgg gtgtcaagat tgccaaagcc tttggactcc acgtgacggt tatcagttcg    720
tctgataaaa agaaagaaga agccatggaa gtcctcggcg ccgatgctta tcttgttagc    780
aaggatactg aaaagatgat ggaagcagca gagagcctag attacataat ggacaccatt    840
ccagttgctc atcctctgga accatatctt gcccttctga agacaaatgg aaagctagtg    900
atgctgggcg ttgttccaga gccgttgcac ttcgtgactc ctctcttaat acttgggaga    960
aggagcatag ctggaagttt cattggcagc atggaggaaa cacaggaaac tctagatttc   1020
tgtgcagaga agaaggtatc atcgatgatt gaggttgtgg gcctggacta catcaacacg   1080
gccatggaaa ggttggagaa gaacgatgtc cgttacagat ttgtggtgga tgttgctaga   1140
agcaagttgg ataattagtc tgcaatcaat caatcagatc aatgcctgca tgcaagatga   1200
atagatctgg actagtagct taacatgaaa gggaaattaa atttttattt aggaactcga   1260
tactggtttt tgttacttta gtttagcttt tgtgaggttg aaacaattca gatgtttttt   1320
taacttgtat atgtaaagat caatttctcg tgacagtaaa taataatcca atgtcttctg   1380
ccaaattaat atatgtattc gtatttttat atgaaaaaaa aaaaaaaaaa aaaaaaaaaa   1440
aaaaaaaaaa aaaaaaaaaa                                               1460
```

<210> SEQ ID NO 96
<211> LENGTH: 788
<212> TYPE: DNA
<213> ORGANISM: Pinus radiata

<400> SEQUENCE: 96

```
ataagactct cgagaaggtc tatgtccccg aggagggggt tctcaactta atcgcagaga     60
caccatttcc agctaatatt ggcatagcaa ttggtcattc tatctttgtc aaaggagatc    120
aaacaaattt tgaaattgga cctaatggtg tggaggctag tcagctatac ccagatgtga    180
aatataccac tgtcgatgag tacctcagca aatttgtgtg aagtatgcga gattctcttc    240
cacatgcttc agagatacat aacagtttca atcaatgttt gtcctaggca tttgccaaat    300
tgtgggttat aatccttcgt aggtgtttgg cagaacagaa cctcctgttt agtatagtat    360
gacgagctag gcactgcaga tccttcacac ttttctcttc cataagaaac aaatactcac    420
ctgtggtttg ttttctttct ttctggaact ttggtatggc aataatgtct ttggaaaccg    480
cttagtgtgg aatgctaagt actagtgtcc agagttctaa gggagttcca aaatcatggc    540
tgatgtgaac tggttgttcc agagggtgtt tacaaccaac agttgttcag tgaataattt    600
tgttagagtg tttagatcca tctttacaag gctattgagt aaggttggtg ttagtgaacg    660
gaatgatgtc aaatcttgat gggctgactg actctcttgt gatgtcaaat cttgatggat    720
tgtgtctttt tcaatggtaa aaaaaaaaaa aaaaaaaaaa aaaaaaaaaa aaaaaaaaaa    780
aaaaaaaa                                                             788
```

<210> SEQ ID NO 97
<211> LENGTH: 577
<212> TYPE: DNA
<213> ORGANISM: Pinus radiata

<400> SEQUENCE: 97

```
gcccgacggc cacttgttgg acgccatgga agctctccgg aaagccggga ttctggaacc     60
```

```
gtttaaactg cagcccaagg aaggactggc tctcgtcaac ggcacagcgg tgggatccgc    120

cgtggccgcg tccgtctgtt ttgacgccaa cgtgctgggc gtgctggctg agattctgtc    180

tgcgctcttc tgcgaggtga tgcaagggaa accggagttc gtagatccgt taacccacca    240

gttgaagcac cacccagggc agatcgaagc cgcggccgtc atggagttcc tcctcgacgg    300

tagcgactac gtgaaagaag cagcgcggct tcacgagaaa gacccgttga gcaaaccgaa    360

acaagaccgc tacgctctgc gaacatcgcc acagtggttg gggcctccga tcgaagtcat    420

ccgcgctgct actcactcca tcgagcggga gatcaattcc gtcaacgaca atccgttaat    480

cgatgtctcc agggacatgg ctctccacgg cggcaacttc cagggaacac ccatcggagt    540

ttccatggac aacatgcgaa tctctttggc agccgtc                             577
```

<210> SEQ ID NO 98
<211> LENGTH: 492
<212> TYPE: DNA
<213> ORGANISM: Pinus radiata

<400> SEQUENCE: 98

```
tacctggcca accccgtcac gactcacgtc cagagcgccg aacaacacaa ccaggatgtc     60

aattccctcg gcttgatctc cgccagaaag actgccgagg ccgttgagat tttaaagctg    120

atgttcgcta catatctggt ggccttatgc caggcgatcg atctccggca cctggaagaa    180

aacatgcgat ccgttgtgaa gcacgtagtc ttgcaggccg caagaaagac actgtgcact    240

gcagaagacg gaagcctcca cgacaccgga ttttgcgaga aggagctcct gcaagtcatc    300

gatcatcagc ccgttttctc gtacatcgac gatcccacaa atccatcata cgcgcttatg    360

ctccaactca gagaagtgct cgtagatgag gctctcaaat catcttgccc agacgggaat    420

gacgaatccg atcacaattt gcagcccgct gagagcgctg gagctgctgg aatattaccc    480

aattgggtgt tt                                                        492
```

<210> SEQ ID NO 99
<211> LENGTH: 391
<212> TYPE: DNA
<213> ORGANISM: Pinus radiata

<400> SEQUENCE: 99

```
cgttttccca aaggccattt tcgggcaggg ctacggcgca tgacagaagc aggcccggtg     60

ctggcaatga acctagcctt cgcaaagaat cctttccccg ccaaatctgg ctcctgcgga    120

acagtcgtcc ggaacgctca aataaagatc ctcgattaca ggaactggcg agtctctccc    180

gcacaatcaa gccggcgaaa tctgcatccg cggacccgaa ataatgaaag gatatattaa    240

cgacccggaa tccacggccg ctacaatcga tgaagaaggc tggctccaca caggcgacgt    300

cgggtacatt gacgatgacg aagaaatctt catagtcgac agagtaaagg agattatcaa    360

tataaaggct tccaggtgga tcctgctaat c                                   391
```

<210> SEQ ID NO 100
<211> LENGTH: 567
<212> TYPE: DNA
<213> ORGANISM: Eucalyptus grandis

<400> SEQUENCE: 100

```
ctgaatttc cctaactaga aataaagaga ttatatacat acacgagcaa agcgctctcc     60

tccagttgtc ttccttcgtt cgctcatctc tcctcgtaca ttattagcat acgacctctt    120

gtatcggacc cggatccgct atcgttaacg tacacacgtt ctagtgctga atggagatgg    180
```

agagcaccac cggcaccggc aacggccttc acagcctctg cgccgccggg agccaccatg 240
ccgacccact gaactggggg gcggcggcag cagccctcac agggagccac ctcgacgagg 300
tgaagcggat ggtcgaggag taccggaggc cggcggtgcg cctcggcggg gagtccctca 360
cgatagccca ggtggcggcg gtggcgagtc aggagggggt aggggtcgag ctctcggagg 420
cggcccgtcc cagggtcaag gccagcagcg actgggtcat ggagagcatg aacaagggaa 480
ctgacagcta cggggtcaca ccgggttcgg cggcaacttc tcaaccggag gccgaagcaa 540
ggcggtcctt ttcagaagga acttata 567

<210> SEQ ID NO 101
<211> LENGTH: 612
<212> TYPE: DNA
<213> ORGANISM: Eucalyptus grandis

<400> SEQUENCE: 101
aaagcaacac attgaactct ctctctctct ctctctctct ctctctctct cccccacccc 60
cccttcccaa ccccacccac atacagacaa gtagatacgc gcacacagaa gaagaaaaga 120
tgggggtttc aatgcagtca atcgcactag cgacggttct ggccgtccta acgacatggg 180
cgtggagggc ggtgaactgg gtgtggctga ggccgaagag gctcgagagg cttctgagac 240
agcaaggtct ctccggcaag tcctacacct tcctggtcgg cgacctcaag gagaacttgc 300
ggatgctcaa ggaagccaag tccaagccca tcgccgtctc cgatgacatc aagcctcgtc 360
tcttgccttt cttgcatcaa tccttccaaa cctatggcaa agactcgttc acatggatgg 420
gcccaacacc aagagtgaac attacgaacc cggaacaaat aaaggaggta ttctctaaga 480
tatatgacta tcccaagcca gcctccaatc ccctggtgaa gttgctcgct gatggactcg 540
cgaaccatga gggcgagaaa tgggctcggc accgaaagat tatcaatcca gcattccaca 600
tggagaagtt ga 612

<210> SEQ ID NO 102
<211> LENGTH: 455
<212> TYPE: DNA
<213> ORGANISM: Eucalyptus grandis

<400> SEQUENCE: 102
tgtctctctc tctctctctc tctgtaaacc accatgctct tcctcactca tctcctagca 60
gttctagggg ttgtgttgct cctgctaatt ctatggaggg caagatcttc tccgaacaaa 120
cccaaaggta ctgccttacc cccggagctg ccgggcgcat ggccgatcat aggccacatc 180
cacttgctgg gcggcgagac ccgctggcc aggaccctgg ccgccatggc ggacaagcag 240
ggcccgatgt ttcggatccg tctcggagtc cacccggcga ccatcataag cagccgtgag 300
gcggtccggg agtgcttcac cacccacgac aaggacctcg cttctcgccc caaatccaag 360
gcgggaatcc acttgggcta cggtatgcc ggttttggct tcgtagaata cggggacttt 420
tggcgcgaga tgaggaagat caccatgctc gagct 455

<210> SEQ ID NO 103
<211> LENGTH: 1866
<212> TYPE: DNA
<213> ORGANISM: Eucalyptus grandis

<400> SEQUENCE: 103
cgggctcgtg gctcggctcc ggcgcaagcc gcccttccca ccgggcccga ggggcctccc 60
ggtcatcggg aacatgctca tgatgggcga gctcacccac cgcggcctcg cgagtctggc 120

-continued

```
gaagaagtat ggcgggatct tccacctccg catgggcttc ctgcacatgg ttgccgtgtc    180

gtcccccgac gtggcccgcc aggtcctcca ggtccacgac gggatcttct cgaaccggcc    240

tgccaccatc gcgatcagct acctcacgta tgaccgggcc gacatggcct tcgcgcacta    300

cggcccgttc tggcggcaga tgcggaagct gtgcgtgatg aagctcttca gccggaagcg    360

ggctgagtcg tgggagtcgg tccgcgatga ggtggacacg atggtgcgca ccgtcgcggg    420

cagcgagggg accgccgtga acatcggcga gctcgtgttc gagctcacgc gggacatcat    480

ctaccgcgcg gccttcgcac gagctcgacc gagggccagg acgagttcat cagcatactg    540

caggagttct cgaaattatt tggcgccttc aacatagccg attttatccc gtacctgagc    600

tggatcgatc cgcaagggct caccgccagg cttgtcaagg cgcgccagtc gctggacggg    660

ttcatcgacc acattataga tgatcacatg gacaagaaga gaaacaagac gagttccggt    720

ggaggcgatc aagatgtcga taccgacatg gtcgacgatc tgctggcctt ctacagcgac    780

gaagcgaagg tgaacgagtc cgacgatttg cagaactcga tcaggctaac gagagacaac    840

atcaaggcca tcatcatgga cgtgatgttc ggcgggacgg agactgtggc gtcggctatc    900

gagtgggcca tggcggagct catgcgaagc cccgaggacc tgaagaaggt ccagcaagaa    960

ctcgcggatg tcgtgggcct agaccggaga gtcgaggaga gcgacttcga gaagctgacc   1020

tatctcaagt gctgcctcaa agagaccctc cgcctccacc cgccgatccc gctgctcctc   1080

cacgagacgg cagaggacgc cgtgatctcc ggctaccgca tccccgcacg gtcccgggtc   1140

atgatcaatg catgggccat cgggcgtgac cccggctcgt ggaccgaacc tgacaagttc   1200

aaaccgtccc ggttcctgga gtcaggcatg cccgactaca aggggagcaa cttcgagttc   1260

atccctttcg ggtcgggccg gaggtcgtgc ccagggatgc agctcgggct ctacgcgctc   1320

gacatggccg tggcccacct cctgcactgc ttcacgtggg aactgcccga cgggatgaag   1380

ccgagcgaga tggacatggg cgacgtcttc gggctcaccg cgccgaggtc cacccggctc   1440

gtggcggtgc cgactccgag gttggtgggg gctctatatt gagcaagcaa atggagggtc   1500

gggttggggg gtgcgaggag gggaacgtat ttttcagctc ctggagggct gcaagatttg   1560

gagtgcataa acccatccat acaagggcaa aagagggtgg tgccaaaatg atttgcatgg   1620

atttttcgat ttttgttttg tattataaaa aaggtcaaat aaccgaagag gacaagaaag   1680

acaagaaaaa gaattgagac ggaacttgaa tcaatgttgt tctgttctct ctttctattt   1740

ctttgtggat attacaagac ttatctcatt tggtgggctt ttcttttctt gtgatttctt   1800

tgatcttgtc atacacaaat aaatatggaa tgaagaaacc tttccatcaa aaaaaaaaaa   1860

aaaaaa                                                              1866
```

<210> SEQ ID NO 104
<211> LENGTH: 519
<212> TYPE: DNA
<213> ORGANISM: Eucalyptus grandis

<400> SEQUENCE: 104

```
cacgagctcg tgagccttcc cggagacaag gccatcttac ttcgcaacaa attgcgtccg     60

cactcctttc tcaagaaacc tagtcatcca agaagcagag cattgcaact gcaaacagcc    120

aaagcccaaa ctcgtacaga aggagagaga gagagagaat agaagcatga gtgcatgcac    180

gaaccaagca atcacgacgg ccagtgaaga tgaagagttc ttgttcgcca tggaaatgaa    240

tgctctgata gcactcccct tggtcttgaa ggccaccatc gaactgggga tcctcgaaat    300

actggccgag tgcgggccta tggctccact ttcgcctgct cagattgcct cccgtctctc    360
```

cgcaaagaac ccggaagccc ccgtaaccct tgaccggatc ctccggtttc tcgccagcta 420
ctccatcctc tcttgcactc tcgcccaaga cacagaaggc aaccccctga ggctttacgg 480
tttgggaccc aaaagcaaac acttcgtcag agcccatgg 519

<210> SEQ ID NO 105
<211> LENGTH: 594
<212> TYPE: DNA
<213> ORGANISM: Eucalyptus grandis

<400> SEQUENCE: 105
ccaaccctgg accaggtact tttggcaggc ggtccattgc ccttcaaacc ggtccaaacc 60
ggaccatcac tgtccttata tacgttgcat catgcctgct catagaactt aggtcaactg 120
caacatttct tgatcacaac atattacaat attcctaagc agagagagag agagagagag 180
agagagagag agagagagag tttgaatcaa tggccaccgc cggagaggag agccagaccc 240
aagccgggag gcaccaggag gttggccaca agtctctcct tcagagtgat gctctttacc 300
aatatatttt ggagaccagc gtgtacccaa gagagcctga gcccatgaag gagctcaggg 360
aaataacagc aaaacatcca tggaacataa tgacaacatc agcagacgaa gggcagttct 420
tgaacatgct tctcaagctc atcaacgcca agaacaccat ggagattggt gtcttcactg 480
gctactctct cctcgccacc gctcttgctc ttcctgatga cggaaagatt ttggctatgg 540
acattaacag agagagctat gaacttggcc tgccggtcat ccaaaaagcc ggtg 594

<210> SEQ ID NO 106
<211> LENGTH: 407
<212> TYPE: DNA
<213> ORGANISM: Eucalyptus grandis

<400> SEQUENCE: 106
ccgttttatt tcctctgatt tcctttgctc gagtctcgcg gaagagagag aagagaggag 60
aggagagaat gggttcgacc ggatccgaga cccagatgac cccgacccaa gtctcggacg 120
aggaggcgaa cctcttcgcc atgcagctgg cgagcgcctc cgtgctcccc atggtcctca 180
aggccgccat cgagctcgac ctcctcgaga tcatggccaa ggccgggccg ggcgcgttcc 240
tctccccggg ggaagtcgcg gcccagctcc cgacccagaa ccccgaggca cccgtaatgc 300
tcgaccggat cttccggctg ctggccagct actccgtgct cacgtgcacc ctccgcgacc 360
tccccgatgg caaggtcgag cggctctacg gcttagcgcc ggtgtgc 407

<210> SEQ ID NO 107
<211> LENGTH: 1630
<212> TYPE: DNA
<213> ORGANISM: Eucalyptus grandis

<400> SEQUENCE: 107
ccgttttatt tcctctgctt tcctttgctc gagtctcgcg gaagagagag aagagaggag 60
aggagagaat gggttcgacc ggatccgaga cccagatgac cccgacccaa gtctcggacg 120
aggaggcgaa cctcttcgcc atgcagctgg cgagcgcctc cgtgctcccc atggtcctca 180
aggccgccat cgagctcgac ctcctcgaga tcatggccaa ggccgggccg ggcgcgttcc 240
tctccccggg ggaagtcgcg gcccagctcc cgacccagaa ccccgaggca cccgtcatgc 300
tcgaccggat cttccggctg ctggccagct actccgtgct cacgtgcacc ctccgcgacc 360
tccccgatgg caaggtcgag cggctctacg gcttagcgcc ggtgtgcaag ttcttggtca 420
agaacgagga cggggtctcc atcgccgcac tcaacttgat gaaccaggac aaaatcctca 480

-continued

```
tggaaagctg gtattacctg aaagatgcgg tccttgaagg cggaatccca ttcaacaagg    540
cgtacgggat gaccgcgttc gagtatcatg gcaccgaccc gcgattcaac aagatcttta    600
accggggaat gtctgatcac tccaccatta ctatgaagaa gatactggaa acatacaagg    660
gcttcgaggg cctcgagacc gtggtcgatg tcggaggcgg cactggggcc gtgctcagca    720
tgatcgttgc caaataccca tcgatgaaag ggatcaactt cgacctgcct cacgtgattg    780
aagacgctcc acccccttcct ggtgtcaagc acgtcggagg cgacatgttc gtcagcgttc    840
caaagggaga tgccattttc atgaagtgga tatgccatga ctggagtgac gaccattgcg    900
cgaagttcct caagaactgc tacgatgcgc ttcccaacaa tggaaaggtg atcgttgcag    960
agtgcgtact ccctgtgtac ccagacacga gcctagcgac caagaatgtg atccacatcg   1020
actgcatcat gttggcccac aacccaggcg ggaaagagag gacacagaag gagttcgagg   1080
cattggccaa aggggccgga tttcagggct tccaagtcat gtgctgcgct ttcggcactc   1140
acgtcatgga gttcctgaag accgcttgat ctgctcctct gtggtgatgt tcatggttct   1200
tggatttgaa aggtcgtgaa ggagcccttt tctcacagtt ggcttcggca taccaagttc   1260
ttctcataaa aggaaacaat aagaagcgac tgtatgatgg cgcaagtgga agttacaaga   1320
tttgttgttt tatgtctata aagttttgag tcttctgcat actgatttca cagaatgtgt   1380
aacgaaacgg cgtatatgga tgtgcctgaa tgatggaaat tgtgatattc tgtcttcttt   1440
ttcagtaaat cacttcgaac aaaagttgtg ttgctcgtgg caaccaggaa aaaatctgtg   1500
ggtgactttg agttaaagcc tgtcattcac aaaccccatg gcattgcctt tggtcagggg   1560
tcagccaagc cggaagcgtc aacgtgaaaa gatcctcaag ggtccattaa aatccccaca   1620
aacccagagc                                                          1630
```

<210> SEQ ID NO 108
<211> LENGTH: 1248
<212> TYPE: DNA
<213> ORGANISM: Eucalyptus grandis

<400> SEQUENCE: 108

```
atcactaacc atctgccttt cttcatcttc tttcttctgc ttctcctccg tttcctcgtt     60
tcgatatcgt gaaaggagtc cgtcgacgac aatggccgag aagagcaagg tcctgatcat    120
cggagggacg ggctacatcg gcaagttcat cgtggaagcg agtgcaaaag cagggcatcc    180
cacgttcgcg ctggttaggc agagcacggt ctccgacccc gtcaagggcc agctcgtcga    240
gagcttcaag aacttgggcg tcactctgct catcggtgat ctgtacgatc atgagagctt    300
ggtgaaggca atcaagcaag ccgacgtggt gatatcgaca gtggggcaca tgcaaatggc    360
ggatcagacc aagatcgtcg acgccattaa ggaagctggc aacgttaaga gattctttcc    420
ttccgaattc ggcaatgatg tggacagggt gcatgctgtg gagccagcga agtctgcttt    480
tgaattgaag gcccagatcc gccgtgccgt ggaggcggca ggcatccctt acacctacgt    540
cccatgtggc tgcttcgccg gctacttcct cccaacactg gcgcagcagg aggtcactgc    600
tcctccgaag gacaaagtca ccgtcatggg tgacggaaat gcaaaggcaa ttttcaacaa    660
ggaagatgac attgcggcct tcaccatcaa ggctgtggat gatccgagat cgctgaacaa    720
gatcctttac atcaggcctc ctaagaacgt ttactcattc aatgagcttg ttgccttgtg    780
ggagaagaaa attggcaaga ccctcgagaa gatttacctt cctgaagagc aaatcctgaa    840
gcaaatccag gagtccccaa ttcccatcaa tgtcatatta gcagtgaacc attcaatctt    900
tgttaagggc gacggtgcca attttgagat cgaggagtct tttggtgtcg aggcttctga    960
```

gctgtaccca gatgtgaagt acactacagt ggaagaatac ctcgaaaatt ttgtctaaat 1020
taaggccatg cgtctcctgt tcttcaagga gtgagttacc gtgactctgg tggacagtcg 1080
atatgtatta aaaggctgta cacctaaaga atatcaaagg tcacggtctt atttagaatt 1140
gtctctgatg tcatattctt cttggtcttc ttggacatgt atttgctttc ctttgccgtg 1200
gtatccatga atttcccagg ttgttgaaat taaaaaaaaa aaaaaaaa 1248

<210> SEQ ID NO 109
<211> LENGTH: 481
<212> TYPE: DNA
<213> ORGANISM: Eucalyptus grandis

<400> SEQUENCE: 109
gttaatggca gtgcagcctc aacaccaccc accttcctcc atctctctcc tcccttcttc 60
tttctctgac ttcaatggca gccgactcca tgcttgcgtt cagtataaga ggaaggtggg 120
gcagcctaaa ggggcactgc gggtcactgc atcaagcaat aagaagatcc tcatcatggg 180
aggcacccgt ttcatcggtg tgtttttgtc gagactactt gtcaaagaag gtcatcaggt 240
cactttgttt accagaggaa aagcacccat cactcaacaa ttgcctggtg agtcggacaa 300
ggacttcgct gatttttcat ccaagatcct gcatttgaaa ggagacagaa aggattttga 360
ttttgttaaa tctagtcttg ctgcagaagg ctttgacgtt gtttatgaca ttaacggcga 420
gaggcggatg aagtcgcacc aattttggat gcctgccaaa ccttgaacca gtcaactact 480
g 481

<210> SEQ ID NO 110
<211> LENGTH: 458
<212> TYPE: DNA
<213> ORGANISM: Eucalyptus grandis

<400> SEQUENCE: 110
cataagctct cccgtaatcc tcacatcaca tggcgaagag caaggtcctc gtcgttggcg 60
gcactggcta cctcgggcgg aggttcgtga gggcgagcct ggaccagggc caccccacgt 120
acgtcctcca gcgtccggag accggcctcg acattgagaa gctccagacg ctactgcgct 180
tcaagaggcg tggcgcccaa ctcgtcgagg cctcgttctc agacctgagg agcctcgtcg 240
acgctgtgag gcgggtcgat gtcgtcgtct gtgccatgtc gggggtccac ttccggagcc 300
acaacatcct gatgcagctc aagctcgtgg aggctatcaa agaagctgga aatgtcaagc 360
ggtttttgcc gtcagagttc ggaatggacc cggccctcat gggtcatgca attgagccgg 420
gaagggtcac gttcgatgag aaatggaggt gagaaaag 458

<210> SEQ ID NO 111
<211> LENGTH: 448
<212> TYPE: DNA
<213> ORGANISM: Eucalyptus grandis

<400> SEQUENCE: 111
aggaggcacc tcctcgaaac gaagaagaag aaggacgaag gacgaaggag acgaaggcga 60
gaatgagcgc ggcgggcggt gccgggaagg tcgtgtgcgt gaccggggcg tccggttaca 120
tcgcctcgtg gctcgtcaag ctcctcctcc agcgcggcta caccgtcaag gccaccgtcc 180
gcgatccgaa tgatccaaaa aagactgaac atttgcttgg acttgatgga gcgaaagata 240
gacttcaact gttcaaagca aacctgctgg aagagggttc atttgatcct attgttgagg 300
gttgtgcagg cgtttttcac actgcctctc ccttttatca tgatgtcaag gatccgcagg 360

```
cagaattact tgatccggct gtgaagggaa cactcaatgt cctgaagtca tgttccaaag    420

accttctctg cagcgtgtgg cttgacat                                       448


<210> SEQ ID NO 112
<211> LENGTH: 578
<212> TYPE: DNA
<213> ORGANISM: Eucalyptus grandis

<400> SEQUENCE: 112

gttgaacctc ccgtcctcgg ctctgctcgg ctcgtcaccc tcttcgcgct cccgcatact     60

ccaccaccgc gtacagaaga tgagctcgga gggtgggaag gaggattgcc tcggttgggc    120

tgcccgggac ccttctgggt tcctctcccc ctacaaattc acccgcaggg ccgtgggaag    180

cgaagacgtc tcgattaaga tcacgcactg tggagtgtgc tacgcagatg tggcttggac    240

taggaatgtg cagggacact ccaagtatcc tctggtgcca gggcacgaga tagttggaat    300

tgtgaaacag gttggctcca gtgtccaacg cttcaaagtt ggcgatcatg tgggggtggg    360

aacttatgtc aattcatgca gagagtgcga gtattgcaat gacaggctag aagtccaatg    420

tgaaaagtcg gttatgactt ttgatggaat tgatgcagat ggtacagtga caaagggagg    480

atattctagt cacattgtcg tccatgaaag gtattgcgtc aggattccag aaaactaccc    540

gatggatcta gcagcgcatt tgctctgtgc tggatcac                            578


<210> SEQ ID NO 113
<211> LENGTH: 454
<212> TYPE: DNA
<213> ORGANISM: Eucalyptus grandis

<400> SEQUENCE: 113

aactcatctt gaaatgtcat tggagtcatc atcctctagt gagaagaaac aaatgggttc     60

cgccggattc gaatcggcca caaagccgca cgccgtttgc attccctacc ctgcacaaag    120

ccacattggc gccatgctca agctagcaaa gctcctccat cacaagggct tccacatctc    180

cttcgtcaac accgagttca accaccggcg gctcgccagg gctcgaggcc ccgagttcac    240

aaatggaatg ctgagcgact ttcagttcct gacaatcccc gatggtcttc ctccttcgga    300

cttggatgcg atccaagaca tcaagatgct ctgcgaatcg tccaggaact atatggtcag    360

ccccatcaac gatcttgtat cgagcctggg ctcgaacccg agcgtccctc cggtgacttg    420

catcaatctc ggatggtttc atgacactcg tgac                                454


<210> SEQ ID NO 114
<211> LENGTH: 479
<212> TYPE: DNA
<213> ORGANISM: Eucalyptus grandis

<400> SEQUENCE: 114

catgattgag ggaatcaagg actcttcagg actcatcctg aacacatttg aagatctcga     60

gcagcccgct ctttctttac tccgccaaga agatccaatc gcagttttcg caattggccc    120

attacacaaa tgcggtccat cttcatcggg aagtctcttg gcagaagacc ggagttgcat    180

ttcctggctg gacaagcaag cccctaactc agtggtctat gtgagttttg ggagcatcgc    240

ctctgtgaac gagtcggaat tttccgaaat agctttaggt ttagccgata gccagcagcc    300

attcttgtgg gtggttcgac ccgggtcagt gagcggctcg gaactcttag agaatttgcc    360

cggttgcttt ctggaggcat tacaggagag ggggaagatt gtgaaatggg cgcctcaaca    420

tgaagtgctg gctcatcggg gtgtcggagc gttttggact cacaatggat ggaactcca     479
```

<210> SEQ ID NO 115
<211> LENGTH: 420
<212> TYPE: DNA
<213> ORGANISM: Eucalyptus grandis

<400> SEQUENCE: 115
caacattgtg tttagagaga ggagagagaa ggcaaacacg cccgttttcg ttttactaag 60
agaagatggt gagcgttgtg gctggtagag tcgagagctt gtcgagcagt ggcattcagt 120
cgatcccgca ggagtatgtg aggccgaagg aggagctcac aagcattggc gacatcttcg 180
aggaggagaa gaagcatgag ggccctcagg tcccgaccat cgacctcgag gacatagcgt 240
ctaaagaccc cgtggtgagg gagaggtgcc acgaggagct caggaaggct gccaccgact 300
ggggcgtcat gcacctcgtc aaccatggga tccccaacga cctgattgag cgtgtcaaga 360
aggctggcga ggtgttcttc aacctcccga tcgaggagaa ggagaagcat gccaacgacc 420

<210> SEQ ID NO 116
<211> LENGTH: 679
<212> TYPE: DNA
<213> ORGANISM: Eucalyptus grandis

<400> SEQUENCE: 116
ctaagagagg agaggagagg agcaagatgg cactagcagg agctgcactg tcaggaaccg 60
tggtgagctc cccctttgtg aggatgcagc ctgtgaacag actcagggca ttccccaatg 120
tgggtcaggc cctgtttggt gtcaactctg gccgtggcag agtgactgcc atggccgctt 180
acaaggtcac cctgctcacc cctgaaggca aagtcgaact cgacgtcccc gacgatgttt 240
acatcttgga ctacgccgag gagcaaggca tcgacttgcc ctactcctgc cgtgccggct 300
cttgctcctc ctgcgcgggc aaggtcgtgg cggggagcgt cgaccagagc gacggcagct 360
tcctggatga tgatcagatt gaggaaggtt gggtcctcac ttgtgtcgcc taccctaagt 420
ctgaggtcac cattgagacc cacaaggaag aggagctcac tgcttgaagc tctcctatat 480
ttgcttttgc ataaatcagt ctcactctac gcaactttct ccactctctc cccccttcac 540
tacatgtttg ttagttcctt tagtctcttc ctttttact gtacgaggga tgatttgatg 600
ttattctgag tctaatgtaa tggcttttct ttttcctatt tctgtatgag gaaataaaac 660
tcatgctcta aaaaaaaaa 679

<210> SEQ ID NO 117
<211> LENGTH: 763
<212> TYPE: DNA
<213> ORGANISM: Eucalyptus grandis

<400> SEQUENCE: 117
catacaacta cactgcgacg ccgccgcaga acgcgagcgt gccgaccatg aacggcacca 60
aggtctaccg gttgccgtat aacgctacgg tccagctcgt tttacaggac accgggataa 120
tcgcgccgga gacccacccc atccatctgc acggattcaa cttcttcggt gtgggcaaag 180
gagtggggaa ttatgaccca aagaaggatc ccaagaagtt caatctggtt gacccagtgg 240
agaggaacac cattggaatc ccatctggtg gatggatagc catcagattc acagcagaca 300
atccaggagt ttggttcctg cactgccatc tggaagtgca cacaacttgg ggactgaaga 360
tggcattctt ggtggacaat gggaaggggc ctaaagagac cctgcttcca cctccaagtg 420
atcttccaaa atgttgatca tttgatcatg aggacgacaa gcgattacta atgacaccaa 480
gttagtggaa tcttctcttt gaaaaagaag aagaagagca agaagaataa gaaagatgag 540
gagagaagcc atagaagatt tgaccaagaa gagagagggc aataaaccaa agagaccctt 600
gagatcacga catcccgcaa ttgtttctag agtaatagaa ggatttactc cgacactgct 660
acaataaatt aaggaagaca aggaatttgg tttttttcat tggaggagtg taatttgttt 720
tttggcaagc tcatcacatg aatcacatgg aaaaaaaaaa aaa 763

<210> SEQ ID NO 118
<211> LENGTH: 538
<212> TYPE: DNA
<213> ORGANISM: Eucalyptus grandis

<400> SEQUENCE: 118
atcaagagtt tgagtctaaa ccttgtctaa tcctctctcg catagtcatt tggagacgaa 60
gtgctgatcg gccgcagctg cattctcttc gtaaaacatg acggctgtcg gcaaaacctc 120
tttcctcttg ggagctctcc tcctcttctc tgtggcggtg acattggcag atgcaaaagt 180
ttactaccat gattttgtcg ttcaagcgac caaggtgaag aggctgtgca cgacccacaa 240
caccatcacg gtgaacgggc aattcccggg tccgactttg gaagttaacg acggcgacac 300
cctcgttgtc aatgtcgtca acaaagctcg ctacaacgtc accattcact ggcacggcgt 360
ccggcaggtg agatctggtt gggccgatgg gccggaattt gtgactcaat gcccgattag 420
acccggcgga agttacacgt accgtttcac catccaagga caggtaggaa cgctgtggtg 480
gcatgcacat agctcttggc taagagcgac tgtgtatggt gctctggcat tcgtccaa 538

<210> SEQ ID NO 119
<211> LENGTH: 515
<212> TYPE: DNA
<213> ORGANISM: Eucalyptus grandis

<400> SEQUENCE: 119
ctctctctct ctctctctct gtgtgttcat tctcgttgag ctcgtggtcg cctcccgcca 60
tggatccgca caagtaccgt ccatccagtg ctttcaacac ttctttctgg actacgaact 120
ctggtgctcc tgtctggaac aataactctt cgttgactgt tggaagcaga ggtccaattc 180
ttcttgagga ttatcacctc gtggagaaac ttgccaactt tgatagggag aggattccag 240
agcgtgtggt gcatgccaga ggagccagtg caaagggatt ctttgaggtc actcatgaca 300
tttcccagct tacctgtgct gatttccttc gggcaccagg agttcaaaca cccgtgattg 360
tccgtttctc cactgtcatc cacgaaaggg gcagccctga aaccctgagg gaccctcgag 420
gttttgctgt gaagttctac acaagagagg gtaactttga tctggtggga aacaatttcc 480
ctgtcttctt tgtccgtaat gggataaatt ccccg 515

<210> SEQ ID NO 120
<211> LENGTH: 458
<212> TYPE: DNA
<213> ORGANISM: Eucalyptus grandis

<400> SEQUENCE: 120
gctccctctc gtactgccat actcctgggc cgggattcgg atagggtttt gcggcgatcc 60
atttctcgat tcaaggggaa gaatcatggg gaagtcctac ccgaccgtga gcgaggagta 120
caagaaggct gtcgagaaat gcaagaagaa gttgagaggc ctcatcgctg agaagagctg 180
cgctccgctc atgctccgca tcgcgtggca ctccgccggt accttcgatg tgaagacgaa 240
gaccggaggc ccgttcggga ccatgaagca cgccgcggag ctcagccacg ggccaacag 300 cgggctcgac gttgccgatc aggtcttgca gccgatcaag gatcagttcc ccgtcatcac 360
ttatgctgat ttctaccagc tggctggcgt cgttgctgtg gaagttactg gtggacctga 420
agttgctttt cacccaggaa gagaggcaaa ccacaacc 458

<210> SEQ ID NO 121
<211> LENGTH: 1243
<212> TYPE: DNA
<213> ORGANISM: Eucalyptus grandis

<400> SEQUENCE: 121
ctcccacttc tgtctcgcca ccattactag cttcaaagcc cagatctcag tttcgtgctc 60
tcttcgtcat ctctgcctct tgccatggat ccgtacaagt atcgcccgtc cagcgcttac 120
gattccagct tttggacaac caactacggt gctcccgtct ggaacaatga ctcatcgctg 180
actgttggaa ctagaggtcc gattctcctg gaggactacc atctgattga gaaacttgcc 240
aacttcgaga gagagaggat tcctgagcgg gtggtccatg cacggggagc cagcgcgaaa 300
gggttcttcg aggtcaccca cgacatctct cacttgacct gtgctgattt cctccgggct 360
cctggagtcc agacgcccgt catcgtccgt ttctccaccg tcatccacga gcgcggcagc 420
cccgaaaccc tcagggaccc tcgtggtttt gcagtgaagt tctacaccag agagggaaac 480
tttgatctgg tggggaacaa tttcccagtc ttcttcgttc gcgatgcaat gaaattcccg 540
gacgcgatcc atgcgttcaa gccgaacccg aagtctaaca tccaggagat gtggagaatc 600
atcgatttct tctcccacca gcccgagagt ctgtccacgt tcgcgtggtt cttcgatgat 660
gtgggcattc ctcaggacta caggcacatg gagggattcg gtgtgcacgc tttcaccttc 720
atcaacaaga ccggaaagac gaattacgtt aaattccact ggaagccaac ttgcggggtg 780
aagtgcttgc tggaggagga ggcgatcctc attggaggat cgaaccacag ccatgcgacc 840
aaggatcttt atgactcgat cgctgctggc aactacccgg agtggaagct ctacatccaa 900
gtgatggatc cwgctcttga agacagcttc gacttcgatc cgctggatat gacgaaggaa 960
tggcctgagg acatcttgcc tctgcaacca gtaggccgct tggtgctgaa caaaaacgtc 1020
gataacttct tcgctgagaa tgagcagcta gcgtttaacc cagcatttgt ggtccctggc 1080
atctattact ccaatgataa gcttctccaa gctaggattt tcgcctattc tgatactcac 1140
cgatatcgcc ttggaccaaa ctaccttcaa ctccccgtta atgtcccaag tgcgtcatca 1200
caacaaccac catgatggtt tcatgaatat catgcacagg gat 1243

<210> SEQ ID NO 122
<211> LENGTH: 404
<212> TYPE: DNA
<213> ORGANISM: Pinus radiata

<400> SEQUENCE: 122
gacaaggtca taggccctct cttcaaatgc ttggatgggt ggaaaggaac tcctggccca 60
ttctgaaata aataatcttc caagatcgcc tttatacaac gactgctatg atttgagtcc 120
tcggatcttt ttgttgatgc agttgtttac cgatctggaa tttgattggt cataaagctt 180
gattttgttt ttctttcttt tgttttatac tgctggattt gcatcccatt ggatttgcca 240
gaaatatgta agggtggcag atcatttggg tgatctgaaa catgtaaaag tggcggatca 300
tttgggtagc atgcagatca gttgggtgat cgtgtactgc tttcactatt acttacatat 360
ttaaagatcg ggaataaaaa catgatttta attgaaaaaa aaaa 404

<210> SEQ ID NO 123
<211> LENGTH: 415
<212> TYPE: DNA

<213> ORGANISM: Pinus radiata

<400> SEQUENCE: 123
caaggaagaa aatatggttg cagcagcaga aattacgcag gccaatgaag ttcaagttaa 60
aagcactggg ctgtgcacgg acttcggctc gtctggcagc gatccactga actgggttcg 120
agcagccaag gccatggaag gaagtcactt tgaagaagtg aaagcgatgg tggattcgta 180
tttgggagcc aaggagattt ccattgaagg gaaatctctg acaatctcag acgttgctgc 240
cgttgctcga agatcgcaag tgaaagtgaa attggatgct gcggctgcca aatctagggt 300
cgaggagagt tcaaactggg ttctcaccca gatgaccaag ggacggata cctatggtgt 360 cactactggt ttcggagcca cttctcacag gagaacgaac cagggagccg agctt 415

<210> SEQ ID NO 124
<211> LENGTH: 1659
<212> TYPE: DNA
<213> ORGANISM: Pinus radiata

<400> SEQUENCE: 124
gttgcaggtc ggggatgatt tgaatcacag aaacctcagc gattttgcca agaaatatgg 60
caaaatcttt ctgctcaaga tggccagag gaatcttgtg gtagtttcat ctcccgatct 120
cgccaaggag gtcctgcaca cccagggcgt cgagtttggg tctcgaaccc ggaacgtggt 180
gttcgatatc ttcacgggca aggggcagga catggtgttc accgtctatg gagatcactg 240
gagaaagatg cgcaggatca tgactgtgcc tttctttacg aataaagttg tccagcacta 300
cagattcgcg tgggaagacg agatcagccg cgtggtcgcg gatgtgaaat cccgcgccga 360
gtcttccacc tcgggcattg tcatccgtag gcgcctccag ctcatgatgt ataatattat 420
gtataggatg atgttcgaca ggagattcga atccgaggac gacccgcttt tcctcaagct 480
caaggccctc aacggagagc gaagtcgatt ggcccagagc tttgagtaca attatgggga 540
tttcattccc attcttaggc ccttcctcag aggttatctc agaatctgca atgagattaa 600
agagaaacgg ctctctcttt tcaaggacta cttcgtggaa gagcgcaaga agctcaacag 660
taccaagact agtaccaaca ccggggagct caagtgtgca atggaccata ttttagatgc 720
tcaggacaag ggagagatca atgaggataa tgttttgtac atcgttgaga acatcaacgt 780
tgcagcaatt gagacaacgc tgtggtcgat ggaatgggga atagcggagc tggtgaacca 840
ccaggacatt cagagcaagg tgcgcgcaga gctggacgct gttcttggac caggcgtgca 900
gataacggaa ccagacacga caaggttgcc ctaccttcag gcggttgtga aggaaaccct 960
tcgtctccgc atggcgatcc cgttgctcgt cccccacatg aatctccacg acgccaagct 1020
cgggggctac gatattccgg cagagagcaa gatcctggtg aacgcctggt ggttggccaa 1080
caaccccgcc aactggaaga accccgagga gttccgcccc gagcggttct tcgaggagga 1140
gaagcacacc gaagccaatg gcaacgactt caaattcctg ccttgcggtg tggggaggag 1200
gagctgcccg ggaatcattc tggcgctgcc tctcctcgca ctctccatcg gaagacttgt 1260
tcagaacttc caccttctgc cgccgcccgg gcagagcaaa gtggatgtca ctgagaaggg 1320
cgggcagttc agccttcaca ttctcaacca ttctctcatc gtcgccaagc ccatagcttc 1380
tgcttaatcc caacttgtca gtgactggta tataaatgcg cgcacctgaa caaaaaacac 1440
tccatctatc atgactgtgt gtgcgtgtcc actgtcgagt ctactaagag ctcatagcac 1500
ttcaaaagtt tgctaggatt tcaataacag acaccgtcaa ttatgtcatg tttcaataaa 1560
agtttgcata aattaaatga tatttcaata tactattttg actctccacc aattggggaa 1620

-continued ttttactgct aaaaaaaaaa aaaaaaaaaa aaaaaaaaa 1659

<210> SEQ ID NO 125
<211> LENGTH: 461
<212> TYPE: DNA
<213> ORGANISM: Pinus radiata

<400> SEQUENCE: 125
atttccatgg cgattccgtt tggcttcaat tcgtttcctc tggctgtcct cgtcctcgtt 60
ttccttgttc ttcctccgac tttttctctg gaagatatgg cgtaatagga acctgccgcc 120
aggacccccg gcatggccga tcgtagggaa cgtccttcag attggatttt ccagcggcgc 180
gttcgagacc tcagtgaaga aattccatga gagatacggt ccaatattca ctgtgtggct 240
cggttcccgc cctctgctga tgatcaccga ccgcgagctt gcccacgagg cgctcgtaca 300
gaagggctcc gtcttcgctt gaccgcccgc ccgccctcgg gatgcagaaa atcttcagta 360
gcaaccagca caacatcact tcggctgaat acggcccgct gtggcggagc ttcgcaggaa 420
tctggttaaa gaagccctga gacttcggcg atgaaggctt t 461

<210> SEQ ID NO 126
<211> LENGTH: 569
<212> TYPE: DNA
<213> ORGANISM: Pinus radiata

<400> SEQUENCE: 126
acccagtgac cttcaggcct gagagatttc ttgaggaaga tgttgatatt aagggccatg 60
attacaggct actgccattc ggtgcagggc gcaggatctg ccctggtgca caattgggta 120
ttaatttagt tcagtctatg ttgggacacc tgcttcatca tttcgtatgg gcacctcctg 180
agggaatgaa ggcagaagac atagatctca cagagaatcc agggcttgtt actttcatgg 240
ccaagcctgt gcaggccatt gctattcctc gattgcctga tcatctctac aagcgacagc 300
cactcaattg atcaattgat ctgatagtaa gtttgaattt tgttttgata caaaacgaaa 360
taacgtgcag tttctccttt tccatagtca acatgcagct ttctttctct gaagcgcatg 420
cagctttctt tctctgaagc ccaacttcta gcaagcaata actgtatatt ttagaacaaa 480
tacctattcc tcaaattgag tatttctctg taggcgatgt tcacttgtgc aatttgcaag 540
atatagtaaa gtttactcta aaaaaaaaa 569

<210> SEQ ID NO 127
<211> LENGTH: 661
<212> TYPE: DNA
<213> ORGANISM: Pinus radiata

<400> SEQUENCE: 127
gttttatctg aaggacgctg tgcttgaagg ctcccagcca ttcaccaaag cccatggaat 60
gaatgcgttc gagtacccgg ccatcgatca gagattcaac aagattttca acagggctat 120
gtctgagaat tctaccatgt tgatgaacaa gattttggat acttacgagg gttttaagga 180
ggttcaggag ttggtggatg tgggaggagg tattgggtcg actctcaatc tcatagtgtc 240
taggtatccc cacatttcag gaatcaactt cgacttgtcc catgtgctgg ccgatgctcc 300
tcactaccca gctgtgaaac atgtgggtgg agacatgttt gatagtgtac caagtggcca 360
agctattttt atgaagtgga ttctgcatga ttggagcgat gatcattgca ggaagctttt 420
gaagaattgt cacaaggcgt tgccagagaa ggggaaggtg attgcggtgg acaccattct 480
cccagtggct gcagagacat ctccttatgc tcgtcaggga tttcatacag atttactgat 540
gttggcatac aacccagggg gcaaggaacg cacagagcaa gaatttcaag atttagctaa 600
ggagacggga tttgcaggtg gtgttgaacc tgtatgttgt gtcaatggaa tgtgggtaat 660
g 661

<210> SEQ ID NO 128
<211> LENGTH: 427
<212> TYPE: DNA
<213> ORGANISM: Pinus radiata

<400> SEQUENCE: 128
aatttttctg tggtaagcat atctatggct caaaccagag agaaggacga tgtcagcata 60
acaaactcca aaggattggt atgcgtgaca ggagcggctg gttacttggc atcttggctt 120
atcaagcgtc tcctccagtg tggttaccaa gtgagaggaa ctgtgcggga tcctggcaat 180
gagaaaaaga tggctcattt atggaagtta gatggggcga aagagagact gcaactaatg 240
aaagctgatt taatggacga gggcagcttc gatgaggtca tcagaggctg ccatggtgtt 300
tttcacacag cgtctccagt cgtgggtgtc aaatcagatc ccaagatatg gtatgctctg 360
gccaagactt tagcagaaaa agcagcatgg gattttgccc aagaaaacca tctggacatg 420
gttgcag 427

<210> SEQ ID NO 129
<211> LENGTH: 1412
<212> TYPE: DNA
<213> ORGANISM: Pinus radiata

<400> SEQUENCE: 129
gaaaacatca tccaggcatt ttggaaattt agctcgccgg ttgattcagg atcctgcaat 60
ggcttttggc gaagagcaga ctgccttgcc acaagaaacg cctttgaatc ctccggtcca 120
tcgaggaaca gtgtgcgtta caggagctgc tgggttcata gggtcatggc tcatcatgcg 180
attgcttgag cgaggatata gtgttagagc aactgtgcga gacactggta atcctgtaaa 240
gacaaagcat ctgttggatc tgccgggggc aaatgagaga ttgactctct ggaaagcaga 300
tttggatgat gaaggaagct ttgatgctgc cattgatggg tgtgagggtg ttttccatgt 360
tgccactccc atggatttcg agtccgagga tcccgagaat gagataatta agccaacaat 420
caacggggtc ttgaatgtta tgagatcgtg tgcaaaagcc aagtccgtga agcgagttgt 480
tttcacgtca tctgctggga ctgtgaattt tacagatgat ttccaaacac caggcaaagt 540
ttttgacgaa tcatgctgga ccaacgtgga tctttgcaga aaagttaaaa tgacaggatg 600
gatgtacttt gtatcgaaga cattagcaga gaaagctgct tgggattttg cagaggagaa 660
caagatcgat ctcattactg ttatccccac attggtcgtt ggaccattca ttatgcagac 720
catgccaccg agcatgatca cagccttggc actgttaacg cggaatgaac cccactacat 780
gatactgaga caggtacagc tggttcactt ggatgatctc tgtatgtcac atatctttgt 840
atatgaacat cctgaagcaa agggcagata catctcttcc acatgtgatg ctaccattgt 900
ccaagtggcc aagatgctgg ctcagaaata cccagagtac aatgtaccaa ccacgttcaa 960
ggatgcggat gagtccctgc cggccgtgcc attttcgtca aagaagctcc ttgatttggg 1020
cttcaagttc aactacacca tggaagagat gtttgatggg gccattaagt gctgcagaga 1080
gaaaggattg ctgcctgaga aagcatcttt ctgataagta tctactgatg cagcatacac 1140
acaccgttgg catgtgtggt ttgtgtaaga catggtggca gtggagaaat aatggatcaa 1200
atttggttta tagaaaacag caggaattac tacttgcaag agtgacttat gtgacatgat 1260
atagaaataa gaagaatacc ggctgatcgc tgttgtttat taatgcgaat tttattgatg 1320
ttgacaaggt cataccaggg ctcctggaat gctacatatg tacggctgat tctagctcca 1380
gtaatataat ttttcaaatt ctaaaaaaaa aa 1412

<210> SEQ ID NO 130
<211> LENGTH: 666
<212> TYPE: DNA
<213> ORGANISM: Pinus radiata

<400> SEQUENCE: 130
atcaattttt gcatattatt aaaaagtaag tgtattcgtt ctctatattg atcagtcaca 60
gagtcatggc cagttgtggt tccgagaaag taagagggtt gaatggagat gaagcatgcg 120
aagagaacaa gagagtggtt tgtgtaactg gggcaaatgg gtacatcggc tcttggctgg 180
tcatgagatt actggaacat ggctattatg ttcatggaac tgttagggac ccagaagaca 240
cagggaaggt tgggcatttg ctgcggctcc caggggcaag tgagaagcta aagctgttca 300
aggcagagct taacgacgaa atggcctttg atgatgctgt gagcggttgt caaggggttt 360
tccacgttgc caagcctgtt aatctggact caaacgctct tcagggggag gttgttggtc 420
ctgcggtgag gggaacagta aatctgcttc gagcctgcga acgatcgggc actgtgaaac 480
gagtgataca tacctcgtcc gtttcagcag tgagattcac tgggaaacct gacccccctg 540
atactgtgct ggatgaatct cattggactt cggtcgagta ttgcagaaag acaaagatgg 600
tcggatggat gtactacatc gccaacactt atgcagaaga gggagcccat aagttcggat 660
cagaga 666

<210> SEQ ID NO 131
<211> LENGTH: 478
<212> TYPE: DNA
<213> ORGANISM: Pinus radiata

<400> SEQUENCE: 131
gctggttcaa gtgtcagccc aatggcctcc cctacagaga atccccagat ttcagaagag 60
ctgctaaatc atgagatcca tcaaggaagt acagtatgtg tgacaggagc tgctggcttc 120
ataggatcat ggctcgtcat gcgtttgctt gagcgaggat atactgttag aggaactgtg 180
cgagacactg gtaatccggt gaagacgaag catctattgg atctgcctgg ggcgaatgag 240
aggttaactc tctggaaagc agatttggat gatgaaggaa gctttgacgc cgccattgat 300
ggttgtgagg gagttttcca tgttgccact cccatggatt ttgaatccga ggaccccgag 360
aacgagataa ttaaacccgc tgtcaatggg atgttgaatg ttttgagatc gtgtgggaaa 420
accaagtcta tgaagcgagt tgttttcacg tcgtctgctg ggactctgct ttttacgg 478

<210> SEQ ID NO 132
<211> LENGTH: 510
<212> TYPE: DNA
<213> ORGANISM: Pinus radiata

<400> SEQUENCE: 132
cttgttcaaa gtcacatatc ttattttctt tgtgatatct gcaatttcca agcttttcgt 60
ctacctccct gaaaagatga gcgaggtatg cgtgacagga ggcacaggct tcatagctgc 120
ttatctcatt cgtagtcttc tccagaaagg ttacagagtt cgcactacag ttcgcaaccc 180
agataatgtg gagaagttta gttatctgtg ggatctgcct ggtgcaaacg aaagactcaa 240
catcgtgaga gcagatttgc tagaggaagg cagttttgat gcagcagtag atggtgtaga 300
tggagtattc catactgcat cacctgtctt agtcccatat aacgagcgct tgaaggaaac 360
cctaatagat ccttgtgtga agggcactat caatgtcctc aggtcctgtt caagatcacc 420
ttcagtaaag cgggtggtgc ttacatcctc ctgctcatca ataccgatac gactataata 480
gcttagagcg ttccctgctg gactgagtca 510

<210> SEQ ID NO 133
<211> LENGTH: 890
<212> TYPE: DNA
<213> ORGANISM: Pinus radiata

<400> SEQUENCE: 133
tcctaattgt tcgatcctcc cttttaaagc ccttccctgg ccttcattcc aggtcacaga 60
gttgttcatg cagtgctagc aggaggagca gcgttgcaat tggggaaaat tccaaaatca 120
ataacgagag gacagaagta agtttgtgga aatagcaacc atgccggtgt ttccttctgg 180
tctggacccc tctgaggaca atggcaagct cgtttgtgtc atggatgcgt ccagttatgt 240
aggtttgtgg attgttcagg gccttcttca acgaggctat tcagtgcatg ccacggtgca 300
gagagacgct ggcgaggttg agtctctcag aaaattgcat ggggatcgat tgcagatctt 360
ctatgcagat gtcttggatt atcacagcat tactgatgcg ctcaagggct gttctggtct 420
gtctatacct ttgagcaccc tcagagtgct gcaggctatg atgaagtgat ggcagaaatt 480
gaagtacaag cagcccacaa tgcactggaa gcgtgtgctc agactgagac cattgagaaa 540
gttgtgttca cttcttctgt ggctgcagca atttggagag aagatggaga ctacaaggtt 600
aatgcccttg acgagaggca ttggagtgat gcaaatcttt gcaggaaatt gaagttgtgg 660
tacgcattag ccaagacact gtcagagaag gctgcatggg cgctggcaat ggacagaggg 720
ttgaatatgg tgacaatcaa cgcatctctg attgtaggac ctggcatcac atacaaaagc 780
tcaggatcta ccattgcata tcttaaaggg gctgcacaaa tgtatgagaa gggcacttta 840
gctagtgtgg acataaggtt tctagcggat gcacatatat gcgcttatga 890

<210> SEQ ID NO 134
<211> LENGTH: 955
<212> TYPE: DNA
<213> ORGANISM: Pinus radiata

<400> SEQUENCE: 134
aatcactgac cttcacatat ttattccaat tctaatatct ctactcgctg tctacctgat 60
ttttcagtgg cgaaccaact tgacagggtt ggacatggcc aacagcagca agattctgat 120
tattggagga acaggctaca ttggtcgtca tataaccaaa gccagccttg ctcttggtca 180
tcccacattc cttcttgtca gagagacctc cgcttctaat cctgagaagg ctaagcttct 240
ggaatccttc aaggcctcag gtgctattat actccatgga tctttggagg accatgcaag 300
tcttgtggag gcaatcaaga aagttgatgt agttatctcg gctgtcaagg gaccacagct 360
gacggatcaa cagaatatta tcaaggctat taaggaggtt ggaaccatca agaggttttt 420
gccatctgag ttcgggaatg acgttgatag aacccatgca gtggagcctg caaagaccat 480
gtttgctacc aaagcgaaaa ttcgcagggc cattgaggca gaaggcatcc cttacacatt 540
tgtctctagc aactgttttg ctgggttgtt cttgccaagt ttggggcagc caggccttac 600 cgcccccgcca agggataaag ttgtgatatc tggagatgga aatgccaaag ttgtttttgt 660
gaaggaggag gatataggga cattcaccat caaggcagtg gatgacccta gaactctaaa 720
caagatcctg tatttgaggc ttcctgccaa cacatattct cttaacgagc ttgtagctgt 780

-continued

```
gtgggagaag aagattggca agtctctgga gaagacctat ataccagagg aagaggtcct    840

gaaaaaaatt gcagagtcgc cattcccact caatgctata atgtcaaccg gccactctat    900

ttttgtgaaa ggggatcaaa caaattttga aatcggacct gatggtgtgg aggct         955
```

<210> SEQ ID NO 135
<211> LENGTH: 1024
<212> TYPE: DNA
<213> ORGANISM: Pinus radiata

<400> SEQUENCE: 135

```
agagggttat atatcttgat tctgacctga ttgtcgtcga cgacattgcc aagctctggg      60

ccacggattt ggaatctcgt gtcctcgggg caccagagta ctgcaaggcg aatttcacaa    120

agtatttcac cgataatttc tggtgggatc ccgcattatc caagaccttt gagggaaaaa    180

aaccctgcta cttcaacaca ggcgtaatgg tgatcgatct tgaaaaatgg cgggcagggg    240

aattcacaag aaagatcgaa atctggatgg acatacagaa ggaacgccgt atctatgagc    300

tcggatcatt accgccattt ttactggtat ttgctggttt ggttaagcaa gtcgatcatc    360

gttggaatca gcacggttta ggcggagata atttgcaagg cctttgccga gatcttcacc    420

ctggacctgt cagtttgttg cattggagtg gtaagggcaa accttggcta cgcctggaat    480

gccaagcgga cttgccctct ggatacttta tgggctcctt atgatcttta tcgatcaacg    540

tattacctaa atgggtgaga gagcctctct cctcggggtg ctttttatcg aattaaacct    600

gatttgataa aatgccaaat agaactttac gcctatgcat ctttcagttt tgaatttcaa    660

ttctggtaac gaatagaaga aaacaatagc acagccacag gcaggacaaa tccatcatga    720

gggaccaatc gtttgaattt agtattaata aggttgttcc atataacgcc tgtgaagaat    780

gatattgtgg actgatctat ttatatttgt actgccatgc catcctcagc cagcagagag    840

gcaagcaatg ccgctgcaag tcatgtaggg aaggcgttgt gaactcaatt ttcggcgact    900

gtacaggatg taaatttttg gaacattaat atcattatga taagttcctg aaccaacaac    960

tgtataatac cttataaatg tatctgcaac tccatttttg cataaaaaaa aaaaaaaaaa   1020

aaaa                                                                1024
```

<210> SEQ ID NO 136
<211> LENGTH: 497
<212> TYPE: DNA
<213> ORGANISM: Pinus radiata

<400> SEQUENCE: 136

```
agaacataaa tccgaacaat gaacttgcaa atttcctgca ttgccatcgc cagcccaaga      60

aacttttggc cgcaaagcaa tctgtacact ttctctctca ttccttgcta caagcatgga    120

tataggttct aggggtcttg gggctcctg atgcccaatt gttgctgtgc ttggcatgac     180

ccaaacatgc aagagatctg tagtcagtag tcttgttgga tctatagctt ttagaaaaga    240

gtcacgtcct tttagggtaa catcattcca accatatcca gttccaccac cggctacacc    300

ttcaacggga ggaggagcaa gatattcagc attgctttgg gcaccagatg gataggcatt    360

attttccatc ggaattcagc cgagctcgcc ccctcagtcc aatcgtcgtg aaaatccctc    420

aaaattgggc aattctggct cgaaatcgcc aaattatggg ctacaacagg attaaaattg    480

cacagaaatc tgccagt                                                   497
```

<210> SEQ ID NO 137
<211> LENGTH: 528
<212> TYPE: DNA

<213> ORGANISM: Pinus radiata

<400> SEQUENCE: 137
ggcaatccga gcctagccaa ccaacttggc agcaaggagc acagggagtt ggcgagagaa 60
gctgttagga aatctttggt attgttgaaa aatgggaagt cagccaacaa gcctttgctc 120
cctttggaga agaatgcttc caaggttctt gttgcaggaa cccatcctga taatctgggt 180
tatcagtgtg gtggatggac gatggaatgg caaggattaa gtggaaacat aaccgtagga 240
actacaattc tggaagctat caaactagct gtcagcccct ctactgaagt ggtttatgag 300
caaaatccag atgctaacta tgtcaaagga caagggtttt catatgccat tgtggttgtg 360
ggtgaggcac catacgcaga aacgtttgga gacaatctta atttgaccat tcccctaggc 420
ggaggggaca cgattaagac ggtctgtggc tccttgaaat gccttgtaat cttgatatct 480
ggaaggccac ttgttattga accttatctt ccattggtgg atcgtttt 528

<210> SEQ ID NO 138
<211> LENGTH: 424
<212> TYPE: DNA
<213> ORGANISM: Pinus radiata

<400> SEQUENCE: 138
aaaaaacaaa tgttagctag cctagtgatg agctttacgt atacctggcc ttttatacat 60
ggatctgagt ttttatgcag gtgtagagcc ttttgttact ctgtatcact gggacttgcc 120
acaagctctg gaggacgaat acggtggatt tcgtagcaaa aaagttgtgg atgactttgg 180
catattctca gaagaatgct ttcgtgcttt tggagaccgt gtgaagtact gggtaactgt 240
taacgaaccg ttgatcttct catatttttc ttacgatgtg gggcttcacg caccgggccg 300
ctgttcgcct ggatttggaa actgcactgc gggaaattca gcgacagagc cttatattgt 360
agcccataac atgcttcttg cacatagtac cgctgttaaa aatatatagc ataaataccc 420
aggg 424

<210> SEQ ID NO 139
<211> LENGTH: 404
<212> TYPE: DNA
<213> ORGANISM: Pinus radiata

<400> SEQUENCE: 139
gctaccatct tccctcataa tattgggctt ggagctacca gggatcctga tctggctaga 60
agaatagggg ctgctacggc tttggaagtt cgagctactg gcattcaata cacatttgct 120
ccatgtgttg ctgtttgcag agatcctcga tggggccgct gctatgagag ctacagtgag 180
gatccaaaaa ttgtcaaggc catgactgag attatcgttg gcctgcaagg gaatcctcct 240
gctaattcta caaaaggggg gccttttata gctggacagt caaatgttgc agcttgtgct 300
aagcattttg tgggttatgg tggaacaacc aaaggtatcg atgagaataa tactgttatc 360
aactatcaag ggttatttca acattccaaa ttacccccaa tttt 404

<210> SEQ ID NO 140
<211> LENGTH: 437
<212> TYPE: DNA
<213> ORGANISM: Pinus radiata

<400> SEQUENCE: 140
cctagaattc tatggtgaaa attgttggga caaggctgcc caagtttaca aaggaacagt 60
cccaaatggt taaaggttca atagactatc taggcgttaa ccaatacact gcttattaca 120
tgtatgatcc taaacaacct aaacaaaatg taacagatta ccagactgga ctggaataca 180
ggctttgcat atgctcgcaa tggagtgcct attggaccaa gggcgaactc caattggctt 240
tacattgtgc cttggggtct atacaaggcc gtcacatacg taaaagaaca ctatggaaat 300
ccaactatga ttctctctga aaatggaatg gacgacctgg aaacgtgaca cttccagcag 360
gactgcatga taccatcagg ggtaactact ataaaagcta tttgcaaaat ttgattaatg 420
cacgtgaatg accgggg 437

<210> SEQ ID NO 141
<211> LENGTH: 470
<212> TYPE: DNA
<213> ORGANISM: Pinus radiata

<400> SEQUENCE: 141
gatacatcca agctgagaat ggaagagatt aatggtgata acgcagtaag gaggagctgc 60
tttcctccag gtttcatgtt tggatagca acttctgctt atcagtgtga aggagctgcc 120
aacgaaggtg gaaaaggccc aagcatctgg gactcatttt cacgaacacc aggcaaaatt 180
cttgatggaa gcaacggtga tgtagcagtg gatcagtatc atcgttataa ggcagatgta 240
aaactgatga aagatatggg cgtggctacc tacagattct cgatttcatg gcctcgtata 300
tttccaaagg gaaaaggaga gatcaatgag gaaggagtag cctattacaa taacctcatc 360
aatgaactcc tccagaatgg aatccaagcg tctgtcaact ttgtttcact gggatactcc 420
ccagtctctg gaggatgaat atggcggatt tctgaggcca accattgtga 470

<210> SEQ ID NO 142
<211> LENGTH: 413
<212> TYPE: DNA
<213> ORGANISM: Pinus radiata

<400> SEQUENCE: 142
ataagactaa ttttccagac aatcctccat tcccattcaa ttacactggt actccaccca 60
ataatacaca ggctgtgaat gggactagag taaaagtcct tccctttaac acaactgttc 120
aattgattct tcaagacacc agcatcttca gcacagacag ccaccctgtc catctccatg 180
gtttcaattt ctttgtggtg ggccaaggtg ttggaaacta caatgaatca acagatgcac 240
caaattttaa cctcattgac cctgtcgaga gaaacactgt gggagttccc aaaggaggtt 300
gggctgctat aagatttcgt gcagacaatc caggggtttg gttcatgcac tgtcatttgg 360
aggttcacac atcgtgggga ctgaaaatgg cgtgggtagt aaagaacgga aaa 413

<210> SEQ ID NO 143
<211> LENGTH: 457
<212> TYPE: DNA
<213> ORGANISM: Pinus radiata

<400> SEQUENCE: 143
aaaacctttt cagacgaatg ttctgatgct cggccccggc cagacaacag acatacttct 60
cactgccaat caggctacag gtagatacta catggctgct cgagcatatt ccaacgggca 120
aggagttccc ttcgataaca ccactaccac tgccatttta gaatacgagg gaagctctaa 180
gacttcaact ccagtcatgc ctaatcttcc attctataac gacaccaaca gtgctactag 240
cttcgctaat ggtcttagaa gcttgggctc acacgaccac ccagtcttcg ttcctcagag 300
tgtggaggag aatctgttct acaccatcgg tttggggttg atcaaatgtc cggggcagtc 360
ttgtggaggt ccaacggatc aagatttgca gcaagtatga atacatatca tttgtcccgc 420
aaccacttct tccaatcctt caagctcagc attttgg 457

<210> SEQ ID NO 144
<211> LENGTH: 598
<212> TYPE: DNA
<213> ORGANISM: Pinus radiata

<400> SEQUENCE: 144
gttcggcact gagagatcca tttctttcaa tgttgagaca gtgagtagta ttagtttgat 60
atctctttca ggaatatatc gtgcttgcag gatctttagt ttctgcaaca atgtcgttgc 120
aatcagtgcg tctatcttct gttctccttg ttttgctact agcatttgtt gcttacttag 180
ttgctgtaac aaacgcagat gtccacaatt ataccttcat tattagaaag aagacagtta 240
ccaggctatg caataagcgt ataatcgcca ccgtcaatgg acagctacca ggcccaacta 300
ttcatgtacg tgatggagac gttgttaata tcaaagctta taacaaagct gggtacaatg 360
ccactcttca ctggcatgga gtcgagcagt tgcgtacagg atgggccgat ggacctgcat 420
atgttacaca gtgccccatt ccaccaggtg gtcgttatac atacagattc accatttctg 480
aacaggaagg caccgtgtgg tggcacgctc atgtgtcatg gctccgagct acggtgcatg 540
gagctttcgt aatccttcct aagagaggca aaccatatcc ctttcctaaa ccccgtgc 598

<210> SEQ ID NO 145
<211> LENGTH: 1080
<212> TYPE: DNA
<213> ORGANISM: Pinus radiata

<400> SEQUENCE: 145
aagatcttgg ttcgagtctc tcagctctct ccaaaggaat tttgtgggtc atttgcaggt 60
gaagacacca tggtgaaggc ttatcccacc gtaagcgagg agtacaaggc tgccattgac 120
aaatgcaaga ggaagctccg agctctcatt gcagagaaga actgtgcgcc gatcatggtt 180
cgaatcgcat ggcacagcgc tgggacttac gatgtcaaga ccaagaccgg agggcccttc 240
gggacgatga gatatggggc cgagcttgcc cacggtgcta acagtggtct ggacatcgca 300
gttaggctcc tggagccaat caaggaacag ttccccataa tcacctatgc tgacctttat 360
cagttggctg gtgtggtggc tgttgaagtg accgggggac ctgacattcc gttccatcct 420
ggaagagaag acaagcctga gcctccagaa gaaggccgcc ttcctgatgc tacaaaagga 480
cctgatcatc tgagggatgt ttttggtcac atggggttga atgataagga aattgtggcc 540
ttgtctggtg cccacacctt ggggagatgc cacaaggaga gatctggttt tgaaggacca 600
tggacctcta accccttat ctttgacaac tcttacttca cagagcttgt gactggagag 660
aaggaaggcc tgcttcagtt gccatctgat aaggcactgc ttgctgatcc tagttttgca 720
gtttatgttc agaagtatgc acaggacgaa gacgctttct ttgctgacta tgcggaagct 780
cacctgaagc tttctgaact tgggtttgct gatgcgtaga ttcatacctt ctgcagagac 840
aattccttgc tagatagctt cgttttgtat ttcatctaat cttttcgatt atatagtcac 900
atagaagttg gtgttatgcg ccatagtgat acttgaacct acatgttttt gaaaagtatc 960
gatgttcttt aaaatgaaca ttgaatacaa cattttggaa tctggttgtg ttctatcaag 1020
cgcatatttt aatcgaatgc ttcgttcctg ttaaaaaaaa aaataaaata aaaaaaaaaa 1080

<210> SEQ ID NO 146
<211> LENGTH: 701
<212> TYPE: DNA
<213> ORGANISM: Pinus radiata

<400> SEQUENCE: 146
gtagtttcgt tttacaacaa tctcaggttt tgaatctcag aatagttgcg aaaggaagcg 60
atgacgaagt acgtgatcgt tagctccatt gtatgtttct ttgtatttgt ttctgcgtgc 120
ataatttctg tcaatggatt agttgtccat gaagatgatc tgtcaaagcc tgtgcatggg 180
ctttcgtgga cattttataa ggacagttgc cccgacttgg aggccatagt gaaatcggta 240
cttgagccgg cgttggacga agatatcact caggccgcag gttgctgaga cttcatttcc 300
atgactgttt tgtgcagggt tgcgatgggt ccgtgttgct gacaggaact aaaagaaacc 360
ccgagtgagc aacaggctca gccaaactta acactaagag cccgggcctt gcagctgatc 420
gacgaaatta aaaccgctgt agaagctagc tgcagtgggg ttgtaacttg tgcagacatt 480
ctggctttgg ctgctcgtga ctccgtcgct caggaggccc aaaatttcca gtaccacttg 540
gccgcagaga tagcctaaag tttgccagtc aatccgtagt tctcgccaat ataccaactc 600
caactttaaa tttgacacag ctgatgaaca tttttggctc caaaggattc agtttggccg 660
aaatggttgc tctttcaggt ggacacacaa tcggcattgg t 701

<210> SEQ ID NO 147
<211> LENGTH: 338
<212> TYPE: DNA
<213> ORGANISM: Pinus radiata

<400> SEQUENCE: 147
ctcaattctg tgctgctctg ctcgctcagg gccgggtctg ctattctgct catgcacaag 60
tttgagatcg ggagcctgct ggatctggtg cagaggttca aggtcacggt agcgcctgtc 120
gtgcctccca ttgttctcgc ctttgccaag aacgcgctcg tggaaagcta tgatctgtcg 180
tccattaggg ttgtgctgtc cggtgccgcg cctctcggaa aggagctgga ggatgcatta 240
aggctacgac ttcccaaagc cacttttggt cagggatacg gtatgacaga ggcaggaccg 300
gtgctatcaa tgtgtctggc cttcgctaag gagccctt 338

<210> SEQ ID NO 148
<211> LENGTH: 357
<212> TYPE: DNA
<213> ORGANISM: Pinus radiata

<400> SEQUENCE: 148
ctcaattctg tgctgctctg ctcgctcagg gccgggtctg ctattctgct catgcacaag 60
tttgagatcg ggagcctgct ggatctggtg cagaggttca aggtcacggt agcgcctgtc 120
gtgcctccca ttgttctcgc ctttgccaag aacgcgctcg tggaaagcta tgatctgtcg 180
tccattaggg ttgtgctgtc cggtgccgcg cctctcggaa aggagctgga ggatgcatta 240
aggctacgac ttcccaaagc cacttttggt cagggatacg gtatgacaga ggcaggaccg 300
gtgctatcaa tgtgtctggc cttcgctaag gagccctttc cgatgaagtc cgggtcg 357

<210> SEQ ID NO 149
<211> LENGTH: 470
<212> TYPE: DNA
<213> ORGANISM: Eucalyptus grandis
<220> FEATURE:
<221> NAME/KEY: misc_feature
<222> LOCATION: (353)..(353)
<223> OTHER INFORMATION: n is a, c, g, or t
<220> FEATURE:
<221> NAME/KEY: misc_feature
<222> LOCATION: (437)..(437)
<223> OTHER INFORMATION: n is a, c, g, or t

<400> SEQUENCE: 149
gagaaattca caagcttcac agcacgagag ttaaagagcg agacacggtt tgatccagtg 60
aagggccggc ccccggagat ggcgaagacg ctcaccgcgc tggctggggg agaagaccct 120
ccagtccaaa gttcgtccgc gataaggatg agcgccccac ggtggcctac aaccagttca 180
gcaacgtgat ccccgtgata tccctggcgg ggattgacga ggccggcggc cggaagggcc 240
gagatctgca agaagatcgt ggaggcgtgc gaggactggg gcgtcttcca ggtggttgac 300
cacggggttg atacggggct catcactgac atgacccggc tcgcgcgtaa gtncttcgct 360
ctgccctcgg aggaaaagct ccggttcgac atgactggcg gaaaaagggg gggttatcgt 420
ctccagcatc tcaaggngaa caagttcagg actggtgcaa aagtacgaac 470

<210> SEQ ID NO 150
<211> LENGTH: 380
<212> TYPE: DNA
<213> ORGANISM: Eucalyptus grandis

<400> SEQUENCE: 150
ggaggtcggt gacagagcag tacagcgaga agctcatggc cctcgcttgc aagctcttgg 60
aggtcctctc ggaggcaatg ggactggaga aggaggcact gaccaaggca tgcgtggaca 120
tggaccagaa ggtggtggtc aactactacc ccaaatgccc gcagcccgac ctcacgctcg 180
ggctgaagcg ccacactgac ccgggaacca tcactcttct gctccaggac caggtggggg 240
gcctccaggc caccagagat ggcggcaaga gctggatcac cgtccagcct gtggaagggg 300
cttttgtggt caacctaggc gatcatggtc atttcctgag caacgggagg ttcaagaacg 360
cggaccacca ggcggtggtg 380

<210> SEQ ID NO 151
<211> LENGTH: 349
<212> TYPE: DNA
<213> ORGANISM: Pinus radiata
<220> FEATURE:
<221> NAME/KEY: misc_feature
<222> LOCATION: (212)..(212)
<223> OTHER INFORMATION: n is a, c, g, or t

<400> SEQUENCE: 151
ttggactcca tacctctcgt ggacctccaa ggtcttttac gcgattctgc tagagcccac 60
gttattcaac aaattggccg ggcctgcgct gaatatggct tcttccagat aatcaatcat 120
ggcatcccag atgcagttat caacaggatg ctggaagtag cgaaggagtt tttcagaatg 180
cctgtggagg accgaatgga atactattcc gncgatccgt ccagaaaaac acgtttgtcg 240
acgagcttca acatccataa agaacaagtc ttcaactggg gggctatctc agacatcatt 300
gttatccgtt agaagatcat gttcacactt ggccttcaaa acctgcggg 349

<210> SEQ ID NO 152
<211> LENGTH: 427
<212> TYPE: DNA
<213> ORGANISM: Pinus radiata
<220> FEATURE:
<221> NAME/KEY: misc_feature
<222> LOCATION: (234)..(234)
<223> OTHER INFORMATION: n is a, c, g, or t
<220> FEATURE:
<221> NAME/KEY: misc_feature
<222> LOCATION: (240)..(240)
<223> OTHER INFORMATION: n is a, c, g, or t

<400> SEQUENCE: 152

```
atggtctggg cagcatacgg aggacgatgg aagatggaac gcaaggtgtg caacatgcac      60

atgttgggag ggaaggcgtt ggaagattgg cagccggtga gggacgccga aatgggcttc     120

atgctccgga atattctcag tcactcgcag cgcggcgaga cggtgaatgt gccggacctc     180

ctgaacatct gcgccgccaa catgatcggg cagatcattc taagcaagcg ggtnttcgan     240

acagaagggg acgaggccaa cgagttcaag gacatggtgg tggaactcat gacctgcgct     300

ggatacttca atatcggaga cttcattcca tcgctagcgt ggatggactt gcagggcatt     360

cagcggggta tgaagaagct ccacaagaaa tgggacgcac tcatacagag gattattgat     420

taacacc                                                               427


<210> SEQ ID NO 153
<211> LENGTH: 298
<212> TYPE: DNA
<213> ORGANISM: Eucalyptus grandis
<220> FEATURE:
<221> NAME/KEY: misc_feature
<222> LOCATION: (214)..(214)
<223> OTHER INFORMATION: n is a, c, g, or t

<400> SEQUENCE: 153

gttaccaaag ggcagcaacg tattcttaaa catgggttct atccacaggg atcccaagat      60

ttgggacaaa ccgttggagt ttagacccga gaggttcttg gaaggtccta gcaagtatga     120

tttctcaggt aacaacttcg catacatgcc attcggttct ggtcgaaggg tgtgtgcagg     180

gcttgcgctg gcagagagga tgctaccata tgtnttggcc tctcttttgc actcattcaa     240

gtgggaaata ccaccagggt ctgagctgga tttacctgga caagttcggc cttgtggt       298


<210> SEQ ID NO 154
<211> LENGTH: 251
<212> TYPE: DNA
<213> ORGANISM: Eucalyptus grandis

<400> SEQUENCE: 154

gacttcaaag ggcaggattt tgagctgata cccttcggtg caggtagaag gagctgcccg      60

gctattgcat ttggaaatgc cagtgttgag cttgctttag ctcaacttct tcacagtttc     120

gattgggagc ttcctgatgg gatccagcct agggacttgg atatgaccga agtttttggc     180

atcacaatgc acagaattgc caacctcatg gttgtagcca aaccccgctt ctcctagacg     240

atactcgtgc c                                                          251


<210> SEQ ID NO 155
<211> LENGTH: 411
<212> TYPE: DNA
<213> ORGANISM: Pinus radiata
<220> FEATURE:
<221> NAME/KEY: misc_feature
<222> LOCATION: (198)..(198)
<223> OTHER INFORMATION: n is a, c, g, or t

<400> SEQUENCE: 155

acggggctcc ggtgacgaga tactggcagg tcgttgaagc tggttggagg ttcgaatatc      60

cgagagggat cctgtttctt gtccccttac cttggttttc ctcatccttc cgaatgcagt     120

ctaattcgaa gaccgtggaa gagcggcgcc cggggcctgg gtaagagctt gctggagata     180

tctcggcttg actatgtntt ggctcttttc gtgaatggca agggggatct aggggcgatg     240

atggggtcgg ctgtcgtttt gagggaaaat tcgcaactgt tgatggtctt gactacatct     300

ctggccgtct tgattggttg cgttttgttc tttgtttggc ggagaggggg atcggctccc     360
```

tcgaagcagc cggagaagcc aactcccctg gtgaaagaag aggaagagga g 411

<210> SEQ ID NO 156
<211> LENGTH: 404
<212> TYPE: DNA
<213> ORGANISM: Pinus radiata

<400> SEQUENCE: 156
gctgaagtta ataaaactaa gtacattgag gttgacatgg aggcagaatt ttcaaatcta 60
gctttggaca ttattggatt gtgtgtattt aactatgatt ttggatccgt tactcgagaa 120
tcaccagtaa tcaaggcagt ctatggtaca ttgtttgaag ctgagcatag atcaaccttt 180
tacataccat actggaaatt tccgctggca agatggttag ttcctcgcca acgaaagttc 240
catgaagacc taaaggtcat taatgaatgt cttgataatc tgatagcagg ggccaaggaa 300
acaagacagg aagacgatat cgaggctctt caaggaagag attactctaa agtgaaatat 360
gcaagtttgc tcagatttct agttgatatg agggagaaga tgtt 404

<210> SEQ ID NO 157
<211> LENGTH: 259
<212> TYPE: DNA
<213> ORGANISM: Pinus radiata
<220> FEATURE:
<221> NAME/KEY: misc_feature
<222> LOCATION: (116)..(116)
<223> OTHER INFORMATION: n is a, c, g, or t
<220> FEATURE:
<221> NAME/KEY: misc_feature
<222> LOCATION: (246)..(246)
<223> OTHER INFORMATION: n is a, c, g, or t

<400> SEQUENCE: 157
ccaatcatcg gcaatttcca ccaagtgaga cttcctcttc accgtgctct caaaaatctt 60
gctgagaaat atggtcccat tttgtttctg cgctttggct ctgtacccac tgtggntgtt 120
tcttcatctg agatggccaa acactttctt aaaactcatg atttgatatt tgccagccga 180
cctccaacat cggtaggaaa atatttcttc tataacttca aagatattgc cttcagtcct 240
tatggngatc actggagga 259

<210> SEQ ID NO 158
<211> LENGTH: 338
<212> TYPE: DNA
<213> ORGANISM: Pinus radiata

<400> SEQUENCE: 158
aatggcagtt gggggtcaag gaaatgtggt ctcagcttgc aggcagccat ggaagctaca 60
atcgtctggt gggtgttttg gtagtaatag tttctctggc agttttttat ttgaagagta 120
gaggttcgaa gaagcgtctg cctccagggc cgaagggtgg cctctggttg gaaatttgtt 180
tcaggttgca ttctccggga agcccttcat gtatgtggtg cgagatctga gggagcagtt 240
tggctcgatt ttcacgctcc aaatggggca aaaaacgccc caaattacca cctccccgaa 300
atttccaaca cggggcctct taaaaaagag ggggcccc 338

<210> SEQ ID NO 159
<211> LENGTH: 539
<212> TYPE: DNA
<213> ORGANISM: Pinus radiata
<220> FEATURE:
<221> NAME/KEY: misc_feature
<222> LOCATION: (22)..(22)
<223> OTHER INFORMATION: n is a, c, g, or t
<220> FEATURE:

<221> NAME/KEY: misc_feature
<222> LOCATION: (358)..(358)
<223> OTHER INFORMATION: n is a, c, g, or t
<220> FEATURE:
<221> NAME/KEY: misc_feature
<222> LOCATION: (387)..(387)
<223> OTHER INFORMATION: n is a, c, g, or t
<220> FEATURE:
<221> NAME/KEY: misc_feature
<222> LOCATION: (397)..(397)
<223> OTHER INFORMATION: n is a, c, g, or t

<400> SEQUENCE: 159
aatgtggccg aggagttcct gnaagactca tggatctggc tttcgccagc agacctccaa 60
ccatcggtaa cgaatatttt ggtataattc ctccgacgtc gcattttccc cctatggtcc 120
ttactggagg cagatgcgta aaatctgtgt gttaaagttg ctgagctcaa gacgcataga 180
ttccttccgc cacataagag aagaggaagt ctcttctatg gttcgctcta ttgctaattc 240
ggatctgcat cctgtgaaca ttagcagggc cgtgtcagcc cttgggattg atataatctg 300
caggatggcc ttcggtaaaa agtactgtga ccaagaccta attggtggca ttgggatnaa 360
gtcaatgata aaggaaacgt ttgtgtnagc agggtcnttg aacatgggag attttatacc 420
atacttggca tggattgatc ttcaaggtct caaccgtcga ttgaagaaca tacacaagat 480
ccaagacgac ttgttagggg aagatactag aggcacacgc ttcgccaacc gcagaataa 539

<210> SEQ ID NO 160
<211> LENGTH: 310
<212> TYPE: DNA
<213> ORGANISM: Pinus radiata
<220> FEATURE:
<221> NAME/KEY: misc_feature
<222> LOCATION: (16)..(16)
<223> OTHER INFORMATION: n is a, c, g, or t

<400> SEQUENCE: 160
cgaatgggtg gtcggnaaag accgcacagt aaaggagtct gatttggtaa gtctgaaata 60
ccttcagtgt gtggtgaaag agacgctacg attatacccg ggaggacctc tagcacttcc 120
ccatgagtct gtggaggctg tgacagtaga agggtactat atacctaaga agacgatgct 180
gttggtgaat gtgtgggcta taggaaggga ccccaaagtg tgggggattg atgcttcaga 240
attcaagcca gagagattta tggaggaatt aggtgggcat ctgcatgata atgtcatgga 300
tttagcaggc 310

<210> SEQ ID NO 161
<211> LENGTH: 412
<212> TYPE: DNA
<213> ORGANISM: Eucalyptus grandis

<400> SEQUENCE: 161
cgccacctcc ctcctcctct tccccctcct cctgctcctc ctggtcgccc cgcaaaagcc 60
ctccgcctct gtccgcagtc accgccagcc atggatctcc tcctcctgga gaagaccctc 120
ctgggcctct tcgccgccgc catcgtggcc atcgcggtct ccaagctccg gggcaagcgg 180
ttccgcctcc ccccgggccc cctccccgtg cccatcttcg gcaactggct ccaggtcggc 240
gacgacctca accaccgcaa cctcaccgac ctcgccaaga ggttcggcga catcctcctc 300
ctccgcatgg ggcagcgcaa cctcgtggtc gtctcgtccc cggacctctc caaggaggtg 360
ctccacacgc agggcgtcga gttcgggtcc cgcacccgga acgtcgtctt ct 412

<210> SEQ ID NO 162

<211> LENGTH: 329
<212> TYPE: DNA
<213> ORGANISM: Pinus radiata

<400> SEQUENCE: 162
acttttacaa tgagtgatca caaacaattt tttccaaaat tcataacaaa attttggata 60
cagtgcatat tcgggcaaac aatctgacgg acttcaaaac tactgacaac aaaacaaacc 120
atctggggat gaattacaat ggaaatccac acttcatttg gctgcaactg tatatataaa 180
gtgtttattg cttccagctc ctccagactt tggaagaaat tctatatttt tttttcagga 240
tctgagcttc aggctattgg tttggccaca acaacggagt ggttgagaat gtgcaggctg 300
aattgccctc ctttctctgt cacatccac 329

<210> SEQ ID NO 163
<211> LENGTH: 475
<212> TYPE: DNA
<213> ORGANISM: Pinus radiata

<400> SEQUENCE: 163
atttgcgtca gtctctacct ttgcctgcaa cattcacagt cgctgatgga gggcctcccg 60
cagcaactgt cctgtgctta ctctgggctt tcttcatgat atggtttttg ggcaagagaa 120
gaactagtgc cacgctgcca ccaggaccct atgcatggcc catcatagga aacctctacc 180
aattaatact gcccgctcac cgttctctta gaggccttgc tgacaaatat ggtcccatta 240
tgtttctgcg cttaggctct gtccctaccg tcgtcgtttc ttcttctgag acggccaaag 300
agtttctcaa aactcatgac ttgatttttg ccagccgacc cccaacagcc gctgggagat 360
tgatgttttc caactctaaa gacgtggtgt tcgctccgta tggagatcac tggaggcaaa 420
tgagaaaaat atgcgtgtta gaactactga ctgccaaaag aatcgagctc gtgcc 475

<210> SEQ ID NO 164
<211> LENGTH: 372
<212> TYPE: DNA
<213> ORGANISM: Pinus radiata
<220> FEATURE:
<221> NAME/KEY: misc_feature
<222> LOCATION: (22)..(22)
<223> OTHER INFORMATION: n is a, c, g, or t

<400> SEQUENCE: 164
tggaaataca gttcgactct gngatttcat aaaatatgat gaggaaagga gaatcaggtg 60
gatttgaggt taagggatgg gctgccatgg atgactccgg cgtcctctcg cctttcaact 120
ttactcgcag gaaaacggga tcccacgatg tactttcaag gtagcatact gtggaatctg 180
tcactccgat ctgcatcaaa ttcggaatga atggaaaaat tccctatacc caaatgggtt 240
ccaggccacg aaatcgtagg aactgttgct tgaagttcgg tcagaagtga agaattttgg 300
ctggctggag aatcggcggt gggtgtaagg gttgcatggg tttggaggtg ccagccaatt 360
ggtgaattct tg 372

<210> SEQ ID NO 165
<211> LENGTH: 307
<212> TYPE: DNA
<213> ORGANISM: Eucalyptus grandis

<400> SEQUENCE: 165
tctctctctc tctccctctt gagagtgttg aagtgttagg atgaggattc gagtgccgtc 60
gatgctgttg ttgtggtcac tgttgggcct cgtggcgagg tcgacaatgg ccgaagagac 120

-continued

```
ggtgatcccc gagacaacgc gtttcgacac cggtgggctg agcagatcgg ccttcccgaa    180

gggcttcgtc tgggggacgg cgacctcggc ttatcaagtc gaaggcatgg ccgacaaaga    240

gggacgcggg cctagcatct gggacgtctt cgtcaagatt ccaggaattg tggccggtaa    300

tgcaact                                                              307
```

<210> SEQ ID NO 166
<211> LENGTH: 454
<212> TYPE: DNA
<213> ORGANISM: Eucalyptus grandis

<400> SEQUENCE: 166

```
gaagaaatta ggtttcttgt tgcggctttt ggtagtgggt ctggtgatag cagagacggt     60

ccatggtgct tatgagttca gcagatacga ctttcctcct ggctttgtgt ttggtgctgg    120

cacttcagct tatcaggtcg aaggagcagc aaatgaggat gggaagactc caagtataat    180

ggacacctgg gcccactctg actcagggat tacaagcgga gcaaatggag atattgcctg    240

tgatcaatat cacaaataca aggtagatgt ccaactcatg gcagaaatgg gattagacgc    300

ataccggttt tccatctcat ggtcaaggct catcccaaat gggagaggct ctgtgaatcc    360

gaagggattg cagtactaca acaacctcat caatgaactg atcagccatg ggattgaacc    420

cgcacgtgac cctgcaccat tttgatctgc caca                                454
```

<210> SEQ ID NO 167
<211> LENGTH: 433
<212> TYPE: DNA
<213> ORGANISM: Pinus radiata

<400> SEQUENCE: 167

```
gagaagcaat aggaaaatat ggccctggag aatggtgaaa gaagcagagt actgatcatt     60

ggaggaaccg gttattttgg cagaaggtta gtgaaggcca gccttgcctt cggacatgag    120

acttatgtcc agtatcgtgc ccaggcagcc tctgatatca acaaagtgga gacgcttatt    180

tccttcaaat ctcaaggagc acacctggtg gatgcttcca ttgacaatca cacaagcctc    240

gtaaatgccg tgaaacgagt ggaagttgta atatcggcga tgggtgccga gggtctgaga    300

gaggggcagc tgaaagtgat cgaggccatt aaagaggcag gaaccgtcaa gcgctttctt    360

ccttctgagt tcgggatggc ccagacagaa tggtgcacgc catctatccg ggcaacgagg    420

ttttctctga taa                                                       433
```

<210> SEQ ID NO 168
<211> LENGTH: 330
<212> TYPE: DNA
<213> ORGANISM: Pinus radiata

<400> SEQUENCE: 168

```
cggggagctt gacttgggac tggaaagcag cgggcatcgt ttcctgtggg ttctccgcgg     60

tcatccttcc aatccaaact tatctgcgct gctgcccccg ggtttcgaac agcggaccaa    120

agatcgtggt ctcgtggtta cctcatgggc tccgcaggtt tctatccttg cacacccgtc    180

aacaggaggt tttgtgagtc actgcggttg gaactcgatg ctggagagca tttggtttgg    240

agttcccatt atcgcttggc ccctccaagc tgaccaaagg ccgatcgggt tactttctgg    300

tgaatgatag tagaatagac ggtaggcttg                                     330
```

<210> SEQ ID NO 169
<211> LENGTH: 398
<212> TYPE: DNA

<213> ORGANISM: Eucalyptus grandis

<400> SEQUENCE: 169
ggaaaatttg gtatcggtag agagatcctg tgagatcgac gcgtgggtcg accttcaaaa 60
tttgacccgt gaggtgatct ctcgaacagc gtttggcagt agcttcgaag aaggcaaaag 120
gatctccgaa cttcaggggg aacaagccca gctcacgata atagcccttc aatcggtcta 180
catccctggt tggaggtttg tgccaactaa gatgaacagg aggatgaaga gcatagataa 240
ggaagtgcgg gctctgctca tggacatcat ccgcagaaga gagaaagcaa taagggaagg 300
ggaagctgct ggcgatgatc tgctggggct gttgctggag tcaaacatga aggagaatgt 360
cgggatgagc cttcacgatg tgatggacgg agttgcag 398

<210> SEQ ID NO 170
<211> LENGTH: 432
<212> TYPE: DNA
<213> ORGANISM: Eucalyptus grandis
<220> FEATURE:
<221> NAME/KEY: misc_feature
<222> LOCATION: (214)..(214)
<223> OTHER INFORMATION: n is a, c, g, or t

<400> SEQUENCE: 170
gttaccaaag ggcagcaacg tattcttaaa catgggttct atccacaggg atcccaagat 60
ttgggacaaa ccgttggagt ttagacccga gaggttcttg gaaggtccta gcaagtatga 120
tttctcaggt aacaacttcg catacatgcc attcggttct ggtcgaaggg tgtgtgcagg 180
gcttgcgctg gcagagagga tgcaaccata tgtnttggcc tctcttttgc actcattcaa 240
gtgggaaata ccaccagggt ctgagctgga tttactggac aagttcggcc ttgtggtcaa 300
gaaaatgaag ccccttgtcg ccattccaag accaagattg tccactctgg agctctacat 360
gtcgagatag atatttcatt agagtcccaa agctcttcat ttcaattcta agaaataaac 420
gtatcctgcc ag 432

<210> SEQ ID NO 171
<211> LENGTH: 303
<212> TYPE: DNA
<213> ORGANISM: Eucalyptus grandis
<220> FEATURE:
<221> NAME/KEY: misc_feature
<222> LOCATION: (105)..(105)
<223> OTHER INFORMATION: n is a, c, g, or t

<400> SEQUENCE: 171
ccatcgcggc cctggcccgg acctacgggc cgctcatgca cctgcggctc gggttcgtac 60
gacgtggtgg tggccgcgtc ggcctccgtg gccgccgagt tcctnaagac ccacgacgcc 120
aacttctcga gccggccgcc caactccggg gcgaacacat cgcgtacaac taccaggacc 180
tgatgttcgc gccctacggc ccgcggtggc ggatgctaag gaagataagc tccgtccacc 240
tcttctccgg caaggctctt aagcattaca gacacgttcg ccagaaaaag gtcgcaatcc 300
tca 303

<210> SEQ ID NO 172
<211> LENGTH: 518
<212> TYPE: DNA
<213> ORGANISM: Pinus radiata

<400> SEQUENCE: 172
cattagatat atatatatag acacgcattt acgatatcat tgcaacaatg tcattggtag 60
gctgggttgt ttttctaatc gctttgattt cgtatttggc tgccatcaca aatgcagcaa 120
tcgtcaatta taccttcatc attgaagcga agacagttac caggctatgc aaggagaata 180
caataatcac cgtcaatggg cagctaccag gtccgaccat ctatgtccat gacggagaca 240
ctgttattgt tgaaacttat aacaaggccg agtacaatgc cactcttcac tggcatggag 300
tggagcagtt gcgtacacca tgggctgatg gacctgcata tgttactcaa tgtcccattc 360
caccaggtgg tcgttataca tacagattca acatctctgg acaagaagga accgtgtggt 420
ggcatgccca ttactcatgg ctccgagcta cggtccatgg agcttttgta atccttccta 480
aggaaggaag ctcatatccc ttttctaaac ccaatgcc 518

<210> SEQ ID NO 173
<211> LENGTH: 309
<212> TYPE: DNA
<213> ORGANISM: Eucalyptus grandis
<220> FEATURE:
<221> NAME/KEY: misc_feature
<222> LOCATION: (284)..(284)
<223> OTHER INFORMATION: n is a, c, g, or t
<220> FEATURE:
<221> NAME/KEY: misc_feature
<222> LOCATION: (294)..(294)
<223> OTHER INFORMATION: n is a, c, g, or t

<400> SEQUENCE: 173
gccgctgatc ctaggattga gatctgcatg ctccccgtgg gtgatggcat cactctctgc 60
cgtcggatca gctgagcatc taatctcaag tccttatgat cagggttcat tcttaatgta 120
gaacccacga aaaagagagg gatttatgta tatcttgttg ctgtttcttt tccatgaacc 180
tagaaacggg attcgcaatt aaatgccaaa ttatgttgct gtttctcttt agtgctctcg 240
atttcttttt atttttaat ttttttgatc agtttcttcg aatnatctca agtncttcca 300
aaaaaaaaa 309

<210> SEQ ID NO 174
<211> LENGTH: 381
<212> TYPE: DNA
<213> ORGANISM: Eucalyptus grandis

<400> SEQUENCE: 174
taagacgaag aaatggaaac aacggccaag ccatcgcgaa acgcctttcc gcatatggaa 60
tgcactatat ttgatcttcc gcatgtggtg gccaatttag aagttagcga gaacgtgaga 120
tgtgttcctg ggacatgttt tgagtccata ccaccagcag atgcaataat attgaagtgg 180
atactccatg attggagcga tgaagacgct gtgaagatac tgaagcgatg caaggaggcc 240
ttaggcaagg gcaagggcaa gaaacagaag gtaattataa ttgacatggt gatggacaac 300
acgaagagcg ccaaagagac ggtcgaaacc cagctcttct atgacatgtt gattgatgaa 360
ccctcgccgt cgggaaaggg g 381

<210> SEQ ID NO 175
<211> LENGTH: 236
<212> TYPE: DNA
<213> ORGANISM: Pinus radiata
<220> FEATURE:
<221> NAME/KEY: misc_feature
<222> LOCATION: (37)..(37)
<223> OTHER INFORMATION: n is a, c, g, or t

<400> SEQUENCE: 175
tgaattacca catgcggctg atagatctgg tgaaggncgg aggattgatt gcgtatgaca 60
atactctgtg gcaaggatcc gttgcgcttc ccccagaagt cgccatgagc gaaggcatga 120
gttatgggga agacagagag catatgttgg aactaaacag ggcccttgct gcagaccctc 180
gcatcgagat tgctcagatc ccaattgccg atggagtgac gctgtgcagg cgcctt 236

<210> SEQ ID NO 176
<211> LENGTH: 404
<212> TYPE: DNA
<213> ORGANISM: Pinus radiata
<220> FEATURE:
<221> NAME/KEY: misc_feature
<222> LOCATION: (122)..(122)
<223> OTHER INFORMATION: n is a, c, g, or t
<220> FEATURE:
<221> NAME/KEY: misc_feature
<222> LOCATION: (254)..(254)
<223> OTHER INFORMATION: n is a, c, g, or t
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (349)..(349)
<223> OTHER INFORMATION: n is a, c, g, or t
<220> FEATURE:
<221> NAME/KEY: misc_feature
<222> LOCATION: (374)..(374)
<223> OTHER INFORMATION: n is a, c, g, or t

<400> SEQUENCE: 176
gtcgggaatt ccacttacca gaccattaat tcacgattca tcccacctca gcctggaaat 60
ttggtctgaa tctggagccc aatactgtac aagtagcctt ggtctcttcg ggaatccgtg 120
tntggaaaga agaaattgag atccggccaa agatggttgc agggtcagac ctgggcgctg 180
tgcaggccaa tggaaatcaa aatggaaatg gatttcatca tgtgcattct gttgatctct 240
gcattcagaa tggnccagac cctctgaact gggggcaggc tgccaaggcc ctgcagggct 300
cccactttga agaagtgaag ctcatggtgg ngtcctattt cggatccgng gaagtttcca 360
ttgaaggcaa atcngtcaca atcgcggatg tgaccgcagt tgcc 404

<210> SEQ ID NO 177
<211> LENGTH: 415
<212> TYPE: DNA
<213> ORGANISM: Pinus radiata
<220> FEATURE:
<221> NAME/KEY: misc_feature
<222> LOCATION: (20)..(20)
<223> OTHER INFORMATION: n is a, c, g, or t

<400> SEQUENCE: 177
cccaacgcta tgcgtctgan caggcaactt tcttcagtgc atttgtggcg gccatggata 60
aattgggcag tgtgggtgta aaaactggca cacaggggga ggtcaggagg agatgtgatg 120
cgttcaattg agaagagtaa agttcaaatt ctctccatta ttaaggtggg attgtatgca 180
tggttgagat taatgaacgg aacaaagaaa atttaatgtt ttgtaactag tgagattgat 240
gaattgaata aagaattttt cctgtcctct gattcaacct gttttgcact ctgtgaagca 300
ctttacagtc tggactctgg aaggaatcca tcaaatcgtg actaagaaaa gggtaatgat 360
tttaaagaga ttccgttgcg ctcattccat tgggggattc ctgaaaatat ctgcc 415

<210> SEQ ID NO 178
<211> LENGTH: 409
<212> TYPE: DNA
<213> ORGANISM: Pinus radiata

<400> SEQUENCE: 178
gatgggcgcg caattctttt cagccggctg gtgtagttgc tgttgaggtt acgggaggtc 60
ccacaattga gtttgtccct ggtcgtaagg attcactggc atcaccacga gaagggcggc 120
ttcctgatgc gaagaaaggt tcacaacacc taagggatat cttttatagg atgggcctat 180
ctgacaagga tatagttgct ctttctggag cgcacaccat tgggaaaagc acatccagaa 240
aggtcaggct ttgatggagc atggaccgag cagcctctga agtttgataa ttcatatttt 300
gtagagcttc tcaaaggcga gtctgaagga ttactccaat tgcctacgga caaatgcttg 360
gtagaggatc ccagtttccg cccttatgtg gatctttatg ccaaggatg 409

<210> SEQ ID NO 179
<211> LENGTH: 411
<212> TYPE: DNA
<213> ORGANISM: Eucalyptus grandis
<220> FEATURE:
<221> NAME/KEY: misc_feature
<222> LOCATION: (393)..(393)
<223> OTHER INFORMATION: n is a, c, g, or t

<400> SEQUENCE: 179
agagcttctc ccagagaggc ctctctatgg aagatctcgt cgctctttcg ggaggccaca 60
cactaggatt ttcccactgc tcctccttcg caggcaggat ccgcaacttc aacaccacgc 120
acgacatcga cccatcgatg cacccatccc tggcagcgag cctaagaggc gtgtgcccga 180
gcaagaacag gccaaaaaac gcagggacca ccatggaccc ttcctcgacc accttcgaca 240
acacgtacta cgggctgatc ctccagggga agggcctgtt ctcttcggac caggccctcc 300
tggcagtgcc caagacgaag gatctggtcg agaagttcgc aggctcgcac aaggaattca 360
cggatgcatt cgtcaagtcc atgatcaaga ttnagcagca tcacaggcgg a 411

<210> SEQ ID NO 180
<211> LENGTH: 334
<212> TYPE: DNA
<213> ORGANISM: Pinus radiata

<400> SEQUENCE: 180
gcatcatggg aagtacaact gggaagaaga gacagcctaa cagcaagcaa aacagcagca 60
aataacaaca ttccagcccc cacatcaaat gttgcaacac ttaactccaa gtttcagaat 120
gtaggcctca ctgaacaaga catggtcaca ctctcaggag cccatacaat aggaaaggcg 180
cgttgtgcaa cattcaactc taggctcacg ggacaaccgg atcccactct tcagaaagag 240
tttttgacat cgctccaaca aatctgcttt caagggctag ccagtaataa caacaccgta 300
acttcactgg atgtggagac tcccgtcatt tttg 334

<210> SEQ ID NO 181
<211> LENGTH: 343
<212> TYPE: DNA
<213> ORGANISM: Pinus radiata

<400> SEQUENCE: 181
atttcgctga actggatctg gatcgaagaa ggtattgcat atcaaagaaa gaggcaaata 60
tgactccggc cactgttttg ctttctatat ttgtgattgt atatggtagt gctgtgaacg 120
ctctgccaac tcccgtggcg ggtctttcgt ggacgttcta caacacaagt tgcccgtcat 180
tggagtcgat agtgcggaag cgcatggaag cctatttgag tgcagacatc acacaagctg 240
caggattgct gaggctccac ttccacgact gttttgtcca gggatgcgac gggtctgtgt 300
tgctgaactc aacatcgggg gagcaaacag ttgcgcccaa ctt 343

<210> SEQ ID NO 182
<211> LENGTH: 443
<212> TYPE: DNA
<213> ORGANISM: Pinus radiata
<220> FEATURE:
<221> NAME/KEY: misc_feature
<222> LOCATION: (164)..(164)
<223> OTHER INFORMATION: n is a, c, g, or t

<400> SEQUENCE: 182
atttcgctga actggatctg gatcgaagaa ggtattgcat atcaaagaaa gacgcaaata 60
tgactccggc cactgttttg ctttctatat ttgtgattgt atatggtagt gctgtgaacg 120
ctctgccaat tcccgtggcg ggtctttcgt ggaccgtttt acancacaag ttgcccgtca 180
ttggagtcga tagtgcggaa gcgcatggaa gcctatttga gtgcagacat cacacaagct 240
gcaggattgc tgaggctcca cttccacgac tgttttgtcc agggatgcga cgggtctgtg 300
ttgctgaact caacatcggg ggagcaaaca gttgcgccca acttatcact cagagcggag 360
gctctgaaaa tcatcaatga catcaaagag aacgtagaag cggcgtgcag cggaactgtg 420
tcgtgtgcag acattcttgc ctt 443

<210> SEQ ID NO 183
<211> LENGTH: 243
<212> TYPE: DNA
<213> ORGANISM: Pinus radiata

<400> SEQUENCE: 183
acattgatga ttgtgctacg cgtatttttt tcaatctcta gcacttggga aggtctggag 60
gaggcggctc caaggttgcc tgagggccgt gaccgttctt cactataaac accatattca 120
gtccccatac taaatggtcg tctaaatggc agtggagaaa ccacactcct ggattgtcag 180
ctttgaatct tatcgcaacc caaccgctca caggagctat tactgtgttg cgtagtgggg 240
atc 243

<210> SEQ ID NO 184
<211> LENGTH: 473
<212> TYPE: DNA
<213> ORGANISM: Pinus radiata

<400> SEQUENCE: 184
ggtggcccct agaagaaaca cactcagaga gtttgatcta taagaggaga gattcactcc 60
aaaatgcaca gggagattca ctccaccatc aaattttaat cattggcctt tttcctctca 120
acggccgatg gcgtaaacac gcgtaagcaa acaccaagat cctgaaacag tcgactgatc 180
gattcagaat aatttgaaag gaaactggac tactcaatca atttgttgac atttatcaag 240
aaatggatga ttcagtacag gaggtatcca aggaaggcaa tcaatgggca ggattcattg 300
agggtgagaa tgtaatccga agaggaaggg agattcttct acagcatgat aaccgggagg 360
cacataactg ggagtcacat aaacataagt ggtggccaca tttggaagaa aaaatcccgc 420
acattgccaa agcaggattt acatctatat ggctgccgcc tgcttttgat tcg 473

<210> SEQ ID NO 185
<211> LENGTH: 641
<212> TYPE: DNA
<213> ORGANISM: Pinus radiata

<400> SEQUENCE: 185

```
ggcaccgagc tgggataccc ctgctgcgac ttgatccctt ttgaacagga attatttaat     60

tttcctaatt attttagttt gcaaggaaac ttgactactc catcaatttg tttacagttt    120

tcgaaaaatg ggctatccag ttcaggaggt atccaaggaa cacgatcaat gggcaggatt    180

tgttgaaggt gaaagtgtgc ttcaaagagg aagggagatt cttctccagg gttttaactg    240

ggagtcacat aaatacaagt ggtggccaaa tttggaagaa aagatcccgc acattgctaa    300

agcaggattt acatctgtat ggctgccacc tgcttttgat tctgctgcac cccaaggtta    360

cttgccccga aacatttatt ctctgaactc tgcatatggt tcagaatatc agctgaaaag    420

cttacttatg acaatgcgaa agaaaaatgt gagagccatg gctgacatag ttatcaatca    480

tcgcatggga agctctcagg ggtttggagg cttgtataat cgctattatg gttgcctgcc    540

ttgggatgaa cgtgctgtta cacgttgttc tggtggactt ggaaactgga gcacagggga    600

taattttcat ggagtaccaa acgttgatca cacccaagat t                        641
```

<210> SEQ ID NO 186
<211> LENGTH: 655
<212> TYPE: DNA
<213> ORGANISM: Pinus radiata

<400> SEQUENCE: 186

```
agaatggcca agtttcgatc tctgtcttta ttgttatggt tctcctgcat catagtcaat     60

gcagcctctc ctgcacaagc agaagctaca acgcctcctc tgaataccct cttacttcag    120

ggcttcaatt gggattcagc ccagagttct actccttggt ataatgtatt gaagggaatt    180

gtagacgatg cagcggacgc cggcattacg tacgtctggt ttccgccgcc ctcacaatcc    240

ggcgcccctc aaggttattt gccagcgaag ctctatgatt tagactcgtc ctacgggagc    300

gagcaacaac taaaggatgc cgtgaatgcg ttccaccaaa agggaattgc gattatgggc    360

gacatcgtga taaaccatcg gaacgggacg aagcaggacg ataaaggata ttggtgcgtg    420

tttgagggcg ggaaggggga cggtactctg gactggggac cctgggcggt caccgtgaag    480

gaccaaccat atccgttgtg cggctccggc caggcggaca ccggagggga cttcaagtac    540

gccccggacg tggaccacac caatcccaag atacagcaag atttgtcgga gtggatgaat    600

tggctcaagt ccatgtcgga tttgatggct ggaggttcga ctacgtcaag gctac         655
```

<210> SEQ ID NO 187
<211> LENGTH: 438
<212> TYPE: DNA
<213> ORGANISM: Eucalyptus grandis

<400> SEQUENCE: 187

```
ctggggtggg gaggctggtc gacgtgggcg ggagcgcggg ggactgcctc cggatgatca     60

tggggaagca cacgcacgtc cgggaaggga tcaacttcga cttgcccgag gtcgtggcca    120

aagcgcctcc cattcctggg gtgacccatg ttggtggcga catgttcaag tccatccctg    180

ctggtgatgc cattttcatg aggtggatac tgacgacatg gacggacgac gagtgcaagc    240

agatactgga aaactgcttc aaggcactcc ctgcgggagg gaagctgatt gcctgcgagc    300

cggtgctacc gcagcactca gatgatagcc acaggactcg agcacttctt gagggcgaca    360

tcttcgtgat gaccatctac agggccaagg gcaagcatag gactgagcag gaattccagc    420

agctcgggct ctctaccg                                                  438
```

<210> SEQ ID NO 188
<211> LENGTH: 597
<212> TYPE: DNA

<213> ORGANISM: Eucalyptus grandis

<400> SEQUENCE: 188
acccaacaat ggccgacaac caagaacgcg aagggcgcga tcaagaagag gaagtcggga 60
agctggcggt ccagctggcc agcgcggtgg tgctcccgat gaccctcaag tcggccctcg 120
agctcggcat catcgacgcc ctcgtctccg ccggtgggtt cctctcggct gccgagatag 180
cgagccgggt tggcgccaag aacccggggg ccccagtcct ggtggaccgg atgatgcgcc 240
tcctggcgag ccacggcgtg atcgagtggc ggttgaggag gggcgacggc aacggagatg 300
gaggggagag agagtacggt ccaggaccca tgtgcaggtt ctttgccaag gaccaagaag 360
gtggagatgt tggtcctctg tttctgctaa ttcacgacaa ggtcttcatg gagagttggt 420
accacttgaa cgatgtcatc atggaaggag gggttccgtt cgagagggca tacgggatga 480
cggcgttcga gtatcctgcc gttgacgata ggttcaatca agttttcaac cgggccatgg 540
cgagtcatac ttccctcatc atgaagaaaa tactcgatgt ctacagaggg tttgaag 597

<210> SEQ ID NO 189
<211> LENGTH: 470
<212> TYPE: DNA
<213> ORGANISM: Eucalyptus grandis

<400> SEQUENCE: 189
cccgaccccg ctttacatga acaagatcct cgagtcgtac cgtgggtttg agggcgcaaa 60
gacgattgcc gacctaggtg gcggcgtcgg ccagaacctt cggctcatat tggacaagtt 120
cccaaatctc aggggcatac tctatgatct gcctcatgtg atcaaagatg cacctgccca 180
tcctcgtatg gagcgtgtcg gaggagacct gttaaagtct gttccgaaag cagatatact 240
cttcatgaag tggcttttcc atggtctacg agacgatttc tgcaaaatgc tactccagaa 300
ctgttacgag gcgctgccac caaatggcaa ggtggtcatc gtggacccga tccttcccga 360
ataccccgag acagacatag tgtcgaggaa ctcgttcacc tccgacatga tcatgctata 420
cacgagccct ggagaagacc ggacgaggaa agagctggag gtgctcgcac 470

<210> SEQ ID NO 190
<211> LENGTH: 499
<212> TYPE: DNA
<213> ORGANISM: Eucalyptus grandis

<400> SEQUENCE: 190
gtccagtttt cagccgtgct atgaagaagc caacagttta gaccgttgga ttcagcctcc 60
gtcggatctg cttcataata tgtccgataa agaactattt tggagagcga cccttgttcc 120
taaaatcaag aagtatccat tcagaagagt tccaaaaatt gctttcatgt tcttgaccaa 180
gggtccattg ccgctggctc ctctttggga gaggttcttc aagggccatg aggggcttta 240
ttcgatctat attcattccc atccatcatt ccatgcccac tttcatcctt ggtcggtatt 300
taacaggaga caaatcccaa gtcaggtgtc tgagtggggc aggatgagca tgtgtgatgc 360
agagaaaaga ctcctagcca acgcattgct agacatatcc aatgagcggt tcattcttct 420
ttctgaatca tgcattccgc tgtataactt cagcctcatc tatcactaca ttatgaagtc 480
cggatatagc ttcatgggt 499

<210> SEQ ID NO 191
<211> LENGTH: 1036
<212> TYPE: DNA
<213> ORGANISM: Eucalyptus grandis

<400> SEQUENCE: 191
ggcaagtggt ggctggaatt cacacccatt gcgctctctc tctctctcta gatcctatct 60
cgaaagccaa aagaaaagac agtcggaaga aaaaatataa aaaaaaacat gagttcgaag 120
gaagccccag tcattacaac ttcccatgaa gatgaagaaa ttttgaatgc ctttgaggtc 180
ccctcaatgg cttttgttcc catggtcttg aaaggcgtcc atgagctggg gattcttgaa 240
ttgctggcca agggtgacca gctctctccg ttggacatcg tggcccgcct ctctatcgac 300
aacccggccg caccggacac gatcgaccgg atgctgcggc tccttgcgag ttactccatc 360
ttatcgtgca ctctcgtgga ggataaagaa ggccgccccc agaggctcta cggcctcggg 420
cctcggagca agttcttttt ggaccagaat ggagcttcta ctttaccaac tcatatgcta 480
ctccaagaaa agactctcct ggaatgctgg aactgcctta aagatgcagt taaggaagga 540
ggggcagatc ctttcacccg caggcacggc atgaacgtgt tcgactacat gggccaggac 600
ccgagattca acgacctgta caacaagtcg atgaggaccg ggtcggcgat ttacatgccc 660
aagatcgctc agcattatcg tgggttttca aaggcgaaga cggtcgtcaa tgtgggcggt 720
ggcatcggcg agaccctgaa aaccatactc tccaagaatc cccacatccg cgccatcaac 780
tacgacttgc ctcatgtgat cgcaactgct cctcccattc ctggtattac gcatgttgga 840
ggagacattc taaagtccgt ccctaaagcg gatgtccatt tcctgaagtc ggttctccat 900
cgcggggatg atgagttctg cgtgaaggtg ctcaagaatt gctgggaggc attgccgccg 960
acggggaaag tggtgatcgt ggaggaagtg accccggagt atcctgggac cgacgatgtc 1020
tcacagacca cgctct 1036

<210> SEQ ID NO 192
<211> LENGTH: 682
<212> TYPE: DNA
<213> ORGANISM: Pinus radiata

<400> SEQUENCE: 192
agacgttgga ggaggtatag gctctgcctt gtccatcatt gtgaaggaac atccacacat 60
tcgtggcatt aatctcgatc tgcctcatgt cattgccact gcgcctctca taactggggt 120
ggagcacatg gagggaaata tgttcgagca catacccttct gccgatgcag tcatgatgaa 180
gtggatcctc catgactggg cggacgagga gtgtgtgaaa ttgctgagaa gaagctacga 240
cgcaacgcca gcgaagggaa aggtgttaat tgtggaagca gttgttgagg gagacaaaga 300
aggtgaaagc atgtcgaggc gattgggatt gttatatgat atatcgatga tggcttacac 360
aactggtggg aaggagagaa cagaggaaga attcaaaggg ttgttccagc gcgcagggtt 420
caagagccac accatcatca agttgccttt ccttcagtcg ctcatagtgc tgtccaaagc 480
ctaataagct attgcgcttc cgattatcgt tacaataacg ttggttttgc tggggttgtt 540
atcatgcagt atatgaccta tgttttatgt tatctggcag tataagattt ctgaagacat 600
ggttgaaatt attgtgagat tttaaagata tttatccatc ataaaaataa tggaatatga 660
taatattttt acaaaaaaaa aa 682

<210> SEQ ID NO 193
<211> LENGTH: 399
<212> TYPE: DNA
<213> ORGANISM: Eucalyptus grandis

<400> SEQUENCE: 193
agcgtctaat ggttcctatt tagaagttca gaaagtctct gtctttccta ccttgcgggg 60
tagtctcttc ggacgtactc aaacatggag caaggctggg acaagggcga gatcctggca 120
agcaaagctc tctcgaagta catattggag accaatgcat atccgagaga gcacgagcag 180
ctgaaagaac tcagggaggc cacggtccag aagtaccaaa tccggagtat aatgaacgtg 240
ccggttgatg aggggcagct gatctccatg atgttgaagc tcatgaatgc gaagaagaca 300
atcgagatcg gagtcttcac cggctactct cttctgacca ccgcacttgc acttccggcc 360
gacggcaaga taatagcgat agaccaggat aaggaggcc 399

<210> SEQ ID NO 194
<211> LENGTH: 399
<212> TYPE: DNA
<213> ORGANISM: Eucalyptus grandis

<400> SEQUENCE: 194
cggacgtact cagacatgga gcgaggcggg gacaagggcg agatcctggc aagcaaagct 60
ctctcgaagt acatattgga gacgaatgca tatccgagag agcacgagca gctaaaagaa 120
ctcagggagg ccacggtcca aaagtaccaa atgcggagta taatgagcgt gccggctgat 180
gaggggcagc taatctccat gatgttgaag ctcatgaatg cgaagaaaac aatcgagatc 240
ggagtcttca cgggctattc tcttctcacc accgcacttg cacttccggc cgacggcaag 300
ataatagcaa tagacccgga taaggaggcc tatgaaattg gcctgccata tatcaaaaaa 360
gccggagtcg atcataagat caacttcatc cagtcggat 399

<210> SEQ ID NO 195
<211> LENGTH: 296
<212> TYPE: DNA
<213> ORGANISM: Eucalyptus grandis

<400> SEQUENCE: 195
ttgcagtaca tattggagac gaatgcatat ccgagagagc acgagcagct gaaagaactc 60
agggaggcca cagtccagaa gtaccaaatc cggagtataa tgaacgtgcc ggctgacgag 120
gggcagctaa tctccatgat gttgaagctc atgaatgcga agaagacgat cgagatcgga 180
gtcttcaccg gctgttctct tctcaccacc gcacttgcac ttccggccga tggcaagata 240
atagcgatag acccggataa ggaggcctat gaaattggcc taccatatat ccgaaa 296

<210> SEQ ID NO 196
<211> LENGTH: 474
<212> TYPE: DNA
<213> ORGANISM: Eucalyptus grandis

<400> SEQUENCE: 196
gcgccaccac caaacgctca ccttctcatc atcagccctc tgtctctgtc tctgtctctc 60
gattctccgc cccgccacga caatggaggc gaagccgtcg gagcagcccc gcgagttcat 120
cttccggtcg aagctccccg acatctacat tcccgacaac ctctccctcc acgcctactg 180
cttcgagaac atctccgagt tcgccgaccg cccctgcgtc atcaacgggg ccaccggccg 240
gacctacacc tatgccgagg tcgagctgat ctcccgccgg gtctcagccg gcctcaacgg 300
gctcggcgtc ggacagggcg acgtgatcat gctgctcctc cagaactgcc ctgagttcgt 360
gttcgcgttc ctcggcgcgt cctaccgggg cgccatcagc acgaccgcga acccgttcta 420
caccccgggc gagatcgcca agcaggcctc agctgcccgg gccaagatcg tgat 474

<210> SEQ ID NO 197
<211> LENGTH: 543
<212> TYPE: DNA

<213> ORGANISM: Eucalyptus grandis

<400> SEQUENCE: 197
gttcgccgac aaggtgaggc cgttcgcgga ggagaacggg gtgaaggtcg tgtgcatcga 60
taccgcgccg gagggctgcc tgcacttctc ggaattgatg caggcggacg agaacgccgc 120
ccccgcggcg gacgtcaagc cggacgacgt cttggcgctc ccctattcgt cgggcacgac 180
ggggcttccc aagggagtga tgcttacgca caggggtcaa gtgaccagcg tggcgcagca 240
ggtcgacgga gacaacccca acttgtactt ccacaaggag gacgtgatcc tgtgcacgct 300
cccgttgttc cacatatact ccctcaactc ggtgatgttc tgcgcgctcc gtgtcggcgc 360
cgccatcctg atcatgcaga agttcgagat cgtggcgctg atggagctcg tgcagcggta 420
ccgggtgacg atcctgccca ttgtcccgcc gatcgtgctg gagatcgcaa agagcgccga 480
ggtggaccgg tacgacctgt cgtcgatccg gaccatcatg tcgggtgcgg cccgatgggg 540
aag 543

<210> SEQ ID NO 198
<211> LENGTH: 564
<212> TYPE: DNA
<213> ORGANISM: Eucalyptus grandis

<400> SEQUENCE: 198
ctggacaact agttgcagga gttgaagctc aagttatcag cgtggataca ctaaaatctc 60
ttccccctaa tcagttaggg gaaatatggg ttcgtggacc taacatgatg aaaggatatt 120
ataacaatcc acaagcaact aaattgacaa ttgataacaa gggttgggtg cacactggag 180
accttggata ttttgatgag gaagggcaac tatatgttgt tgatcgaatc aaagagctca 240
tcaagtacaa aggttttcag attgctccag ctgagcttga aggactcctt ctttcacatc 300
ctgaaatttt agatgctgtt gtcattccat ttcctgatgc tgaagctggt gaagttccta 360
ttgcatatgt cgttcgctca cctaccagct ctctaactga agaggaagtc cagaaattca 420
ttgccaatca ggttgcacca ttcaaaagac taaggagggt gacattcgtc aacagcgtcc 480
caaagtctgc ttccggcaaa attttgagac gtgagctgat tgcaaaagta cgagcaaaga 540
tataactgtg catgctcgat gcgt 564

<210> SEQ ID NO 199
<211> LENGTH: 455
<212> TYPE: DNA
<213> ORGANISM: Pinus radiata

<400> SEQUENCE: 199
ggctactttg atgaggaagg aggattattt attgtggatc gtattaaaga actaatcaaa 60
tacaaaggtt tccaggttgc ccctgctgag ttggagggca tattgttgac acatccccaa 120
attgcagatg ctggagttat tccccttcct gatctaaaag ctggagaggt tccaatagca 180
tatgttgtac gtacccctgg aagctctttg acggaaaagg atgccatgga ttatgttgcc 240
aagcaggtcg caccatttaa aaggttgcat agagtcaatt ttgtagactc tatacccaag 300
tctgcctcag ggaagattct tcgacgagag cttattgcta aggccaaatc aaaattgtaa 360
gcaaagaaat atatcatttt ttctggtatc atgatacaaa gttgcacaaa cttatttgta 420
agtgtcaccc cagatgaaca aggaatttgt tccgc 455

<210> SEQ ID NO 200
<211> LENGTH: 569
<212> TYPE: DNA

<213> ORGANISM: Pinus radiata

<400> SEQUENCE: 200

```
gtcgtctgta aattactctg tgagtgttta gtgttttctt ctcttattga tttcagggga     60
caagtaggtg ggggtggggg agcttaagtc aaatctagtg ctttctctgt aagattttcc    120
ctttttttttc ttgctaagag tagccatgat tgaggtacag tcagctcccc ccatggcacg    180
gtccactgag aacgagaata accagcatga tgccgaagaa ggggcggtat tgaatgaggg    240
cggcatggat tttctgtatc ggtcaaagct tccagacata gatattccat accatcttcc    300
attgcactcg tattgcttcg agaaactgga cgagctcaga gagaagccat gtctgataca    360
ggggtcgaac gggaagattt acagctatgg cgaagtggaa ttgatatctc gcaaggtggc    420
ctcgggtttg gccaaattgg gattcaaaaa gggggacgtg gtcatgctgc tgctgcccaa    480
ttgccccgaa tttgtctttg ttttcctagg ggcgtccatg gctggtgcca ttgccaccac    540
ggcgaaccct ttttacactc cctccgata                                      569
```

<210> SEQ ID NO 201
<211> LENGTH: 993
<212> TYPE: DNA
<213> ORGANISM: Eucalyptus grandis

<400> SEQUENCE: 201

```
tgaccatcct ccggcaatgg ctcttcacat cctcttcaca tggcttgctc tttcccttcc     60
tctcctcctc ctcctcctcc tctcagtgaa aaacttcaat aacaaaaaga agaacctccc    120
tccagggcct ccatcacttc ccatcatagg caacttccac cagctcggcc ccctgcctca    180
tcagtctctg tggaaactct ccagacgata tggccccgtc atgctcatcc gcctcggtgg    240
cacccctacc atcgtaatct cctcccctga tgctgccagg gaggtcctca agacccacga    300
ccttgatagt tgcagtcgcc cgcagatggt cggcccggga cgcctctcct atgactccct    360
cgacatggcc ttcgtggagt acggcgatta ctggagggag ttaaggacgc tgtgtgtgct    420
cgagctgttt agcatgaagc gagtccagtc cttccgatac atcagggaag aggaggtggg    480
atctatgatc gaatcgatcg caaaatcagc agagagcgga actccggtta atatgagcga    540
gaagttcatg gctctgacgg ctaacttcac ttgcagggtc gcatttggga agccatttca    600
ggggacggag ttggaagacg aagggttcat ggatatggtt cacgagggaa tggcgatgtt    660
gggaagcttc tcggcatctg attatttccc tcgactcggc tggattgtgg acaggttcac    720
ggggctccat tcgaggttgg agaagagctt tcgcaatttg gacgatctct atcagaaggt    780
gatcgaagag catcggaatg cgaataagag caacgaggga aaggaggaca ttgtcgatgt    840
gctgctgaag atggagaaag atcagactga gctcgcgggg gtccggctca aggaagataa    900
catcaaggcc atcttgatga atatatttct cggaggagtg gacaccggtg cagtgtcatg    960
gactggacaa tggctgagct cgctaggaac ccg                                 993
```

<210> SEQ ID NO 202
<211> LENGTH: 349
<212> TYPE: DNA
<213> ORGANISM: Eucalyptus grandis

<400> SEQUENCE: 202

```
ggacggagtt ggaagacgaa gggttcatgg atatggttca cgagggaatg gcgatgttgg     60
gaagcttctc ggcatctgat tatttccctc gactcggctg gattgtggac aggttcacgg    120
ggctccattc gaggttggag aagagctttc gcaatttgga cgatctctat cagaaggtga    180
```

tcgaagagca tcggaatgcg aataagagca acgagggaaa ggaggacatt gtcgatgtgc 240
tgctgaagat ggagaaagat cagactgagc tcgcgggtgt ccggctcaag gaagataaca 300
tcaaggccat cttgatggta tatcatacaa tctctacgta ttacttaat 349

<210> SEQ ID NO 203
<211> LENGTH: 432
<212> TYPE: DNA
<213> ORGANISM: Eucalyptus grandis

<400> SEQUENCE: 203
cttggtcgta gcagctttgc tgattgttct cttgaggagc aagtctagga aaagaaagag 60
caacctccca ccgagccctc ctaagttgcc gatcatcggc aatcttcacc agcttggcaa 120
atcgccacac atatctctcc atcgccttgc gagaaactac gggccaatca tgtccttgca 180
gctcggcgaa gtcccaacca tagtcgtttc ctcagccgca atggccaagg aggtgatgaa 240
aacccatgac ctagtgctcg caaaccgccc tcagatcttc tctgccaagc acttgtttta 300
tgactgcaca gacatggcct tctctcccta tggcgcttat tggaggcaca taaggaaaat 360
ctgcatactt gaagtgctta gcgcaaaacg ggttcagtca tttagtcatg tcagggagga 420
agaagttgct cg 432

<210> SEQ ID NO 204
<211> LENGTH: 407
<212> TYPE: DNA
<213> ORGANISM: Eucalyptus grandis

<400> SEQUENCE: 204
ctcaccttca aatgcctccg cttcctcttc tcctctgccg ccgctactaa ccttcacctt 60
ccgccatcac cgccgaagct ccctatcatc gggaacctcc accagctcag tgatcaccct 120
caccgctcgc tccaagccct gtcgagacgc tatggcccct tgatgatgct ccacttcgga 180
agcgtgcccg tcctcgtcgt atcttccgcc gactgtgcac gggacatctt gaagacccac 240
gacctcattt tctccgaccg acccaggtca accctgtcgg agaggctttt gtaccaccgc 300
aaggacgtgg ctctggcgcc gtttggcgag tactggaggg aaatgaggag catctgtgtc 360
ctccagctgc tgagcaacaa gagggtccac tcgtttcgga cggtcca 407

<210> SEQ ID NO 205
<211> LENGTH: 384
<212> TYPE: DNA
<213> ORGANISM: Eucalyptus grandis

<400> SEQUENCE: 205
gggaaattac cccacaggtc gctggatcga ctctccaaaa catatggccc cctcatgtat 60
atgagactcg gatccatgcc atgcgtggtc ggctcatccg ctgagatggc ccgagagttt 120
ctcaagaccc acgatctcac attctcgtcc cgaccccgtg tggcggccgg gaaatacact 180
gtttacaact actccgacat cacctggtct ccctacggag agcactggcg tctcgccaga 240
aaaatctgcc tcatggagct cttcagtgcc aaacgcctcg aatctttcga gtacatcaga 300
gtagaagagg tcgcccggat gctgagttcc gtcttcgaaa ccagccggca gggccttcct 360
gtagaaatca gggaagagac gact 384

<210> SEQ ID NO 206
<211> LENGTH: 543
<212> TYPE: DNA
<213> ORGANISM: Eucalyptus grandis

<400> SEQUENCE: 206
ataaataaga atggtgaacg agttagggtc ggaaaagccc tttctggtat gcctagagtt 60
ttatatgaaa ctcgctattg ctctagttgc gttggtggtg gcatggagct tcttcgtcaa 120
gggaagaaat aggaagctgc ccccgggacc gttctctttg cccatcatcg gaaatctcca 180
tttgctggga cagcttccac accgagcact gaccgctctt tctctcaaat tcgggcctct 240
tatgtcgctt cgcctcggct ctgctcttac attagtagtc tcttcacctg atatggccaa 300
ggagtttctg aagacacatg atctgctttt tgctagcaga cctccatccg cggctactaa 360
ttatttttgg tataattgca ctgacatcgg ttttgctccg tatggcgctt actggaggca 420
agtgcgtaag gtgtgcgttt tacagttgct gagctccaga cgcttggatt atttccgctt 480
tataagagaa gaggaggtct ctgctatgat tcattctatt gctcattccg atcatcctgt 540
aaa 543

<210> SEQ ID NO 207
<211> LENGTH: 1320
<212> TYPE: DNA
<213> ORGANISM: Eucalyptus grandis

<400> SEQUENCE: 207
tcatcacttg catttggcca gcacatcata gctacctctt atagctgtaa tcttcaccaa 60
attggagaga tgagcttcca gaaccagctc ttcatcttct gcacgttgct actagggttt 120
ctgaagttgg cagaaggcaa aacgaggcac tacaccttcc atatcgattc ccataacatg 180
acgaggctgt gccacacgag gagtgtgctg agtgtaaaca agcagtatcc agggccgccg 240
cttgtggcga gggaaggcga caacatcctc gtcaaggtgg tgaatcatgt tgccgccaac 300
gtcacgattc actggcatgg ggttcggcaa ctgaggacgg gatgggcgga tggaccggct 360
tacgtaaccc agtgtcccat acagaccaac cagagctaca cctacaactt caccctcacc 420
ggccagagag gaacgctgct gtggcacgcg cacgtctcgt ggctaagatc gagcatccac 480
ggccccatca tcatcctccc caagcggaac gagtcctacc cgttcgagaa accctccaag 540
gaagtcccca taatatttgg agagtggttt aatgtagacc ccgaagcggt catcgcccaa 600
gctcttcaga gtggaggagg tcccaatgtc tccgatgcct ataccatcaa tggccttcca 660
ggacccttgt acaattgctc ctctaaagac accttcaagt tgaaggtgaa acctgggaag 720
acatacctcc tccggctgat caacgctgca ctcaacgacg agctcttctt cagcatagcc 780
aaccacgcag tcaccgtcgt cgaggttgat gccgtgtaca ctaagccctt ttctgcgggc 840
tgcctccacc taaccccggg ccaaaccatg aatgtcctcc tcaagacaaa aaccgacttt 900
cccaactcca ccttcctcat ggcagcgtgg ccctatttca ccggcatggg cactttcgac 960
aattccaccg tcgccggaat ccttgagtac gaacatccaa agagctcaaa ttacccgccg 1020
ctcaagaagc tcccccaata taaaccaact ctccctccca tgaacagcac cggttttgtc 1080
gccaaattta cagggcaatt gcgtagtttg gccagcgcta agtttcctgc caacgtgcca 1140
caaaaggttg acagaaaatt cttcttcacc gtcggccttg ggaccagtcc gtgccccaaa 1200
aacaccacgt gtcaaggacc aaatggcacg aaattcgccg catcagtcaa caacatatcg 1260
tttgtgctgc cgtccgtcgc tctcctgcag gctcacttct tcggccagtc caacggagtg 1320

<210> SEQ ID NO 208
<211> LENGTH: 980
<212> TYPE: DNA
<213> ORGANISM: Eucalyptus grandis

<400> SEQUENCE: 208
ctccggccgt ggttgagggc agagtccgta actacacatt caatgtggta atgaagaata 60
ccacgagact gtgttcgagc aagcccatcg tgaccgtgaa cgggatgttc ccgggaccca 120
ctctctatgc tagggaagat gacaccgtgc tcgtgagggt ctctaaccgt gtcaaataca 180
atgtcaccat ccattggcat ggtatccggc agttgaggac ggggtgggcc gacgggccag 240
catacattac ccaatgcccg atccagccgg gccaaagcta tgtgtacaat ttcaccatca 300
cgggccaacg gggcaccctc ctgtggcatg cacacatact ctggctcagg gcaaccctgc 360
acggagccat tgtcatcttg cccaagcgtg gtgttccata ccctttccct aaaccccaca 420
aggaagttgt tgtcgtattg ggcgaatggt ggaaatctga tacagaaggt gtgatcagtc 480
aagccatcaa gtccggatta gcaccgaatg tctccgatgc tcacacgatc aatggccatc 540
cagggccaag ttccaattgc ccttcccagg gtggatttac gttgcctgtt gagagtggca 600
agaagtacat gctgcgaatc atcaacgctg cgctcaatga ggagctcttc ttcaagattg 660
ccgggcacca gctgaccatc gtggaggtcg acgccaccta cgtcaagcct ttcaagaccg 720
acacgatcgt gattgcacct ggccaaacca ccaatgccct catctccacc gaccagagct 780
ctggcaagta catggtcgcc gcctcccctt ttatggactc cccgatcgcc gtcgacaaca 840
tgaccgcgac cgccacatta cactactctg gcacgcttgc tgcgacctcc acgaccctca 900
ccaagactcc cccacaaaac gcgaccgctg tggccaacaa tttcgttaac tcgctccgga 960
gcctcaactc gaagaggtac 980

<210> SEQ ID NO 209
<211> LENGTH: 305
<212> TYPE: DNA
<213> ORGANISM: Eucalyptus grandis

<400> SEQUENCE: 209
gaggctgtgt tcgagcaagc ccatcgtgac cgtgaatggg atgttcccgg gacccactct 60
ctacgctagg gaagacgaca ccgtgctcgt gagggtctcc aaccgtgtca aatacaatgt 120
caccatccat tggcatggta ttcggcagct gaggtcgggg tgggccgacg ggccggcata 180
catcacccaa tgcccaattc agccaggcca aagctatgtg tacaatttca ccatcacggg 240
ccaacggggc accctccttt ggcatgcgca catactctgg ctcagggcaa ccctgcacgg 300
agcca 305

<210> SEQ ID NO 210
<211> LENGTH: 411
<212> TYPE: DNA
<213> ORGANISM: Eucalyptus grandis

<400> SEQUENCE: 210
ttaccgtcga tcacagcctc cttttcacag ttggactagg aatcaaccct tgcccttcct 60
gcaaagctgg caacggaagc agagtcgtgg caagcatgaa caacgtgaca ttcgtgatgc 120
cgacgacagc cattctccaa gcacatttct tcaacaaaag cggcgtcttc acgagcgatt 180
tccccggtaa cccgccaacc attttcaact acacggggtc accgccatca aatttgcgga 240
ccacaagcgg gacaaaggtg taccggttgc gttataactc gacggtccag ctggtgtttc 300
aagacaccgg gattatcgcc ccagagaacc acccaattca tcttcacggg ttcaatttct 360
tcgccattgg gaagggatta ggaaattata atccgaaagt ggatcagaag a 411

<210> SEQ ID NO 211

<211> LENGTH: 311
<212> TYPE: DNA
<213> ORGANISM: Eucalyptus grandis

<400> SEQUENCE: 211
cacaaggaag ttgttgtcgt attgggcgaa tggtggaagt ctgatacaga agctgtgatc 60
aatcaagcca tcaagtccgg attggcaccg aatgtctcgg atgctcacac gatcaatggc 120
catccagggc caagttccaa ttgcccttcc cagggtggat ttacattgcc tgttgagagt 180
ggcaagaagt acatgctccg aatcatcaat gctgcgctca atgaggagct cttcttcaag 240
attgctgggc accagctgac catcgtggag gtcgacgcca cctacgtcaa gcctttcaag 300
accaacacgg g 311

<210> SEQ ID NO 212
<211> LENGTH: 334
<212> TYPE: DNA
<213> ORGANISM: Eucalyptus grandis

<400> SEQUENCE: 212
agcgtggcgt tccatatcct ttccctaaac cccacaagga agttgttgtc gtattgggcg 60
aatggtggaa gtctgataca gaagctgtga tcaatcaagc catcaagtcc ggattggcac 120
cgaatgtctc ggatgctcac acgatcaatg gccatccagg gccaagttcc aattgccctt 180
cccagggtgg atttacattg cctgttgaga gtggcaagaa gtacatgctc cgaatcatca 240
atgctgcgct caatgaggag ctcttcttca agattgctgg gcaccagctg accatcgtgg 300
aggtcgacgc cacctacgtc aagcctttca agac 334

<210> SEQ ID NO 213
<211> LENGTH: 1374
<212> TYPE: DNA
<213> ORGANISM: Eucalyptus grandis

<400> SEQUENCE: 213
accgaacgtg tccgacgctt ataccatcaa cggtcaacct ggagatctct acaactgctc 60
aagcaaagac accgtcatag ttccgatcga ttccggggag acccacctcc tccgagtcat 120
caacgctgcg ctcaatcagg aactcttctt caccgtagcg aaccataggt tcactgtggt 180
cggtgccgac gcctcctacc tgaaaccctt caccacctcg gtgatcatgc ttgggccagg 240
ccaaacgacg gatgtattga tctctggaga ccagcccccg gctcggtact acatggcggc 300
cgaaccctac cagagtgctc agggagcgcc ttttgacaac accacgacca cggccatact 360
ggagtacaag tccgccccgt gccccgccaa gggcatatcg agcaagccag tcatgccaac 420
cctaccggct ttcaacgaca cggctaccgt cacagccttc attcagagct tcaggagccc 480
aaataaggtt gacgtcccga ccgacatcga cgaaaacctc tttatcacgg tcggcctagg 540
actcttcaac tgcccaaaga atttcggtag cagtaggtgc caggggccga atgggacccg 600
tttcacggcc agcatgaaca acgtgtcctt cgtgctgccg tctaatgtct cgatcctgca 660
agcctacaag cagggcgtgc ctggagtttt taccaccgat ttccctgcta accccccctgt 720 ccagttcgat tacacgggga acgtgagccg ctcgctgtgg cagcccgttc cggggaccaa 780
ggtgtacaag ttgaagtacg ggtctagagt acagattgtc ttgcaaggaa ccaacataca 840
aacggccgag aaccacccga tccacattca cgggtacgat ttctacatcc tcgccacagg 900
cttcgggaac ttcaaccccc agaaagatac agcgaagttc aaccttgtcg acccgccaat 960
gaggaacaca gttggcgtct ctgtgaacgg gtgggctgtc attagatttg tcgccgacaa 1020

-continued

```
tccaggtgct tggttgatgc actgtcactt ggatgttcac atcacctggg gattggccgt   1080

ggttttcctt gtcgagaatg gagttggcga attgcaatct ctacagcctc ctcctgcaga   1140

tttgcctcca tgttaaaaga tctgcggctg acagatagtc ctccacgaga aattcataac   1200

gcccacaaca cgggcctatt ctaattttct tcttcttctt tcacctttcc gttttcgttt   1260

cgcggagttt cagttcagtg attgtttccc ctgaattcag ggagccacca gttgtttgct   1320

tgtctcatac tttttttat agataaaatt gtcttgcata aaaaaaaaaa aaaa          1374
```

```
<210> SEQ ID NO 214
<211> LENGTH: 418
<212> TYPE: DNA
<213> ORGANISM: Eucalyptus grandis

<400> SEQUENCE: 214

atcctgtctc agtctccatc atcacttgcg ccaagtaaca tctgatttcg aggaagacga     60

ggagcgcaaa atgggctccg ctactgctgc tggtgcctcg gtttcgtcgc gaatgattct    120

gatgagagcc gccttcttca cactgtgcgc tctcgtgttc ttgccggctc ttgctcaggc    180

gaagcacgga ggtgtcacca ggcattacaa gtttgatatc aagatgcaga atgtgacgag    240

gttgtgccag acgaagagca ttgtcacggt caatggccag ctcccggggc ctcgaatcat    300

cgctagagaa ggcgaccggc tcctaatcaa agtcgttaac aatgtccagt acaatgtcac    360

aatccactgg catggagtcc gacaactcag aagcgggtgg gctgacggac cggcatac      418
```

```
<210> SEQ ID NO 215
<211> LENGTH: 466
<212> TYPE: DNA
<213> ORGANISM: Eucalyptus grandis

<400> SEQUENCE: 215

ccggatcgag tgattagtac aagttcaatt ttgtatcagg gagagagagg gacgatggga     60

acatttctag ggttcgcagt cactgcgacc ctgctcttct gcgtggctca aggcgaagtc    120

ctcttttatg attttgtggt aaatgagaca cctattgaga tgctatgtga gacaaatcgg    180

agcgtactaa ctgtgaacgg tctatttcct gggccggaga tccatgctca caagggtgac    240

actatttacg ttaatgtcac caacttagga ccttatggag tcactattca ctggcatgga    300

gtgagacaaa tacggtatcc ttggtctgat ggcccagaat atgtcacgca atgcccccatc    360

cctacaaact cgagctttct tcaaaaaatc aaactcaccg aggaagaggg cacggtgtgg    420

tggcacgccc acagcgactg gtcacgtgcc acaatacatg gcctat                   466
```

```
<210> SEQ ID NO 216
<211> LENGTH: 757
<212> TYPE: DNA
<213> ORGANISM: Eucalyptus grandis

<400> SEQUENCE: 216

tcgggttctt tgtacaactt aatcggttgt atgtggatac agtgcagaaa ctgcccacga     60

attcagaatc aaatattatg agatgctcca cagttccccg gtttaagtac cttcccatca    120

gtgtacctgc attgtcttca aggaggacat ctaaagcaac tactgtaaga ctttggaccg    180

gcacgagcac aagtctcctt ctttgttctg gatcaagtga ttgttacaag ttcatttttc    240

tcttgttgag agagagagag agatgggaac atttctaggg tttgtggtca ccatgaccct    300

gctcttttgc atggctcaag gcgaagtcat ctactatgat ttcgtggtga aggagacacc    360

tattcagatg ttatgtggga cgaatcagac cgtattgact gtgaatggtc tgtttcctgg    420
```

-continued

```
gccagagatt catgctcaca aaggcgacac catctacgtt aatgtcacca acacaggacc    480

ttatggagtc actattcatt ggcatggagt gagacaaata agatatccct ggtccgacgg    540

cccggagtac atcacacaat gcccaatccc tacaaactca agtttccttc aaaaaatcat    600

actcactgaa gaagagggca cactatggtg gcacgctcat agtgactgga cacgtgccac    660

tatacacggc cctataatca ttttgcctgt caacggcacc aactaccctt acaagtttga    720

cgaacaacac acaatcgtga tatctgaatg gtatgca                             757
```

<210> SEQ ID NO 217
<211> LENGTH: 251
<212> TYPE: DNA
<213> ORGANISM: Eucalyptus grandis

<400> SEQUENCE: 217

```
acacaagtct ccttctttgt tctggatcaa gtgattgtta caagttcatt tttctcttgt     60

tgagagagag agatgggaac atttctaggg tttgtggtca ccatgaccct gctcttttgc    120

atggctcaag gcgaagtcct ctactatgat ttcgtggtga aggagacacc tattcagatg    180

ttatgtggga cgaatcagac cgtattgact gtgaatggtc tgtttcctgg gccagagatt    240

catgctcaca a                                                         251
```

<210> SEQ ID NO 218
<211> LENGTH: 762
<212> TYPE: DNA
<213> ORGANISM: Pinus radiata

<400> SEQUENCE: 218

```
gcctggcagt aatgtctaat gaacaactcc tggaatttgc ttggggattg gcttccagta     60

accaatcctt cttgtgggtt gtgaggtcag atatcgtgca tggtgaatct gccatattac    120

ccaaagagtt cattgaggaa accaaggata gaggtatgct ggtgggttgg gcgcctcaga    180

taaaggtact gtcgcaccca tctgtgggag gatttctaac tcacagcggt tggaactcta    240

cattggaaag cattagtgcg ggtgtgccaa tgatgtgctg gcccttcttt gccgagcaag    300

aaacaaatgc taaatttgtg tgtgaagagt ggggaatagg aatgcaggtg aagaaaatgg    360

tgaagagaga agagttggcg atactggtga ggaattcgat caaaggtgaa gaaggagatg    420

aaatgaggaa aagaattgga aaactgaagg aaactgccaa gcgagcagtt agtgaaggag    480

gctcttctaa gaacaactta gacaagttac tccatcatat attcctcaag ggaatgcatc    540

aaatgatagt ccagaatgtt gaagcaaaca attagttaga agagaacgtg taggacgaac    600

gaaaacatcc cagtacccca agcgttcata tttctgcatt tcgcattaaa tttactttgt    660

attgttccgc acatatgtat tttcaggttg tcaggtttcc ccagagttga acctcatttt    720

caattagatt gtttcacgtc tttacggcgc agggggttgt ga                       762
```

<210> SEQ ID NO 219
<211> LENGTH: 1144
<212> TYPE: DNA
<213> ORGANISM: Eucalyptus grandis

<400> SEQUENCE: 219

```
aaatagctca aaggttagtg tcgcgaccta aattggtgtc aacagctagc caatggagtc     60

ctgctctatt tcgctatttt ggctgggcct cctcctcccg gcacttctag ttttccttct    120

caaccgtcgg aagcgcacca agcttccccc tcagccccca gcatggcccg tgatcggcaa    180

cattttcgac ctcgggacca tgccgcacca gaacctccac aacctccgag ccaagcatgg    240
```

gcctgtcttg tggttgaagc tcggttccgt gaacaccatg gtgatccaat cagctcgagc 300
ggccatggag ttattcaagg gccatgactt cgtgttcgca gaccgcaagt gttcccaagc 360
gtttactgct ctcggctatg accaaggctc gctcgctctt ggtcgtcatg gtgactactg 420
gcgcgctctc cggcgtctct gctccgcgga gctcctcgtg aacaagcgcg tcaacgatac 480
ggcccacctc aggcaaaagt gtgtcgacag catgatcatg tatatagaag aagaaatggc 540
agtcaaacaa gcaacaaaag ggcaaggaat cgacttatct cacttcctct ttctcctggc 600
atttaatgtg gtgggcaaca tggtgctctc acgggatcta ttggacccaa aatcgaagga 660
tgggcccgag ttctacgacg ccatgaaccg gttcatggag tgggctggca agcccaacgt 720
agccgacttc atgccatggt tgaaatggtt ggatccgcag ggatcaagg caggcatggc 780 gaaggacatg ggtcgagcca tgaggattgc cgaaggcttt gtgaaagaga ggttggagga 840
gcgaaagcta aggggagaga tgagaacaac gaatgatttc ttggacgcag tattggatta 900
tgagggcgat ggaaaagaag gccctcacaa tatctcttcc cagaacataa atataatcat 960
tctggaaatg tttttcgccg gatcggagag tacaagtagc accatcgagt gggcgatggc 1020
ggagctactc cgccaacccg agtcaatgaa aaaggccaaa gatgagattg accaggttgt 1080
ggggttgaac agaaagctcg aggaaaatga cacggaaaag atgccatttt tgcaagccgt 1140
ggtg 1144

<210> SEQ ID NO 220
<211> LENGTH: 563
<212> TYPE: DNA
<213> ORGANISM: Eucalyptus grandis

<400> SEQUENCE: 220
agctcaaagc ttagccaatg gagtcctgct ctatttcgct attttggctg ggcctcctcc 60
tcccggcact tctagttttc cttctcaacc gtcggaagcg caccaagctt ccccctcagc 120
ccccagcatg gcccgtgatc ggcaacattt tcgacctcgg gaccatgccg caccagaacc 180
tccacaacct ccgagccaag catgggcctg tcttgtggtt gaagctcggt tccgtgaaca 240
ccatggtgat ccaatcagct caagcggcca tggagttatt caagggccat gacttcgtgt 300
tcgcggaccg caagtgttcc caagcgttta ctgctcttgg ctatgaccaa ggctcgctcg 360
ctcttggtcg tcatggtgac tactggcgcg ctctccggcg tctctgctcc gcggagctcc 420
tcgtgaacaa gcgcgtcaac gagacggccc acctcaggca aaagtgtgtc gacagcatga 480
tcatgtacat agaggaagaa atggcagtca aacaagcaac aaaagggcaa ggaatcgact 540
tatctcactt cctctttctc ctg 563

<210> SEQ ID NO 221
<211> LENGTH: 447
<212> TYPE: DNA
<213> ORGANISM: Eucalyptus grandis

<400> SEQUENCE: 221
taatgaaggc ccaagatgag attgattcta tgattggcca tgatagtttg ttagaagaat 60
cggatgtttc aaaactacct taccttcagt gcattatctt ggagaccctt cgactaaaca 120
cgacggcacc acttctcctc ccacacgcgt catcggctga ttgcactata ggaggatact 180
tcgtcccacg cgacactatt gtgatggtga atgcatgggc cattcacaaa gaccctcagt 240
tgtgggagga tccattgagc ttcaagcctg aaaggttcga gggcaatggc agcgaaaagc 300
aacaaaagct actattgcct tttggactgg gacggagggc atgccctggt gcccccttgg 360

-continued ctcatcgggt catggggtgg acgttgggct tgttgattca gtgttttgat tggaaaagag 420
taagcgaaga agagattgac atgacgg 447

<210> SEQ ID NO 222
<211> LENGTH: 494
<212> TYPE: DNA
<213> ORGANISM: Eucalyptus grandis

<400> SEQUENCE: 222
ttaccttggc gatttcctgc ccatactaaa gttggtcgat tacaatggag tcaagaagag 60
ggtggttgag ctgaaagaga aattcgatgc gttcattcag ggcttgatca acgagcaccg 120
gaggaagaag ggcgacccag agctcgcaga cagcatgatc agtcatcttc tgcatctaca 180
agaatctcag ccggaagact actcggactc catgatcaaa gggcttgtcc ttgttttgtt 240
agttgcggga acagacacgt catcgcttac attagaatgg ataatgacaa acttactaaa 300
caatcctgaa aagttagaga aggcccgaaa tgagattgat tctgttattg gccacgatcg 360
tctggtagaa gaatcggatg tttcgaatct accttacctt cagtgcatca tcttagagac 420
ccttcgacta aacaccacgg tgccacttct cgtcccgcac gcatcatcag ctgattgcac 480
cattggtgga tact 494

<210> SEQ ID NO 223
<211> LENGTH: 492
<212> TYPE: DNA
<213> ORGANISM: Eucalyptus grandis

<400> SEQUENCE: 223
gttgtcagat gcgatcccgg ctcttggctg gttggactca ggtggctata gacgatcgat 60
ggacgagaca gcgaaagagt tggatgtttt ggctcagggg tggctagagg agcatagaag 120
gaagagattg tcctgcccca aagacgacag agagcaagat ttcatggatt ggatgatcaa 180
cgccctcgaa ggtcggaatt ttccagattt tgacgcggat acagttatta aggcgacttg 240
tttgaacatg ataatagcgg ggactgatac ttcgacggtg gcgatcacct gggcgctatc 300
gctgctaatg aacaaccgtc gtgcattgaa gaaggcgcaa caagagctgg acacccatgt 360
tggcaggagt aggcccgtgg aagagtccga tgtgaaaaac ttgacctacc tccaagccat 420
cgtcaaggaa gcactgcgtt tatatcctcc agtaccggtg aacggcctta gaagctccat 480
ggaagagtgc ac 492

<210> SEQ ID NO 224
<211> LENGTH: 391
<212> TYPE: DNA
<213> ORGANISM: Pinus radiata

<400> SEQUENCE: 224
gcaggcttcc tccgggacct ccagggtggc cgattgtggg aaacctgttc cagttgggta 60
acaaacccca cgaagctctc ttccacctcg ctcagaagta cggccctctc atgtgtgtct 120
ctctcggaat gaaaactaca gtggtagtct cctctccggc catggcaaag caagttctca 180
agacccatga ccatgttttt gcgggccgaa cggtcataca gtcagttcag tgcctttctt 240
acgacaagtc ctcagtaatt tgggcccaat atggatccca ctggcgtttg ctcagacgca 300
tatccaatac aaagctcttc agcgtcaaga ggttagaagc cctggaacat ttgagaagag 360
atgaagtatt ccgaacaatc aagcagattc t 391

<210> SEQ ID NO 225

<211> LENGTH: 536
<212> TYPE: DNA
<213> ORGANISM: Pinus radiata

<400> SEQUENCE: 225
ctcgtttatt tacaagctgc ggtgaaagaa actcttcgac tccatccatc cgggccttta 60
ttggtgcgcc atttatttgg taccgcgtcc tgcaatgtat tggggtatga aatcccgcag 120
aatactctcg ttctcgtgaa tgtttgggcg attgggagga accctaagtc atgggaggac 180
gccgaagttt tcaagccaga gagattcatg gaaaaagttg ggtctgaagt agatgcaaat 240
ggagatcaaa actttgggtg ccttctcttc ggagcagggc ggagaagatg cccaggacag 300
caattgggaa cgcttcttgt agagtttggg ttggcacagc tgttgcactg cttcaactgg 360
aggcttccct tggatgacat aaatggcgaa aatcaagaag tggatatgaa tgaaatgttt 420
aatggagtca cgctgcgcaa agctcgtgag ctctcggcta ttccgacacc acgccttgaa 480
tgcattgctc acctgaaata ggtcatcagg tttcgagtga aacctgtgga gataga 536

<210> SEQ ID NO 226
<211> LENGTH: 463
<212> TYPE: DNA
<213> ORGANISM: Pinus radiata

<400> SEQUENCE: 226
gaaaggtacc gtcccgcttg aaaaatatct acagctttta gattggacgc aattataaac 60
attttattcc agtttgtatg tgttatctct gatcgtgttg gagatgtgtg gctgagccta 120
atcatgcatg gagcaacttg tccaggaaaa gaaaaggcag actgccccccg gggcctttct 180 cgttgcccat tatcggcaat cttcacatgc taggaaagat tcctcaccga tcactggcag 240
agctgtctat gaaatacggg cctctcctgt ctctccgcct cggctctact cccgccttag 300
tcgtctcttc tccagaaata gccagtgaat ttctcaaaac ccatgatcag ctttttgcca 360
gcagaattcc ctctgctgct attaaggtat tgacctacaa tttgtccggc ctcatatttt 420
ccccgtatgg cccttgctgg aggcaagtgc gtaaactttg cgt 463

<210> SEQ ID NO 227
<211> LENGTH: 463
<212> TYPE: DNA
<213> ORGANISM: Pinus radiata

<400> SEQUENCE: 227
ggctgagcct aatcatggtt attacatatc ttgaaccttt gtagtagatg ttgtttgtgg 60
atatagctaa tatcaaattg tttgagatag atgtttgctg gtagatatag ctagattagt 120
acagtgaacc atctaaaaaa ctggcgatgg agtttgtaga gttttgtata acactcgtca 180
ctgctcttct ttttgttgta ttggtagcag catggagcaa cttgttcagg aaaagaaaag 240
gcagactgcc cccggggcct ttctcgttgc ccattatcgg caatcttcac atgctaggaa 300
agattcctca ccgatcactg gcagagctgt ctatgaaata cgggcctctc ctgtctctcc 360
gcctcggctc tactcccgcc ttagtcgtct cttctccaga aatagccagt gaatttctca 420
aaacccatga tcagcttttt gccagcagaa ttccctctgc tgc 463

<210> SEQ ID NO 228
<211> LENGTH: 463
<212> TYPE: DNA
<213> ORGANISM: Pinus radiata

<400> SEQUENCE: 228

```
gaattgcttt ctgcgtgtcc agttcatgaa tgcccatact tttattttaa tctcgctact     60

gttattcttc tgggcgtggt gacgggatgg ggtttcttat tccggggaag aaaacagaag    120

cttcctccgg ggccttttca gtggccgatt gttggaaacc ttcacatgat gggagagctt    180

ccacaccaag caattacagc tctctctatg aaatatgggc ctctcatgtc tctccgcctc    240

ggctcctatc tcactttggt cgtttcttct ccagatgtgg ccgaggagtt cctgaagact    300

catgatctgg ctttcgccag cagacctcca accatcggta cgaagtactt ttggtataat    360

tcctccgacg tcgcattttc cccctatggt ccttactgga ggcagatgcg taaaatctgt    420

gtgttacagt tgctgagctc aagacgcata gattccttcc gcc                     463
```

<210> SEQ ID NO 229
<211> LENGTH: 463
<212> TYPE: DNA
<213> ORGANISM: Pinus radiata

<400> SEQUENCE: 229

```
actgtgacca agacctaatt ggtggcattg ggatcaagtc aatgataaag gaaacgtttg     60

tgttagcagg gtctttgaac atgggagatt ttataccata cttggcatgg attgatcttc    120

aaggtctcaa ccgtcgattg aagaacatac acaagatcca agacgacttg ttagggaaga    180

tactagagga acacgcttcg ccaccgcaga ataaccccaa ctacatgcca gatctcgtgg    240

atgttttgct cgcggcctct gcggatgaag atctggagtt cgaaattact cgagacaata    300

taaaatctgt catctatgta tatattgtcc atgcaattat tagatttcaa tgacttaaat    360

aaaacatgac acggtgatta tatcttgaca tttgttttgg atttgttttg ttggtaggat    420

atcttgtccg ctggttcgga ctcgtcgtct gcaagcatag agt                     463
```

<210> SEQ ID NO 230
<211> LENGTH: 543
<212> TYPE: DNA
<213> ORGANISM: Pinus radiata

<400> SEQUENCE: 230

```
ggcaccagac gagctggaac gtgtcgttgg attgggtcgt atggtaaggg aatctgatct     60

gcctcgtctc gtttatttac aagctgtggt gaaagaaact ctgaggctat acccacaggg    120

gccgatttta ttccgccact tgtcttcgga gccctgcaat gtcctgggct atgaaatctc    180

tcaaaacact caagttctgg ttaatatttg ggcgattgga aggaactctg agtcatggga    240

agatgccgga agcttcaaac ctgagagatt catggaaaga gttgggtctg aggtagatac    300

aaatggagat caaaattctg cgtggcttcc cttcggagca gggaggagaa gatgcccagg    360

acagcaattg ggaacgcttg ttgcagaaat tgggctggca cagctcttgc actgtttcaa    420

atggaggctt cccgaagctg atatggatgg cccaaatcaa gaacttgaca tgatggaaag    480

gtttaatgga atcacatcgc cgagggctaa ggaactgttt gcgattccga caccccgcct    540

tga                                                                  543
```

<210> SEQ ID NO 231
<211> LENGTH: 381
<212> TYPE: DNA
<213> ORGANISM: Pinus radiata

<400> SEQUENCE: 231

```
ggaatcctct ttgatatgtt gctcggtggg tcagacacag cgcctacaat aatagagtgg     60

gcaatatcgg aggcgctgat aaaccctcca gtgatgaaga aacttcagga cgagctggaa    120
```

-continued

```
cgcgtcgttg gattggatcg catggcatgc gaatctgatc tgcctcagct cgtttattta    180

caagctatgg taaaagaaac gcttcgactt cacccagcgg ggcctctttt gaaccgtcgc    240

ttatccgctg agtcctgcaa tgtgttgggg tacgaattcc ctaaaaacac tcgtgttctc    300

gttaatgctt gggcgattgg gaggaaccca aagttatggg aggacgctga actttcaag     360

ccagaaagat tcacgggaag a                                              381


<210> SEQ ID NO 232
<211> LENGTH: 384
<212> TYPE: DNA
<213> ORGANISM: Pinus radiata

<400> SEQUENCE: 232

ccacttcggc aacagttgaa tgggcaatgg ctgagcttat cagaaaacca acgctactga     60

aaaaggccca ggcagagctg gatgaggttg ttggtcgaga gaagagaatg gaggaatcag    120

acatagcaaa attgccctat ctacaagcag tagtgaagga ggtactcaga ttgcacccag    180

cagctccact gataattcct cgaagagcag acaactctgc cgagattggt ggatatgttg    240

tcccagagaa cacgcaggtg tttgtgaata tctggggcat cggaagagat cccaacgttt    300

ggaaggaacc tctgaaattc aaaccggaaa ggtttttaga ctgtaatact gactacagag    360

gccaggattt tgaactgata ccat                                           384


<210> SEQ ID NO 233
<211> LENGTH: 405
<212> TYPE: DNA
<213> ORGANISM: Pinus radiata

<400> SEQUENCE: 233

gagaagatga agtttccgct atgattcgct ctattgttaa ttcagatgcc cacaaggact     60

ctcgtcctgt caacatcaag caacttgcgt catcccttgt gacagctata gtcttgagga    120

tgaccttcgg taaaaagtat tcggaccggg attcaggagc attcagttca atgatcaaag    180

aaagtttact gttactcggc tcctttaata ttggagaata cataccttac ttgaactgga    240

tggatttgca aggtctcaac cgccggctga agaagctacg tacaacacaa gaccagttgc    300

tagagaaagt aatagaggaa catgctgccc agaatcggag caacatgacg catgatcttg    360

tggatgcctt acttgcagcc tctgcggata aagatagaga gctcc                    405


<210> SEQ ID NO 234
<211> LENGTH: 348
<212> TYPE: DNA
<213> ORGANISM: Eucalyptus grandis

<400> SEQUENCE: 234

catatacgat caagagagtt tgctgaatgc aattaagcag gttgatgtgg taatctctgc     60

tgtggggcaa gcacaaacgg aggaccaaga ccggattgtt gctgccatca aagcagccgg    120

gaatatcaag agattcttgc cttcagagtt tggaaatgat gtggatcgtg tccatgctgt    180

ggagccagta aaaactggat ttgctctcaa ggccaagatc cgccgccttg ttgaggccga    240

gggaatccct tatacctatg tgtcttctaa ctcttttgca ggttactacc ttcaaacatt    300

gtcacagccc ggggctacag ctccccctag agataacgtt gttatctt                 348


<210> SEQ ID NO 235
<211> LENGTH: 640
<212> TYPE: DNA
<213> ORGANISM: Eucalyptus grandis
```

<400> SEQUENCE: 235
ctgtgtgtta agctagtagt cagtcaagca ttgaaggcat gaacacctta aagacatgaa 60
cagatgaaga tttggagtct caattatact gtgtgttaag ctagtagtca gtcaagcatt 120
gaaggcatga acaccttaaa gacatgaaca gatgaagatt tggagtctca atggtattat 180
tgcctacctt atctccagtc acagcagagt cgcttctaga aaccgatcga gttcgccgga 240
aaacaccgcg cctccgccgt gaaaaccact cagagatggc tgcgaagagc aaggtcctgg 300
tgatcggagg cactggatac atcggaaagt tcatcgtgga agccagtgct aagtccggtc 360
gccctacctt cgctctcgcg agggagtcca ctctctccaa ccccgccaag gccaagatcg 420
tcgaaggttt caagagcctc ggcgtcactt tagttcacgg agacatatac gatcaagaga 480
gtctattgaa tgcgatcaag caggtcgatg tggtaatctc tgctgtgggg cgagcacaaa 540
tagaggacca agacaggatt gttgctgcca tcaaagcagc cgggaatatc aagagatttg 600
tgccttcaga gtttggaaac aacgtggatc gtgtccatgc 640

<210> SEQ ID NO 236
<211> LENGTH: 464
<212> TYPE: DNA
<213> ORGANISM: Eucalyptus grandis

<400> SEQUENCE: 236
gtctcgagtt ttttcttatt taattaattt tctttttaga gattcttgcc ttcagagttt 60
ggaaatgatg tggatcgtgt ccatgctgtg gagccagtaa aaactggatt tgctctcaag 120
gccaagatcc gccgcctcgt tgaggccgag ggaatccctt atacctatgt gtcttctaac 180
tcttttgcag gttactacct tcaaacattg tcacagcccg gggctacagc tccccctaga 240
gataacgttg ttatcttagg ggatggaaat gccaaagtgg tgtttaacaa ggaggatgac 300
atcggcacct ataccatcaa agctgtggat gatccaagga ccttgaacaa aattctgtac 360
atcaggcctc ctgccaacac ctactcaatg aatgagctcg tgtctttgtg ggagagaaag 420
atcggcaagg ctctggagag ggtgtatgtt ccagaggagc aaat 464

<210> SEQ ID NO 237
<211> LENGTH: 315
<212> TYPE: DNA
<213> ORGANISM: Eucalyptus grandis

<400> SEQUENCE: 237
cttctagaaa ccgatcgagt tcgccggaaa acaccgcgcc tccgccgtga aaaccacttc 60
agagatggcc gcgaagagca aggtcctggt gatcggaggc actggttaca tcggaaagtt 120
catcgtggaa gccagtgcta agtccggtcg ccctaccttc gttctcgcga gggagtccac 180
tctctccaac cccgccaagg ccaagatcgt ccaaggtttc aagagcctcg gcgtcacttt 240
agttcacgga gacatatacg atcaagagag tctgttgaat gcgatcaagc aggtcgatgt 300
ggtaatctct gctga 315

<210> SEQ ID NO 238
<211> LENGTH: 376
<212> TYPE: DNA
<213> ORGANISM: Eucalyptus grandis

<400> SEQUENCE: 238
caaagtcacg tcagagaccg atcaagttcg ccggaaaaca ccacgcgcgc tatgaaaaga 60
ccctccaaga tggcagagat gagcagagtc ttggtgattg gaggcgccgg atacatcgga 120

-continued

```
aagttcattg tgaaagcgtg tgctaagtcc ggtcacccta cctttgttct cgagacggag    180

tccactctct ccaaccccgc caacgccgaa atcatcaaag gtttcaagag cttaggcgtg    240

aacctagtcc atggagacat atacgatcaa aaaagtctgt tgagtgcgat taagcaagtt    300

gatgtggtaa tatctactgt ggggcaagca cagctagaag accaagacag gattgttgca    360

gccatcaaag cagccg                                                     376
```

```
<210> SEQ ID NO 239
<211> LENGTH: 297
<212> TYPE: DNA
<213> ORGANISM: Eucalyptus grandis

<400> SEQUENCE: 239

atcaagttcg ccggaaaaca ccacgcccgc tgtgaaaaga ccctccaaga tggcagagat     60

gagcagagtc ttggtgatcg gaggcgccgg atacatcgga aagttcatcg tgaaagcgtg    120

tgctaagtcc ggtcacccta cctttgttct cgagacggag tccactctct ccaaccccgc    180

caacgccgaa atcatcaaag gtttcaagag cttaggcgtg aacctagtcc atggagacat    240

atacgatcaa aagagtctgt tgagtgcgat taagcaagtt gatgtggtaa tctctac      297
```

```
<210> SEQ ID NO 240
<211> LENGTH: 951
<212> TYPE: DNA
<213> ORGANISM: Pinus radiata

<400> SEQUENCE: 240

tctcgcacag ttgacgacgt tttcttgtat ttgtagcgtt cggcacgatc ggggaaaaac     60

gatggcatgc gctactgatg ttgcacgtca gtttctgcca tgcgtccaac ccgtgccgtc    120

cagcatggga ggagagaccg cccggtcgat caacctcacc tgcaatggcc tctccccgcc    180

tcaaccgcag tacaacgccg agaacaacca tgatcaggac accacagttg ccacaagggt    240

tctcattatt ggcgccaccg ggttcatcgg tcggtttgtt gcagaggcca gtgtgaaatc    300

cgggcgccca acttatgccc ttgtgcggcc gacaacatta agttcgaagc ccaaggtcat    360

tcagtctctg gtggattcgg gtattcaagt tgtttatgga tgtctacatg atcacaattc    420

tttggtgaaa gccatcaggc aggttgacgt tgttatttct actgttggtg gagccctaat    480

tcttgatcag ctcaagattg tggatgccat caaggaagtt ggcactgtca agagatttct    540

tccttcagag tttggacacg atgtagaccg agcagatccc gtagagcctg ctcttagttt    600

ttacatagaa aagagaaaag tccggcgtgc agtggaggaa gcaaagattc cttacacata    660

catctgctgc aactccatag ctggctggcc atactattat cacacacatc caactgagct    720

ccccccacca aaggaacagt ttgagatcta tggggatgga agcgttaaag cctttttcgt    780

tactggggac gatattggcg cgtataccat gaaagctgtg gatgaccctc gtactctgaa    840

caagtctatt catttcagac caccaaagaa ttttctcaac ttaaacgaac tcgcagacat    900

atgggagaat aagattaaca gaactctgcc aagagtatct gtctcagcag a             951
```

```
<210> SEQ ID NO 241
<211> LENGTH: 371
<212> TYPE: DNA
<213> ORGANISM: Pinus radiata

<400> SEQUENCE: 241

tttagctgac attttattaa ttcaaagtgg caagatgaca ggtctcaagg actctgctaa     60

tagggttttg ataataggag gcacgggata cattgggaaa tacatggcaa aagccagcgt    120
```

ttcacagggc tatccaacct acgttcttgt ccgtcctgct acagcagctg cccctgattc 180
cttcaaagca aagctacttc agcaattcaa agatattggc attcatattc ttgaaggatc 240
attagatgat cacaacagcc ttgtggatgc aatcaagcaa gtagacatag taatatccgc 300
agttgccatt cctcagcatt tggatcagtt taatatcata aacgccatta aggatgttgg 360
aatggaaata t 371

<210> SEQ ID NO 242
<211> LENGTH: 687
<212> TYPE: DNA
<213> ORGANISM: Eucalyptus grandis

<400> SEQUENCE: 242
taatggcgag ctccacccgt ctcactactg tgagagggac ctgctcaaag tggtcgaccg 60
cgagcatgtg ttcacctacg ctgatgacgc ctgcagcgcc acctacccgc tgatgcagaa 120
gctgaggcaa gtcctggtcg accaggcact ggtgaatggc gagagcgagc tgaacccgag 180
cacttcgatc ttccaaaaga tcgtggcctt cgaggaggag ctcaaggccc agttgccgaa 240
ggacgtcgag ggcgttcgag tccagtacga gacaggcaac ctcgccatcc ccaaccagat 300
caaggaatgc aggtcctatc cattgtacaa gctggtgagg gaggagctgg ggactgccct 360
gctcacgggc gagggcgtga tatcccctgg cgaggacttc gacaaggtct tcactgcgat 420
ctgtgctgga aaactgattg atccgctgct ggagtgccta agcggttgga acggtgctcc 480
tcttcccatc tcttaggaat tgtcctatat tctttctcct tctttttccc tttccgttac 540
ttgccaagta aatctcatgt atccaatctt ttctatcaag agacaattgt atttcttgtt 600
ttctgtttgg tcctttttgt ctcctcccaa gtgaagaaat tggagaatat aagtaattga 660
gtaaattttt acatggaaaa aaaaaaa 687

<210> SEQ ID NO 243
<211> LENGTH: 344
<212> TYPE: DNA
<213> ORGANISM: Eucalyptus grandis

<400> SEQUENCE: 243
tcctggtcga ccaggcactg gtgaatggcg agagcgagct gaacccgagc acttcgatct 60
tccaaaagat cgtggccttc gaggaggagc tcaaggccca gttgccgaag gacgtcgagg 120
gcgttcgagt ccagtacgag acaggaaacc tcgccatccc caaccagatc aaggaatgca 180
ggtcctatcc attgtacaag ctggtgaggg aggagctggg gactgccctg ctcacgggcg 240
agggcgtgat atcccctggc gaggacttcg acaaggtctt cactgcgatc tgtgctggaa 300
aactgattga tccgctgctg gagtgcctaa gcggttggaa cggt 344

<210> SEQ ID NO 244
<211> LENGTH: 681
<212> TYPE: DNA
<213> ORGANISM: Eucalyptus grandis

<400> SEQUENCE: 244
cccaagcctg gattacggct tcaagggagc tgagatcgcc atggcctcat actgctcgga 60
gctgcagttc cttgccaacc ctgtgaccaa ccatgtccag agcgcggagc aacacaacca 120
ggacgtgaac tccttgggcc tgatctcgtc gaggaagact gccgaggcca tcgatgtgct 180
gaagctcatg tcctccacct tcctggtcgc cctgtgccag gccatcgacc tgaggcacct 240
ggaagagaac ctcaagagcg tggtcaagaa cacggtgaac caagtggcca agaaggtcct 300

```
ctacgtcggg tccaacggcg agctccaccc gtcgcggttc agcgagaaag acctgatcaa    360

ggtggtcgac cgggagtacg tcttcgccta catcgatgac ccctgcagcg ccacgtaccc    420

cctgatgcag aaactgaggc aggtcctcgt ggacgatgcg ctggacgacg tcgaccggga    480

gaagaacccc agcacctcca tcttccagaa gattggggct ttcgaggagg agctcaaggc    540

actcctcccg aaggaggtcg agaacgcgag agctcagttc gagagcggga actcggcgat    600

cgctaacaag atcagggggt gcaggtcgta cccattgtac aggttcgtga gggaagagct    660

cgggaccggt ttgctcacgg g                                              681
```

<210> SEQ ID NO 245
<211> LENGTH: 1455
<212> TYPE: DNA
<213> ORGANISM: Eucalyptus grandis

<400> SEQUENCE: 245

```
tttgcaatcc tctgaatttt ccctaactag aaataaagag attatataca tacacgagca     60

aagcgctctc ctccagttgt cttccttcgt tcgctcatct ctcctcgtac attattagca    120

tacgacctct tgtatcggac ccggatccgc tatcgttaac gtacacacgt tctagtgctg    180

aatggagatg gagagcacca ccggcaccgg caacggcctt cacagcctct gcgccgccgg    240

gagccaccat gccgacccac tgaactgggg ggcggcggca gcagccctca cagggagcca    300

cctcgacgag gtgaagcgga tggtcgagga gtaccggagg ccggcggtgc gcctcggcgg    360

ggagtccctc acgatagccc aggtggcggc ggtggcgagt caggaggggg taggggtcga    420

gctctcggag gcggcccgtc ccagggtcaa ggccagcagc gactgggtca tggagagcat    480

gaacaaggga actgacagct acggggtcac caccgggttc ggcgccactt ctcaccggag    540

gacgaagcaa ggcggtgctt tgcagaagga acttataagg ttcttgaatg ccgggatctt    600

cggcaacggc acggagtcgt gccacaccct gcctcaatcc tccacccgag ccgccatgct    660

cgtccgggtc aacaccctcc tccagggcta ctccggcatc cgttttgaga tcctcgaggc    720

catcaccaag ttcctcaacc acaacatcac cccgtgcctg cccctcaggg gcaccatcac    780

tgcctcaggc gacttggtcc ccctctccta cattgccggg ctcctgacgg gccggcccaa    840

ctccaaggcc gtcgggcctg atgggaagtc cctggacgct gtcgaggcct tccggctcgc    900

cgggattgac acgggcttct tcgagctgca gccaaaggaa gggttggcgc tcgtgaacgg    960

cacggcagtc gggtctggcc tggcttccat cgtcctcttc gaggccaaca tactcgcggt   1020

cctgtccgag gtcctgtcag cgatcttcgc agaggtgatg caggggaagc cggagttcac   1080

agaccacttg acgcataaat tgaagcacca tcccgggcag attgagtctg cggctataat   1140

ggagcacatt ttggatggaa gcgcttacgt gaaggctgct aaaaagttgc acgagatgga   1200

tccgctccag aagccaaagc aggacaggta cgctctcagg acttctcccc agtggctagg   1260

gccccagatt gaggtgatcc gagcggcaac caagatgatt gagagggaaa tcaattcggt   1320

caatgacaac ccgctgatcg atgtcgcgag gaacaaggcc ctgcacggtg ggaacttcca   1380

ggggaccccg attggtgtct ccatggacaa cactcgcctg gcggttgcgt ccatagggaa   1440

gctcatgttc gcgca                                                    1455
```

<210> SEQ ID NO 246
<211> LENGTH: 294
<212> TYPE: DNA
<213> ORGANISM: Eucalyptus grandis

<400> SEQUENCE: 246

-continued caacagtggc atcacgccgt gcttgccgct ccgcggctcg atctccgcct ctggtgactt 60
ggtacccttt tcctacatcg cgggtctttt gacgggacgt cccaattcca aagcggtcgg 120
acccgctggg gagaccctca cggccaaaca agcctttgag ctcgctggga tcagtggtgg 180
attcttcgag ttgcagccga aggaaggact tgcccttgtg aatgggacgg gagttgggtc 240
tgccttagct gccatagtgc tttttgaagc taatatgctc actgtcctct caga 294

<210> SEQ ID NO 247
<211> LENGTH: 1520
<212> TYPE: DNA
<213> ORGANISM: Pinus radiata

<400> SEQUENCE: 247
gtgatctggt tcccctgtct tatattgctg ggctcttgac cgggaggcct aattccagag 60
tcagatccag agatggaatt gaaatgagcg gagccgaagc gctcaagaaa gtgggcctgg 120
aaaagccctt tgaattgcag cctaaagaag gtctggccat tgtcaatggc acttcagtgg 180
gagcagcact ggcttccatt gtgtgtttcg atgccaatgt tcttgctctg ctctctgaag 240
taatctctgc catgttctgc gaggttatga atgggaagcc tgagtttaca gatccattaa 300
ctcacaagct gaagcaccat cctggccaaa tggaagctgc agcgatcatg gagtatgtct 360
tggacgggag tcttatatga aacacgctgc taagctccat gagatgaatc ctctgcagaa 420
gccaaagcag gatcgctatg cgcttcgcac ttcgcctcag tggctcggcc ctcaggtgga 480
gattatcaga tctgcaactc acatgattga gcgggaaatc aattctgtga atgacaatcc 540
agtaattgat gttgccagag acaaagctct acatggaggg aatttccagg gcacacctat 600
tggtgtttcc atggataatc ttcgtctgtc aatttcagca attgggaaat tgatgttcgc 660
tcaattctca gagcttgtga atgattacta caatggaggc ttgccttcga atctgagtgg 720
tgggcctaat cccagcctgg attatggact gaaaggggcc gagatcgcta tggcttctta 780
cacttctgag cttctttacc tggcaaatcc tgtcaccagc catgtacaga gcgccgaaca 840
gcataaccag gatgtcaatt ctctgggtct cgtttcagct agaaaatctg ccgaggccat 900
cgatattctg aagctgatgc tctccacata cctgacagct ctgtgccagg ctgtggattt 960
aaggcatctg gaggaaaaca tgctggccac tgtgaagcag attgtttctc aggtagccaa 1020
gaaaaccctg agcacagggc tcaacgggga gcttttgcca ggccgtttct gcgaaaagga 1080
tttgctccag gtagtggata acgaacatgt tttctcttac attgacgatc cgtgcaatgc 1140
cagctaccca ttgactcaga aactgagaaa catcctggtg gaacatgcct tcaagaacgc 1200
agaaggtgag aaggatccca acacttccat tttcaataag attcctgtgt ttgaagccga 1260
gctgaaggca cagcttgaac cgcaagttag tctggccaga gaaagttatg acaaagggac 1320
cagccctctg cccaacagga tccaggaatg caggtcttat cctctctatg aatttgtgag 1380
aaaccagctc ggtacccttc aggcatggtt attccatata aatattgtaa tgagatgttt 1440
aattatttac tgctctcttt tttttccgga gcttgcgacc gccttcgatt ccgtgcacta 1500
cgcgaggacg aagcctctgt 1520

<210> SEQ ID NO 248
<211> LENGTH: 449
<212> TYPE: DNA
<213> ORGANISM: Pinus radiata

<400> SEQUENCE: 248
ctctcattct gaggttcatc tggctgaagt ttgaactgtg ctcgaattct gaggttcatc 60

-continued

```
gtgcagaagt ttgattcgtg aattatttgt ttgtttaatt atagtgcaca tggcgcctca    120

ggaattcaca ggcgaagtga aattctgtgc gggaaatggc ggtacggcgt ctttgaacga    180

tccgctgaat tgggcagccg cagcggagtc catgaaggga tctcacttcg aggaagttaa    240

acgaatgtgg gaggagtttc gttctccagt tgtgaggctc cagggatccg gtctcacgat    300

tgcccaggtg gcagccgtgg ccaggagaac gggatccgtg agagtcgaac ttgagaccgg    360

cgcgaaggcg cgggtagatg agagcagtaa ttgggtgatg gacagtatgg cgaacgggac    420

ggatagctat ggcgttacga cggggttcg                                      449
```

<210> SEQ ID NO 249
<211> LENGTH: 512
<212> TYPE: DNA
<213> ORGANISM: Eucalyptus grandis

<400> SEQUENCE: 249

```
gaacttggtg aagttaggaa gtatactagg catggccatc ggtgttgcac tcttcagctc     60

gcttcttgta ctttcatttg tctctccaat ctcttcacta agttccaatt actacgacaa    120

gacctgtccc aatgctgagt tgatcgtcgc aaatgctgtc aagaatgcgg caatgaagga    180

caaaaccgtt ccggctgctc ttctgcggat gcattttcac gactgtttca ttaggggttg    240

cgatgcgtcg gtgcttttaa actccaaagg aagcaacaaa gcggagaagg atggacctcc    300

taatgtctct ctgcactcat tttttgtaat cgacaatgcc aaaaaggagt tggaagcttc    360

ttgccccggc gtggtttcat gtgcggacat cttggcacta gctgctagag attccgtcgt    420

actgtccgga ggtccgactt gggatgtgcc caagggaagg aaggatggaa gaacatcaaa    480

agccagcgag acgactcaac tcccagcacc ac                                  512
```

<210> SEQ ID NO 250
<211> LENGTH: 354
<212> TYPE: DNA
<213> ORGANISM: Eucalyptus grandis

<400> SEQUENCE: 250

```
ctggtaatca ccatagttgt cttctttggg cacataggag actcagaagg aggggacttg     60

aggaagaatt tctacaagag cgcatgtcct cttgctgagg aaatagtgaa gaatgtcacg    120

tggaagcatg ccgccagtaa ctcagctttg cccgccaagt tcctgaggat gcatttccac    180

gattgcttcg ttaggggttg cgatggctca gttttgctag actcgacggc gaacaacaag    240

gcggagaagg tggcggttcc gaaccagtcg ctaaccgggt tcgacgtaat agacgagatc    300

aaggagaagc tggaggaaac atgccctggg gtcgtctctt gtgccgacat cctg          354
```

<210> SEQ ID NO 251
<211> LENGTH: 195
<212> TYPE: DNA
<213> ORGANISM: Pinus radiata

<400> SEQUENCE: 251

```
aacgctgacc ctatcgcggt tatagacgaa gcactcagca ctggtggtgc gcccaatttg     60

tcggatgcat ataccctaaa tggacagcca ggagacctgt ataactgctc tagggcagga    120

acattccggt ttctggtcaa acaaggagaa acttaccttc tacggatggt caatgctgca    180

ctcaatagtg cccac                                                     195
```

<210> SEQ ID NO 252
<211> LENGTH: 377
<212> TYPE: DNA

<213> ORGANISM: Pinus radiata

<400> SEQUENCE: 252
ccaaacccca tggagaaact ccgctcataa taggagaatg gtggaacgct gaccctattg 60
cggttataga tgaagcactc cgcactggtg gtgcgcccaa tttgtcggat gcatataccc 120
taaatggaca gccaggagac ctgtataact gctctagggc aggaacattt cggtttcctg 180
taaaacaagg agaaacttac cttctccgga tggtcaatgc tgcactcaat agtgcccact 240
ttttcaagat cgcaggccac aaatttacag tagtagctgt ggatgcttcc tacaccaagc 300
catacaaaca gatgtaatcg ccattgctcc cggtcagact actgatgttc tcgtcacggc 360
cgaccaacct gtgggca 377

<210> SEQ ID NO 253
<211> LENGTH: 387
<212> TYPE: DNA
<213> ORGANISM: Pinus radiata

<400> SEQUENCE: 253
gatgcccaca ccattaatgg aaagccaggg ccactcttca aatgccctac caaagatact 60
tttgtggttc cagtggaaca tgggaagact taccttcttc gaatcatcaa cgcagctctc 120
aatgacgagc tctttttga tgttgcaaac catcatctga aagtggtgga gattgacgca 180
gtatacacaa agccactaat aacgaactca atagtaattg ctccaggcca gaccacaaat 240
gccttgatcc acaccaacaa aaggagtggc aggtatttca tggctgctcg ctcattcatg 300
gacgcgcccg tctccgtcga caataaaacc gccacagcca ttttgcagta cgtcaattca 360
atacaaattc tgttataatg cccagca 387

<210> SEQ ID NO 254
<211> LENGTH: 534
<212> TYPE: DNA
<213> ORGANISM: Pinus radiata

<400> SEQUENCE: 254
aacatgatgg cgcccatggc cggagcagag tacggaataa agctgattat tcagttgctt 60
gttgtactac ttgctgttca acttgttgca gggaaaacga ccagacatta ctcattccat 120
gtgaggttga agaacgttac tcgtctctgc cacacaaagc cattgattac agtcaatggg 180
aaatctcctg gacctaaagt agtcgtccgt gagggagata gagtcatcat caaagttcat 240
aatcatgtta gcaataatgt ctcaattcac tggcatggag ttcgacaatt gaggtctggt 300
tgggcagatg gccctgctta cataacccaa tgcccaattc aaacgggaca gacttatgtt 360
tataacttca ctgtcacagg acagagggga actctctggt ggcacgctca catctcttgg 420
ctaagagcga gcgtatatgg cgctttcatc atctatccta aacgccatgt tccttatcca 480
tttccaaagc catacaaaga agtccctctg attctcgggg aatggtggaa tgca 534

<210> SEQ ID NO 255
<211> LENGTH: 1076
<212> TYPE: DNA
<213> ORGANISM: Pinus radiata

<400> SEQUENCE: 255
gcccaattcc accaggtggt cgttacacat atagattcaa catctctggt caagaaggaa 60
cggtttggtg gcatgcccat tactcatggc tccgagctac tgtgcatgga gcttttgtaa 120
tccttcctaa gaaaggaagc tcatatccct tttctaaacc gcatgctgaa attcctatta 180

-continued taataggtga atggtggaac gctaacccca tcgccgttat agacgaagcg gttcgcacag 240
gtggtgcgcc taatttatcc gatgccttca ccataaatgg acagccagga gatctgttta 300
actgctctac ctcgggaaca tttcgcctcc ctgtagaaag cggagaaacg taccttctgc 360
ggattgtgaa tgctgcactc aatagcgggc actttttcaa gatagcaggc cacgaattta 420
cagtggtagc tgtggatgct tgttacacca agccatacaa aacagatgta ctcgtcatat 480
ctgccggcca gacgacagat gttcttatca cggccaacca gtctgtgggc agatactata 540
tggccgcccg agcgtatcaa aatcaggcgg caggcgattt cactaacacc acaacaactg 600
ccattctaga gtacattgga agtgaaaatt ctactcgccc aattttgcct agccttccag 660
cctacaacga cactgccact gtcactagat ttagcagagc actgcgaagt ctggcatccc 720
aggagcaccc tgtgaatgtt ccgcacacaa tagatgaaag cctcatctca actgttggac 780
tggggctact tccgtgtggc gctgggaata cctgtgaagg tcccaacgga acgaggctga 840
gtgcaagtat caacaacata tcgtatgtag agcccacgat ctcgttgctt caagcatatt 900
attacactgc caatggtatc tttacggggg attttccatc aaaacctgaa gttagattca 960
actacacggg ggacgatata ccccgaaaat tttgggctcc ggaccccgca acaaaagtga 1020
aggtgctcga atacaactcc acagtgcagc tcgtttttca gtcaacaaac atcttc 1076

<210> SEQ ID NO 256
<211> LENGTH: 483
<212> TYPE: DNA
<213> ORGANISM: Pinus radiata

<400> SEQUENCE: 256
atttcgcagg gaaactgtaa tacagcatat ttcaagaagc tttctttcga aaatggtgat 60
ctcaaaatat gcagcagcga tgtcgtgctt gctcatcgca gtagttgcat tagaggttgg 120
ggcagaaacg agacattaca aatttgacat aaaattcaag aacgttactc gtttatgcca 180
cacaaagccg atagttacag cgaatggcaa gttcccaggc ccaacaatat atgcacgaga 240
aggagacaca gtcactgtga aagtaaccaa tcacgtgaca tacaacgtgt ccatacactg 300
gcacgggata aggcagttgc ggactgggtg ggctgatggg cctgcttata ttacgcagtg 360
ccccattcaa acaggccaaa cttatgtata taactttaca atcacagggc agcgaggcac 420
acttttctgg cacgctcaca ttctctggtt acgtgcaaca ttgaatgggc ccatcgtcat 480
tct 483

<210> SEQ ID NO 257
<211> LENGTH: 470
<212> TYPE: DNA
<213> ORGANISM: Pinus radiata

<400> SEQUENCE: 257
ggttgttgtt taagtacaag gatgaacatg tcgagatcaa aggcgttgct ctgcccttcc 60
ccagctcatg tgaagtacgt gctaattgtc atcctgttga ttattatgat tcagtgcccg 120
gatatagtag caggaaagca tgcgcagaca accaggcatt acaagttcaa cgtgaggcta 180
agcaatgtga cacgtctttg ccgcacgaaa cctttgatta cagtgaatgg aaagtatcca 240
ggacctacag ttgttgctcg cgagggagat cgggtaatta taaaacttgt aaaccacgtg 300
aaggacaacg tcactattca ctggcatggc gttcgacagc tgagatcggg atgggcggat 360
ggtcctggtt atatcactca atgtccactt caaaccggaa tgagttacgt ttataatttc 420
accatcgtag ggcagagagg aactctatgg tggcacgcac acatttcttg 470

<210> SEQ ID NO 258
<211> LENGTH: 472
<212> TYPE: DNA
<213> ORGANISM: Pinus radiata

<400> SEQUENCE: 258
agttatccag caggctcttc aaacaggagg tggtccaaat gtatctgatg cctatactat 60
aaatggactt cctggaccac tttacaactg ttccaatgag acatttgttt tgaaagtgca 120
tcctggacaa acatatcttc ttcgtatcat caatgctgca ctcaatgatg aactcttcct 180
tgccattgca aatcacagtt taacagttgt ggaggtggat gcagtgtatg tcaagccttt 240
ccagacagat actcttctta taaccccagg gcagactacc aatgttttac ttactgctaa 300
tgctactagt ggtaaaaata aacaatttgt catagctgct agtccttttg ttaccggttc 360
agggacattt gataattcca ctgttgcagg aattgtgagt tataattctc ataagtttaa 420
aaattcttcc accattattc tgccaaaact cccatccttc aatgatacaa at 472

<210> SEQ ID NO 259
<211> LENGTH: 405
<212> TYPE: DNA
<213> ORGANISM: Pinus radiata

<400> SEQUENCE: 259
caggacaaac cacgaatgtt ttgctcgagg ctaacaaaag atctggaagt tatttcgtgg 60
ctgctcggcc attcatggat gcacctgtga cagtgaacaa caagaccgca actgccattt 120
tgcactacat cggcaggaat tctgaatcag atattcccgc cgttaatcct ctcatgccac 180
gacttcctct cctcaacgac actgcgtttg caacgagttt cacctccaag ctcagaagct 240
tgaattctgt tcagtttccc gcaaaagtcc cgcagacaat agatcgcaat ctcttcttcg 300
cagtggggct tgcgacggag tcttgtcaga cctgtaacgg tggcctccgt gcttccgcat 360
caatcaacaa cataagcttc gtcatgccca gcatttctct tctgg 405

<210> SEQ ID NO 260
<211> LENGTH: 1352
<212> TYPE: DNA
<213> ORGANISM: Pinus radiata

<400> SEQUENCE: 260
acaccactta tccctttacc tttaccaggc cgcatcgcca gattcccatt cttctaggag 60
aatggtggaa taggaatccc atggacgttg tgaatcaagc aacccaaaca ggagctgccc 120
ccaacgtttc agatgcattt actataaatg gacaaccagg cgacctatac aaatgttcta 180
cttcagatac ctttagcgtg tcgatgaaag gtggggaaac taatcttcta cgtgttatca 240
acgctgcact caatactgac ctattcttct ccattgctag ccacacaatg acagttgtcg 300
ctgtggatgc cttgtataca aaaccttttc agacgaatgt tctgatgctc ggccccggcc 360
agacaacaga catacttctc actgccaatc aggctacagg tagatactac atggctgctc 420
gagcatattc cagcgggcaa ggagttccct tcgataacac cactaccact gccattttag 480
aatacgaggg aagctctaag acttcaactc cagtcatgcc taatcttcca ttctataacg 540
acaccaacag tgctactagc ttcgctaatg gtcttagaag cttgggctca cacgaccacc 600
cagtcttcgt tcctcagagt gtggaggaga atctgttcta caccatcggt ttggggttga 660
tcaaatgtcc ggggcagtct tgtggaggtc ccaacggatc aagatttgca gcaagtatga 720
ataacatatc atttgtcccg ccaaccactt cttccatcct tcaagctcag cattttggca 780

```
tgaaaggagt attctccgcg gacttccccg ataacccttc cgtgggattt gattataccg    840

cacagaacat cagcagagac ctctggtccc ctgtgaaagc cacaagagtg aaagttctta    900

aatataactc gacggtgcaa gtaattcttc aaggaaccaa tatatttgcg ggtgaaagcc    960

atcctatcca tctccatggt tatgacttct acatcgtggg agcaggcttt ggcaattata   1020

acgcacaaac cgatcctcac aagttcaacc tggtggatcc tcctatgcgc aacactgtga   1080

acgttccagt caatggctgg gctgcaataa gattcgtggc tgacaatcct ggagcttggg   1140

tgatgcactg ccacttggac gtgcacataa catggggatt ggccatggtg tttgtggtta   1200

acaatggacc tgacgctctt ttgagtctcc agtcacctcc cagagatctt ccgctatgct   1260

gaggaaaact gtgatgcata gcgatcctct attggtccca cttcattctt tttccttctc   1320

gtcactttgc tccttccatc gtttatgtct at                                 1352
```

<210> SEQ ID NO 261
<211> LENGTH: 337
<212> TYPE: DNA
<213> ORGANISM: Pinus radiata

<400> SEQUENCE: 261

```
ttcttaacta taacgcgaca gttcaagtaa ttctccaggg aacaaatata tttgctggtg     60

aaagccatcc tatccatctc catggttatg acttttacat cgtgggagca gggtttggta    120

attataatgc acaaacagat cctcagaagt tcaacctggt ggatcctcct atgcgcaaca    180

ctgtgaacgt tccagtcaat ggctgggctg ccataagatt cgttgctgac aatcctggag    240

cttgggtgat gcactgccac ttagacgtgc acataacatg gggttggcg atggtttttg     300

tggttaacaa tggacctgat cctcttttga gtctcca                            337
```

<210> SEQ ID NO 262
<211> LENGTH: 279
<212> TYPE: DNA
<213> ORGANISM: Pinus radiata

<400> SEQUENCE: 262

```
acaagagtga aagttcttaa ttataacaca acggtgcaag taattcttca aggaacaaat     60

atatttgcgg gtgaaagcca tcctattcat ctccatggtt atgacttcta catagtggga    120

gcaggatttg gcaattataa tccacaaacc gatcctcaaa agttcaacct ggcggatcct    180

cctatgcgca acactgtaaa cgttccagtt aatggctggg ctgcaataag attcgtggcc    240

gacaatcctg gcgcttgggt gatgcactgc cacttggac                           279
```

<210> SEQ ID NO 263
<211> LENGTH: 279
<212> TYPE: DNA
<213> ORGANISM: Pinus radiata

<400> SEQUENCE: 263

```
aaaacctttt cagacgaatg ttctgatgct cggccccggc cagacaacag acatagcggc     60

cgcgtcgacc aacttgcaga tacctttagc gtgtcgatga aaggtgggga aactaatctt    120

ctacgtgtta tcaacgctgc actcaatact gacctattct tctccattgc tagccacaca    180

atgacagttg tcgctgtgga tgccttgtat acaaaacctt ttcagacgaa tgttctgatg    240

ctcggccccg gccagacaac agacatagcg gccgcgaat                           279
```

<210> SEQ ID NO 264
<211> LENGTH: 474
<212> TYPE: DNA

<213> ORGANISM: Pinus radiata

<400> SEQUENCE: 264
ccctgactct acaatcaata cgtcgttcct gcaacagtta caagggcagt gtcctcgggc 60
tggtggagac gagttgcctt cgtctcttga ctacgtaacg ccagcccgtt ttgataacac 120
ttactttgcc aacttgaagc agcagaaggg tgttctgcac tctgatcgca cgctatacga 180
tcccgcagcc tcagggtctg taactagcag tacagttgat catttctctt ctgatcagac 240
tgctttcttc gaaagcttca aaggagccat gatcaaaatg gggaacctca gcccttcggc 300
cggaacgcaa ggagaaatcc ggcgggactg cagaaaagta aattagagag ctcctagcct 360
tcatccagag gcatcaacca tgaggataag ttggataaat tatcttgtct taatatcagg 420
ttggatttag tggtataata tcgggttgga tttagtggta aaaaaaaaaa aaaa 474

<210> SEQ ID NO 265
<211> LENGTH: 1790
<212> TYPE: DNA
<213> ORGANISM: Pinus radiata

<400> SEQUENCE: 265
ggcacgaggc aaacttggtc gtttgtttag gttttgctgc aggtgaacac taatatggaa 60
ggccagattg cagcattaag caaagaagat gagttcattt ttcacagccc ttttcctgca 120
gtacctgttc cagagaatat aagtcttttc cagtttgttc tggaaggtgc tgagaaatac 180
cgtgataagg tggccctcgt ggaggcctcc acagggaagg agtacaacta tggtcaggtg 240
atttcgctca caaggaatgt tgcagctggg ctcgtggaca aaggcattca aaagggcgat 300
gttgtatttg ttctgcttcc aaatatggca gaataccccca ttattgtgct gggaataatg 360
ttggccggcg cagtgttttc tggggcaaat ccttctgcac acatcaatga agttgaaaaa 420
catatccagg attctggagc aaagattgtt gtgacagttg ggtctgctta tgagaaggtg 480
aggcaagtga aactgcctgt tattattgca gataacgagc atgtcatgaa cacaattcca 540
ttgcaggaaa tttttgagag aaactatgag gccgcagggc cttttgtaca aatttgtcag 600
gatgatctgt gtgcactccc ttattcctct ggcaccacag ggcctctaa aggtgtcatg 660 ctcactcaca gaaatctgat tgcaaatctg tgctctagct tgtttgatgt ccatgaatct 720
cttgtaggaa atttcaccac gttggggctg atgccattct ttcacatata tggcatcacg 780
ggcatctgtt gcgccactct tcgcaacgga ggcaaggtcg tggtcatgtc cagattcgat 840
ctccgacact ttatcagttc tttgattact tatgaggtca acttcgcgcc tattgtcccg 900
cctataatgc tctccctcgt taaaaatcct atcgttaacg agttcgatct cagccgcttg 960
aaactcaaag ctgtcatgac tgcggctgct ccactggcgc cggatctact gcgagcgttc 1020
gaggaaaaat tccctggggt tgaggttcaa gaggcctatg gtcttacgga acacagttgc 1080
atcacattga ctcattgcgc tcccggaaac atacgtggga gagccaagaa gagttcggtt 1140
ggttttatta ttcccaatct ggaggtgaag tttattgatc ccgaaactgg aaagtcattg 1200
cccaggaatt ccatcgggga ggtgtgcgtc agaagccaat gtgtcatgcg agggtattac 1260
aagaaaccga cagaaaccga gaaaacagtg gacagcgacg gctggctgca tactggggat 1320
gtcggtttca tagatgatga cgacgacgta ttcatcgtcg acagaattaa agagctgatc 1380
aaatacaaag gttttcaggt tgctcctgca gaactggaag ccattctact ttctcatcca 1440
tcagtggaag acgcagcagt ggttcccttta cctgatgagg aagcagggga gattccagcg 1500
gcgtgcgtgg tgatggcagc cagtgctacg gagacggagg acgacatttc gaagtttgtg 1560

-continued gcgtcgcagg tggctacata caagagggtg agactggtga agtttgtgtc caccattcct 1620
aaatcttctt ccggaaagat cctgcgcaga cttctgagag ataatctccg tgaaacgctc 1680
aaaaaccagc accaaccatt gtccacttag gctttgcagc gttatatata aataaataat 1740
caaacatcta gggatgggat tatagcccca taacatacat tttgaaattc 1790

<210> SEQ ID NO 266
<211> LENGTH: 2043
<212> TYPE: DNA
<213> ORGANISM: Eucalyptus grandis

<400> SEQUENCE: 266
gcgccaccac caaacgctca ccttctcatc atcagccctc tgtctctgtc tctgtctctc 60
gattctccgc cccgccacga caatggaggc gaagccgtcg gagcagcccc gcgagttcat 120
cttccggtcg aagctccccg acatctacat tcccgacaac ctctccctcc acgcctactg 180
cttcgagaac atctccgagt tcgccgaccg cccctgcgtc atcaacgggg ccaccggccg 240
gacctacacc tatgccgagg tcgagctgat ctcccgccgg gtctcagccg gcctcaacgg 300
gctcggcgtc ggacagggcg acgtgatcat gctgctcctc cagaactgcc ctgagttcgt 360
gttcgcgttc ctcggcgcgt cctaccgggg cgccatcagc acgaccgcga acccgttcta 420
caccccgggc gagatcgcca agcaggcctc agctgcccgg gccaagatcg tgatcacgca 480
ggccgcgttc gccgacaagg tgaggccgtt cgcggaggag aacggggtga aggtcgtgtg 540
catcgatacc gcgccggagg gctgcctgca cttctcggaa ttgatgcagg cggacgagaa 600
cgccgccccc gcggcggacg tcaagccgga cgacgtcttg gcgctcccct attcgtcggg 660
cacgacgggg cttcccaagg gagtgatgct tacgcacagg ggtcaagtga ccagcgtggc 720
gcagcaggtc gacggagaca accccaactt gtacttccac aaggaggacg tgatcctgtg 780
cacgctcccg ttgttccaca tatactccct caactcggtg atgttctgcg cgctccgtgt 840
cggcgccgcc atcctgatca tgcagaagtt cgagatcgtg gcgctgatgg agctcgtgca 900
gcggtaccgg gtgacgatcc tgcccattgt cccgccgatc gtgctggaga tcgccaagag 960
cgccgaggtg gaccggtacg acctgtcgtc gatccggacc atcatgtcgg gtgcggcccc 1020
gatggggaag gagctcgagg acaccgtgcg agccaagctg cccaatgcca agctcggaca 1080
gggctatggg atgacggagg cgggcccggt gctggcaatg tgcccggcat ttgcaaagga 1140
gccgttcgag atcaagtcag gcgcatgcgg gaccgtcgtg aggaacgcgg agatgaagat 1200
cgtcgacccg gagacagggg cctcgctccc gcggaaccag gccggcgaga tctgcatccg 1260
gggtcaccag atcatgaaag gttatctgaa cgacgccgag gcgaccgcaa ataccataga 1320
caaagaaggg tggctgcaca ccggcgacat cggctacata gacgatgacg acgagctctt 1380
cattgtcgat cggttgaagg aactcatcaa gtacaagggc ttccaggttg ctccggccga 1440
gctagaggca atgctgattg cacacccaag tatctcggat gccgctgttg tgccgatgaa 1500
ggatgaggtt gccggtgagg ttcctgttgc attcgtggtg aaatccaatg gttccgtaat 1560
caccgaggac gaaatcaagc aatacatctc gaagcaggtc gtgttttaca agaggatcaa 1620
gcgggttttc ttcacggacg caattccgaa agccccctcc ggaaaaatct tgaggaagga 1680
cctaagagca aagttggcct ctggtgttta caattaattt ctcataccct tttctttttc 1740
aaccctgccc ctgtacttgc ttaaagaccc atgtagttga aatgaatgta acctcttcgg 1800
aggggccaaa tatggaaggg ggaaagaaag acatatggcg atgatttgat ttcacatgct 1860
attgtaatgt atttattgtt tcaattccga attagacaaa gtgcttaaag ctctcttttc 1920

-continued

```
ggattttttt tttcattaat gtataataat tgcggacatt acaatatact gtacaacgtg   1980

atttgagctt gatgaattac aagattggaa gaacttcgaa gacaaaaaaa aaaaaaaaaa   2040

aaa                                                                 2043
```

<210> SEQ ID NO 267
<211> LENGTH: 92
<212> TYPE: PRT
<213> ORGANISM: Pinus radiata

<400> SEQUENCE: 267

```
Lys Glu Thr Gly Leu Leu Asn Gln Phe Val Asp Ile Tyr Gln Glu Met
1               5                   10                  15

Asp Asp Ser Val Gln Glu Val Ser Lys Glu Gly Asn Gln Trp Ala Gly
            20                  25                  30

Phe Ile Glu Gly Glu Asn Val Ile Arg Arg Gly Arg Glu Ile Leu Leu
        35                  40                  45

Gln His Asp Asn Arg Glu Ala His Asn Trp Glu Ser His Lys His Lys
    50                  55                  60

Trp Trp Pro His Leu Glu Glu Lys Ile Pro His Ile Ala Lys Ala Gly
65                  70                  75                  80

Phe Thr Ser Ile Trp Leu Pro Pro Ala Phe Asp Ser
                85                  90
```

<210> SEQ ID NO 268
<211> LENGTH: 182
<212> TYPE: PRT
<213> ORGANISM: Pinus radiata

<400> SEQUENCE: 268

```
Leu Leu His Gln Phe Val Tyr Ser Phe Arg Lys Met Gly Tyr Pro Val
1               5                   10                  15

Gln Glu Val Ser Lys Glu His Asp Gln Trp Ala Gly Phe Val Glu Gly
            20                  25                  30

Glu Ser Val Leu Gln Arg Gly Arg Glu Ile Leu Leu Gln Gly Phe Asn
        35                  40                  45

Trp Glu Ser His Lys Tyr Lys Trp Trp Pro Asn Leu Glu Glu Lys Ile
    50                  55                  60

Pro His Ile Ala Lys Ala Gly Phe Thr Ser Val Trp Leu Pro Pro Ala
65                  70                  75                  80

Phe Asp Ser Ala Ala Pro Gln Gly Tyr Leu Pro Arg Asn Ile Tyr Ser
                85                  90                  95

Leu Asn Ser Ala Tyr Gly Ser Glu Tyr Gln Leu Lys Ser Leu Leu Met
            100                 105                 110

Thr Met Arg Lys Lys Asn Val Arg Ala Met Ala Asp Ile Val Ile Asn
        115                 120                 125

His Arg Met Gly Ser Ser Gln Gly Phe Gly Gly Leu Tyr Asn Arg Tyr
    130                 135                 140

Tyr Gly Cys Leu Pro Trp Asp Glu Arg Ala Val Thr Arg Cys Ser Gly
145                 150                 155                 160

Gly Leu Gly Asn Trp Ser Thr Gly Asp Asn Phe His Gly Val Pro Asn
                165                 170                 175

Val Asp His Thr Gln Asp
            180
```

<210> SEQ ID NO 269
<211> LENGTH: 218
<212> TYPE: PRT

<213> ORGANISM: Pinus radiata

<400> SEQUENCE: 269

```
Arg Met Ala Lys Phe Arg Ser Leu Ser Leu Leu Leu Trp Phe Ser Cys
1               5                   10                  15

Ile Ile Val Asn Ala Ala Ser Pro Ala Gln Ala Glu Ala Thr Thr Pro
            20                  25                  30

Pro Leu Asn Thr Leu Leu Leu Gln Gly Phe Asn Trp Asp Ser Ala Gln
        35                  40                  45

Ser Ser Thr Pro Trp Tyr Asn Val Leu Lys Gly Ile Val Asp Asp Ala
    50                  55                  60

Ala Asp Ala Gly Ile Thr Tyr Val Trp Phe Pro Pro Pro Ser Gln Ser
65                  70                  75                  80

Gly Ala Pro Gln Gly Tyr Leu Pro Ala Lys Leu Tyr Asp Leu Asp Ser
                85                  90                  95

Ser Tyr Gly Ser Glu Gln Gln Leu Lys Asp Ala Val Asn Ala Phe His
            100                 105                 110

Gln Lys Gly Ile Ala Ile Met Gly Asp Ile Val Ile Asn His Arg Asn
        115                 120                 125

Gly Thr Lys Gln Asp Asp Lys Gly Tyr Trp Cys Val Phe Glu Gly Gly
    130                 135                 140

Lys Gly Asp Gly Thr Leu Asp Trp Gly Pro Trp Ala Val Thr Val Lys
145                 150                 155                 160

Asp Gln Pro Tyr Pro Leu Cys Gly Ser Gly Gln Ala Asp Thr Gly Gly
                165                 170                 175

Asp Phe Lys Tyr Ala Pro Asp Val Asp His Thr Asn Pro Lys Ile Gln
            180                 185                 190

Gln Asp Leu Ser Glu Trp Met Asn Trp Leu Lys Ser Met Ser Asp Leu
        195                 200                 205

Met Ala Gly Gly Ser Thr Thr Ser Arg Leu
    210                 215
```

<210> SEQ ID NO 270
<211> LENGTH: 145
<212> TYPE: PRT
<213> ORGANISM: Eucalyptus grandis

<400> SEQUENCE: 270

```
Gly Val Gly Arg Leu Val Asp Val Gly Gly Ser Ala Gly Asp Cys Leu
1               5                   10                  15

Arg Met Ile Met Gly Lys His Thr His Val Arg Glu Gly Ile Asn Phe
            20                  25                  30

Asp Leu Pro Glu Val Val Ala Lys Ala Pro Pro Ile Pro Gly Val Thr
        35                  40                  45

His Val Gly Gly Asp Met Phe Lys Ser Ile Pro Ala Gly Asp Ala Ile
    50                  55                  60

Phe Met Arg Trp Ile Leu Thr Thr Trp Thr Asp Asp Glu Cys Lys Gln
65                  70                  75                  80

Ile Leu Glu Asn Cys Phe Lys Ala Leu Pro Ala Gly Gly Lys Leu Ile
                85                  90                  95

Ala Cys Glu Pro Val Leu Pro Gln His Ser Asp Asp Ser His Arg Thr
            100                 105                 110

Arg Ala Leu Leu Glu Gly Asp Ile Phe Val Met Thr Ile Tyr Arg Ala
        115                 120                 125

Lys Gly Lys His Arg Thr Glu Gln Glu Phe Gln Gln Leu Gly Leu Ser
    130                 135                 140
```

Thr
145

<210> SEQ ID NO 271
<211> LENGTH: 198
<212> TYPE: PRT
<213> ORGANISM: Eucalyptus grandis

<400> SEQUENCE: 271

Pro Thr Met Ala Asp Asn Gln Glu Arg Glu Gly Arg Asp Gln Glu Glu
1 5 10 15

Glu Val Gly Lys Leu Ala Val Gln Leu Ala Ser Ala Val Val Leu Pro
20 25 30

Met Thr Leu Lys Ser Ala Leu Glu Leu Gly Ile Ile Asp Ala Leu Val
35 40 45

Ser Ala Gly Gly Phe Leu Ser Ala Ala Glu Ile Ala Ser Arg Val Gly
50 55 60

Ala Lys Asn Pro Gly Ala Pro Val Leu Val Asp Arg Met Met Arg Leu
65 70 75 80

Leu Ala Ser His Gly Val Ile Glu Trp Arg Leu Arg Arg Gly Asp Gly
85 90 95

Asn Gly Asp Gly Gly Glu Arg Glu Tyr Gly Pro Gly Pro Met Cys Arg
100 105 110

Phe Phe Ala Lys Asp Gln Glu Gly Gly Asp Val Gly Pro Leu Phe Leu
115 120 125

Leu Ile His Asp Lys Val Phe Met Glu Ser Trp Tyr His Leu Asn Asp
130 135 140

Val Ile Met Glu Gly Gly Val Pro Phe Glu Arg Ala Tyr Gly Met Thr
145 150 155 160

Ala Phe Glu Tyr Pro Ala Val Asp Asp Arg Phe Asn Gln Val Phe Asn
165 170 175

Arg Ala Met Ala Ser His Thr Ser Leu Ile Met Lys Lys Ile Leu Asp
180 185 190

Val Tyr Arg Gly Phe Glu
195

<210> SEQ ID NO 272
<211> LENGTH: 156
<212> TYPE: PRT
<213> ORGANISM: Eucalyptus grandis

<400> SEQUENCE: 272

Pro Thr Pro Leu Tyr Met Asn Lys Ile Leu Glu Ser Tyr Arg Gly Phe
1 5 10 15

Glu Gly Ala Lys Thr Ile Ala Asp Leu Gly Gly Gly Val Gly Gln Asn
20 25 30

Leu Arg Leu Ile Leu Asp Lys Phe Pro Asn Leu Arg Gly Ile Leu Tyr
35 40 45

Asp Leu Pro His Val Ile Lys Asp Ala Pro Ala His Pro Arg Met Glu
50 55 60

Arg Val Gly Gly Asp Leu Leu Lys Ser Val Pro Lys Ala Asp Ile Leu
65 70 75 80

Phe Met Lys Trp Leu Phe His Gly Leu Arg Asp Asp Phe Cys Lys Met
85 90 95

Leu Leu Gln Asn Cys Tyr Glu Ala Leu Pro Pro Asn Gly Lys Val Val
100 105 110

```
Ile Val Asp Pro Ile Leu Pro Glu Tyr Pro Glu Thr Asp Ile Val Ser
        115                 120                 125

Arg Asn Ser Phe Thr Ser Asp Met Ile Met Leu Tyr Thr Ser Pro Gly
    130                 135                 140

Glu Asp Arg Thr Arg Lys Glu Leu Glu Val Leu Ala
145                 150                 155


<210> SEQ ID NO 273
<211> LENGTH: 166
<212> TYPE: PRT
<213> ORGANISM: Eucalyptus grandis

<400> SEQUENCE: 273

Ser Ser Phe Gln Pro Cys Tyr Glu Glu Ala Asn Ser Leu Asp Arg Trp
1               5                   10                  15

Ile Gln Pro Pro Ser Asp Leu Leu His Asn Met Ser Asp Lys Glu Leu
            20                  25                  30

Phe Trp Arg Ala Thr Leu Val Pro Lys Ile Lys Lys Tyr Pro Phe Arg
        35                  40                  45

Arg Val Pro Lys Ile Ala Phe Met Phe Leu Thr Lys Gly Pro Leu Pro
    50                  55                  60

Leu Ala Pro Leu Trp Glu Arg Phe Phe Lys Gly His Glu Gly Leu Tyr
65                  70                  75                  80

Ser Ile Tyr Ile His Ser His Pro Ser Phe His Ala His Phe His Pro
                85                  90                  95

Trp Ser Val Phe Asn Arg Arg Gln Ile Pro Ser Gln Val Ser Glu Trp
            100                 105                 110

Gly Arg Met Ser Met Cys Asp Ala Glu Lys Arg Leu Leu Ala Asn Ala
        115                 120                 125

Leu Leu Asp Ile Ser Asn Glu Arg Phe Ile Leu Leu Ser Glu Ser Cys
    130                 135                 140

Ile Pro Leu Tyr Asn Phe Ser Leu Ile Tyr His Tyr Ile Met Lys Ser
145                 150                 155                 160

Gly Tyr Ser Phe Met Gly
                165


<210> SEQ ID NO 274
<211> LENGTH: 328
<212> TYPE: PRT
<213> ORGANISM: Eucalyptus grandis

<400> SEQUENCE: 274

Ile Leu Ser Arg Lys Pro Lys Glu Lys Thr Val Gly Arg Lys Asn Ile
1               5                   10                  15

Lys Lys Asn Met Ser Ser Lys Glu Ala Pro Val Ile Thr Thr Ser His
            20                  25                  30

Glu Asp Glu Glu Ile Leu Asn Ala Phe Glu Val Pro Ser Met Ala Phe
        35                  40                  45

Val Pro Met Val Leu Lys Gly Val His Glu Leu Gly Ile Leu Glu Leu
    50                  55                  60

Leu Ala Lys Gly Asp Gln Leu Ser Pro Leu Asp Ile Val Ala Arg Leu
65                  70                  75                  80

Ser Ile Asp Asn Pro Ala Ala Pro Asp Thr Ile Asp Arg Met Leu Arg
                85                  90                  95

Leu Leu Ala Ser Tyr Ser Ile Leu Ser Cys Thr Leu Val Glu Asp Lys
            100                 105                 110

Glu Gly Arg Pro Gln Arg Leu Tyr Gly Leu Gly Pro Arg Ser Lys Phe
```

```
        115                 120                 125

Phe Leu Asp Gln Asn Gly Ala Ser Thr Leu Pro Thr His Met Leu Leu
    130                 135                 140

Gln Glu Lys Thr Leu Leu Glu Cys Trp Asn Cys Leu Lys Asp Ala Val
145                 150                 155                 160

Lys Glu Gly Gly Ala Asp Pro Phe Thr Arg Arg His Gly Met Asn Val
                165                 170                 175

Phe Asp Tyr Met Gly Gln Asp Pro Arg Phe Asn Asp Leu Tyr Asn Lys
            180                 185                 190

Ser Met Arg Thr Gly Ser Ala Ile Tyr Met Pro Lys Ile Ala Gln His
        195                 200                 205

Tyr Arg Gly Phe Ser Lys Ala Lys Thr Val Val Asn Val Gly Gly Gly
    210                 215                 220

Ile Gly Glu Thr Leu Lys Thr Ile Leu Ser Lys Asn Pro His Ile Arg
225                 230                 235                 240

Ala Ile Asn Tyr Asp Leu Pro His Val Ile Ala Thr Ala Pro Pro Ile
                245                 250                 255

Pro Gly Ile Thr His Val Gly Gly Asp Ile Leu Lys Ser Val Pro Lys
            260                 265                 270

Ala Asp Val His Phe Leu Lys Ser Val Leu His Arg Gly Asp Asp Glu
        275                 280                 285

Phe Cys Val Lys Val Leu Lys Asn Cys Trp Glu Ala Leu Pro Pro Thr
    290                 295                 300

Gly Lys Val Val Ile Val Glu Glu Val Thr Pro Glu Tyr Pro Gly Thr
305                 310                 315                 320

Asp Asp Val Ser Gln Thr Thr Leu
                325


<210> SEQ ID NO 275
<211> LENGTH: 160
<212> TYPE: PRT
<213> ORGANISM: Pinus radiata

<400> SEQUENCE: 275

Asp Val Gly Gly Gly Ile Gly Ser Ala Leu Ser Ile Ile Val Lys Glu
1               5                   10                  15

His Pro His Ile Arg Gly Ile Asn Leu Asp Leu Pro His Val Ile Ala
            20                  25                  30

Thr Ala Pro Leu Ile Thr Gly Val Glu His Met Glu Gly Asn Met Phe
        35                  40                  45

Glu His Ile Pro Ser Ala Asp Ala Val Met Met Lys Trp Ile Leu His
    50                  55                  60

Asp Trp Ala Asp Glu Glu Cys Val Lys Leu Leu Arg Arg Ser Tyr Asp
65                  70                  75                  80

Ala Thr Pro Ala Lys Gly Lys Val Leu Ile Val Glu Ala Val Val Glu
                85                  90                  95

Gly Asp Lys Glu Gly Glu Ser Met Ser Arg Arg Leu Gly Leu Leu Tyr
            100                 105                 110

Asp Ile Ser Met Met Ala Tyr Thr Thr Gly Gly Lys Glu Arg Thr Glu
        115                 120                 125

Glu Glu Phe Lys Gly Leu Phe Gln Arg Ala Gly Phe Lys Ser His Thr
    130                 135                 140

Ile Ile Lys Leu Pro Phe Leu Gln Ser Leu Ile Val Leu Ser Lys Ala
145                 150                 155                 160
```

<210> SEQ ID NO 276
<211> LENGTH: 112
<212> TYPE: PRT
<213> ORGANISM: Eucalyptus grandis

<400> SEQUENCE: 276

Ser Leu Arg Thr Tyr Ser Asn Met Glu Gln Gly Trp Asp Lys Gly Glu
1               5                   10                  15

Ile Leu Ala Ser Lys Ala Leu Ser Lys Tyr Ile Leu Glu Thr Asn Ala
            20                  25                  30

Tyr Pro Arg Glu His Glu Gln Leu Lys Glu Leu Arg Glu Ala Thr Val
        35                  40                  45

Gln Lys Tyr Gln Ile Arg Ser Ile Met Asn Val Pro Val Asp Glu Gly
    50                  55                  60

Gln Leu Ile Ser Met Met Leu Lys Leu Met Asn Ala Lys Lys Thr Ile
65                  70                  75                  80

Glu Ile Gly Val Phe Thr Gly Tyr Ser Leu Leu Thr Thr Ala Leu Ala
                85                  90                  95

Leu Pro Ala Asp Gly Lys Ile Ile Ala Ile Asp Gln Asp Lys Glu Ala
            100                 105                 110

<210> SEQ ID NO 277
<211> LENGTH: 133
<212> TYPE: PRT
<213> ORGANISM: Eucalyptus grandis

<400> SEQUENCE: 277

Arg Thr Tyr Ser Asp Met Glu Arg Gly Gly Asp Lys Gly Glu Ile Leu
1               5                   10                  15

Ala Ser Lys Ala Leu Ser Lys Tyr Ile Leu Glu Thr Asn Ala Tyr Pro
            20                  25                  30

Arg Glu His Glu Gln Leu Lys Glu Leu Arg Glu Ala Thr Val Gln Lys
        35                  40                  45

Tyr Gln Met Arg Ser Ile Met Ser Val Pro Ala Asp Glu Gly Gln Leu
    50                  55                  60

Ile Ser Met Met Leu Lys Leu Met Asn Ala Lys Lys Thr Ile Glu Ile
65                  70                  75                  80

Gly Val Phe Thr Gly Tyr Ser Leu Leu Thr Thr Ala Leu Ala Leu Pro
                85                  90                  95

Ala Asp Gly Lys Ile Ile Ala Ile Asp Pro Asp Lys Glu Ala Tyr Glu
            100                 105                 110

Ile Gly Leu Pro Tyr Ile Lys Lys Ala Gly Val Asp His Lys Ile Asn
        115                 120                 125

Phe Ile Gln Ser Asp
    130

<210> SEQ ID NO 278
<211> LENGTH: 98
<212> TYPE: PRT
<213> ORGANISM: Eucalyptus grandis

<400> SEQUENCE: 278

Leu Gln Tyr Ile Leu Glu Thr Asn Ala Tyr Pro Arg Glu His Glu Gln
1               5                   10                  15

Leu Lys Glu Leu Arg Glu Ala Thr Val Gln Lys Tyr Gln Ile Arg Ser
            20                  25                  30

Ile Met Asn Val Pro Ala Asp Glu Gly Gln Leu Ile Ser Met Met Leu
        35                  40                  45

```
Lys Leu Met Asn Ala Lys Lys Thr Ile Glu Ile Gly Val Phe Thr Gly
    50                  55                  60

Cys Ser Leu Leu Thr Thr Ala Leu Ala Leu Pro Ala Asp Gly Lys Ile
65                  70                  75                  80

Ile Ala Ile Asp Pro Asp Lys Glu Ala Tyr Glu Ile Gly Leu Pro Tyr
                85                  90                  95

Ile Arg


<210> SEQ ID NO 279
<211> LENGTH: 157
<212> TYPE: PRT
<213> ORGANISM: Eucalyptus grandis

<400> SEQUENCE: 279

Arg His His Gln Thr Leu Thr Phe Ser Ser Ser Ala Leu Cys Leu Cys
1               5                   10                  15

Leu Cys Leu Ser Ile Leu Arg Pro Ala Thr Thr Met Glu Ala Lys Pro
            20                  25                  30

Ser Glu Gln Pro Arg Glu Phe Ile Phe Arg Ser Lys Leu Pro Asp Ile
        35                  40                  45

Tyr Ile Pro Asp Asn Leu Ser Leu His Ala Tyr Cys Phe Glu Asn Ile
    50                  55                  60

Ser Glu Phe Ala Asp Arg Pro Cys Val Ile Asn Gly Ala Thr Gly Arg
65                  70                  75                  80

Thr Tyr Thr Tyr Ala Glu Val Glu Leu Ile Ser Arg Arg Val Ser Ala
                85                  90                  95

Gly Leu Asn Gly Leu Gly Val Gly Gln Gly Asp Val Ile Met Leu Leu
            100                 105                 110

Leu Gln Asn Cys Pro Glu Phe Val Phe Ala Phe Leu Gly Ala Ser Tyr
        115                 120                 125

Arg Gly Ala Ile Ser Thr Thr Ala Asn Pro Phe Tyr Thr Pro Gly Glu
    130                 135                 140

Ile Ala Lys Gln Ala Ser Ala Ala Arg Ala Lys Ile Val
145                 150                 155


<210> SEQ ID NO 280
<211> LENGTH: 180
<212> TYPE: PRT
<213> ORGANISM: Eucalyptus grandis

<400> SEQUENCE: 280

Phe Ala Asp Lys Val Arg Pro Phe Ala Glu Glu Asn Gly Val Lys Val
1               5                   10                  15

Val Cys Ile Asp Thr Ala Pro Glu Gly Cys Leu His Phe Ser Glu Leu
            20                  25                  30

Met Gln Ala Asp Glu Asn Ala Ala Pro Ala Ala Asp Val Lys Pro Asp
        35                  40                  45

Asp Val Leu Ala Leu Pro Tyr Ser Ser Gly Thr Thr Gly Leu Pro Lys
    50                  55                  60

Gly Val Met Leu Thr His Arg Gly Gln Val Thr Ser Val Ala Gln Gln
65                  70                  75                  80

Val Asp Gly Asp Asn Pro Asn Leu Tyr Phe His Lys Glu Asp Val Ile
                85                  90                  95

Leu Cys Thr Leu Pro Leu Phe His Ile Tyr Ser Leu Asn Ser Val Met
            100                 105                 110

Phe Cys Ala Leu Arg Val Gly Ala Ala Ile Leu Ile Met Gln Lys Phe
        115                 120                 125
```

```
Glu Ile Val Ala Leu Met Glu Leu Val Gln Arg Tyr Arg Val Thr Ile
    130                 135                 140

Leu Pro Ile Val Pro Pro Ile Val Leu Glu Ile Ala Lys Ser Ala Glu
145                 150                 155                 160

Val Asp Arg Tyr Asp Leu Ser Ser Ile Arg Thr Ile Met Ser Gly Ala
                165                 170                 175

Ala Arg Trp Gly
            180
```

<210> SEQ ID NO 281
<211> LENGTH: 180
<212> TYPE: PRT
<213> ORGANISM: Eucalyptus grandis

<400> SEQUENCE: 281

```
Gly Gln Leu Val Ala Gly Val Glu Ala Gln Val Ile Ser Val Asp Thr
1               5                   10                  15

Leu Lys Ser Leu Pro Pro Asn Gln Leu Gly Glu Ile Trp Val Arg Gly
            20                  25                  30

Pro Asn Met Met Lys Gly Tyr Tyr Asn Asn Pro Gln Ala Thr Lys Leu
        35                  40                  45

Thr Ile Asp Asn Lys Gly Trp Val His Thr Gly Asp Leu Gly Tyr Phe
    50                  55                  60

Asp Glu Glu Gly Gln Leu Tyr Val Val Asp Arg Ile Lys Glu Leu Ile
65                  70                  75                  80

Lys Tyr Lys Gly Phe Gln Ile Ala Pro Ala Glu Leu Glu Gly Leu Leu
                85                  90                  95

Leu Ser His Pro Glu Ile Leu Asp Ala Val Val Ile Pro Phe Pro Asp
            100                 105                 110

Ala Glu Ala Gly Glu Val Pro Ile Ala Tyr Val Val Arg Ser Pro Thr
        115                 120                 125

Ser Ser Leu Thr Glu Glu Glu Val Gln Lys Phe Ile Ala Asn Gln Val
    130                 135                 140

Ala Pro Phe Lys Arg Leu Arg Arg Val Thr Phe Val Asn Ser Val Pro
145                 150                 155                 160

Lys Ser Ala Ser Gly Lys Ile Leu Arg Arg Glu Leu Ile Ala Lys Val
                165                 170                 175

Arg Ala Lys Ile
            180
```

<210> SEQ ID NO 282
<211> LENGTH: 119
<212> TYPE: PRT
<213> ORGANISM: Pinus radiata

<400> SEQUENCE: 282

```
Gly Tyr Phe Asp Glu Glu Gly Gly Leu Phe Ile Val Asp Arg Ile Lys
1               5                   10                  15

Glu Leu Ile Lys Tyr Lys Gly Phe Gln Val Ala Pro Ala Glu Leu Glu
            20                  25                  30

Gly Ile Leu Leu Thr His Pro Gln Ile Ala Asp Ala Gly Val Ile Pro
        35                  40                  45

Leu Pro Asp Leu Lys Ala Gly Glu Val Pro Ile Ala Tyr Val Val Arg
    50                  55                  60

Thr Pro Gly Ser Ser Leu Thr Glu Lys Asp Ala Met Asp Tyr Val Ala
65                  70                  75                  80
```

Lys Gln Val Ala Pro Phe Lys Arg Leu His Arg Val Asn Phe Val Asp
85 90 95

Ser Ile Pro Lys Ser Ala Ser Gly Lys Ile Leu Arg Arg Glu Leu Ile
100 105 110

Ala Lys Ala Lys Ser Lys Leu
115

<210> SEQ ID NO 283
<211> LENGTH: 152
<212> TYPE: PRT
<213> ORGANISM: Pinus radiata

<400> SEQUENCE: 283

Asp Phe Pro Phe Phe Phe Leu Leu Arg Val Ala Met Ile Glu Val Gln
1 5 10 15

Ser Ala Pro Pro Met Ala Arg Ser Thr Glu Asn Glu Asn Asn Gln His
20 25 30

Asp Ala Glu Glu Gly Ala Val Leu Asn Glu Gly Gly Met Asp Phe Leu
35 40 45

Tyr Arg Ser Lys Leu Pro Asp Ile Asp Ile Pro Tyr His Leu Pro Leu
50 55 60

His Ser Tyr Cys Phe Glu Lys Leu Asp Glu Leu Arg Glu Lys Pro Cys
65 70 75 80

Leu Ile Gln Gly Ser Asn Gly Lys Ile Tyr Ser Tyr Gly Glu Val Glu
85 90 95

Leu Ile Ser Arg Lys Val Ala Ser Gly Leu Ala Lys Leu Gly Phe Lys
100 105 110

Lys Gly Asp Val Val Met Leu Leu Leu Pro Asn Cys Pro Glu Phe Val
115 120 125

Phe Val Phe Leu Gly Ala Ser Met Ala Gly Ala Ile Ala Thr Thr Ala
130 135 140

Asn Pro Phe Tyr Thr Pro Ser Asp
145 150

<210> SEQ ID NO 284
<211> LENGTH: 330
<212> TYPE: PRT
<213> ORGANISM: Eucalyptus grandis

<400> SEQUENCE: 284

Asp His Pro Pro Ala Met Ala Leu His Ile Leu Phe Thr Trp Leu Ala
1 5 10 15

Leu Ser Leu Pro Leu Leu Leu Leu Leu Leu Leu Ser Val Lys Asn Phe
20 25 30

Asn Asn Lys Lys Lys Asn Leu Pro Pro Gly Pro Pro Ser Leu Pro Ile
35 40 45

Ile Gly Asn Phe His Gln Leu Gly Pro Leu Pro His Gln Ser Leu Trp
50 55 60

Lys Leu Ser Arg Arg Tyr Gly Pro Val Met Leu Ile Arg Leu Gly Gly
65 70 75 80

Thr Pro Thr Ile Val Ile Ser Ser Pro Asp Ala Ala Arg Glu Val Leu
85 90 95

Lys Thr His Asp Leu Asp Ser Cys Ser Arg Pro Gln Met Val Gly Pro
100 105 110

Gly Arg Leu Ser Tyr Asp Ser Leu Asp Met Ala Phe Val Glu Tyr Gly
115 120 125

Asp Tyr Trp Arg Glu Leu Arg Thr Leu Cys Val Leu Glu Leu Phe Ser

```
    130                 135                 140

Met Lys Arg Val Gln Ser Phe Arg Tyr Ile Arg Glu Glu Glu Val Gly
145                 150                 155                 160

Ser Met Ile Glu Ser Ile Ala Lys Ser Ala Glu Ser Gly Thr Pro Val
                165                 170                 175

Asn Met Ser Glu Lys Phe Met Ala Leu Thr Ala Asn Phe Thr Cys Arg
            180                 185                 190

Val Ala Phe Gly Lys Pro Phe Gln Gly Thr Glu Leu Glu Asp Glu Gly
        195                 200                 205

Phe Met Asp Met Val His Glu Gly Met Ala Met Leu Gly Ser Phe Ser
    210                 215                 220

Ala Ser Asp Tyr Phe Pro Arg Leu Gly Trp Ile Val Asp Arg Phe Thr
225                 230                 235                 240

Gly Leu His Ser Arg Leu Glu Lys Ser Phe Arg Asn Leu Asp Asp Leu
                245                 250                 255

Tyr Gln Lys Val Ile Glu Glu His Arg Asn Ala Asn Lys Ser Asn Glu
            260                 265                 270

Gly Lys Glu Asp Ile Val Asp Val Leu Leu Lys Met Glu Lys Asp Gln
        275                 280                 285

Thr Glu Leu Ala Gly Val Arg Leu Lys Glu Asp Asn Ile Lys Ala Ile
    290                 295                 300

Leu Met Asn Ile Phe Leu Gly Gly Val Asp Thr Gly Ala Val Ser Trp
305                 310                 315                 320

Thr Gly Gln Trp Leu Ser Ser Leu Gly Thr
                325                 330


<210> SEQ ID NO 285
<211> LENGTH: 115
<212> TYPE: PRT
<213> ORGANISM: Eucalyptus grandis

<400> SEQUENCE: 285

Thr Glu Leu Glu Asp Glu Gly Phe Met Asp Met Val His Glu Gly Met
1               5                   10                  15

Ala Met Leu Gly Ser Phe Ser Ala Ser Asp Tyr Phe Pro Arg Leu Gly
            20                  25                  30

Trp Ile Val Asp Arg Phe Thr Gly Leu His Ser Arg Leu Glu Lys Ser
        35                  40                  45

Phe Arg Asn Leu Asp Asp Leu Tyr Gln Lys Val Ile Glu Glu His Arg
    50                  55                  60

Asn Ala Asn Lys Ser Asn Glu Gly Lys Glu Asp Ile Val Asp Val Leu
65                  70                  75                  80

Leu Lys Met Glu Lys Asp Gln Thr Glu Leu Ala Gly Val Arg Leu Lys
                85                  90                  95

Glu Asp Asn Ile Lys Ala Ile Leu Met Val Tyr His Thr Ile Ser Thr
            100                 105                 110

Tyr Tyr Leu
        115


<210> SEQ ID NO 286
<211> LENGTH: 143
<212> TYPE: PRT
<213> ORGANISM: Eucalyptus grandis

<400> SEQUENCE: 286

Leu Val Val Ala Ala Leu Leu Ile Val Leu Leu Arg Ser Lys Ser Arg
1               5                   10                  15
```

```
Lys Arg Lys Ser Asn Leu Pro Pro Ser Pro Pro Lys Leu Pro Ile Ile
            20                  25                  30

Gly Asn Leu His Gln Leu Gly Lys Ser Pro His Ile Ser Leu His Arg
        35                  40                  45

Leu Ala Arg Asn Tyr Gly Pro Ile Met Ser Leu Gln Leu Gly Glu Val
    50                  55                  60

Pro Thr Ile Val Val Ser Ser Ala Ala Met Ala Lys Glu Val Met Lys
65                  70                  75                  80

Thr His Asp Leu Val Leu Ala Asn Arg Pro Gln Ile Phe Ser Ala Lys
                85                  90                  95

His Leu Phe Tyr Asp Cys Thr Asp Met Ala Phe Ser Pro Tyr Gly Ala
            100                 105                 110

Tyr Trp Arg His Ile Arg Lys Ile Cys Ile Leu Glu Val Leu Ser Ala
        115                 120                 125

Lys Arg Val Gln Ser Phe Ser His Val Arg Glu Glu Glu Val Ala
    130                 135                 140
```

<210> SEQ ID NO 287
<211> LENGTH: 135
<212> TYPE: PRT
<213> ORGANISM: Eucalyptus grandis

<400> SEQUENCE: 287

```
Leu Thr Phe Lys Cys Leu Arg Phe Leu Phe Ser Ser Ala Ala Ala Thr
1               5                   10                  15

Asn Leu His Leu Pro Pro Ser Pro Pro Lys Leu Pro Ile Ile Gly Asn
            20                  25                  30

Leu His Gln Leu Ser Asp His Pro His Arg Ser Leu Gln Ala Leu Ser
        35                  40                  45

Arg Arg Tyr Gly Pro Leu Met Met Leu His Phe Gly Ser Val Pro Val
    50                  55                  60

Leu Val Val Ser Ser Ala Asp Cys Ala Arg Asp Ile Leu Lys Thr His
65                  70                  75                  80

Asp Leu Ile Phe Ser Asp Arg Pro Arg Ser Thr Leu Ser Glu Arg Leu
                85                  90                  95

Leu Tyr His Arg Lys Asp Val Ala Leu Ala Pro Phe Gly Glu Tyr Trp
            100                 105                 110

Arg Glu Met Arg Ser Ile Cys Val Leu Gln Leu Leu Ser Asn Lys Arg
        115                 120                 125

Val His Ser Phe Arg Thr Val
    130                 135
```

<210> SEQ ID NO 288
<211> LENGTH: 128
<212> TYPE: PRT
<213> ORGANISM: Eucalyptus grandis

<400> SEQUENCE: 288

```
Gly Lys Leu Pro His Arg Ser Leu Asp Arg Leu Ser Lys Thr Tyr Gly
1               5                   10                  15

Pro Leu Met Tyr Met Arg Leu Gly Ser Met Pro Cys Val Val Gly Ser
            20                  25                  30

Ser Ala Glu Met Ala Arg Glu Phe Leu Lys Thr His Asp Leu Thr Phe
        35                  40                  45

Ser Ser Arg Pro Arg Val Ala Ala Gly Lys Tyr Thr Val Tyr Asn Tyr
    50                  55                  60
```

Ser Asp Ile Thr Trp Ser Pro Tyr Gly Glu His Trp Arg Leu Ala Arg
65 70 75 80

Lys Ile Cys Leu Met Glu Leu Phe Ser Ala Lys Arg Leu Glu Ser Phe
85 90 95

Glu Tyr Ile Arg Val Glu Glu Val Ala Arg Met Leu Ser Ser Val Phe
100 105 110

Glu Thr Ser Arg Gln Gly Leu Pro Val Glu Ile Arg Glu Glu Thr Thr
115 120 125

<210> SEQ ID NO 289
<211> LENGTH: 179
<212> TYPE: PRT
<213> ORGANISM: Eucalyptus grandis

<400> SEQUENCE: 289

Ile Arg Met Val Asn Glu Leu Gly Ser Glu Lys Pro Phe Leu Val Cys
1 5 10 15

Leu Glu Phe Tyr Met Lys Leu Ala Ile Ala Leu Val Ala Leu Val Val
20 25 30

Ala Trp Ser Phe Phe Val Lys Gly Arg Asn Arg Lys Leu Pro Pro Gly
35 40 45

Pro Phe Ser Leu Pro Ile Ile Gly Asn Leu His Leu Leu Gly Gln Leu
50 55 60

Pro His Arg Ala Leu Thr Ala Leu Ser Leu Lys Phe Gly Pro Leu Met
65 70 75 80

Ser Leu Arg Leu Gly Ser Ala Leu Thr Leu Val Val Ser Ser Pro Asp
85 90 95

Met Ala Lys Glu Phe Leu Lys Thr His Asp Leu Leu Phe Ala Ser Arg
100 105 110

Pro Pro Ser Ala Ala Thr Asn Tyr Phe Trp Tyr Asn Cys Thr Asp Ile
115 120 125

Gly Phe Ala Pro Tyr Gly Ala Tyr Trp Arg Gln Val Arg Lys Val Cys
130 135 140

Val Leu Gln Leu Leu Ser Ser Arg Arg Leu Asp Tyr Phe Arg Phe Ile
145 150 155 160

Arg Glu Glu Glu Val Ser Ala Met Ile His Ser Ile Ala His Ser Asp
165 170 175

His Pro Val

<210> SEQ ID NO 290
<211> LENGTH: 440
<212> TYPE: PRT
<213> ORGANISM: Eucalyptus grandis

<400> SEQUENCE: 290

Ser Ser Leu Ala Phe Gly Gln His Ile Ile Ala Thr Ser Tyr Ser Cys
1 5 10 15

Asn Leu His Gln Ile Gly Glu Met Ser Phe Gln Asn Gln Leu Phe Ile
20 25 30

Phe Cys Thr Leu Leu Leu Gly Phe Leu Lys Leu Ala Glu Gly Lys Thr
35 40 45

Arg His Tyr Thr Phe His Ile Asp Ser His Asn Met Thr Arg Leu Cys
50 55 60

His Thr Arg Ser Val Leu Ser Val Asn Lys Gln Tyr Pro Gly Pro Pro
65 70 75 80

Leu Val Ala Arg Glu Gly Asp Asn Ile Leu Val Lys Val Val Asn His
85 90 95

```
Val Ala Ala Asn Val Thr Ile His Trp His Gly Val Arg Gln Leu Arg
            100                 105                 110

Thr Gly Trp Ala Asp Gly Pro Ala Tyr Val Thr Gln Cys Pro Ile Gln
        115                 120                 125

Thr Asn Gln Ser Tyr Thr Tyr Asn Phe Thr Leu Thr Gly Gln Arg Gly
    130                 135                 140

Thr Leu Leu Trp His Ala His Val Ser Trp Leu Arg Ser Ser Ile His
145                 150                 155                 160

Gly Pro Ile Ile Ile Leu Pro Lys Arg Asn Glu Ser Tyr Pro Phe Glu
                165                 170                 175

Lys Pro Ser Lys Glu Val Pro Ile Ile Phe Gly Glu Trp Phe Asn Val
            180                 185                 190

Asp Pro Glu Ala Val Ile Ala Gln Ala Leu Gln Ser Gly Gly Gly Pro
        195                 200                 205

Asn Val Ser Asp Ala Tyr Thr Ile Asn Gly Leu Pro Gly Pro Leu Tyr
    210                 215                 220

Asn Cys Ser Ser Lys Asp Thr Phe Lys Leu Lys Val Lys Pro Gly Lys
225                 230                 235                 240

Thr Tyr Leu Leu Arg Leu Ile Asn Ala Ala Leu Asn Asp Glu Leu Phe
                245                 250                 255

Phe Ser Ile Ala Asn His Ala Val Thr Val Val Glu Val Asp Ala Val
            260                 265                 270

Tyr Thr Lys Pro Phe Ser Ala Gly Cys Leu His Leu Thr Pro Gly Gln
        275                 280                 285

Thr Met Asn Val Leu Leu Lys Thr Lys Thr Asp Phe Pro Asn Ser Thr
    290                 295                 300

Phe Leu Met Ala Ala Trp Pro Tyr Phe Thr Gly Met Gly Thr Phe Asp
305                 310                 315                 320

Asn Ser Thr Val Ala Gly Ile Leu Glu Tyr Glu His Pro Lys Ser Ser
                325                 330                 335

Asn Tyr Pro Pro Leu Lys Lys Leu Pro Gln Tyr Lys Pro Thr Leu Pro
            340                 345                 350

Pro Met Asn Ser Thr Gly Phe Val Ala Lys Phe Thr Gly Gln Leu Arg
        355                 360                 365

Ser Leu Ala Ser Ala Lys Phe Pro Ala Asn Val Pro Gln Lys Val Asp
    370                 375                 380

Arg Lys Phe Phe Phe Thr Val Gly Leu Gly Thr Ser Pro Cys Pro Lys
385                 390                 395                 400

Asn Thr Thr Cys Gln Gly Pro Asn Gly Thr Lys Phe Ala Ala Ser Val
                405                 410                 415

Asn Asn Ile Ser Phe Val Leu Pro Ser Val Ala Leu Leu Gln Ala His
            420                 425                 430

Phe Phe Gly Gln Ser Asn Gly Val
        435                 440
```

<210> SEQ ID NO 291
<211> LENGTH: 326
<212> TYPE: PRT
<213> ORGANISM: Eucalyptus grandis

<400> SEQUENCE: 291

```
Pro Ala Val Val Glu Gly Arg Val Arg Asn Tyr Thr Phe Asn Val Val
1               5                   10                  15

Met Lys Asn Thr Thr Arg Leu Cys Ser Ser Lys Pro Ile Val Thr Val
            20                  25                  30
```

Asn Gly Met Phe Pro Gly Pro Thr Leu Tyr Ala Arg Glu Asp Asp Thr
35 40 45

Val Leu Val Arg Val Ser Asn Arg Val Lys Tyr Asn Val Thr Ile His
50 55 60

Trp His Gly Ile Arg Gln Leu Arg Thr Gly Trp Ala Asp Gly Pro Ala
65 70 75 80

Tyr Ile Thr Gln Cys Pro Ile Gln Pro Gly Gln Ser Tyr Val Tyr Asn
85 90 95

Phe Thr Ile Thr Gly Gln Arg Gly Thr Leu Leu Trp His Ala His Ile
100 105 110

Leu Trp Leu Arg Ala Thr Leu His Gly Ala Ile Val Ile Leu Pro Lys
115 120 125

Arg Gly Val Pro Tyr Pro Phe Pro Lys Pro His Lys Glu Val Val Val
130 135 140

Val Leu Gly Glu Trp Trp Lys Ser Asp Thr Glu Gly Val Ile Ser Gln
145 150 155 160

Ala Ile Lys Ser Gly Leu Ala Pro Asn Val Ser Asp Ala His Thr Ile
165 170 175

Asn Gly His Pro Gly Pro Ser Ser Asn Cys Pro Ser Gln Gly Gly Phe
180 185 190

Thr Leu Pro Val Glu Ser Gly Lys Lys Tyr Met Leu Arg Ile Ile Asn
195 200 205

Ala Ala Leu Asn Glu Glu Leu Phe Phe Lys Ile Ala Gly His Gln Leu
210 215 220

Thr Ile Val Glu Val Asp Ala Thr Tyr Val Lys Pro Phe Lys Thr Asp
225 230 235 240

Thr Ile Val Ile Ala Pro Gly Gln Thr Thr Asn Ala Leu Ile Ser Thr
245 250 255

Asp Gln Ser Ser Gly Lys Tyr Met Val Ala Ala Ser Pro Phe Met Asp
260 265 270

Ser Pro Ile Ala Val Asp Asn Met Thr Ala Thr Ala Thr Leu His Tyr
275 280 285

Ser Gly Thr Leu Ala Ala Thr Ser Thr Thr Leu Thr Lys Thr Pro Pro
290 295 300

Gln Asn Ala Thr Ala Val Ala Asn Asn Phe Val Asn Ser Leu Arg Ser
305 310 315 320

Leu Asn Ser Lys Arg Tyr
325

<210> SEQ ID NO 292
<211> LENGTH: 101
<212> TYPE: PRT
<213> ORGANISM: Eucalyptus grandis

<400> SEQUENCE: 292

Arg Leu Cys Ser Ser Lys Pro Ile Val Thr Val Asn Gly Met Phe Pro
1 5 10 15

Gly Pro Thr Leu Tyr Ala Arg Glu Asp Asp Thr Val Leu Val Arg Val
20 25 30

Ser Asn Arg Val Lys Tyr Asn Val Thr Ile His Trp His Gly Ile Arg
35 40 45

Gln Leu Arg Ser Gly Trp Ala Asp Gly Pro Ala Tyr Ile Thr Gln Cys
50 55 60

Pro Ile Gln Pro Gly Gln Ser Tyr Val Tyr Asn Phe Thr Ile Thr Gly
65 70 75 80

Gln Arg Gly Thr Leu Leu Trp His Ala His Ile Leu Trp Leu Arg Ala
85 90 95

Thr Leu His Gly Ala
100

<210> SEQ ID NO 293
<211> LENGTH: 136
<212> TYPE: PRT
<213> ORGANISM: Eucalyptus grandis

<400> SEQUENCE: 293

Thr Val Asp His Ser Leu Leu Phe Thr Val Gly Leu Gly Ile Asn Pro
1 5 10 15

Cys Pro Ser Cys Lys Ala Gly Asn Gly Ser Arg Val Val Ala Ser Met
20 25 30

Asn Asn Val Thr Phe Val Met Pro Thr Thr Ala Ile Leu Gln Ala His
35 40 45

Phe Phe Asn Lys Ser Gly Val Phe Thr Ser Asp Phe Pro Gly Asn Pro
50 55 60

Pro Thr Ile Phe Asn Tyr Thr Gly Ser Pro Pro Ser Asn Leu Arg Thr
65 70 75 80

Thr Ser Gly Thr Lys Val Tyr Arg Leu Arg Tyr Asn Ser Thr Val Gln
85 90 95

Leu Val Phe Gln Asp Thr Gly Ile Ile Ala Pro Glu Asn His Pro Ile
100 105 110

His Leu His Gly Phe Asn Phe Phe Ala Ile Gly Lys Gly Leu Gly Asn
115 120 125

Tyr Asn Pro Lys Val Asp Gln Lys
130 135

<210> SEQ ID NO 294
<211> LENGTH: 104
<212> TYPE: PRT
<213> ORGANISM: Eucalyptus grandis

<400> SEQUENCE: 294

His Lys Glu Val Val Val Val Leu Gly Glu Trp Trp Lys Ser Asp Thr
1 5 10 15

Glu Ala Val Ile Asn Gln Ala Ile Lys Ser Gly Leu Ala Pro Asn Val
20 25 30

Ser Asp Ala His Thr Ile Asn Gly His Pro Gly Pro Ser Ser Asn Cys
35 40 45

Pro Ser Gln Gly Gly Phe Thr Leu Pro Val Glu Ser Gly Lys Lys Tyr
50 55 60

Met Leu Arg Ile Ile Asn Ala Ala Leu Asn Glu Glu Leu Phe Phe Lys
65 70 75 80

Ile Ala Gly His Gln Leu Thr Ile Val Glu Val Asp Ala Thr Tyr Val
85 90 95

Lys Pro Phe Lys Thr Asn Thr Gly
100

<210> SEQ ID NO 295
<211> LENGTH: 110
<212> TYPE: PRT
<213> ORGANISM: Eucalyptus grandis

<400> SEQUENCE: 295

Arg Gly Val Pro Tyr Pro Phe Pro Lys Pro His Lys Glu Val Val Val

```
1               5                   10                  15

Val Leu Gly Glu Trp Trp Lys Ser Asp Thr Glu Ala Val Ile Asn Gln
            20                  25                  30

Ala Ile Lys Ser Gly Leu Ala Pro Asn Val Ser Asp Ala His Thr Ile
        35                  40                  45

Asn Gly His Pro Gly Pro Ser Ser Asn Cys Pro Ser Gln Gly Gly Phe
    50                  55                  60

Thr Leu Pro Val Glu Ser Gly Lys Lys Tyr Met Leu Arg Ile Ile Asn
65                  70                  75                  80

Ala Ala Leu Asn Glu Glu Leu Phe Phe Lys Ile Ala Gly His Gln Leu
                85                  90                  95

Thr Ile Val Glu Val Asp Ala Thr Tyr Val Lys Pro Phe Lys
            100                 105                 110


<210> SEQ ID NO 296
<211> LENGTH: 384
<212> TYPE: PRT
<213> ORGANISM: Eucalyptus grandis

<400> SEQUENCE: 296

Pro Asn Val Ser Asp Ala Tyr Thr Ile Asn Gly Gln Pro Gly Asp Leu
1               5                   10                  15

Tyr Asn Cys Ser Ser Lys Asp Thr Val Ile Val Pro Ile Asp Ser Gly
            20                  25                  30

Glu Thr His Leu Leu Arg Val Ile Asn Ala Ala Leu Asn Gln Glu Leu
        35                  40                  45

Phe Phe Thr Val Ala Asn His Arg Phe Thr Val Val Gly Ala Asp Ala
    50                  55                  60

Ser Tyr Leu Lys Pro Phe Thr Thr Ser Val Ile Met Leu Gly Pro Gly
65                  70                  75                  80

Gln Thr Thr Asp Val Leu Ile Ser Gly Asp Gln Pro Pro Ala Arg Tyr
                85                  90                  95

Tyr Met Ala Ala Glu Pro Tyr Gln Ser Ala Gln Gly Ala Pro Phe Asp
            100                 105                 110

Asn Thr Thr Thr Thr Ala Ile Leu Glu Tyr Lys Ser Ala Pro Cys Pro
        115                 120                 125

Ala Lys Gly Ile Ser Ser Lys Pro Val Met Pro Thr Leu Pro Ala Phe
    130                 135                 140

Asn Asp Thr Ala Thr Val Thr Ala Phe Ile Gln Ser Phe Arg Ser Pro
145                 150                 155                 160

Asn Lys Val Asp Val Pro Thr Asp Ile Asp Glu Asn Leu Phe Ile Thr
                165                 170                 175

Val Gly Leu Gly Leu Phe Asn Cys Pro Lys Asn Phe Gly Ser Ser Arg
            180                 185                 190

Cys Gln Gly Pro Asn Gly Thr Arg Phe Thr Ala Ser Met Asn Asn Val
        195                 200                 205

Ser Phe Val Leu Pro Ser Asn Val Ser Ile Leu Gln Ala Tyr Lys Gln
    210                 215                 220

Gly Val Pro Gly Val Phe Thr Thr Asp Phe Pro Ala Asn Pro Pro Val
225                 230                 235                 240

Gln Phe Asp Tyr Thr Gly Asn Val Ser Arg Ser Leu Trp Gln Pro Val
                245                 250                 255

Pro Gly Thr Lys Val Tyr Lys Leu Lys Tyr Gly Ser Arg Val Gln Ile
            260                 265                 270

Val Leu Gln Gly Thr Asn Ile Gln Thr Ala Glu Asn His Pro Ile His
```

```
        275                 280                 285

Ile His Gly Tyr Asp Phe Tyr Ile Leu Ala Thr Gly Phe Gly Asn Phe
    290                 295                 300

Asn Pro Gln Lys Asp Thr Ala Lys Phe Asn Leu Val Asp Pro Pro Met
305                 310                 315                 320

Arg Asn Thr Val Gly Val Ser Val Asn Gly Trp Ala Val Ile Arg Phe
                325                 330                 335

Val Ala Asp Asn Pro Gly Ala Trp Leu Met His Cys His Leu Asp Val
            340                 345                 350

His Ile Thr Trp Gly Leu Ala Val Val Phe Leu Val Glu Asn Gly Val
        355                 360                 365

Gly Glu Leu Gln Ser Leu Gln Pro Pro Pro Ala Asp Leu Pro Pro Cys
    370                 375                 380


<210> SEQ ID NO 297
<211> LENGTH: 139
<212> TYPE: PRT
<213> ORGANISM: Eucalyptus grandis

<400> SEQUENCE: 297

Ser Cys Leu Ser Leu His His His Leu Arg Gln Val Thr Ser Asp Phe
1               5                   10                  15

Glu Glu Asp Glu Glu Arg Lys Met Gly Ser Ala Thr Ala Ala Gly Ala
            20                  25                  30

Ser Val Ser Ser Arg Met Ile Leu Met Arg Ala Ala Phe Phe Thr Leu
        35                  40                  45

Cys Ala Leu Val Phe Leu Pro Ala Leu Ala Gln Ala Lys His Gly Gly
    50                  55                  60

Val Thr Arg His Tyr Lys Phe Asp Ile Lys Met Gln Asn Val Thr Arg
65                  70                  75                  80

Leu Cys Gln Thr Lys Ser Ile Val Thr Val Asn Gly Gln Leu Pro Gly
                85                  90                  95

Pro Arg Ile Ile Ala Arg Glu Gly Asp Arg Leu Leu Ile Lys Val Val
            100                 105                 110

Asn Asn Val Gln Tyr Asn Val Thr Ile His Trp His Gly Val Arg Gln
        115                 120                 125

Leu Arg Ser Gly Trp Ala Asp Gly Pro Ala Tyr
    130                 135


<210> SEQ ID NO 298
<211> LENGTH: 155
<212> TYPE: PRT
<213> ORGANISM: Eucalyptus grandis

<400> SEQUENCE: 298

Pro Asp Arg Val Ile Ser Thr Ser Ser Ile Leu Tyr Gln Gly Glu Arg
1               5                   10                  15

Gly Thr Met Gly Thr Phe Leu Gly Phe Ala Val Thr Ala Thr Leu Leu
            20                  25                  30

Phe Cys Val Ala Gln Gly Glu Val Leu Phe Tyr Asp Phe Val Val Asn
        35                  40                  45

Glu Thr Pro Ile Glu Met Leu Cys Glu Thr Asn Arg Ser Val Leu Thr
    50                  55                  60

Val Asn Gly Leu Phe Pro Gly Pro Glu Ile His Ala His Lys Gly Asp
65                  70                  75                  80

Thr Ile Tyr Val Asn Val Thr Asn Leu Gly Pro Tyr Gly Val Thr Ile
                85                  90                  95
```

```
His Trp His Gly Val Arg Gln Ile Arg Tyr Pro Trp Ser Asp Gly Pro
            100                 105                 110

Glu Tyr Val Thr Gln Cys Pro Ile Pro Thr Asn Ser Ser Phe Leu Gln
        115                 120                 125

Lys Ile Lys Leu Thr Glu Glu Glu Gly Thr Val Trp Trp His Ala His
    130                 135                 140

Ser Asp Trp Ser Arg Ala Thr Ile His Gly Leu
145                 150                 155


<210> SEQ ID NO 299
<211> LENGTH: 179
<212> TYPE: PRT
<213> ORGANISM: Eucalyptus grandis

<400> SEQUENCE: 299

Leu Leu Gln Val His Phe Ser Leu Val Glu Arg Glu Arg Glu Met Gly
1               5                   10                  15

Thr Phe Leu Gly Phe Val Val Thr Met Thr Leu Leu Phe Cys Met Ala
            20                  25                  30

Gln Gly Glu Val Ile Tyr Tyr Asp Phe Val Val Lys Glu Thr Pro Ile
        35                  40                  45

Gln Met Leu Cys Gly Thr Asn Gln Thr Val Leu Thr Val Asn Gly Leu
    50                  55                  60

Phe Pro Gly Pro Glu Ile His Ala His Lys Gly Asp Thr Ile Tyr Val
65                  70                  75                  80

Asn Val Thr Asn Thr Gly Pro Tyr Gly Val Thr Ile His Trp His Gly
                85                  90                  95

Val Arg Gln Ile Arg Tyr Pro Trp Ser Asp Gly Pro Glu Tyr Ile Thr
            100                 105                 110

Gln Cys Pro Ile Pro Thr Asn Ser Ser Phe Leu Gln Lys Ile Ile Leu
        115                 120                 125

Thr Glu Glu Glu Gly Thr Leu Trp Trp His Ala His Ser Asp Trp Thr
    130                 135                 140

Arg Ala Thr Ile His Gly Pro Ile Ile Ile Leu Pro Val Asn Gly Thr
145                 150                 155                 160

Asn Tyr Pro Tyr Lys Phe Asp Glu Gln His Thr Ile Val Ile Ser Glu
                165                 170                 175

Trp Tyr Ala


<210> SEQ ID NO 300
<211> LENGTH: 62
<212> TYPE: PRT
<213> ORGANISM: Eucalyptus grandis

<400> SEQUENCE: 300

Glu Arg Glu Met Gly Thr Phe Leu Gly Phe Val Val Thr Met Thr Leu
1               5                   10                  15

Leu Phe Cys Met Ala Gln Gly Glu Val Leu Tyr Tyr Asp Phe Val Val
            20                  25                  30

Lys Glu Thr Pro Ile Gln Met Leu Cys Gly Thr Asn Gln Thr Val Leu
        35                  40                  45

Thr Val Asn Gly Leu Phe Pro Gly Pro Glu Ile His Ala His
    50                  55                  60


<210> SEQ ID NO 301
<211> LENGTH: 190
<212> TYPE: PRT
```

<213> ORGANISM: Pinus radiata

<400> SEQUENCE: 301

Leu Ala Val Met Ser Asn Glu Gln Leu Leu Glu Phe Ala Trp Gly Leu
1 5 10 15

Ala Ser Ser Asn Gln Ser Phe Leu Trp Val Val Arg Ser Asp Ile Val
20 25 30

His Gly Glu Ser Ala Ile Leu Pro Lys Glu Phe Ile Glu Glu Thr Lys
35 40 45

Asp Arg Gly Met Leu Val Gly Trp Ala Pro Gln Ile Lys Val Leu Ser
50 55 60

His Pro Ser Val Gly Gly Phe Leu Thr His Ser Gly Trp Asn Ser Thr
65 70 75 80

Leu Glu Ser Ile Ser Ala Gly Val Pro Met Met Cys Trp Pro Phe Phe
85 90 95

Ala Glu Gln Glu Thr Asn Ala Lys Phe Val Cys Glu Glu Trp Gly Ile
100 105 110

Gly Met Gln Val Lys Lys Met Val Lys Arg Glu Glu Leu Ala Ile Leu
115 120 125

Val Arg Asn Ser Ile Lys Gly Glu Glu Gly Asp Glu Met Arg Lys Arg
130 135 140

Ile Gly Lys Leu Lys Glu Thr Ala Lys Arg Ala Val Ser Glu Gly Gly
145 150 155 160

Ser Ser Lys Asn Asn Leu Asp Lys Leu Leu His His Ile Phe Leu Lys
165 170 175

Gly Met His Gln Met Ile Val Gln Asn Val Glu Ala Asn Asn
180 185 190

<210> SEQ ID NO 302
<211> LENGTH: 365
<212> TYPE: PRT
<213> ORGANISM: Eucalyptus grandis

<400> SEQUENCE: 302

Pro Met Glu Ser Cys Ser Ile Ser Leu Phe Trp Leu Gly Leu Leu Leu
1 5 10 15

Pro Ala Leu Leu Val Phe Leu Leu Asn Arg Arg Lys Arg Thr Lys Leu
20 25 30

Pro Pro Gln Pro Pro Ala Trp Pro Val Ile Gly Asn Ile Phe Asp Leu
35 40 45

Gly Thr Met Pro His Gln Asn Leu His Asn Leu Arg Ala Lys His Gly
50 55 60

Pro Val Leu Trp Leu Lys Leu Gly Ser Val Asn Thr Met Val Ile Gln
65 70 75 80

Ser Ala Arg Ala Ala Met Glu Leu Phe Lys Gly His Asp Phe Val Phe
85 90 95

Ala Asp Arg Lys Cys Ser Gln Ala Phe Thr Ala Leu Gly Tyr Asp Gln
100 105 110

Gly Ser Leu Ala Leu Gly Arg His Gly Asp Tyr Trp Arg Ala Leu Arg
115 120 125

Arg Leu Cys Ser Ala Glu Leu Leu Val Asn Lys Arg Val Asn Asp Thr
130 135 140

Ala His Leu Arg Gln Lys Cys Val Asp Ser Met Ile Met Tyr Ile Glu
145 150 155 160

Glu Glu Met Ala Val Lys Gln Ala Thr Lys Gly Gln Gly Ile Asp Leu
165 170 175

```
Ser His Phe Leu Phe Leu Leu Ala Phe Asn Val Val Gly Asn Met Val
            180                 185                 190

Leu Ser Arg Asp Leu Leu Asp Pro Lys Ser Lys Asp Gly Pro Glu Phe
        195                 200                 205

Tyr Asp Ala Met Asn Arg Phe Met Glu Trp Ala Gly Lys Pro Asn Val
    210                 215                 220

Ala Asp Phe Met Pro Trp Leu Lys Trp Leu Asp Pro Gln Gly Ile Lys
225                 230                 235                 240

Ala Gly Met Ala Lys Asp Met Gly Arg Ala Met Arg Ile Ala Glu Gly
                245                 250                 255

Phe Val Lys Glu Arg Leu Glu Glu Arg Lys Leu Arg Gly Glu Met Arg
            260                 265                 270

Thr Thr Asn Asp Phe Leu Asp Ala Val Leu Asp Tyr Glu Gly Asp Gly
        275                 280                 285

Lys Glu Gly Pro His Asn Ile Ser Ser Gln Asn Ile Asn Ile Ile Ile
    290                 295                 300

Leu Glu Met Phe Phe Ala Gly Ser Glu Ser Thr Ser Ser Thr Ile Glu
305                 310                 315                 320

Trp Ala Met Ala Glu Leu Leu Arg Gln Pro Glu Ser Met Lys Lys Ala
                325                 330                 335

Lys Asp Glu Ile Asp Gln Val Val Gly Leu Asn Arg Lys Leu Glu Glu
            340                 345                 350

Asn Asp Thr Glu Lys Met Pro Phe Leu Gln Ala Val Val
        355                 360                 365


<210> SEQ ID NO 303
<211> LENGTH: 183
<212> TYPE: PRT
<213> ORGANISM: Eucalyptus grandis

<400> SEQUENCE: 303

Pro Met Glu Ser Cys Ser Ile Ser Leu Phe Trp Leu Gly Leu Leu Leu
1               5                   10                  15

Pro Ala Leu Leu Val Phe Leu Leu Asn Arg Arg Lys Arg Thr Lys Leu
            20                  25                  30

Pro Pro Gln Pro Pro Ala Trp Pro Val Ile Gly Asn Ile Phe Asp Leu
        35                  40                  45

Gly Thr Met Pro His Gln Asn Leu His Asn Leu Arg Ala Lys His Gly
    50                  55                  60

Pro Val Leu Trp Leu Lys Leu Gly Ser Val Asn Thr Met Val Ile Gln
65                  70                  75                  80

Ser Ala Gln Ala Ala Met Glu Leu Phe Lys Gly His Asp Phe Val Phe
                85                  90                  95

Ala Asp Arg Lys Cys Ser Gln Ala Phe Thr Ala Leu Gly Tyr Asp Gln
            100                 105                 110

Gly Ser Leu Ala Leu Gly Arg His Gly Asp Tyr Trp Arg Ala Leu Arg
        115                 120                 125

Arg Leu Cys Ser Ala Glu Leu Leu Val Asn Lys Arg Val Asn Glu Thr
    130                 135                 140

Ala His Leu Arg Gln Lys Cys Val Asp Ser Met Ile Met Tyr Ile Glu
145                 150                 155                 160

Glu Glu Met Ala Val Lys Gln Ala Thr Lys Gly Gln Gly Ile Asp Leu
                165                 170                 175

Ser His Phe Leu Phe Leu Leu
            180
```

<210> SEQ ID NO 304
<211> LENGTH: 148
<212> TYPE: PRT
<213> ORGANISM: Eucalyptus grandis

<400> SEQUENCE: 304

```
Met Lys Ala Gln Asp Glu Ile Asp Ser Met Ile Gly His Asp Ser Leu
1               5                   10                  15

Leu Glu Glu Ser Asp Val Ser Lys Leu Pro Tyr Leu Gln Cys Ile Ile
            20                  25                  30

Leu Glu Thr Leu Arg Leu Asn Thr Thr Ala Pro Leu Leu Leu Pro His
        35                  40                  45

Ala Ser Ser Ala Asp Cys Thr Ile Gly Gly Tyr Phe Val Pro Arg Asp
    50                  55                  60

Thr Ile Val Met Val Asn Ala Trp Ala Ile His Lys Asp Pro Gln Leu
65                  70                  75                  80

Trp Glu Asp Pro Leu Ser Phe Lys Pro Glu Arg Phe Glu Gly Asn Gly
                85                  90                  95

Ser Glu Lys Gln Gln Lys Leu Leu Leu Pro Phe Gly Leu Gly Arg Arg
            100                 105                 110

Ala Cys Pro Gly Ala Pro Leu Ala His Arg Val Met Gly Trp Thr Leu
        115                 120                 125

Gly Leu Leu Ile Gln Cys Phe Asp Trp Lys Arg Val Ser Glu Glu Glu
    130                 135                 140

Ile Asp Met Thr
145
```

<210> SEQ ID NO 305
<211> LENGTH: 164
<212> TYPE: PRT
<213> ORGANISM: Eucalyptus grandis

<400> SEQUENCE: 305

```
Tyr Leu Gly Asp Phe Leu Pro Ile Leu Lys Leu Val Asp Tyr Asn Gly
1               5                   10                  15

Val Lys Lys Arg Val Val Glu Leu Lys Glu Lys Phe Asp Ala Phe Ile
            20                  25                  30

Gln Gly Leu Ile Asn Glu His Arg Arg Lys Lys Gly Asp Pro Glu Leu
        35                  40                  45

Ala Asp Ser Met Ile Ser His Leu Leu His Leu Gln Glu Ser Gln Pro
    50                  55                  60

Glu Asp Tyr Ser Asp Ser Met Ile Lys Gly Leu Val Leu Val Leu Leu
65                  70                  75                  80

Val Ala Gly Thr Asp Thr Ser Ser Leu Thr Leu Glu Trp Ile Met Thr
                85                  90                  95

Asn Leu Leu Asn Asn Pro Glu Lys Leu Glu Lys Ala Arg Asn Glu Ile
            100                 105                 110

Asp Ser Val Ile Gly His Asp Arg Leu Val Glu Glu Ser Asp Val Ser
        115                 120                 125

Asn Leu Pro Tyr Leu Gln Cys Ile Ile Leu Glu Thr Leu Arg Leu Asn
    130                 135                 140

Thr Thr Val Pro Leu Leu Val Pro His Ala Ser Ser Ala Asp Cys Thr
145                 150                 155                 160

Ile Gly Gly Tyr
```

<210> SEQ ID NO 306
<211> LENGTH: 163
<212> TYPE: PRT
<213> ORGANISM: Eucalyptus grandis

<400> SEQUENCE: 306

Leu Ser Asp Ala Ile Pro Ala Leu Gly Trp Leu Asp Ser Gly Gly Tyr
1 5 10 15

Arg Arg Ser Met Asp Glu Thr Ala Lys Glu Leu Asp Val Leu Ala Gln
20 25 30

Gly Trp Leu Glu Glu His Arg Arg Lys Arg Leu Ser Cys Pro Lys Asp
35 40 45

Asp Arg Glu Gln Asp Phe Met Asp Trp Met Ile Asn Ala Leu Glu Gly
50 55 60

Arg Asn Phe Pro Asp Phe Asp Ala Asp Thr Val Ile Lys Ala Thr Cys
65 70 75 80

Leu Asn Met Ile Ile Ala Gly Thr Asp Thr Ser Thr Val Ala Ile Thr
85 90 95

Trp Ala Leu Ser Leu Leu Met Asn Asn Arg Arg Ala Leu Lys Lys Ala
100 105 110

Gln Gln Glu Leu Asp Thr His Val Gly Arg Ser Arg Pro Val Glu Glu
115 120 125

Ser Asp Val Lys Asn Leu Thr Tyr Leu Gln Ala Ile Val Lys Glu Ala
130 135 140

Leu Arg Leu Tyr Pro Pro Val Pro Val Asn Gly Leu Arg Ser Ser Met
145 150 155 160

Glu Glu Cys

<210> SEQ ID NO 307
<211> LENGTH: 129
<212> TYPE: PRT
<213> ORGANISM: Pinus radiata

<400> SEQUENCE: 307

Arg Leu Pro Pro Gly Pro Pro Gly Trp Pro Ile Val Gly Asn Leu Phe
1 5 10 15

Gln Leu Gly Asn Lys Pro His Glu Ala Leu Phe His Leu Ala Gln Lys
20 25 30

Tyr Gly Pro Leu Met Cys Val Ser Leu Gly Met Lys Thr Thr Val Val
35 40 45

Val Ser Ser Pro Ala Met Ala Lys Gln Val Leu Lys Thr His Asp His
50 55 60

Val Phe Ala Gly Arg Thr Val Ile Gln Ser Val Gln Cys Leu Ser Tyr
65 70 75 80

Asp Lys Ser Ser Val Ile Trp Ala Gln Tyr Gly Ser His Trp Arg Leu
85 90 95

Leu Arg Arg Ile Ser Asn Thr Lys Leu Phe Ser Val Lys Arg Leu Glu
100 105 110

Ala Leu Glu His Leu Arg Arg Asp Glu Val Phe Arg Thr Ile Lys Gln
115 120 125

Ile

<210> SEQ ID NO 308
<211> LENGTH: 166
<212> TYPE: PRT
<213> ORGANISM: Pinus radiata

<400> SEQUENCE: 308

```
Leu Val Tyr Leu Gln Ala Ala Val Lys Glu Thr Leu Arg Leu His Pro
1               5                   10                  15

Ser Gly Pro Leu Leu Val Arg His Leu Phe Gly Thr Ala Ser Cys Asn
            20                  25                  30

Val Leu Gly Tyr Glu Ile Pro Gln Asn Thr Leu Val Leu Val Asn Val
        35                  40                  45

Trp Ala Ile Gly Arg Asn Pro Lys Ser Trp Glu Asp Ala Glu Val Phe
    50                  55                  60

Lys Pro Glu Arg Phe Met Glu Lys Val Gly Ser Glu Val Asp Ala Asn
65                  70                  75                  80

Gly Asp Gln Asn Phe Gly Cys Leu Leu Phe Gly Ala Gly Arg Arg Arg
                85                  90                  95

Cys Pro Gly Gln Gln Leu Gly Thr Leu Leu Val Glu Phe Gly Leu Ala
            100                 105                 110

Gln Leu Leu His Cys Phe Asn Trp Arg Leu Pro Leu Asp Asp Ile Asn
        115                 120                 125

Gly Glu Asn Gln Glu Val Asp Met Asn Glu Met Phe Asn Gly Val Thr
    130                 135                 140

Leu Arg Lys Ala Arg Glu Leu Ser Ala Ile Pro Thr Pro Arg Leu Glu
145                 150                 155                 160

Cys Ile Ala His Leu Lys
                165


<210> SEQ ID NO 309
<211> LENGTH: 123
<212> TYPE: PRT
<213> ORGANISM: Pinus radiata

<400> SEQUENCE: 309

Ser Cys Trp Arg Cys Val Ala Glu Pro Asn His Ala Trp Ser Asn Leu
1               5                   10                  15

Ser Arg Lys Arg Lys Gly Arg Leu Pro Pro Gly Pro Phe Ser Leu Pro
            20                  25                  30

Ile Ile Gly Asn Leu His Met Leu Gly Lys Ile Pro His Arg Ser Leu
        35                  40                  45

Ala Glu Leu Ser Met Lys Tyr Gly Pro Leu Leu Ser Leu Arg Leu Gly
    50                  55                  60

Ser Thr Pro Ala Leu Val Val Ser Ser Pro Glu Ile Ala Ser Glu Phe
65                  70                  75                  80

Leu Lys Thr His Asp Gln Leu Phe Ala Ser Arg Ile Pro Ser Ala Ala
                85                  90                  95

Ile Lys Val Leu Thr Tyr Asn Leu Ser Gly Leu Ile Phe Ser Pro Tyr
            100                 105                 110

Gly Pro Cys Trp Arg Gln Val Arg Lys Leu Cys
        115                 120


<210> SEQ ID NO 310
<211> LENGTH: 114
<212> TYPE: PRT
<213> ORGANISM: Pinus radiata

<400> SEQUENCE: 310

Tyr Ser Glu Pro Ser Lys Lys Leu Ala Met Glu Phe Val Glu Phe Cys
1               5                   10                  15

Ile Thr Leu Val Thr Ala Leu Leu Phe Val Val Leu Val Ala Ala Trp
            20                  25                  30
```

```
Ser Asn Leu Phe Arg Lys Arg Lys Gly Arg Leu Pro Pro Gly Pro Phe
        35                  40                  45

Ser Leu Pro Ile Ile Gly Asn Leu His Met Leu Gly Lys Ile Pro His
    50                  55                  60

Arg Ser Leu Ala Glu Leu Ser Met Lys Tyr Gly Pro Leu Leu Ser Leu
65                  70                  75                  80

Arg Leu Gly Ser Thr Pro Ala Leu Val Val Ser Ser Pro Glu Ile Ala
                85                  90                  95

Ser Glu Phe Leu Lys Thr His Asp Gln Leu Phe Ala Ser Arg Ile Pro
            100                 105                 110

Ser Ala


<210> SEQ ID NO 311
<211> LENGTH: 154
<212> TYPE: PRT
<213> ORGANISM: Pinus radiata

<400> SEQUENCE: 311

Glu Leu Leu Ser Ala Cys Pro Val His Glu Cys Pro Tyr Phe Tyr Phe
1               5                   10                  15

Asn Leu Ala Thr Val Ile Leu Leu Gly Val Val Thr Gly Trp Gly Phe
            20                  25                  30

Leu Phe Arg Gly Arg Lys Gln Lys Leu Pro Pro Gly Pro Phe Gln Trp
        35                  40                  45

Pro Ile Val Gly Asn Leu His Met Met Gly Glu Leu Pro His Gln Ala
    50                  55                  60

Ile Thr Ala Leu Ser Met Lys Tyr Gly Pro Leu Met Ser Leu Arg Leu
65                  70                  75                  80

Gly Ser Tyr Leu Thr Leu Val Val Ser Ser Pro Asp Val Ala Glu Glu
                85                  90                  95

Phe Leu Lys Thr His Asp Leu Ala Phe Ala Ser Arg Pro Pro Thr Ile
            100                 105                 110

Gly Thr Lys Tyr Phe Trp Tyr Asn Ser Ser Asp Val Ala Phe Ser Pro
        115                 120                 125

Tyr Gly Pro Tyr Trp Arg Gln Met Arg Lys Ile Cys Val Leu Gln Leu
    130                 135                 140

Leu Ser Ser Arg Arg Ile Asp Ser Phe Arg
145                 150


<210> SEQ ID NO 312
<211> LENGTH: 116
<212> TYPE: PRT
<213> ORGANISM: Pinus radiata

<400> SEQUENCE: 312

Cys Asp Gln Asp Leu Ile Gly Gly Ile Gly Ile Lys Ser Met Ile Lys
1               5                   10                  15

Glu Thr Phe Val Leu Ala Gly Ser Leu Asn Met Gly Asp Phe Ile Pro
            20                  25                  30

Tyr Leu Ala Trp Ile Asp Leu Gln Gly Leu Asn Arg Arg Leu Lys Asn
        35                  40                  45

Ile His Lys Ile Gln Asp Asp Leu Leu Gly Lys Ile Leu Glu Glu His
    50                  55                  60

Ala Ser Pro Pro Gln Asn Asn Pro Asn Tyr Met Pro Asp Leu Val Asp
65                  70                  75                  80

Val Leu Leu Ala Ala Ser Ala Asp Glu Asp Leu Glu Phe Glu Ile Thr
                85                  90                  95
```

Arg Asp Asn Ile Lys Ser Val Ile Tyr Val Tyr Ile Val His Ala Ile
100 105 110

Ile Arg Phe Gln
115

<210> SEQ ID NO 313
<211> LENGTH: 180
<212> TYPE: PRT
<213> ORGANISM: Pinus radiata

<400> SEQUENCE: 313

Ala Pro Asp Glu Leu Glu Arg Val Val Gly Leu Gly Arg Met Val Arg
1 5 10 15

Glu Ser Asp Leu Pro Arg Leu Val Tyr Leu Gln Ala Val Val Lys Glu
20 25 30

Thr Leu Arg Leu Tyr Pro Gln Gly Pro Ile Leu Phe Arg His Leu Ser
35 40 45

Ser Glu Pro Cys Asn Val Leu Gly Tyr Glu Ile Ser Gln Asn Thr Gln
50 55 60

Val Leu Val Asn Ile Trp Ala Ile Gly Arg Asn Ser Glu Ser Trp Glu
65 70 75 80

Asp Ala Gly Ser Phe Lys Pro Glu Arg Phe Met Glu Arg Val Gly Ser
85 90 95

Glu Val Asp Thr Asn Gly Asp Gln Asn Ser Ala Trp Leu Pro Phe Gly
100 105 110

Ala Gly Arg Arg Arg Cys Pro Gly Gln Gln Leu Gly Thr Leu Val Ala
115 120 125

Glu Ile Gly Leu Ala Gln Leu Leu His Cys Phe Lys Trp Arg Leu Pro
130 135 140

Glu Ala Asp Met Asp Gly Pro Asn Gln Glu Leu Asp Met Met Glu Arg
145 150 155 160

Phe Asn Gly Ile Thr Ser Pro Arg Ala Lys Glu Leu Phe Ala Ile Pro
165 170 175

Thr Pro Arg Leu
180

<210> SEQ ID NO 314
<211> LENGTH: 127
<212> TYPE: PRT
<213> ORGANISM: Pinus radiata

<400> SEQUENCE: 314

Gly Ile Leu Phe Asp Met Leu Leu Gly Gly Ser Asp Thr Ala Pro Thr
1 5 10 15

Ile Ile Glu Trp Ala Ile Ser Glu Ala Leu Ile Asn Pro Pro Val Met
20 25 30

Lys Lys Leu Gln Asp Glu Leu Glu Arg Val Val Gly Leu Asp Arg Met
35 40 45

Ala Cys Glu Ser Asp Leu Pro Gln Leu Val Tyr Leu Gln Ala Met Val
50 55 60

Lys Glu Thr Leu Arg Leu His Pro Ala Gly Pro Leu Leu Asn Arg Arg
65 70 75 80

Leu Ser Ala Glu Ser Cys Asn Val Leu Gly Tyr Glu Phe Pro Lys Asn
85 90 95

Thr Arg Val Leu Val Asn Ala Trp Ala Ile Gly Arg Asn Pro Lys Leu
100 105 110

Trp Glu Asp Ala Glu Thr Phe Lys Pro Glu Arg Phe Thr Gly Arg
115 120 125

<210> SEQ ID NO 315
<211> LENGTH: 127
<212> TYPE: PRT
<213> ORGANISM: Pinus radiata

<400> SEQUENCE: 315

Thr Ser Ala Thr Val Glu Trp Ala Met Ala Glu Leu Ile Arg Lys Pro
1 5 10 15

Thr Leu Leu Lys Lys Ala Gln Ala Glu Leu Asp Glu Val Val Gly Arg
20 25 30

Glu Lys Arg Met Glu Glu Ser Asp Ile Ala Lys Leu Pro Tyr Leu Gln
35 40 45

Ala Val Val Lys Glu Val Leu Arg Leu His Pro Ala Ala Pro Leu Ile
50 55 60

Ile Pro Arg Arg Ala Asp Asn Ser Ala Glu Ile Gly Gly Tyr Val Val
65 70 75 80

Pro Glu Asn Thr Gln Val Phe Val Asn Ile Trp Gly Ile Gly Arg Asp
85 90 95

Pro Asn Val Trp Lys Glu Pro Leu Lys Phe Lys Pro Glu Arg Phe Leu
100 105 110

Asp Cys Asn Thr Asp Tyr Arg Gly Gln Asp Phe Glu Leu Ile Pro
115 120 125

<210> SEQ ID NO 316
<211> LENGTH: 134
<212> TYPE: PRT
<213> ORGANISM: Pinus radiata

<400> SEQUENCE: 316

Glu Asp Glu Val Ser Ala Met Ile Arg Ser Ile Val Asn Ser Asp Ala
1 5 10 15

His Lys Asp Ser Arg Pro Val Asn Ile Lys Gln Leu Ala Ser Ser Leu
20 25 30

Val Thr Ala Ile Val Leu Arg Met Thr Phe Gly Lys Lys Tyr Ser Asp
35 40 45

Arg Asp Ser Gly Ala Phe Ser Ser Met Ile Lys Glu Ser Leu Leu Leu
50 55 60

Leu Gly Ser Phe Asn Ile Gly Glu Tyr Ile Pro Tyr Leu Asn Trp Met
65 70 75 80

Asp Leu Gln Gly Leu Asn Arg Arg Leu Lys Lys Leu Arg Thr Thr Gln
85 90 95

Asp Gln Leu Leu Glu Lys Val Ile Glu Glu His Ala Ala Gln Asn Arg
100 105 110

Ser Asn Met Thr His Asp Leu Val Asp Ala Leu Leu Ala Ala Ser Ala
115 120 125

Asp Lys Asp Arg Glu Leu
130

<210> SEQ ID NO 317
<211> LENGTH: 115
<212> TYPE: PRT
<213> ORGANISM: Eucalyptus grandis

<400> SEQUENCE: 317

Ile Tyr Asp Gln Glu Ser Leu Leu Asn Ala Ile Lys Gln Val Asp Val
1 5 10 15

```
Val Ile Ser Ala Val Gly Gln Ala Gln Thr Glu Asp Gln Asp Arg Ile
            20                  25                  30

Val Ala Ala Ile Lys Ala Ala Gly Asn Ile Lys Arg Phe Leu Pro Ser
        35                  40                  45

Glu Phe Gly Asn Asp Val Asp Arg Val His Ala Val Glu Pro Val Lys
    50                  55                  60

Thr Gly Phe Ala Leu Lys Ala Lys Ile Arg Arg Leu Val Glu Ala Glu
65                  70                  75                  80

Gly Ile Pro Tyr Thr Tyr Val Ser Ser Asn Ser Phe Ala Gly Tyr Tyr
                85                  90                  95

Leu Gln Thr Leu Ser Gln Pro Gly Ala Thr Ala Pro Pro Arg Asp Asn
            100                 105                 110

Val Val Ile
        115


<210> SEQ ID NO 318
<211> LENGTH: 161
<212> TYPE: PRT
<213> ORGANISM: Eucalyptus grandis

<400> SEQUENCE: 318

Arg Phe Gly Val Ser Met Val Leu Leu Pro Thr Leu Ser Pro Val Thr
1               5                   10                  15

Ala Glu Ser Leu Leu Glu Thr Asp Arg Val Arg Arg Lys Thr Pro Arg
            20                  25                  30

Leu Arg Arg Glu Asn His Ser Glu Met Ala Ala Lys Ser Lys Val Leu
        35                  40                  45

Val Ile Gly Gly Thr Gly Tyr Ile Gly Lys Phe Ile Val Glu Ala Ser
    50                  55                  60

Ala Lys Ser Gly Arg Pro Thr Phe Ala Leu Ala Arg Glu Ser Thr Leu
65                  70                  75                  80

Ser Asn Pro Ala Lys Ala Lys Ile Val Glu Gly Phe Lys Ser Leu Gly
                85                  90                  95

Val Thr Leu Val His Gly Asp Ile Tyr Asp Gln Glu Ser Leu Leu Asn
            100                 105                 110

Ala Ile Lys Gln Val Asp Val Val Ile Ser Ala Val Gly Arg Ala Gln
        115                 120                 125

Ile Glu Asp Gln Asp Arg Ile Val Ala Ala Ile Lys Ala Ala Gly Asn
    130                 135                 140

Ile Lys Arg Phe Val Pro Ser Glu Phe Gly Asn Asn Val Asp Arg Val
145                 150                 155                 160

His


<210> SEQ ID NO 319
<211> LENGTH: 141
<212> TYPE: PRT
<213> ORGANISM: Eucalyptus grandis

<400> SEQUENCE: 319

Arg Phe Leu Pro Ser Glu Phe Gly Asn Asp Val Asp Arg Val His Ala
1               5                   10                  15

Val Glu Pro Val Lys Thr Gly Phe Ala Leu Lys Ala Lys Ile Arg Arg
            20                  25                  30

Leu Val Glu Ala Glu Gly Ile Pro Tyr Thr Tyr Val Ser Ser Asn Ser
        35                  40                  45

Phe Ala Gly Tyr Tyr Leu Gln Thr Leu Ser Gln Pro Gly Ala Thr Ala
```

```
    50                  55                  60

Pro Pro Arg Asp Asn Val Val Ile Leu Gly Asp Gly Asn Ala Lys Val
65                  70                  75                  80

Val Phe Asn Lys Glu Asp Asp Ile Gly Thr Tyr Thr Ile Lys Ala Val
                85                  90                  95

Asp Asp Pro Arg Thr Leu Asn Lys Ile Leu Tyr Ile Arg Pro Pro Ala
            100                 105                 110

Asn Thr Tyr Ser Met Asn Glu Leu Val Ser Leu Trp Glu Arg Lys Ile
        115                 120                 125

Gly Lys Ala Leu Glu Arg Val Tyr Val Pro Glu Glu Gln
    130                 135                 140


<210> SEQ ID NO 320
<211> LENGTH: 102
<212> TYPE: PRT
<213> ORGANISM: Eucalyptus grandis

<400> SEQUENCE: 320

Lys Pro Ile Glu Phe Ala Gly Lys His Arg Ala Ser Ala Val Lys Thr
1               5                   10                  15

Thr Ser Glu Met Ala Ala Lys Ser Lys Val Leu Val Ile Gly Gly Thr
            20                  25                  30

Gly Tyr Ile Gly Lys Phe Ile Val Glu Ala Ser Ala Lys Ser Gly Arg
        35                  40                  45

Pro Thr Phe Val Leu Ala Arg Glu Ser Thr Leu Ser Asn Pro Ala Lys
    50                  55                  60

Ala Lys Ile Val Gln Gly Phe Lys Ser Leu Gly Val Thr Leu Val His
65                  70                  75                  80

Gly Asp Ile Tyr Asp Gln Glu Ser Leu Leu Asn Ala Ile Lys Gln Val
                85                  90                  95

Asp Val Val Ile Ser Ala
            100


<210> SEQ ID NO 321
<211> LENGTH: 125
<212> TYPE: PRT
<213> ORGANISM: Eucalyptus grandis

<400> SEQUENCE: 321

Gln Ser His Val Arg Asp Arg Ser Ser Ser Pro Glu Asn Thr Thr Arg
1               5                   10                  15

Ala Met Lys Arg Pro Ser Lys Met Ala Glu Met Ser Arg Val Leu Val
            20                  25                  30

Ile Gly Gly Ala Gly Tyr Ile Gly Lys Phe Ile Val Lys Ala Cys Ala
        35                  40                  45

Lys Ser Gly His Pro Thr Phe Val Leu Glu Thr Glu Ser Thr Leu Ser
    50                  55                  60

Asn Pro Ala Asn Ala Glu Ile Ile Lys Gly Phe Lys Ser Leu Gly Val
65                  70                  75                  80

Asn Leu Val His Gly Asp Ile Tyr Asp Gln Lys Ser Leu Leu Ser Ala
                85                  90                  95

Ile Lys Gln Val Asp Val Val Ile Ser Thr Val Gly Gln Ala Gln Leu
            100                 105                 110

Glu Asp Gln Asp Arg Ile Val Ala Ala Ile Lys Ala Ala
        115                 120                 125


<210> SEQ ID NO 322
```

<211> LENGTH: 98
<212> TYPE: PRT
<213> ORGANISM: Eucalyptus grandis

<400> SEQUENCE: 322

Ser Ser Ser Pro Glu Asn Thr Thr Pro Ala Val Lys Arg Pro Ser Lys
1               5                   10                  15

Met Ala Glu Met Ser Arg Val Leu Val Ile Gly Gly Ala Gly Tyr Ile
            20                  25                  30

Gly Lys Phe Ile Val Lys Ala Cys Ala Lys Ser Gly His Pro Thr Phe
        35                  40                  45

Val Leu Glu Thr Glu Ser Thr Leu Ser Asn Pro Ala Asn Ala Glu Ile
    50                  55                  60

Ile Lys Gly Phe Lys Ser Leu Gly Val Asn Leu Val His Gly Asp Ile
65                  70                  75                  80

Tyr Asp Gln Lys Ser Leu Leu Ser Ala Ile Lys Gln Val Asp Val Val
                85                  90                  95

Ile Ser

<210> SEQ ID NO 323
<211> LENGTH: 319
<212> TYPE: PRT
<213> ORGANISM: Pinus radiata

<400> SEQUENCE: 323

Lys Asp Pro Leu Ala Gln Leu Thr Thr Phe Ser Cys Ile Cys Ser Val
1               5                   10                  15

Arg His Asp Arg Gly Lys Thr Met Ala Cys Ala Thr Asp Val Ala Arg
            20                  25                  30

Gln Phe Leu Pro Cys Val Gln Pro Val Pro Ser Ser Met Gly Gly Glu
        35                  40                  45

Thr Ala Arg Ser Ile Asn Leu Thr Cys Asn Gly Leu Ser Pro Pro Gln
    50                  55                  60

Pro Gln Tyr Asn Ala Glu Asn Asn His Asp Gln Asp Thr Thr Val Ala
65                  70                  75                  80

Thr Arg Val Leu Ile Ile Gly Ala Thr Gly Phe Ile Gly Arg Phe Val
                85                  90                  95

Ala Glu Ala Ser Val Lys Ser Gly Arg Pro Thr Tyr Ala Leu Val Arg
            100                 105                 110

Pro Thr Thr Leu Ser Ser Lys Pro Lys Val Ile Gln Ser Leu Val Asp
        115                 120                 125

Ser Gly Ile Gln Val Val Tyr Gly Cys Leu His Asp His Asn Ser Leu
    130                 135                 140

Val Lys Ala Ile Arg Gln Val Asp Val Val Ile Ser Thr Val Gly Gly
145                 150                 155                 160

Ala Leu Ile Leu Asp Gln Leu Lys Ile Val Asp Ala Ile Lys Glu Val
                165                 170                 175

Gly Thr Val Lys Arg Phe Leu Pro Ser Glu Phe Gly His Asp Val Asp
            180                 185                 190

Arg Ala Asp Pro Val Glu Pro Ala Leu Ser Phe Tyr Ile Glu Lys Arg
        195                 200                 205

Lys Val Arg Arg Ala Val Glu Glu Ala Lys Ile Pro Tyr Thr Tyr Ile
    210                 215                 220

Cys Cys Asn Ser Ile Ala Gly Trp Pro Tyr Tyr Tyr His Thr His Pro
225                 230                 235                 240

Thr Glu Leu Pro Pro Pro Lys Glu Gln Phe Glu Ile Tyr Gly Asp Gly

```
                245                 250                 255

Ser Val Lys Ala Phe Phe Val Thr Gly Asp Asp Ile Gly Ala Tyr Thr
            260                 265                 270

Met Lys Ala Val Asp Asp Pro Arg Thr Leu Asn Lys Ser Ile His Phe
        275                 280                 285

Arg Pro Pro Lys Asn Phe Leu Asn Leu Asn Glu Leu Ala Asp Ile Trp
    290                 295                 300

Glu Asn Lys Ile Asn Arg Thr Leu Pro Arg Val Ser Val Ser Ala
305                 310                 315


<210> SEQ ID NO 324
<211> LENGTH: 126
<212> TYPE: PRT
<213> ORGANISM: Pinus radiata

<400> SEQUENCE: 324

Leu Asn Ser Leu Ala Asp Ile Leu Leu Ile Gln Ser Gly Lys Met Thr
1               5                   10                  15

Gly Leu Lys Asp Ser Ala Asn Arg Val Leu Ile Ile Gly Gly Thr Gly
            20                  25                  30

Tyr Ile Gly Lys Tyr Met Ala Lys Ala Ser Val Ser Gln Gly Tyr Pro
        35                  40                  45

Thr Tyr Val Leu Val Arg Pro Ala Thr Ala Ala Ala Pro Asp Ser Phe
    50                  55                  60

Lys Ala Lys Leu Leu Gln Gln Phe Lys Asp Ile Gly Ile His Ile Leu
65                  70                  75                  80

Glu Gly Ser Leu Asp Asp His Asn Ser Leu Val Asp Ala Ile Lys Gln
                85                  90                  95

Val Asp Ile Val Ile Ser Ala Val Ala Ile Pro Gln His Leu Asp Gln
            100                 105                 110

Phe Asn Ile Ile Asn Ala Ile Lys Asp Val Gly Met Glu Ile
        115                 120                 125


<210> SEQ ID NO 325
<211> LENGTH: 164
<212> TYPE: PRT
<213> ORGANISM: Eucalyptus grandis

<400> SEQUENCE: 325

Asn Gly Glu Leu His Pro Ser His Tyr Cys Glu Arg Asp Leu Leu Lys
1               5                   10                  15

Val Val Asp Arg Glu His Val Phe Thr Tyr Ala Asp Asp Ala Cys Ser
            20                  25                  30

Ala Thr Tyr Pro Leu Met Gln Lys Leu Arg Gln Val Leu Val Asp Gln
        35                  40                  45

Ala Leu Val Asn Gly Glu Ser Glu Leu Asn Pro Ser Thr Ser Ile Phe
    50                  55                  60

Gln Lys Ile Val Ala Phe Glu Glu Glu Leu Lys Ala Gln Leu Pro Lys
65                  70                  75                  80

Asp Val Glu Gly Val Arg Val Gln Tyr Glu Thr Gly Asn Leu Ala Ile
                85                  90                  95

Pro Asn Gln Ile Lys Glu Cys Arg Ser Tyr Pro Leu Tyr Lys Leu Val
            100                 105                 110

Arg Glu Glu Leu Gly Thr Ala Leu Leu Thr Gly Glu Gly Val Ile Ser
        115                 120                 125

Pro Gly Glu Asp Phe Asp Lys Val Phe Thr Ala Ile Cys Ala Gly Lys
    130                 135                 140
```

Leu Ile Asp Pro Leu Leu Glu Cys Leu Ser Gly Trp Asn Gly Ala Pro
145 150 155 160

Leu Pro Ile Ser

<210> SEQ ID NO 326
<211> LENGTH: 114
<212> TYPE: PRT
<213> ORGANISM: Eucalyptus grandis

<400> SEQUENCE: 326

Leu Val Asp Gln Ala Leu Val Asn Gly Glu Ser Glu Leu Asn Pro Ser
1 5 10 15

Thr Ser Ile Phe Gln Lys Ile Val Ala Phe Glu Glu Glu Leu Lys Ala
20 25 30

Gln Leu Pro Lys Asp Val Glu Gly Val Arg Val Gln Tyr Glu Thr Gly
35 40 45

Asn Leu Ala Ile Pro Asn Gln Ile Lys Glu Cys Arg Ser Tyr Pro Leu
50 55 60

Tyr Lys Leu Val Arg Glu Glu Leu Gly Thr Ala Leu Leu Thr Gly Glu
65 70 75 80

Gly Val Ile Ser Pro Gly Glu Asp Phe Asp Lys Val Phe Thr Ala Ile
85 90 95

Cys Ala Gly Lys Leu Ile Asp Pro Leu Leu Glu Cys Leu Ser Gly Trp
100 105 110

Asn Gly

<210> SEQ ID NO 327
<211> LENGTH: 226
<212> TYPE: PRT
<213> ORGANISM: Eucalyptus grandis

<400> SEQUENCE: 327

Pro Ser Leu Asp Tyr Gly Phe Lys Gly Ala Glu Ile Ala Met Ala Ser
1 5 10 15

Tyr Cys Ser Glu Leu Gln Phe Leu Ala Asn Pro Val Thr Asn His Val
20 25 30

Gln Ser Ala Glu Gln His Asn Gln Asp Val Asn Ser Leu Gly Leu Ile
35 40 45

Ser Ser Arg Lys Thr Ala Glu Ala Ile Asp Val Leu Lys Leu Met Ser
50 55 60

Ser Thr Phe Leu Val Ala Leu Cys Gln Ala Ile Asp Leu Arg His Leu
65 70 75 80

Glu Glu Asn Leu Lys Ser Val Val Lys Asn Thr Val Asn Gln Val Ala
85 90 95

Lys Lys Val Leu Tyr Val Gly Ser Asn Gly Glu Leu His Pro Ser Arg
100 105 110

Phe Ser Glu Lys Asp Leu Ile Lys Val Val Asp Arg Glu Tyr Val Phe
115 120 125

Ala Tyr Ile Asp Asp Pro Cys Ser Ala Thr Tyr Pro Leu Met Gln Lys
130 135 140

Leu Arg Gln Val Leu Val Asp Asp Ala Leu Asp Asp Val Asp Arg Glu
145 150 155 160

Lys Asn Pro Ser Thr Ser Ile Phe Gln Lys Ile Gly Ala Phe Glu Glu
165 170 175

Glu Leu Lys Ala Leu Leu Pro Lys Glu Val Glu Asn Ala Arg Ala Gln
180 185 190

```
Phe Glu Ser Gly Asn Ser Ala Ile Ala Asn Lys Ile Arg Gly Cys Arg
        195                 200                 205

Ser Tyr Pro Leu Tyr Arg Phe Val Arg Glu Glu Leu Gly Thr Gly Leu
    210                 215                 220

Leu Thr
225


<210> SEQ ID NO 328
<211> LENGTH: 424
<212> TYPE: PRT
<213> ORGANISM: Eucalyptus grandis

<400> SEQUENCE: 328

Met Glu Met Glu Ser Thr Thr Gly Thr Gly Asn Gly Leu His Ser Leu
1               5                   10                  15

Cys Ala Ala Gly Ser His His Ala Asp Pro Leu Asn Trp Gly Ala Ala
            20                  25                  30

Ala Ala Ala Leu Thr Gly Ser His Leu Asp Glu Val Lys Arg Met Val
        35                  40                  45

Glu Glu Tyr Arg Arg Pro Ala Val Arg Leu Gly Gly Glu Ser Leu Thr
    50                  55                  60

Ile Ala Gln Val Ala Ala Val Ala Ser Gln Glu Gly Val Gly Val Glu
65                  70                  75                  80

Leu Ser Glu Ala Ala Arg Pro Arg Val Lys Ala Ser Ser Asp Trp Val
                85                  90                  95

Met Glu Ser Met Asn Lys Gly Thr Asp Ser Tyr Gly Val Thr Thr Gly
            100                 105                 110

Phe Gly Ala Thr Ser His Arg Arg Thr Lys Gln Gly Gly Ala Leu Gln
        115                 120                 125

Lys Glu Leu Ile Arg Phe Leu Asn Ala Gly Ile Phe Gly Asn Gly Thr
    130                 135                 140

Glu Ser Cys His Thr Leu Pro Gln Ser Ser Thr Arg Ala Ala Met Leu
145                 150                 155                 160

Val Arg Val Asn Thr Leu Leu Gln Gly Tyr Ser Gly Ile Arg Phe Glu
                165                 170                 175

Ile Leu Glu Ala Ile Thr Lys Phe Leu Asn His Asn Ile Thr Pro Cys
            180                 185                 190

Leu Pro Leu Arg Gly Thr Ile Thr Ala Ser Gly Asp Leu Val Pro Leu
        195                 200                 205

Ser Tyr Ile Ala Gly Leu Leu Thr Gly Arg Pro Asn Ser Lys Ala Val
    210                 215                 220

Gly Pro Asp Gly Lys Ser Leu Asp Ala Val Glu Ala Phe Arg Leu Ala
225                 230                 235                 240

Gly Ile Asp Thr Gly Phe Phe Glu Leu Gln Pro Lys Glu Gly Leu Ala
                245                 250                 255

Leu Val Asn Gly Thr Ala Val Gly Ser Gly Leu Ala Ser Ile Val Leu
            260                 265                 270

Phe Glu Ala Asn Ile Leu Ala Val Leu Ser Glu Val Leu Ser Ala Ile
        275                 280                 285

Phe Ala Glu Val Met Gln Gly Lys Pro Glu Phe Thr Asp His Leu Thr
    290                 295                 300

His Lys Leu Lys His His Pro Gly Gln Ile Glu Ser Ala Ala Ile Met
305                 310                 315                 320

Glu His Ile Leu Asp Gly Ser Ala Tyr Val Lys Ala Ala Lys Lys Leu
                325                 330                 335
```

```
His Glu Met Asp Pro Leu Gln Lys Pro Lys Gln Asp Arg Tyr Ala Leu
            340                 345                 350

Arg Thr Ser Pro Gln Trp Leu Gly Pro Gln Ile Glu Val Ile Arg Ala
        355                 360                 365

Ala Thr Lys Met Ile Glu Arg Glu Ile Asn Ser Val Asn Asp Asn Pro
    370                 375                 380

Leu Ile Asp Val Ala Arg Asn Lys Ala Leu His Gly Gly Asn Phe Gln
385                 390                 395                 400

Gly Thr Pro Ile Gly Val Ser Met Asp Asn Thr Arg Leu Ala Val Ala
                405                 410                 415

Ser Ile Gly Lys Leu Met Phe Ala
            420


<210> SEQ ID NO 329
<211> LENGTH: 97
<212> TYPE: PRT
<213> ORGANISM: Eucalyptus grandis

<400> SEQUENCE: 329

Asn Ser Gly Ile Thr Pro Cys Leu Pro Leu Arg Gly Ser Ile Ser Ala
1               5                   10                  15

Ser Gly Asp Leu Val Pro Phe Ser Tyr Ile Ala Gly Leu Leu Thr Gly
            20                  25                  30

Arg Pro Asn Ser Lys Ala Val Gly Pro Ala Gly Glu Thr Leu Thr Ala
        35                  40                  45

Lys Gln Ala Phe Glu Leu Ala Gly Ile Ser Gly Gly Phe Phe Glu Leu
    50                  55                  60

Gln Pro Lys Glu Gly Leu Ala Leu Val Asn Gly Thr Gly Val Gly Ser
65                  70                  75                  80

Ala Leu Ala Ala Ile Val Leu Phe Glu Ala Asn Met Leu Thr Val Leu
                85                  90                  95

Ser


<210> SEQ ID NO 330
<211> LENGTH: 412
<212> TYPE: PRT
<213> ORGANISM: Pinus radiata

<400> SEQUENCE: 330

Val Tyr Arg Ser Ile Asn Ser Gln Ala Glu Ala Pro Ser Trp Pro Asn
1               5                   10                  15

Gly Ser Cys Ser Asp His Gly Val Cys Leu Gly Arg Glu Ser Tyr Met
            20                  25                  30

Lys His Ala Ala Lys Leu His Glu Met Asn Pro Leu Gln Lys Pro Lys
        35                  40                  45

Gln Asp Arg Tyr Ala Leu Arg Thr Ser Pro Gln Trp Leu Gly Pro Gln
    50                  55                  60

Val Glu Ile Ile Arg Ser Ala Thr His Met Ile Glu Arg Glu Ile Asn
65                  70                  75                  80

Ser Val Asn Asp Asn Pro Val Ile Asp Val Ala Arg Asp Lys Ala Leu
                85                  90                  95

His Gly Gly Asn Phe Gln Gly Thr Pro Ile Gly Val Ser Met Asp Asn
            100                 105                 110

Leu Arg Leu Ser Ile Ser Ala Ile Gly Lys Leu Met Phe Ala Gln Phe
        115                 120                 125

Ser Glu Leu Val Asn Asp Tyr Tyr Asn Gly Gly Leu Pro Ser Asn Leu
```

```
130                 135                 140

Ser Gly Gly Pro Asn Pro Ser Leu Asp Tyr Gly Leu Lys Gly Ala Glu
145                 150                 155                 160

Ile Ala Met Ala Ser Tyr Thr Ser Glu Leu Leu Tyr Leu Ala Asn Pro
                165                 170                 175

Val Thr Ser His Val Gln Ser Ala Glu Gln His Asn Gln Asp Val Asn
            180                 185                 190

Ser Leu Gly Leu Val Ser Ala Arg Lys Ser Ala Glu Ala Ile Asp Ile
        195                 200                 205

Leu Lys Leu Met Leu Ser Thr Tyr Leu Thr Ala Leu Cys Gln Ala Val
    210                 215                 220

Asp Leu Arg His Leu Glu Glu Asn Met Leu Ala Thr Val Lys Gln Ile
225                 230                 235                 240

Val Ser Gln Val Ala Lys Lys Thr Leu Ser Thr Gly Leu Asn Gly Glu
                245                 250                 255

Leu Leu Pro Gly Arg Phe Cys Glu Lys Asp Leu Leu Gln Val Val Asp
            260                 265                 270

Asn Glu His Val Phe Ser Tyr Ile Asp Asp Pro Cys Asn Ala Ser Tyr
        275                 280                 285

Pro Leu Thr Gln Lys Leu Arg Asn Ile Leu Val Glu His Ala Phe Lys
    290                 295                 300

Asn Ala Glu Gly Glu Lys Asp Pro Asn Thr Ser Ile Phe Asn Lys Ile
305                 310                 315                 320

Pro Val Phe Glu Ala Glu Leu Lys Ala Gln Leu Glu Pro Gln Val Ser
                325                 330                 335

Leu Ala Arg Glu Ser Tyr Asp Lys Gly Thr Ser Pro Leu Pro Asn Arg
            340                 345                 350

Ile Gln Glu Cys Arg Ser Tyr Pro Leu Tyr Glu Phe Val Arg Asn Gln
        355                 360                 365

Leu Gly Thr Leu Gln Ala Trp Leu Phe His Ile Asn Ile Val Met Arg
    370                 375                 380

Cys Leu Ile Ile Tyr Cys Ser Leu Phe Phe Pro Glu Leu Ala Thr Ala
385                 390                 395                 400

Phe Asp Ser Val His Tyr Ala Arg Thr Lys Pro Leu
                405                 410
```

<210> SEQ ID NO 331
<211> LENGTH: 132
<212> TYPE: PRT
<213> ORGANISM: Pinus radiata

<400> SEQUENCE: 331

```
Gly Ser Ser Cys Arg Ser Leu Ile Arg Glu Leu Phe Val Cys Leu Ile
1               5                   10                  15

Ile Val His Met Ala Pro Gln Glu Phe Thr Gly Glu Val Lys Phe Cys
            20                  25                  30

Ala Gly Asn Gly Gly Thr Ala Ser Leu Asn Asp Pro Leu Asn Trp Ala
        35                  40                  45

Ala Ala Ala Glu Ser Met Lys Gly Ser His Phe Glu Glu Val Lys Arg
    50                  55                  60

Met Trp Glu Glu Phe Arg Ser Pro Val Val Arg Leu Gln Gly Ser Gly
65                  70                  75                  80

Leu Thr Ile Ala Gln Val Ala Ala Val Ala Arg Arg Thr Gly Ser Val
                85                  90                  95

Arg Val Glu Leu Glu Thr Gly Ala Lys Ala Arg Val Asp Glu Ser Ser
```

```
            100                 105                 110

Asn Trp Val Met Asp Ser Met Ala Asn Gly Thr Asp Ser Tyr Gly Val
        115                 120                 125

Thr Thr Gly Phe
    130


<210> SEQ ID NO 332
<211> LENGTH: 170
<212> TYPE: PRT
<213> ORGANISM: Eucalyptus grandis

<400> SEQUENCE: 332

Asn Leu Val Lys Leu Gly Ser Ile Leu Gly Met Ala Ile Gly Val Ala
1               5                   10                  15

Leu Phe Ser Ser Leu Leu Val Leu Ser Phe Val Ser Pro Ile Ser Ser
            20                  25                  30

Leu Ser Ser Asn Tyr Tyr Asp Lys Thr Cys Pro Asn Ala Glu Leu Ile
        35                  40                  45

Val Ala Asn Ala Val Lys Asn Ala Ala Met Lys Asp Lys Thr Val Pro
    50                  55                  60

Ala Ala Leu Leu Arg Met His Phe His Asp Cys Phe Ile Arg Gly Cys
65                  70                  75                  80

Asp Ala Ser Val Leu Leu Asn Ser Lys Gly Ser Asn Lys Ala Glu Lys
                85                  90                  95

Asp Gly Pro Pro Asn Val Ser Leu His Ser Phe Phe Val Ile Asp Asn
            100                 105                 110

Ala Lys Lys Glu Leu Glu Ala Ser Cys Pro Gly Val Val Ser Cys Ala
        115                 120                 125

Asp Ile Leu Ala Leu Ala Ala Arg Asp Ser Val Val Leu Ser Gly Gly
    130                 135                 140

Pro Thr Trp Asp Val Pro Lys Gly Arg Lys Asp Gly Arg Thr Ser Lys
145                 150                 155                 160

Ala Ser Glu Thr Thr Gln Leu Pro Ala Pro
                165                 170


<210> SEQ ID NO 333
<211> LENGTH: 118
<212> TYPE: PRT
<213> ORGANISM: Eucalyptus grandis

<400> SEQUENCE: 333

Leu Val Ile Thr Ile Val Val Phe Phe Gly His Ile Gly Asp Ser Glu
1               5                   10                  15

Gly Gly Asp Leu Arg Lys Asn Phe Tyr Lys Ser Ala Cys Pro Leu Ala
            20                  25                  30

Glu Glu Ile Val Lys Asn Val Thr Trp Lys His Ala Ala Ser Asn Ser
        35                  40                  45

Ala Leu Pro Ala Lys Phe Leu Arg Met His Phe His Asp Cys Phe Val
    50                  55                  60

Arg Gly Cys Asp Gly Ser Val Leu Leu Asp Ser Thr Ala Asn Asn Lys
65                  70                  75                  80

Ala Glu Lys Val Ala Val Pro Asn Gln Ser Leu Thr Gly Phe Asp Val
                85                  90                  95

Ile Asp Glu Ile Lys Glu Lys Leu Glu Glu Thr Cys Pro Gly Val Val
            100                 105                 110

Ser Cys Ala Asp Ile Leu
        115
```

<210> SEQ ID NO 334
<211> LENGTH: 65
<212> TYPE: PRT
<213> ORGANISM: Pinus radiata

<400> SEQUENCE: 334

```
Asn Ala Asp Pro Ile Ala Val Ile Asp Glu Ala Leu Ser Thr Gly Gly
1               5                   10                  15

Ala Pro Asn Leu Ser Asp Ala Tyr Thr Leu Asn Gly Gln Pro Gly Asp
            20                  25                  30

Leu Tyr Asn Cys Ser Arg Ala Gly Thr Phe Arg Phe Leu Val Lys Gln
        35                  40                  45

Gly Glu Thr Tyr Leu Leu Arg Met Val Asn Ala Ala Leu Asn Ser Ala
    50                  55                  60

His
65
```

<210> SEQ ID NO 335
<211> LENGTH: 104
<212> TYPE: PRT
<213> ORGANISM: Pinus radiata

<400> SEQUENCE: 335

```
Lys Pro His Gly Glu Thr Pro Leu Ile Ile Gly Glu Trp Trp Asn Ala
1               5                   10                  15

Asp Pro Ile Ala Val Ile Asp Glu Ala Leu Arg Thr Gly Gly Ala Pro
            20                  25                  30

Asn Leu Ser Asp Ala Tyr Thr Leu Asn Gly Gln Pro Gly Asp Leu Tyr
        35                  40                  45

Asn Cys Ser Arg Ala Gly Thr Phe Arg Phe Pro Val Lys Gln Gly Glu
    50                  55                  60

Thr Tyr Leu Leu Arg Met Val Asn Ala Ala Leu Asn Ser Ala His Phe
65                  70                  75                  80

Phe Lys Ile Ala Gly His Lys Phe Thr Val Val Ala Val Asp Ala Ser
                85                  90                  95

Tyr Thr Lys Pro Tyr Lys Gln Met
            100
```

<210> SEQ ID NO 336
<211> LENGTH: 125
<212> TYPE: PRT
<213> ORGANISM: Pinus radiata

<400> SEQUENCE: 336

```
Asp Ala His Thr Ile Asn Gly Lys Pro Gly Pro Leu Phe Lys Cys Pro
1               5                   10                  15

Thr Lys Asp Thr Phe Val Val Pro Val Glu His Gly Lys Thr Tyr Leu
            20                  25                  30

Leu Arg Ile Ile Asn Ala Ala Leu Asn Asp Glu Leu Phe Phe Asp Val
        35                  40                  45

Ala Asn His His Leu Lys Val Val Glu Ile Asp Ala Val Tyr Thr Lys
    50                  55                  60

Pro Leu Ile Thr Asn Ser Ile Val Ile Ala Pro Gly Gln Thr Thr Asn
65                  70                  75                  80

Ala Leu Ile His Thr Asn Lys Arg Ser Gly Arg Tyr Phe Met Ala Ala
                85                  90                  95

Arg Ser Phe Met Asp Ala Pro Val Ser Val Asp Asn Lys Thr Ala Thr
```

```
            100                 105                 110

Ala Ile Leu Gln Tyr Val Asn Ser Ile Gln Ile Leu Leu
        115                 120                 125


<210> SEQ ID NO 337
<211> LENGTH: 178
<212> TYPE: PRT
<213> ORGANISM: Pinus radiata

<400> SEQUENCE: 337

Asn Met Met Ala Pro Met Ala Gly Ala Glu Tyr Gly Ile Lys Leu Ile
1               5                   10                  15

Ile Gln Leu Leu Val Val Leu Leu Ala Val Gln Leu Val Ala Gly Lys
            20                  25                  30

Thr Thr Arg His Tyr Ser Phe His Val Arg Leu Lys Asn Val Thr Arg
        35                  40                  45

Leu Cys His Thr Lys Pro Leu Ile Thr Val Asn Gly Lys Ser Pro Gly
    50                  55                  60

Pro Lys Val Val Val Arg Glu Gly Asp Arg Val Ile Ile Lys Val His
65                  70                  75                  80

Asn His Val Ser Asn Asn Val Ser Ile His Trp His Gly Val Arg Gln
                85                  90                  95

Leu Arg Ser Gly Trp Ala Asp Gly Pro Ala Tyr Ile Thr Gln Cys Pro
            100                 105                 110

Ile Gln Thr Gly Gln Thr Tyr Val Tyr Asn Phe Thr Val Thr Gly Gln
        115                 120                 125

Arg Gly Thr Leu Trp Trp His Ala His Ile Ser Trp Leu Arg Ala Ser
    130                 135                 140

Val Tyr Gly Ala Phe Ile Ile Tyr Pro Lys Arg His Val Pro Tyr Pro
145                 150                 155                 160

Phe Pro Lys Pro Tyr Lys Glu Val Pro Leu Ile Leu Gly Glu Trp Trp
                165                 170                 175

Asn Ala


<210> SEQ ID NO 338
<211> LENGTH: 358
<212> TYPE: PRT
<213> ORGANISM: Pinus radiata

<400> SEQUENCE: 338

Pro Ile Pro Pro Gly Gly Arg Tyr Thr Tyr Arg Phe Asn Ile Ser Gly
1               5                   10                  15

Gln Glu Gly Thr Val Trp Trp His Ala His Tyr Ser Trp Leu Arg Ala
            20                  25                  30

Thr Val His Gly Ala Phe Val Ile Leu Pro Lys Lys Gly Ser Ser Tyr
        35                  40                  45

Pro Phe Ser Lys Pro His Ala Glu Ile Pro Ile Ile Ile Gly Glu Trp
    50                  55                  60

Trp Asn Ala Asn Pro Ile Ala Val Ile Asp Glu Ala Val Arg Thr Gly
65                  70                  75                  80

Gly Ala Pro Asn Leu Ser Asp Ala Phe Thr Ile Asn Gly Gln Pro Gly
                85                  90                  95

Asp Leu Phe Asn Cys Ser Thr Ser Gly Thr Phe Arg Leu Pro Val Glu
            100                 105                 110

Ser Gly Glu Thr Tyr Leu Leu Arg Ile Val Asn Ala Ala Leu Asn Ser
        115                 120                 125
```

```
Gly His Phe Phe Lys Ile Ala Gly His Glu Phe Thr Val Val Ala Val
    130                 135                 140

Asp Ala Cys Tyr Thr Lys Pro Tyr Lys Thr Asp Val Leu Val Ile Ser
145                 150                 155                 160

Ala Gly Gln Thr Thr Asp Val Leu Ile Thr Ala Asn Gln Ser Val Gly
                165                 170                 175

Arg Tyr Tyr Met Ala Ala Arg Ala Tyr Gln Asn Gln Ala Ala Gly Asp
            180                 185                 190

Phe Thr Asn Thr Thr Thr Thr Ala Ile Leu Glu Tyr Ile Gly Ser Glu
        195                 200                 205

Asn Ser Thr Arg Pro Ile Leu Pro Ser Leu Pro Ala Tyr Asn Asp Thr
    210                 215                 220

Ala Thr Val Thr Arg Phe Ser Arg Ala Leu Arg Ser Leu Ala Ser Gln
225                 230                 235                 240

Glu His Pro Val Asn Val Pro His Thr Ile Asp Glu Ser Leu Ile Ser
                245                 250                 255

Thr Val Gly Leu Gly Leu Leu Pro Cys Gly Ala Gly Asn Thr Cys Glu
            260                 265                 270

Gly Pro Asn Gly Thr Arg Leu Ser Ala Ser Ile Asn Asn Ile Ser Tyr
        275                 280                 285

Val Glu Pro Thr Ile Ser Leu Leu Gln Ala Tyr Tyr Tyr Thr Ala Asn
    290                 295                 300

Gly Ile Phe Thr Gly Asp Phe Pro Ser Lys Pro Glu Val Arg Phe Asn
305                 310                 315                 320

Tyr Thr Gly Asp Asp Ile Pro Arg Lys Phe Trp Ala Pro Asp Pro Ala
                325                 330                 335

Thr Lys Val Lys Val Leu Glu Tyr Asn Ser Thr Val Gln Leu Val Phe
            340                 345                 350

Gln Ser Thr Asn Ile Phe
        355


<210> SEQ ID NO 339
<211> LENGTH: 160
<212> TYPE: PRT
<213> ORGANISM: Pinus radiata

<400> SEQUENCE: 339

Phe Arg Arg Glu Thr Val Ile Gln His Ile Ser Arg Ser Phe Leu Ser
1               5                   10                  15

Lys Met Val Ile Ser Lys Tyr Ala Ala Ala Met Ser Cys Leu Leu Ile
            20                  25                  30

Ala Val Val Ala Leu Glu Val Gly Ala Glu Thr Arg His Tyr Lys Phe
        35                  40                  45

Asp Ile Lys Phe Lys Asn Val Thr Arg Leu Cys His Thr Lys Pro Ile
    50                  55                  60

Val Thr Ala Asn Gly Lys Phe Pro Gly Pro Thr Ile Tyr Ala Arg Glu
65                  70                  75                  80

Gly Asp Thr Val Thr Val Lys Val Thr Asn His Val Thr Tyr Asn Val
                85                  90                  95

Ser Ile His Trp His Gly Ile Arg Gln Leu Arg Thr Gly Trp Ala Asp
            100                 105                 110

Gly Pro Ala Tyr Ile Thr Gln Cys Pro Ile Gln Thr Gly Gln Thr Tyr
        115                 120                 125

Val Tyr Asn Phe Thr Ile Thr Gly Gln Arg Gly Thr Leu Phe Trp His
    130                 135                 140
```

```
Ala His Ile Leu Trp Leu Arg Ala Thr Leu Asn Gly Pro Ile Val Ile
145                 150                 155                 160


<210> SEQ ID NO 340
<211> LENGTH: 156
<212> TYPE: PRT
<213> ORGANISM: Pinus radiata

<400> SEQUENCE: 340

Gly Cys Cys Leu Ser Thr Arg Met Asn Met Ser Arg Ser Lys Ala Leu
1               5                   10                  15

Leu Cys Pro Ser Pro Ala His Val Lys Tyr Val Leu Ile Val Ile Leu
            20                  25                  30

Leu Ile Ile Met Ile Gln Cys Pro Asp Ile Val Ala Gly Lys His Ala
        35                  40                  45

Gln Thr Thr Arg His Tyr Lys Phe Asn Val Arg Leu Ser Asn Val Thr
    50                  55                  60

Arg Leu Cys Arg Thr Lys Pro Leu Ile Thr Val Asn Gly Lys Tyr Pro
65                  70                  75                  80

Gly Pro Thr Val Val Ala Arg Glu Gly Asp Arg Val Ile Ile Lys Leu
                85                  90                  95

Val Asn His Val Lys Asp Asn Val Thr Ile His Trp His Gly Val Arg
            100                 105                 110

Gln Leu Arg Ser Gly Trp Ala Asp Gly Pro Gly Tyr Ile Thr Gln Cys
        115                 120                 125

Pro Leu Gln Thr Gly Met Ser Tyr Val Tyr Asn Phe Thr Ile Val Gly
    130                 135                 140

Gln Arg Gly Thr Leu Trp Trp His Ala His Ile Ser
145                 150                 155


<210> SEQ ID NO 341
<211> LENGTH: 157
<212> TYPE: PRT
<213> ORGANISM: Pinus radiata

<400> SEQUENCE: 341

Val Ile Gln Gln Ala Leu Gln Thr Gly Gly Gly Pro Asn Val Ser Asp
1               5                   10                  15

Ala Tyr Thr Ile Asn Gly Leu Pro Gly Pro Leu Tyr Asn Cys Ser Asn
            20                  25                  30

Glu Thr Phe Val Leu Lys Val His Pro Gly Gln Thr Tyr Leu Leu Arg
        35                  40                  45

Ile Ile Asn Ala Ala Leu Asn Asp Glu Leu Phe Leu Ala Ile Ala Asn
    50                  55                  60

His Ser Leu Thr Val Val Glu Val Asp Ala Val Tyr Val Lys Pro Phe
65                  70                  75                  80

Gln Thr Asp Thr Leu Leu Ile Thr Pro Gly Gln Thr Thr Asn Val Leu
                85                  90                  95

Leu Thr Ala Asn Ala Thr Ser Gly Lys Asn Lys Gln Phe Val Ile Ala
            100                 105                 110

Ala Ser Pro Phe Val Thr Gly Ser Gly Thr Phe Asp Asn Ser Thr Val
        115                 120                 125

Ala Gly Ile Val Ser Tyr Asn Ser His Lys Phe Lys Asn Ser Ser Thr
    130                 135                 140

Ile Ile Leu Pro Lys Leu Pro Ser Phe Asn Asp Thr Asn
145                 150                 155
```

<210> SEQ ID NO 342
<211> LENGTH: 134
<212> TYPE: PRT
<213> ORGANISM: Pinus radiata

<400> SEQUENCE: 342

Gly Gln Thr Thr Asn Val Leu Leu Glu Ala Asn Lys Arg Ser Gly Ser
1               5                   10                  15

Tyr Phe Val Ala Ala Arg Pro Phe Met Asp Ala Pro Val Thr Val Asn
            20                  25                  30

Asn Lys Thr Ala Thr Ala Ile Leu His Tyr Ile Gly Arg Asn Ser Glu
        35                  40                  45

Ser Asp Ile Pro Ala Val Asn Pro Leu Met Pro Arg Leu Pro Leu Leu
    50                  55                  60

Asn Asp Thr Ala Phe Ala Thr Ser Phe Thr Ser Lys Leu Arg Ser Leu
65                  70                  75                  80

Asn Ser Val Gln Phe Pro Ala Lys Val Pro Gln Thr Ile Asp Arg Asn
                85                  90                  95

Leu Phe Phe Ala Val Gly Leu Ala Thr Glu Ser Cys Gln Thr Cys Asn
            100                 105                 110

Gly Gly Leu Arg Ala Ser Ala Ser Ile Asn Asn Ile Ser Phe Val Met
        115                 120                 125

Pro Ser Ile Ser Leu Leu
    130

<210> SEQ ID NO 343
<211> LENGTH: 419
<212> TYPE: PRT
<213> ORGANISM: Pinus radiata

<400> SEQUENCE: 343

Thr Thr Tyr Pro Phe Thr Phe Thr Arg Pro His Arg Gln Ile Pro Ile
1               5                   10                  15

Leu Leu Gly Glu Trp Trp Asn Arg Asn Pro Met Asp Val Val Asn Gln
            20                  25                  30

Ala Thr Gln Thr Gly Ala Ala Pro Asn Val Ser Asp Ala Phe Thr Ile
        35                  40                  45

Asn Gly Gln Pro Gly Asp Leu Tyr Lys Cys Ser Thr Ser Asp Thr Phe
    50                  55                  60

Ser Val Ser Met Lys Gly Gly Glu Thr Asn Leu Leu Arg Val Ile Asn
65                  70                  75                  80

Ala Ala Leu Asn Thr Asp Leu Phe Phe Ser Ile Ala Ser His Thr Met
                85                  90                  95

Thr Val Val Ala Val Asp Ala Leu Tyr Thr Lys Pro Phe Gln Thr Asn
            100                 105                 110

Val Leu Met Leu Gly Pro Gly Gln Thr Thr Asp Ile Leu Leu Thr Ala
        115                 120                 125

Asn Gln Ala Thr Gly Arg Tyr Tyr Met Ala Ala Arg Ala Tyr Ser Ser
    130                 135                 140

Gly Gln Gly Val Pro Phe Asp Asn Thr Thr Thr Thr Ala Ile Leu Glu
145                 150                 155                 160

Tyr Glu Gly Ser Ser Lys Thr Ser Thr Pro Val Met Pro Asn Leu Pro
                165                 170                 175

Phe Tyr Asn Asp Thr Asn Ser Ala Thr Ser Phe Ala Asn Gly Leu Arg
            180                 185                 190

Ser Leu Gly Ser His Asp His Pro Val Phe Val Pro Gln Ser Val Glu
        195                 200                 205

Glu Asn Leu Phe Tyr Thr Ile Gly Leu Gly Leu Ile Lys Cys Pro Gly
    210                 215                 220

Gln Ser Cys Gly Gly Pro Asn Gly Ser Arg Phe Ala Ala Ser Met Asn
225                 230                 235                 240

Asn Ile Ser Phe Val Pro Pro Thr Thr Ser Ser Ile Leu Gln Ala Gln
                245                 250                 255

His Phe Gly Met Lys Gly Val Phe Ser Ala Asp Phe Pro Asp Asn Pro
            260                 265                 270

Ser Val Gly Phe Asp Tyr Thr Ala Gln Asn Ile Ser Arg Asp Leu Trp
        275                 280                 285

Ser Pro Val Lys Ala Thr Arg Val Lys Val Leu Lys Tyr Asn Ser Thr
    290                 295                 300

Val Gln Val Ile Leu Gln Gly Thr Asn Ile Phe Ala Gly Glu Ser His
305                 310                 315                 320

Pro Ile His Leu His Gly Tyr Asp Phe Tyr Ile Val Gly Ala Gly Phe
                325                 330                 335

Gly Asn Tyr Asn Ala Gln Thr Asp Pro His Lys Phe Asn Leu Val Asp
            340                 345                 350

Pro Pro Met Arg Asn Thr Val Asn Val Pro Val Asn Gly Trp Ala Ala
        355                 360                 365

Ile Arg Phe Val Ala Asp Asn Pro Gly Ala Trp Val Met His Cys His
    370                 375                 380

Leu Asp Val His Ile Thr Trp Gly Leu Ala Met Val Phe Val Val Asn
385                 390                 395                 400

Asn Gly Pro Asp Ala Leu Leu Ser Leu Gln Ser Pro Pro Arg Asp Leu
                405                 410                 415

Pro Leu Cys

<210> SEQ ID NO 344
<211> LENGTH: 111
<212> TYPE: PRT
<213> ORGANISM: Pinus radiata

<400> SEQUENCE: 344

Leu Asn Tyr Asn Ala Thr Val Gln Val Ile Leu Gln Gly Thr Asn Ile
1               5                   10                  15

Phe Ala Gly Glu Ser His Pro Ile His Leu His Gly Tyr Asp Phe Tyr
            20                  25                  30

Ile Val Gly Ala Gly Phe Gly Asn Tyr Asn Ala Gln Thr Asp Pro Gln
        35                  40                  45

Lys Phe Asn Leu Val Asp Pro Pro Met Arg Asn Thr Val Asn Val Pro
    50                  55                  60

Val Asn Gly Trp Ala Ala Ile Arg Phe Val Ala Asp Asn Pro Gly Ala
65                  70                  75                  80

Trp Val Met His Cys His Leu Asp Val His Ile Thr Trp Gly Leu Ala
                85                  90                  95

Met Val Phe Val Val Asn Asn Gly Pro Asp Pro Leu Leu Ser Leu
            100                 105                 110

<210> SEQ ID NO 345
<211> LENGTH: 93
<212> TYPE: PRT
<213> ORGANISM: Pinus radiata

<400> SEQUENCE: 345

Thr Arg Val Lys Val Leu Asn Tyr Asn Thr Thr Val Gln Val Ile Leu

```
1               5                   10                  15

Gln Gly Thr Asn Ile Phe Ala Gly Glu Ser His Pro Ile His Leu His
            20                  25                  30

Gly Tyr Asp Phe Tyr Ile Val Gly Ala Gly Phe Gly Asn Tyr Asn Pro
        35                  40                  45

Gln Thr Asp Pro Gln Lys Phe Asn Leu Ala Asp Pro Pro Met Arg Asn
    50                  55                  60

Thr Val Asn Val Pro Val Asn Gly Trp Ala Ala Ile Arg Phe Val Ala
65                  70                  75                  80

Asp Asn Pro Gly Ala Trp Val Met His Cys His Leu Asp
                85                  90
```

<210> SEQ ID NO 346
<211> LENGTH: 93
<212> TYPE: PRT
<213> ORGANISM: Pinus radiata

<400> SEQUENCE: 346

```
Lys Thr Phe Ser Asp Glu Cys Ser Asp Ala Arg Pro Arg Pro Asp Asn
1               5                   10                  15

Arg His Ser Gly Arg Val Asp Gln Leu Ala Asp Thr Phe Ser Val Ser
            20                  25                  30

Met Lys Gly Gly Glu Thr Asn Leu Leu Arg Val Ile Asn Ala Ala Leu
        35                  40                  45

Asn Thr Asp Leu Phe Phe Ser Ile Ala Ser His Thr Met Thr Val Val
    50                  55                  60

Ala Val Asp Ala Leu Tyr Thr Lys Pro Phe Gln Thr Asn Val Leu Met
65                  70                  75                  80

Leu Gly Pro Gly Gln Thr Thr Asp Ile Ala Ala Ala Asn
                85                  90
```

<210> SEQ ID NO 347
<211> LENGTH: 114
<212> TYPE: PRT
<213> ORGANISM: Pinus radiata

<400> SEQUENCE: 347

```
Pro Asp Ser Thr Ile Asn Thr Ser Phe Leu Gln Gln Leu Gln Gly Gln
1               5                   10                  15

Cys Pro Arg Ala Gly Gly Asp Glu Leu Pro Ser Ser Leu Asp Tyr Val
            20                  25                  30

Thr Pro Ala Arg Phe Asp Asn Thr Tyr Phe Ala Asn Leu Lys Gln Gln
        35                  40                  45

Lys Gly Val Leu His Ser Asp Arg Thr Leu Tyr Asp Pro Ala Ala Ser
    50                  55                  60

Gly Ser Val Thr Ser Ser Thr Val Asp His Phe Ser Ser Asp Gln Thr
65                  70                  75                  80

Ala Phe Phe Glu Ser Phe Lys Gly Ala Met Ile Lys Met Gly Asn Leu
                85                  90                  95

Ser Pro Ser Ala Gly Thr Gln Gly Glu Ile Arg Arg Asp Cys Arg Lys
            100                 105                 110

Val Asn
```

<210> SEQ ID NO 348
<211> LENGTH: 551
<212> TYPE: PRT
<213> ORGANISM: Pinus radiata

<400> SEQUENCE: 348

```
Met Glu Gly Gln Ile Ala Ala Leu Ser Lys Glu Asp Glu Phe Ile Phe
1               5                   10                  15

His Ser Pro Phe Pro Ala Val Pro Val Pro Glu Asn Ile Ser Leu Phe
            20                  25                  30

Gln Phe Val Leu Glu Gly Ala Glu Lys Tyr Arg Asp Lys Val Ala Leu
        35                  40                  45

Val Glu Ala Ser Thr Gly Lys Glu Tyr Asn Tyr Gly Gln Val Ile Ser
    50                  55                  60

Leu Thr Arg Asn Val Ala Ala Gly Leu Val Asp Lys Gly Ile Gln Lys
65                  70                  75                  80

Gly Asp Val Val Phe Val Leu Leu Pro Asn Met Ala Glu Tyr Pro Ile
                85                  90                  95

Ile Val Leu Gly Ile Met Leu Ala Gly Ala Val Phe Ser Gly Ala Asn
            100                 105                 110

Pro Ser Ala His Ile Asn Glu Val Glu Lys His Ile Gln Asp Ser Gly
        115                 120                 125

Ala Lys Ile Val Val Thr Val Gly Ser Ala Tyr Glu Lys Val Arg Gln
    130                 135                 140

Val Lys Leu Pro Val Ile Ile Ala Asp Asn Glu His Val Met Asn Thr
145                 150                 155                 160

Ile Pro Leu Gln Glu Ile Phe Glu Arg Asn Tyr Glu Ala Ala Gly Pro
                165                 170                 175

Phe Val Gln Ile Cys Gln Asp Asp Leu Cys Ala Leu Pro Tyr Ser Ser
            180                 185                 190

Gly Thr Thr Gly Ala Ser Lys Gly Val Met Leu Thr His Arg Asn Leu
        195                 200                 205

Ile Ala Asn Leu Cys Ser Ser Leu Phe Asp Val His Glu Ser Leu Val
    210                 215                 220

Gly Asn Phe Thr Thr Leu Gly Leu Met Pro Phe Phe His Ile Tyr Gly
225                 230                 235                 240

Ile Thr Gly Ile Cys Cys Ala Thr Leu Arg Asn Gly Gly Lys Val Val
                245                 250                 255

Val Met Ser Arg Phe Asp Leu Arg His Phe Ile Ser Ser Leu Ile Thr
            260                 265                 270

Tyr Glu Val Asn Phe Ala Pro Ile Val Pro Pro Ile Met Leu Ser Leu
        275                 280                 285

Val Lys Asn Pro Ile Val Asn Glu Phe Asp Leu Ser Arg Leu Lys Leu
    290                 295                 300

Lys Ala Val Met Thr Ala Ala Ala Pro Leu Ala Pro Asp Leu Leu Arg
305                 310                 315                 320

Ala Phe Glu Glu Lys Phe Pro Gly Val Glu Val Gln Glu Ala Tyr Gly
                325                 330                 335

Leu Thr Glu His Ser Cys Ile Thr Leu Thr His Cys Ala Pro Gly Asn
            340                 345                 350

Ile Arg Gly Arg Ala Lys Lys Ser Ser Val Gly Phe Ile Ile Pro Asn
        355                 360                 365

Leu Glu Val Lys Phe Ile Asp Pro Glu Thr Gly Lys Ser Leu Pro Arg
    370                 375                 380

Asn Ser Ile Gly Glu Val Cys Val Arg Ser Gln Cys Val Met Arg Gly
385                 390                 395                 400

Tyr Tyr Lys Lys Pro Thr Glu Thr Glu Lys Thr Val Asp Ser Asp Gly
                405                 410                 415
```

```
Trp Leu His Thr Gly Asp Val Gly Phe Ile Asp Asp Asp Asp Asp Val
            420                 425                 430

Phe Ile Val Asp Arg Ile Lys Glu Leu Ile Lys Tyr Lys Gly Phe Gln
        435                 440                 445

Val Ala Pro Ala Glu Leu Glu Ala Ile Leu Leu Ser His Pro Ser Val
    450                 455                 460

Glu Asp Ala Ala Val Val Pro Leu Pro Asp Glu Glu Ala Gly Glu Ile
465                 470                 475                 480

Pro Ala Ala Cys Val Val Met Ala Ala Ser Ala Thr Glu Thr Glu Asp
                485                 490                 495

Asp Ile Ser Lys Phe Val Ala Ser Gln Val Ala Thr Tyr Lys Arg Val
            500                 505                 510

Arg Leu Val Lys Phe Val Ser Thr Ile Pro Lys Ser Ser Ser Gly Lys
        515                 520                 525

Ile Leu Arg Arg Leu Leu Arg Asp Asn Leu Arg Glu Thr Leu Lys Asn
    530                 535                 540

Gln His Gln Pro Leu Ser Thr
545                 550


<210> SEQ ID NO 349
<211> LENGTH: 544
<212> TYPE: PRT
<213> ORGANISM: Eucalyptus grandis

<400> SEQUENCE: 349

Met Glu Ala Lys Pro Ser Glu Gln Pro Arg Glu Phe Ile Phe Arg Ser
1               5                   10                  15

Lys Leu Pro Asp Ile Tyr Ile Pro Asp Asn Leu Ser Leu His Ala Tyr
            20                  25                  30

Cys Phe Glu Asn Ile Ser Glu Phe Ala Asp Arg Pro Cys Val Ile Asn
        35                  40                  45

Gly Ala Thr Gly Arg Thr Tyr Thr Tyr Ala Glu Val Glu Leu Ile Ser
    50                  55                  60

Arg Arg Val Ser Ala Gly Leu Asn Gly Leu Gly Val Gly Gln Gly Asp
65                  70                  75                  80

Val Ile Met Leu Leu Leu Gln Asn Cys Pro Glu Phe Val Phe Ala Phe
                85                  90                  95

Leu Gly Ala Ser Tyr Arg Gly Ala Ile Ser Thr Thr Ala Asn Pro Phe
            100                 105                 110

Tyr Thr Pro Gly Glu Ile Ala Lys Gln Ala Ser Ala Ala Arg Ala Lys
        115                 120                 125

Ile Val Ile Thr Gln Ala Ala Phe Ala Asp Lys Val Arg Pro Phe Ala
    130                 135                 140

Glu Glu Asn Gly Val Lys Val Val Cys Ile Asp Thr Ala Pro Glu Gly
145                 150                 155                 160

Cys Leu His Phe Ser Glu Leu Met Gln Ala Asp Glu Asn Ala Ala Pro
                165                 170                 175

Ala Ala Asp Val Lys Pro Asp Asp Val Leu Ala Leu Pro Tyr Ser Ser
            180                 185                 190

Gly Thr Thr Gly Leu Pro Lys Gly Val Met Leu Thr His Arg Gly Gln
        195                 200                 205

Val Thr Ser Val Ala Gln Gln Val Asp Gly Asp Asn Pro Asn Leu Tyr
    210                 215                 220

Phe His Lys Glu Asp Val Ile Leu Cys Thr Leu Pro Leu Phe His Ile
225                 230                 235                 240
```

```
Tyr Ser Leu Asn Ser Val Met Phe Cys Ala Leu Arg Val Gly Ala Ala
                245                 250                 255

Ile Leu Ile Met Gln Lys Phe Glu Ile Val Ala Leu Met Glu Leu Val
            260                 265                 270

Gln Arg Tyr Arg Val Thr Ile Leu Pro Ile Val Pro Pro Ile Val Leu
        275                 280                 285

Glu Ile Ala Lys Ser Ala Glu Val Asp Arg Tyr Asp Leu Ser Ser Ile
    290                 295                 300

Arg Thr Ile Met Ser Gly Ala Ala Pro Met Gly Lys Glu Leu Glu Asp
305                 310                 315                 320

Thr Val Arg Ala Lys Leu Pro Asn Ala Lys Leu Gly Gln Gly Tyr Gly
                325                 330                 335

Met Thr Glu Ala Gly Pro Val Leu Ala Met Cys Pro Ala Phe Ala Lys
            340                 345                 350

Glu Pro Phe Glu Ile Lys Ser Gly Ala Cys Gly Thr Val Val Arg Asn
        355                 360                 365

Ala Glu Met Lys Ile Val Asp Pro Glu Thr Gly Ala Ser Leu Pro Arg
    370                 375                 380

Asn Gln Ala Gly Glu Ile Cys Ile Arg Gly His Gln Ile Met Lys Gly
385                 390                 395                 400

Tyr Leu Asn Asp Ala Glu Ala Thr Ala Asn Thr Ile Asp Lys Glu Gly
                405                 410                 415

Trp Leu His Thr Gly Asp Ile Gly Tyr Ile Asp Asp Asp Asp Glu Leu
            420                 425                 430

Phe Ile Val Asp Arg Leu Lys Glu Leu Ile Lys Tyr Lys Gly Phe Gln
        435                 440                 445

Val Ala Pro Ala Glu Leu Glu Ala Met Leu Ile Ala His Pro Ser Ile
    450                 455                 460

Ser Asp Ala Ala Val Val Pro Met Lys Asp Glu Val Ala Gly Glu Val
465                 470                 475                 480

Pro Val Ala Phe Val Val Lys Ser Asn Gly Ser Val Ile Thr Glu Asp
                485                 490                 495

Glu Ile Lys Gln Tyr Ile Ser Lys Gln Val Val Phe Tyr Lys Arg Ile
            500                 505                 510

Lys Arg Val Phe Phe Thr Asp Ala Ile Pro Lys Ala Pro Ser Gly Lys
        515                 520                 525

Ile Leu Arg Lys Asp Leu Arg Ala Lys Leu Ala Ser Gly Val Tyr Asn
    530                 535                 540


<210> SEQ ID NO 350
<211> LENGTH: 717
<212> TYPE: DNA
<213> ORGANISM: Eucalyptus grandis

<400> SEQUENCE: 350

cctgttttgg caacaactcc agcagctctc tgctcttttt actataaaaa aacccatctt      60

cacttcttct gtacttgcac acgaacatta agcgcttgat cagaacttgt atcagctccc     120

caccaccacc aaacagaaga gaaacagaag aaaaggaaaa gttcgaacaa cttcgaacga     180

tgcgagccct tgctgttgtg ctcggttctg ctatcttgct ggcgtatgtc gcgagcagtg     240

cgggtgcgct gagcttggat tactatgacc agacgtgccc gaagctcgag ttttcggtga     300

ggggggctgt gaagaaagcg atgaagaacg acaacaccgt tcctgctgct ttacttcgca     360

tgcacttcca cgactgcttc atcagaggat gtgacggttc cgtgctcttg aactcgacgg     420

caaagaacac agccgaaaaa gacgggccgc cgaacatctc actccacgca ttctatgtga     480
```

```
tcgaccttgc gaaggaagcg gtggaagctc agtgccctgg ggtcgtctct tgcgccgaca    540
tcttggcctt ggccgctcgg gatgctgtcg ctctgtctgg aggaccgcat tgggatgtgc    600
cgaaaggaag aaaagatggg aggattcgaa agcgaatgac acaaggcaat taccagctcc    660
gaccttcaac atctctcaac tacagcaagc ttctctcaag aggcctttcc atggaga       717
```

<210> SEQ ID NO 351
<211> LENGTH: 369
<212> TYPE: DNA
<213> ORGANISM: Eucalyptus grandis

<400> SEQUENCE: 351

```
ggcgtctctc ctctgtctag tcatgtttct gaaatacctc tccgccgcac tcatctctct     60
tgcaacgatt cgctctgctt acggtgcctc cactccgaag cgaagagcaa catgcgcggg    120
cgggcagacc gtgaaaaacg aggcctgttg cgcctggttc cccgtcctgg aagacattct    180
gcccaacatg ttcgacaacg aatgtggcga cgacgcccat ggcgctctgc gtctgagctt    240
ccacgacgcg atcggtttct ctccttctca aggtggagga ggcgcggacg gatccatttt    300
gtcttcagtg acaccgaact gcagttcccc gcgaacgctg gcctcgacga cccgatcgac    360
actgagctt                                                            369
```

<210> SEQ ID NO 352
<211> LENGTH: 1391
<212> TYPE: DNA
<213> ORGANISM: Eucalyptus grandis

<400> SEQUENCE: 352

```
gaaaaactgt ggtggtgaag ctgcctcgca aagatgtgac gttatctaat cagcgtctcc     60
ctgcccggaa aaagccggaa aaggaactgt tattttcaag cttttatttc accacaatca    120
cggagttata tattatacca agatttccgc gttaacctta cgccggagaa acttcatctg    180
agtgtgtgct cttgctggtt ttcaacagga acatatcgat aatttatgtc atggctacac    240
acgatatggt cggcttttcc gtcgtcgttg tcctccttgc cacttcggtt atcaccactg    300
cccgttgtaa gctctcaccg agtcattatc aatcaacatg tccgaaagca ttgtcgattg    360
ttcgagctgg agtagcaaaa gcaatcaaga atgagacccg gacgggcgcg tccttgcttc    420
ggctgcactt ccatgactgc ttcgtcaatg ggtgcgatgc gtcgatattg ttggatgaca    480
cgcctagctt cgtgggcgag aaaacagcag ctccgaacaa caattccgtg agagggttcg    540
aagtgatcga ccgcatcaag gctagtctgg agaaggagtg ccctggagtg gtttcctgtg    600
cagatatcgt tgccctggct gctcgcgact cagtcgttca tttgggaggt ccttcatgga    660
ccgtaagctt agggagaaag gattccatta ctgctagcag gagccttgct aacacctcca    720
tacctccacc tacttctaat ctcagtgctc tcataaccag cttcgctgct cagggtcttt    780
cagtcaagaa catggtggct ctttctggtt cacataccat tggcctagcg agatgcactt    840
ccttccgaag acggatctac aacgactcga acatagatac atccttcgcc cataaattgc    900
agaagatatg tcccaggatt ggaaatgata gtgtccttca aaggctagac atccaaacgc    960
cgaccttctt tgacaacctt tactaccaca atttactgca gaagaagggc cttcttcact   1020
ctgatcaaga gctcttcaat ggcagttctg tggattcact ggtcaagaag tatgcatgcg   1080
acacaggaaa atttttccga gattttgcca aggcaatgat caaaatgagc gaaattaagc   1140
cccccaaagg aagcaatggt caaataagga aaaattgcag gaaagtgaac taagtatgaa   1200
gctcatatat gcaatttgaa actgccacat atgaacacgg tagtgaaatc agggctcgat   1260
```

aatgtcccct gacaatttgt cgtcatgtat ctgtcttctt gactaatttg tggttgctgc 1320
ttgaaaaata aaggagctcg tctcagtttc tgtaaaaaaa aaaaaaaaaa aaaaaaaaaa 1380
aaaaaaaaaa a 1391

<210> SEQ ID NO 353
<211> LENGTH: 337
<212> TYPE: DNA
<213> ORGANISM: Eucalyptus grandis

<400> SEQUENCE: 353
cagaatgcct agtcgtcatc cgatttgggt aattgtcgcc atagcttttg taaccgcact 60
cgggtgggga agtgcctccg cacaactctc tacaaacttc tactccaaaa gttgtcccaa 120
tgttttgagc acggtgaaat ctgttgtccg gtccgcggtg tcgaaagagc gccgcatggg 180
tgcttctctc ctgcgcctct tctttcatga ttgcttcgtc aatgggtgcg atggctcgat 240
actcctggac gacacatcct cgttccaagg ggagaagacg gccggcccaa ataataagtc 300
tttgagagga tacaacgtca ttgaccggat caagtcc 337

<210> SEQ ID NO 354
<211> LENGTH: 368
<212> TYPE: DNA
<213> ORGANISM: Eucalyptus grandis

<400> SEQUENCE: 354
ctcacttccg agcgcgccat gcagttcacc ttttccgccg ctttcctcgc tctcgtcaca 60
gtcgcggccg ctatgcccac caagcgtgcg gcgtgcagca acggacgaac ggccactcat 120
gcctcgtgct gtgtgtggtt cgacgtcctc gacgatattc aagagaatct gttcgacggt 180
ggagagtgcg gagaggaaac acacgagtct ctgcggctca ctttccacga tgccatcggc 240
ttctccccga gcctgtttct cgagggaaaa ttcggtggtc tcggcgctga tggttccatc 300
atggctcact ctgacatcga gaccgtgttc cccgccaaca atggaattga tgatatcgtc 360
gacgcgca 368

<210> SEQ ID NO 355
<211> LENGTH: 955
<212> TYPE: DNA
<213> ORGANISM: Eucalyptus grandis

<400> SEQUENCE: 355
aagaaactca gacccagacc cagaccacat catggcctcc cgtttcagct ctttcgtttt 60
ggtttctttt cttgtgatag ctgcatcaca tgttcatgtt acgagctctg ctcacttggt 120
gaaggggctc tcgtggtcct tctacgagaa gagctgtccc aaggtggagt ccgtcatcaa 180
gaaacatctc aagaaggtgt tcgaggagga tattggccaa gctgctgggc tgcttcgtct 240
gcacttccat gactgctttg ttaagggatg tgatgcttcg gtgttgctgg atggatcagc 300
cagtggacca agtgagcagg acgctccacc gaaccggagc ttgagaccat cagcattcaa 360
gatcatcgat gacctccgtg agctcgtgga caagaagtgt ggtcgagtag tctcttgtgc 420
tgatatcgca gccattgccg ctcgtgactc cgttgtcctg tcaggcggac ctgagtatga 480
tgtgccgttg ggaaggcggg atggactcac gtttgcgact caaaatgtga ccttagagaa 540
tttacctgca ccaactgaga acgccagtgc aattctctcc gccctagcca agaaaaactt 600
agacgctacc gacgtggtgg ccctctctgg aggccacacc atcgggcttg ggcactgcac 660
ctcctttgag aatcggctct acccgaccca agaccccacg atggagaaga cctttgccca 720

```
tgatctcaag ggcgtgtgcc ccaccacaaa ctccaccaac actacggtct tggacatccg    780

atcacccaac cgattcgaca acaagtactt tgtcgatttg gtgaaccgcc aaggcctgtt    840

cacctcagac caagatctgt atgaggatcc cacaaccagg gacattgtca ctagctttgc    900

cgaggaccag gaattgttct ttgagaagtt tgtcctagcc atgacgaaga tgggg         955

<210> SEQ ID NO 356
<211> LENGTH: 308
<212> TYPE: DNA
<213> ORGANISM: Eucalyptus grandis

<400> SEQUENCE: 356

ctgtgtctag tcatgttcct gaagtatctc tccggcgccc tcgtctccct tgcaacgatc     60

cgcggtgttt gcggtgcttc cgctccgatg cgaagagcaa catgtgcggg tgggcagact    120

gtcaaaaatg cggcatgttg tgcatggttc ccagtactcg acgacatcag ggaaaacttt    180

ttcgacaacg aatgcggcga tgacgcccat gctgccctgc gtctgagttt ccacgatgca    240

atcggtttct ctcgttcgaa aggtggagga ggcgcggacg gatccatcat tgccttcaat    300

aagactga                                                             308

<210> SEQ ID NO 357
<211> LENGTH: 373
<212> TYPE: DNA
<213> ORGANISM: Eucalyptus grandis

<400> SEQUENCE: 357

tcaggtcctt gtcaacatgg cattcaaact cgtggttaat cttgttagtc ttgctctcgc     60

cgtcagtgct gcaaacttca agcgagttgc ttgcccaggt actacggcca cagctcgcaa    120

tccggcgtgc tgcgcattct tctcactgag agatgacttg cttacaaatc tcttcggggg    180

tgtgtgcggc gaagaggcgc acgagtctct ccgattgtct ttccatgatg ccattgcgtt    240

ttcgcccgca ttaattaggc aaggcaaacc gggaggtgga ggtgctgatg gctctatgat    300

tactttccca aacgtcgagc ccaattttaa tgccaacaac ggcattattg attctgtcga    360

ctttttgaca cca                                                       373

<210> SEQ ID NO 358
<211> LENGTH: 417
<212> TYPE: DNA
<213> ORGANISM: Eucalyptus grandis

<400> SEQUENCE: 358

ctcttgtcct gggaccgtgt cttgcgccga cattctcgcc ctcggtgctc aagcttctgt     60

cgttctgtca ggaggtccat cttggagggt gctctcgggg aggagggaca gcttgacggc    120

gaaccaagca ggagcgaaca catcgatacc tagccctttt gattccttgg ctaacctcac    180

ttccaaattc gccgctgttg gcttggacac caatgacctt gtcactcttt ccggagctca    240

cacctttgga cgtgcacagt gcaggacatt cagccctagg ctctacaact tcaacgcgag    300

tggcagccca gatccaacca taagtccttc atacttgacc actctccaac aactttgccc    360

acagaatgga agcggctccg tcctcgccaa cctcgacccg acgaccgtga acacatt       417

<210> SEQ ID NO 359
<211> LENGTH: 659
<212> TYPE: DNA
<213> ORGANISM: Pinus radiata

<400> SEQUENCE: 359
```

cacaatggaa atagtttagg tcagtaatgg aacggatgaa acatattccc ggccttacac 60
tgcagtttca gtctgtgctg atcactggag cggcattgtt tctatggatc cagacatcgg 120
atgctcagga ctgtaatggt ctgagtcatc actattatca gaagtcctgt ccaaatgccc 180
aggctatcat taaatctgta gtttcagatg ctgtcaaaaa ggaagcgaga atggctgctt 240
ccttgcttcg tctgcatttt catgactgtt ttgttcaggg ctgtgatgct tcaattctgc 300
ttgatgacac tgctagtttc acaggggaga agacagcatt acctaacaga aattctgtaa 360
gaggctttga ggtagtggat aagatcaaaa gcaaattgga ggaagcatgt cctggagtgg 420
tctcatgtgc tgacattctt gctgtggcag cccgtgattc agtaggcttt agtgtgggtc 480
cgtattggga ggttctactg ggcaggaggg actcaaagac tgcaagcaag agcggtgcaa 540
acaacgacat tcctgcaccc aactcaaccc atcagactct ggaaaccaaa ttcaacctca 600
aaggtctcaa tgtgcttgac ctagttgctc tatcaaggtc ccataacaat agggttagc 659

<210> SEQ ID NO 360
<211> LENGTH: 669
<212> TYPE: DNA
<213> ORGANISM: Pinus radiata

<400> SEQUENCE: 360
gcggcacgag cggcaaaact aaagctattc gcagcctccc tctatggcga cattagggat 60
ccctctcggc tcactcagcc tgctcctcct cttcttctgc tgcgcacaac gcagtgtggg 120
actgaaggaa aattactacg caacgtcgtg tccgagagca gagcacatag tgaaggagca 180
ggtctacaat ctctaccagg agcacggcaa cactgccgtt tcatggatca gacttatctt 240
ccatgactgc atagttcagt cgtgcgatgc ctccattcta ttagacagta gtggagacgt 300
gcagacagag aaacaatcgg accgaaactt cggaatgcga aacttcaagt atgtggacac 360
cattaaggag gccatcgagg tggaatgtcc tggagtggtg tcgtgtgctg acattattgt 420
tctcgccgca aaggaggcag ctgcaatgct aggaggtcca cgcatcgcgg tgaaaacagg 480
gagacgagac agcagaaaaa gcagtgcagc agtggtggac aaatacgttc cgctgcataa 540
tggcagcatc tcatctcttc tctctgcctt tgcctctgtg ggcatcgatg cggaaggagc 600
tgtggccctt ttaggtttga tacttatcca ttctgtatta cattatacat aaataaaaaa 660
aaaaaaaaa 669

<210> SEQ ID NO 361
<211> LENGTH: 916
<212> TYPE: DNA
<213> ORGANISM: Pinus radiata

<400> SEQUENCE: 361
agcaaattgg ttgcttttgg agcgcttgtt ccaacagcaa aaatggctgt tttgatgaag 60
agctttccgt gcattgctgt cattgtgttc attatctgtt cgattactga tactgtgaat 120
gggaaactga gctccacgtt ttatgataag tcttgtccca aggccctgtc tatagtgcaa 180
gccggggtga agcaagcagt ggctaaggaa aaacgtatgg gggcatcgct tctccgcctt 240
catttccacg actgcttcgt taatggctgc gatgggtctg tactgttgga caattccacg 300
accttcacta gcgagaaata tgctcttccc aataacaatt ccgcgagggg tttcgaggtg 360
atcgatagca taaagagcca actcgagaat gcttgcaccg gcgtcgtttc ttgtgcagac 420
attctcacga ttgctgctcg tgattctgtt gttcagttgg gtggaccttc gtggaaggtg 480
atgttgggga ggcgagactc aacaacagcg agcattagcg gtgcaaacaa taacattccg 540
cctcccactt ccaatctgac gaaactcatt tcactatttc aggcacaggg cctctccaca 600
aaggaaatgg ttgcactctc tggtggtcat accatcgggc aggcgcaatg caagaatttc 660
agagcccata tttacaacga caccaacata gatactacgt acgccacttc attgcgttca 720
aagtgtccta gtaccacagg ctccggagac agcaacctgt cgccactgga ttatacgact 780
cccactgtgt ttgacaaaaa ctattactac aatctgaaaa gcaaaagagg acttctccac 840
tccgaccagg aactcttcaa cggaggctcc actgattcgc atgtgactaa gtacgcctcc 900
aaccagaata ccttct 916

<210> SEQ ID NO 362
<211> LENGTH: 586
<212> TYPE: DNA
<213> ORGANISM: Pinus radiata

<400> SEQUENCE: 362
gcaaacagca accttccctc gccagcttcc agtctcagca cactcatgac agcatttcaa 60
aaacagggtc tctctaccaa ggacctcgtc gcactctcag gtgctcatac aattggtcaa 120
gcacggtgca ccacattcag aactcgcatc tacaacgata ccaacattaa cgctgccttc 180
gctacatctg cgaaggcgaa ctgccccagc actggtggcg acaacaccct ctctcccttg 240
gatgttctca cccctaccac atttgacaac aagtattaca ctaatctgaa aagccaaaag 300
ggacttttcc actccgatca ggagctattt aatggaggtt ccacagactc tagagttagt 360
atctacagca ccagtcaagc cattttcttt actgactttg cagccgccat ggtgaatatg 420
ggtaatatta gtcccctcac tggcaccaac ggcgagatcc gcacaaactg caggaaagtc 480
aattaaaatt tgtaaagatt gtattatcta tagcttttct ctgaagttat aagcgaagct 540
ttacaagaaa gcaataaatt actgtttaat taaaaaaaaa aaaaaa 586

<210> SEQ ID NO 363
<211> LENGTH: 1224
<212> TYPE: DNA
<213> ORGANISM: Pinus radiata

<400> SEQUENCE: 363
ctaccactca atttcgctct tatcttctgt gtttcatcgt tttcttccaa atatgatgat 60
gaggactcta gtgtgcattg ggttaatggc tgtgtttgta gccttcatac atataaacgc 120
tgtgaatggg cagctgagct caacgtttta tgccaaatcg tgtccgaggt tgccatcgat 180
agtgaaatca gtggtgaagc aagcggtagc taaggagaaa agaatgggag cgtccttggt 240
ccgccttcac tttcacgatt gcttcgtcaa cgggtgcgat ggttcaatct tattggatga 300
caacgctacg tttaccggag aaaagactgc aggcccaaac gccaattctg cgagaggctt 360
cgaggtaatt gacagcatta aaactcaagt ggaggcagcc tgcagtggag tcgtgtcgtg 420
tgcagacatt ctcaccattg ctgctcgtga ctctattgtt gaacttcaag gcccaacatg 480
gacggtaatg cttggaaggc gagactccac gactgcgagt ttaagcgctg caaacaacaa 540
cattccatct cccgcttcca gtctgagcac actcatctca tcttttcaag ctcacggtct 600
ttctaccaaa gaccttgttg cactctcagg tgctcataca attggtcaat cacgatgcgc 660
ctttttcaga actcggatct acaacgaaac gaacattaac gctgctttcg ctacatctgt 720
aaaggcaaac tgccccagcg ctggtggcga cagcaacctc tctcccttag atgcggtcac 780
ctcaatcaca tttgacaaca agtattactc taatcttaaa atacagaaag gacttctcca 840
ctccgaccag cagctcttta atggaggttc tacagattct caggttactg cgtacagcag 900
caatcagaac agcttcttta tagactttac agctgccatg gtgaagatgg gaaatattag 960
ccctctcact ggcactaacg ggcaaatccg caaaaactgc aggaagtcca attagtctct 1020
ctgaagattg tattctccgt actctttcag cttatttttt ctttgtaaca ttgattttcg 1080
atcggctagt gagccttcaa atcgaagctc taaaagaaag caataaacta catttctgag 1140
attatgttca gagttgtatg cagttcagac cataattcca attttgcttc ccaaaaaaaa 1200
aagacttgta aaaaaaaaaa aaaa 1224

<210> SEQ ID NO 364
<211> LENGTH: 519
<212> TYPE: DNA
<213> ORGANISM: Pinus radiata

<400> SEQUENCE: 364
aaactgccca agtcaggagg cgacaataac ctgtcaccgt tggatctact gactccaaca 60
acgttcgaca ataaatacta cacaaatctg aagagccaaa agggtcttct ccactcagac 120
cagcagctgt ttaatggcgg ctctgcagat tcccaggtta ctacctacag caccactcag 180
agcaccttct ttaccgactt cgcagcttcc atgttgaata tgggtaatat cagtcccctc 240
actggcacca gcggacaaat ccgcaaaaac tgcagaaaac ctaattgatg cctctcttag 300
gccatatgta ctttactgtt ctcatgggat tatattttga ttgtagaatt atatagatag 360
ttgggagacc tacggctgcg ttagacacta gcaagcctcc aattggatct gtgcgtccct 420
agtttgttga ctatttggtt gatttcgatg taccaagtac aaagtttctc aacagattaa 480
tccaatgaat taggttttat aaaaaaaaaa aaaaaaaaa 519

<210> SEQ ID NO 365
<211> LENGTH: 646
<212> TYPE: DNA
<213> ORGANISM: Pinus radiata

<400> SEQUENCE: 365
aaaccattca aacccaccga agatttcatt gcgtcgcagc atcatgactt cctttacagc 60
aatggcgtca gtcgtgtgca tcgctctgct ctttttttcg accgttgctt ttgctcaact 120
caactcaacg tattatgata cgtcgtgtcc caaactcctg gcaacggtga aggctgcagt 180
gaagacggcg gtggccaatg agaaacgcat gggggcatca ttgctccgtc ttcactttca 240
tgattgtttc gtcaatggtt gcgatgggtc agtgttgttg gacgactctt cgagtctaac 300
tggggaaaag actgctcttc ccaacaacaa ttcgttgagg ggtttcgacg tcatagacac 360
catcaaatca caagtggaag cagtttgcag cggaatcgta tcgtgcgctg acattttggc 420
tattacggct agagattctg tcgtcgaatt gggaggacca acatggacag tgctgcttgg 480
aaggagagac tcagcaactg ccagcctaag cgccgcaaac accaacattc ccgctcccac 540
ttccaatctc agtggtctca tctcatcttt tcaagcacag ggcctttcaa ccaaggatat 600
gattgtccta tcaggtgcac ataccattgg ccaagctcga tgcaca 646

<210> SEQ ID NO 366
<211> LENGTH: 364
<212> TYPE: DNA
<213> ORGANISM: Pinus radiata

<400> SEQUENCE: 366
ccttaatctc ctcttttaca gcccatggtc tttccacaaa ggatctcggt gcactctcgg 60
gagctcatac gattggccaa gcgcggtgca ccacattcag agctcgcgtc tacaacgaat 120

```
ccaacattga cacttccttc gccacttcgg tgaaggcaaa ctggccaagc gctggtggcg    180

acaacaccct ctcgccctta gatctggcca cgcctaccac atttgacaac aagtattaca    240

ctgatttgag aagccaaaag ggacttctgc actccgatca gcaaatgttt agcggagggt    300

ctacaaattc tcaagtcacc acctatagct ccaatcaaaa acaccttctt tacagacttt    360

acag                                                                 364
```

<210> SEQ ID NO 367
<211> LENGTH: 364
<212> TYPE: DNA
<213> ORGANISM: Pinus radiata

<400> SEQUENCE: 367

```
ggaaaaggat caactttcac ttaaaggagg acatcaccca agcggctggt ttgctgcgcg     60

tccatttcca tgactgcttc gttcagggtt gcgacggatc ggttctgttg gacggttctg    120

ccagcggtcc tagcgaacaa gacgctccac cgaacttaac gctgagagca aaagcctttg    180

aaataattaa cgacatcaag aaacatgtgg aaaaggcttg cagcggcgtt gtctcttgcg    240

cggacttgac tgctctcgca gctcgcgagt cggtcagagc agttggagga ccagagtatc    300

gagtgcctct ggggcgcagg gacagcctga aattcgccac acgaaaagtg acccttgcca    360

acct                                                                 364
```

<210> SEQ ID NO 368
<211> LENGTH: 801
<212> TYPE: DNA
<213> ORGANISM: Pinus radiata

<400> SEQUENCE: 368

```
gtcatggctt cgtttacagc aatgcgatct ctggccttta tcgccttgtt gatgtgttcg     60

accgttgcgt acgcgcagct tagcgcaacg ttttataata catcatgtcc caaactactc    120

tcaacggtgc aggccgctgt gaagcaagcg gtggccaacg agaagcgcat gggggcatcg    180

ctcctccgcc ttcactttca cgactgcttc gttaatggtt gcgatgggtc tgtgctgctg    240

gacgactctt cgactctaac tggagagaag accgccgttc ccaacaacaa ttcggcaagg    300

ggtttcgatg tgatagacac catcaagtct caagtggaag cagtttgcag tggagttgtg    360

tcgtgcgcag atattttggc tattgctgct agagattctg ttgtccagtt gggaggccca    420

acatggacag tgcagctggg gaggagagac tccaggactg ccagcctaag tggtgcaaac    480

aacaacattc cggctcctac ttctaatctc agtgctctca tctcattatt tcaagctcag    540

ggtctttcca cgaaggacat ggttgtccta tcaggtgcgc acaccatagg ccaagcgcgg    600

tgcacaagct tcagggcccg catctacaac gaatccaaca ttaatgcagc atacgcaact    660

tccctgaaga caaactgtcc gactacagga agcgacaaca acctgtcacc attggatcgt    720

gttactccca ctacgtttga catcaactac tactcaaatc tgagaagcca aaagggactt    780

ctccactccg accagcagct g                                              801
```

<210> SEQ ID NO 369
<211> LENGTH: 1171
<212> TYPE: DNA
<213> ORGANISM: Pinus radiata

<400> SEQUENCE: 369

```
gccaaataaa gttatctttt ggctttattc cacaagaaaa aaatggctta cctaaggaag     60

agtttcgcct gtatagctgt aatggtgttt atcgtgtgtt ctattacaga tactgtgaat    120
```

```
gggcagctga gctccacgtt ttacgacaaa tcttgcccga cggcactgtc ggtagtgaag    180
gccgcagtga agcaagcggt cgctaacgag aaacggatgg gtgcgtcttt gctccgcctg    240
cactttcacg actgcttcgt taatggttgc gatgggtccg ttctgttgga cgattcttcg    300
accattactg gcgagaagac agctaatccc aatgccaatt ctgcgagggg attcgacgta    360
atagatacca taaagagcaa tgtcgagaaa gcttgcagtg gagtcgtttc ctgtgcagac    420
attctcgcca ttgctgctcg tgattctgtt gttgaactgg gcggtccttc atggacagta    480
atgttgggaa ggcgagactc gacaacagct agcaaaagcg gtgcaaacag taatattccg    540
cctccgactt ccagtctgag caacctcatc tcactattcc aagcgcaggg actctccgca    600
aaggaaatgg ttgcactttc tggcggtcat accatcgggc aggcgcaatg caagaatttc    660
agagcccata tttacaacga gaccaacata gacagtgcgt acgccacttc attgcgttca    720
aagtgtccga gtaccacagg ctccggagac agcaacttgt cgccattgga ttatatgact    780
cccactgtgt ttgacaaaaa ctattacagc gacctgaaaa gccaaaaagg acttctccac    840
tccgaccagg aactcttcaa cggaggctcc actgattcac aggtgactac gtacgcctcc    900
aaccagaaca ccttcttctc cgatttttgct gcggccatgg ttaagatggg aaatatcaaa    960
cctcttaccg gcaccagcgg acagatccca aagaactgca ggaagccaaa ctaattatga   1020
tcactgtcga attatcatca ctccgttgca ctgcctttta attgtaaaag taacgtttcg   1080
actgatttca gtctatggat accatatgct gatggagctt gtcatgaata aataagttca   1140
taactttacc atcattaaaa aaaaaaaaaa a                                  1171

<210> SEQ ID NO 370
<211> LENGTH: 1073
<212> TYPE: DNA
<213> ORGANISM: Pinus radiata

<400> SEQUENCE: 370

atcagattaa gagtgcactt gagaaggagt gcccaaaaac tgtatcgtgt gcagatattc     60
tcgctattgc atctcgtgat tcagtggtcc tgagtggagg gctgggctgg gaagttttac    120
tggggaggag agattcgaag agtgcaagtt tgagtgggtc caacaacaat atcccggcgc    180
ccaactcaac tctgcagacg cttactacca agttcaaact acaaggtcta gatgaggtag    240
acttggtatc cctttcaggg agtcacacca tcggcctatc tcgatgcaca agtttcaggc    300
agaggcttta caaccagagt ggaaatgggc tgccagactt cactctaaac aggggttact    360
atgctcggct gaaatccgga tgtccaaaat ctggaggaga taataacttg ttcccattgg    420
atttcgtgac tcctaccaaa ttcgataact actacttcaa gagcttgctg agcggtcaag    480
ggctgttgaa cacagacgaa gaattgttcg caaagggctc agggaagacg aaggagctag    540
ttaaacttta tgcagcaaat gaggagctct ttctcaaaca gtttgcatta tctatggtga    600
agatgggaaa catcaagcct cttacaggca ccgtgggaga aatcagggtc aactgtcgta    660
aggttaacag ttgatcgttt taatttaatc attttccatc tcttgcattg cattttgtta    720
catctccctt cttagctgcc atcaaattgc attactagat catccttccc atggctttca    780
gttgtaacag gttgaataaa attgccactt ctgaattatt aaacttctga ttgggctgga    840
cgatagaggg aaacttcaac gtcccaatca aattgtcatg taagaaatat ctcgggcagt    900
aaactcagag tggtaaatca agattgttga ataaaatgtt agctcttcgt taatggctgt    960
ggagaaggtc aacactcctc gtgtgtttag ctatgtgtct gtttattaac gcttgcgagt   1020
tttgatgtaa tggaaatcgt gtcttcaaca agaataaaaa aaaaaaaaaa aaa          1073
```

<210> SEQ ID NO 371
<211> LENGTH: 1522
<212> TYPE: DNA
<213> ORGANISM: Pinus radiata

<400> SEQUENCE: 371
gaaaggcctg tcgatttcct ccatttgaat cgacaggatc gaagaatcta ttttacatca 60
aagcaaagcc aaagctgtgg ccgacatggg caagtttatc acggctctgg cttctgttat 120
tctctgcgtg tttgtgatct atggcggcgc tgtcaatgct ctgcccagtc ccgtggctgg 180
tctttcttgg acgttctaca gctcgagttg cccgtccttg gagtccatag tgtgggagcg 240
catggaagcc tatttgagtg cagacatcac acaggctgca ggattgttga ggctccactt 300
ccacgactgc tttgtccagg gatgcgatgg gtcggtgttg ttgaacgcaa cgtcaggtga 360
gcaaacggct cccccaaact tatcactcag agcgcaggct ttaaagatta ttaacgacat 420
caaagagaac gtcgaagccg cctgcagcgg aattgtgtcg tgtgccgaca ttgttacttt 480
agcagctcgt gactccgttg taatggctgg aggaccgttc taccccttac cactcggccg 540
cagggacagc cttaccttcg ccaatcgatc gaccgttctc gccaatttgc catccccaac 600
ctccaatgta acggggctca tcagtgtttt gggtcccaaa ggcttgaatt tcacagatct 660
ggtggccctc tcaggaggac atacaattgg cagaagcaac tgctcctcct tcgacaacag 720
actatataac agcaccaccg gtacacaaat gcgggatccc acgatggacc agagtttcgc 780
taagaatctt tatctcacct gccctaccag taccaccgtt aacaccacca aattggatat 840
tcgcactcca aatgtgttcg acaacaaata ctacgtcgat ctcctcaacc gacagaccct 900
cttcacttct gaccagactc tttacaccga cactcgaacc cgcgacattg tgatcaattt 960
tgcggtgaat cagagcctct tctttgaaca gtttgtgctg agcatgctca aaatggggca 1020
gctggatgtg ctcacaggaa gcgagggaga gatccgtaag aactgctggg ctgcgaatcc 1080
ttcaacattt tcgattatgg atccagaggc gtctcaagaa tcaacatctt actctatgtg 1140
agattagggt tatgagcgaa tctcaaatat aagcaagcag cgttaattcc cagcaaagtc 1200
taataaatat atatataacc ggcatcttgt aaaccctttg caatgctggt tctacaaatt 1260
actttttccc ttttgacctt ctgaaagagc agaaatcaag cctgaataca gtgcattctc 1320
gttgaaaata aatagcgttt cttgttgata atcagatttc caaccgattc cggcaatttc 1380
caataagaaa ctttactgaa tttaaactca aatgctggcc aattttgttt agggcgtttt 1440
tgaaatcgtt ggactgttat ctttggaaac ctacattaga cttatattta tctaaaatat 1500
tgcacccaaa aaaaaaaaaa aa 1522

<210> SEQ ID NO 372
<211> LENGTH: 311
<212> TYPE: DNA
<213> ORGANISM: Pinus radiata

<400> SEQUENCE: 372
ctcaatttcg ctcttatctt ctgtgtttca tcgttttctt cccaatatga tgatgaggac 60
tctagtgtgc attgggttaa tggctgtgtt tgtagccttc atacatataa acgcttgaat 120
gggcagctga gctcaacgtt ttatgccaaa tcgtgtccga ggttgccatc gatagtgaaa 180
tcagtggtga agcaagcggt cgctaaggag aaaagaatgg gagcgtcctt ggtccgcctt 240
cactttcacg attgcttcgt caatgggtgc gatggttcaa tcttattgga tgacaacgcg 300
acgtttaccg g 311

<210> SEQ ID NO 373
<211> LENGTH: 474
<212> TYPE: DNA
<213> ORGANISM: Pinus radiata

<400> SEQUENCE: 373
catcgatgct atcaagacag ccctcgagag ttcttgcaac gccactgttt cttgcgcaga 60
tattctcgct attgcagcgc gggattcagt ataccttagc ggtgggcctt actggcaagt 120
gcagatgggg agaagagatg gcaccactgc cagcaaaagt gcagcaaatg ccgacatccc 180
ttctcctatt gagtcgcttg gttcactcat atcccaattc caaggtgttg ggctttctgt 240
tcatgatctt gtagtgcttt caggggctca caccataggc cgtgcccact gtggcacctt 300
cagctcacgc ctattcaatt tcagcggctc aaacagtgcg gacccaacta ttcaccaatc 360
tctactgcaa gacctgcata gtttatgccc agatggaaac agtgatccaa ataccctggc 420
gccactggac cctgtgacca aagacaagct ccataatgtg tatttcagaa atct 474

<210> SEQ ID NO 374
<211> LENGTH: 353
<212> TYPE: DNA
<213> ORGANISM: Pinus radiata

<400> SEQUENCE: 374
ctttctgtta cggatgtcgt tgctttgtca gggggacata caattgggcg agctcggtgc 60
acagtgttca gcggtagact ctacaatttc agcggaacgg gcagtccgga tccgacactg 120
aattcctcct atctatccac cttgcaaagc acgtgcccgc agaatggaag cgcgaatacg 180
ttaacgtcac tggatccagg gactccaaat acgttcgaca acaactactt tgcaaatctg 240
cagattgaga tgggtctgct tcagtcgatc aagaacttct ttccacatcg ggagcaagca 300
ccatctctac tgtcaatgat tatgccagta gtcaatccga tttcttcttc aac 353

<210> SEQ ID NO 375
<211> LENGTH: 461
<212> TYPE: DNA
<213> ORGANISM: Pinus radiata

<400> SEQUENCE: 375
caaagcagag ttgcgtttga agcgcaagaa atggccgctt taatgaaaag ctccgcatgc 60
attgctgtaa ttgtgtttat tgtgtgttcg attaataaca ctgtgcatgg gcagctgagc 120
tcaacatttt atgacaaatc ttgcccgacg gtgctgtcgg tagtgaaagc cggggtgaag 180
caagcggtcg ccaaggagca aaggatgggg gcgtcgcttc tccgacttca cttccacgac 240
tgcttcgtta atggttgcga tgggtccgtt ctgttggatg actcttcgaa aattactggc 300
gagaaaacgg ctattcccaa tgccaattcg gcgagggggt tcgatgtgat cgataccata 360
aagagtcagg tcgagaaatc ttgcagcgca gtcgtttcct gttctgacat tctagccatt 420
gctgctcgtg attctgttgt tgaactgggc ggcccttcat g 461

<210> SEQ ID NO 376
<211> LENGTH: 179
<212> TYPE: PRT
<213> ORGANISM: Eucalyptus grandis

<400> SEQUENCE: 376

Met Arg Ala Leu Ala Val Val Leu Gly Ser Ala Ile Leu Leu Ala Tyr
1               5                   10                  15

```
Val Ala Ser Ser Ala Gly Ala Leu Ser Leu Asp Tyr Tyr Asp Gln Thr
            20                  25                  30

Cys Pro Lys Leu Glu Phe Ser Val Arg Gly Ala Val Lys Lys Ala Met
        35                  40                  45

Lys Asn Asp Asn Thr Val Pro Ala Ala Leu Leu Arg Met His Phe His
    50                  55                  60

Asp Cys Phe Ile Arg Gly Cys Asp Gly Ser Val Leu Leu Asn Ser Thr
65                  70                  75                  80

Ala Lys Asn Thr Ala Glu Lys Asp Gly Pro Pro Asn Ile Ser Leu His
                85                  90                  95

Ala Phe Tyr Val Ile Asp Leu Ala Lys Glu Ala Val Glu Ala Gln Cys
            100                 105                 110

Pro Gly Val Val Ser Cys Ala Asp Ile Leu Ala Leu Ala Ala Arg Asp
        115                 120                 125

Ala Val Ala Leu Ser Gly Gly Pro His Trp Asp Val Pro Lys Gly Arg
    130                 135                 140

Lys Asp Gly Arg Ile Arg Lys Arg Met Thr Gln Gly Asn Tyr Gln Leu
145                 150                 155                 160

Arg Pro Ser Thr Ser Leu Asn Tyr Ser Lys Leu Leu Ser Arg Gly Leu
                165                 170                 175

Ser Met Glu


<210> SEQ ID NO 377
<211> LENGTH: 115
<212> TYPE: PRT
<213> ORGANISM: Eucalyptus grandis

<400> SEQUENCE: 377

Met Phe Leu Lys Tyr Leu Ser Ala Ala Leu Ile Ser Leu Ala Thr Ile
1               5                   10                  15

Arg Ser Ala Tyr Gly Ala Ser Thr Pro Lys Arg Arg Ala Thr Cys Ala
            20                  25                  30

Gly Gly Gln Thr Val Lys Asn Glu Ala Cys Cys Ala Trp Phe Pro Val
        35                  40                  45

Leu Glu Asp Ile Leu Pro Asn Met Phe Asp Asn Glu Cys Gly Asp Asp
    50                  55                  60

Ala His Gly Ala Leu Arg Leu Ser Phe His Asp Ala Ile Gly Phe Ser
65                  70                  75                  80

Pro Ser Gln Gly Gly Gly Gly Ala Asp Gly Ser Ile Leu Ser Ser Val
                85                  90                  95

Thr Pro Asn Cys Ser Ser Pro Arg Thr Leu Ala Ser Thr Thr Arg Ser
            100                 105                 110

Thr Leu Ser
        115


<210> SEQ ID NO 378
<211> LENGTH: 315
<212> TYPE: PRT
<213> ORGANISM: Eucalyptus grandis

<400> SEQUENCE: 378

Met Val Gly Phe Ser Val Val Val Val Leu Leu Ala Thr Ser Val Ile
1               5                   10                  15

Thr Thr Ala Arg Cys Lys Leu Ser Pro Ser His Tyr Gln Ser Thr Cys
            20                  25                  30

Pro Lys Ala Leu Ser Ile Val Arg Ala Gly Val Ala Lys Ala Ile Lys
        35                  40                  45
```

```
Asn Glu Thr Arg Thr Gly Ala Ser Leu Leu Arg Leu His Phe His Asp
    50                  55                  60

Cys Phe Val Asn Gly Cys Asp Ala Ser Ile Leu Leu Asp Asp Thr Pro
65                  70                  75                  80

Ser Phe Val Gly Glu Lys Thr Ala Ala Pro Asn Asn Asn Ser Val Arg
                85                  90                  95

Gly Phe Glu Val Ile Asp Arg Ile Lys Ala Ser Leu Glu Lys Glu Cys
            100                 105                 110

Pro Gly Val Val Ser Cys Ala Asp Ile Val Ala Leu Ala Ala Arg Asp
        115                 120                 125

Ser Val Val His Leu Gly Gly Pro Ser Trp Thr Val Ser Leu Gly Arg
    130                 135                 140

Lys Asp Ser Ile Thr Ala Ser Arg Ser Leu Ala Asn Thr Ser Ile Pro
145                 150                 155                 160

Pro Pro Thr Ser Asn Leu Ser Ala Leu Ile Thr Ser Phe Ala Ala Gln
                165                 170                 175

Gly Leu Ser Val Lys Asn Met Val Ala Leu Ser Gly Ser His Thr Ile
            180                 185                 190

Gly Leu Ala Arg Cys Thr Ser Phe Arg Arg Arg Ile Tyr Asn Asp Ser
        195                 200                 205

Asn Ile Asp Thr Ser Phe Ala His Lys Leu Gln Lys Ile Cys Pro Arg
    210                 215                 220

Ile Gly Asn Asp Ser Val Leu Gln Arg Leu Asp Ile Gln Thr Pro Thr
225                 230                 235                 240

Phe Phe Asp Asn Leu Tyr Tyr His Asn Leu Leu Gln Lys Lys Gly Leu
                245                 250                 255

Leu His Ser Asp Gln Glu Leu Phe Asn Gly Ser Ser Val Asp Ser Leu
            260                 265                 270

Val Lys Lys Tyr Ala Cys Asp Thr Gly Lys Phe Phe Arg Asp Phe Ala
        275                 280                 285

Lys Ala Met Ile Lys Met Ser Glu Ile Lys Pro Pro Lys Gly Ser Asn
    290                 295                 300

Gly Gln Ile Arg Lys Asn Cys Arg Lys Val Asn
305                 310                 315
```

<210> SEQ ID NO 379
<211> LENGTH: 111
<212> TYPE: PRT
<213> ORGANISM: Eucalyptus grandis

<400> SEQUENCE: 379

```
Met Pro Ser Arg His Pro Ile Trp Val Ile Val Ala Ile Ala Phe Val
1               5                   10                  15

Thr Ala Leu Gly Trp Gly Ser Ala Ser Ala Gln Leu Ser Thr Asn Phe
            20                  25                  30

Tyr Ser Lys Ser Cys Pro Asn Val Leu Ser Thr Val Lys Ser Val Val
        35                  40                  45

Arg Ser Ala Val Ser Lys Glu Arg Arg Met Gly Ala Ser Leu Leu Arg
    50                  55                  60

Leu Phe Phe His Asp Cys Phe Val Asn Gly Cys Asp Gly Ser Ile Leu
65                  70                  75                  80

Leu Asp Asp Thr Ser Ser Phe Gln Gly Glu Lys Thr Ala Gly Pro Asn
                85                  90                  95

Asn Lys Ser Leu Arg Gly Tyr Asn Val Ile Asp Arg Ile Lys Ser
            100                 105                 110
```

<210> SEQ ID NO 380
<211> LENGTH: 116
<212> TYPE: PRT
<213> ORGANISM: Eucalyptus grandis

<400> SEQUENCE: 380

```
Met Gln Phe Thr Phe Ser Ala Ala Phe Leu Ala Leu Val Thr Val Ala
1               5                   10                  15

Ala Ala Met Pro Thr Lys Arg Ala Ala Cys Ser Asn Gly Arg Thr Ala
            20                  25                  30

Thr His Ala Ser Cys Cys Val Trp Phe Asp Val Leu Asp Asp Ile Gln
        35                  40                  45

Glu Asn Leu Phe Asp Gly Gly Glu Cys Gly Glu Glu Thr His Glu Ser
    50                  55                  60

Leu Arg Leu Thr Phe His Asp Ala Ile Gly Phe Ser Pro Ser Leu Phe
65                  70                  75                  80

Leu Glu Gly Lys Phe Gly Gly Leu Gly Ala Asp Gly Ser Ile Met Ala
                85                  90                  95

His Ser Asp Ile Glu Thr Val Phe Pro Ala Asn Asn Gly Ile Asp Asp
            100                 105                 110

Ile Val Asp Ala
        115
```

<210> SEQ ID NO 381
<211> LENGTH: 308
<212> TYPE: PRT
<213> ORGANISM: Eucalyptus grandis

<400> SEQUENCE: 381

```
Met Ala Ser Arg Phe Ser Ser Phe Val Leu Val Ser Phe Leu Val Ile
1               5                   10                  15

Ala Ala Ser His Val His Val Thr Ser Ser Ala His Leu Val Lys Gly
            20                  25                  30

Leu Ser Trp Ser Phe Tyr Glu Lys Ser Cys Pro Lys Val Glu Ser Val
        35                  40                  45

Ile Lys Lys His Leu Lys Lys Val Phe Glu Glu Asp Ile Gly Gln Ala
    50                  55                  60

Ala Gly Leu Leu Arg Leu His Phe His Asp Cys Phe Val Lys Gly Cys
65                  70                  75                  80

Asp Ala Ser Val Leu Leu Asp Gly Ser Ala Ser Gly Pro Ser Glu Gln
                85                  90                  95

Asp Ala Pro Pro Asn Arg Ser Leu Arg Pro Ser Ala Phe Lys Ile Ile
            100                 105                 110

Asp Asp Leu Arg Glu Leu Val Asp Lys Lys Cys Gly Arg Val Val Ser
        115                 120                 125

Cys Ala Asp Ile Ala Ala Ile Ala Ala Arg Asp Ser Val Val Leu Ser
    130                 135                 140

Gly Gly Pro Glu Tyr Asp Val Pro Leu Gly Arg Arg Asp Gly Leu Thr
145                 150                 155                 160

Phe Ala Thr Gln Asn Val Thr Leu Glu Asn Leu Pro Ala Pro Thr Glu
                165                 170                 175

Asn Ala Ser Ala Ile Leu Ser Ala Leu Ala Lys Lys Asn Leu Asp Ala
            180                 185                 190

Thr Asp Val Val Ala Leu Ser Gly Gly His Thr Ile Gly Leu Gly His
        195                 200                 205
```

```
Cys Thr Ser Phe Glu Asn Arg Leu Tyr Pro Thr Gln Asp Pro Thr Met
    210                 215                 220

Glu Lys Thr Phe Ala His Asp Leu Lys Gly Val Cys Pro Thr Thr Asn
225                 230                 235                 240

Ser Thr Asn Thr Thr Val Leu Asp Ile Arg Ser Pro Asn Arg Phe Asp
                245                 250                 255

Asn Lys Tyr Phe Val Asp Leu Val Asn Arg Gln Gly Leu Phe Thr Ser
            260                 265                 270

Asp Gln Asp Leu Tyr Glu Asp Pro Thr Thr Arg Asp Ile Val Thr Ser
        275                 280                 285

Phe Ala Glu Asp Gln Glu Leu Phe Phe Glu Lys Phe Val Leu Ala Met
    290                 295                 300

Thr Lys Met Gly
305


<210> SEQ ID NO 382
<211> LENGTH: 98
<212> TYPE: PRT
<213> ORGANISM: Eucalyptus grandis

<400> SEQUENCE: 382

Met Phe Leu Lys Tyr Leu Ser Gly Ala Leu Val Ser Leu Ala Thr Ile
1               5                   10                  15

Arg Gly Val Cys Gly Ala Ser Ala Pro Met Arg Arg Ala Thr Cys Ala
            20                  25                  30

Gly Gly Gln Thr Val Lys Asn Ala Ala Cys Cys Ala Trp Phe Pro Val
        35                  40                  45

Leu Asp Asp Ile Arg Glu Asn Phe Phe Asp Asn Glu Cys Gly Asp Asp
    50                  55                  60

Ala His Ala Ala Leu Arg Leu Ser Phe His Asp Ala Ile Gly Phe Ser
65                  70                  75                  80

Arg Ser Lys Gly Gly Gly Gly Ala Asp Gly Ser Ile Ile Ala Phe Asn
                85                  90                  95

Lys Thr


<210> SEQ ID NO 383
<211> LENGTH: 119
<212> TYPE: PRT
<213> ORGANISM: Eucalyptus grandis

<400> SEQUENCE: 383

Met Ala Phe Lys Leu Val Val Asn Leu Val Ser Leu Ala Leu Ala Val
1               5                   10                  15

Ser Ala Ala Asn Phe Lys Arg Val Ala Cys Pro Gly Thr Thr Ala Thr
            20                  25                  30

Ala Arg Asn Pro Ala Cys Cys Ala Phe Phe Ser Leu Arg Asp Asp Leu
        35                  40                  45

Leu Thr Asn Leu Phe Gly Gly Val Cys Gly Glu Glu Ala His Glu Ser
    50                  55                  60

Leu Arg Leu Ser Phe His Asp Ala Ile Ala Phe Ser Pro Ala Leu Ile
65                  70                  75                  80

Arg Gln Gly Lys Pro Gly Gly Gly Gly Ala Asp Gly Ser Met Ile Thr
                85                  90                  95

Phe Pro Asn Val Glu Pro Asn Phe Asn Ala Asn Asn Gly Ile Ile Asp
            100                 105                 110

Ser Val Asp Phe Leu Thr Pro
        115
```

<210> SEQ ID NO 384
<211> LENGTH: 138
<212> TYPE: PRT
<213> ORGANISM: Eucalyptus grandis

<400> SEQUENCE: 384

```
Ser Cys Pro Gly Thr Val Ser Cys Ala Asp Ile Leu Ala Leu Gly Ala
1               5                   10                  15

Gln Ala Ser Val Val Leu Ser Gly Gly Pro Ser Trp Arg Val Leu Ser
            20                  25                  30

Gly Arg Arg Asp Ser Leu Thr Ala Asn Gln Ala Gly Ala Asn Thr Ser
        35                  40                  45

Ile Pro Ser Pro Phe Asp Ser Leu Ala Asn Leu Thr Ser Lys Phe Ala
    50                  55                  60

Ala Val Gly Leu Asp Thr Asn Asp Leu Val Thr Leu Ser Gly Ala His
65                  70                  75                  80

Thr Phe Gly Arg Ala Gln Cys Arg Thr Phe Ser Pro Arg Leu Tyr Asn
                85                  90                  95

Phe Asn Ala Ser Gly Ser Pro Asp Pro Thr Ile Ser Pro Ser Tyr Leu
            100                 105                 110

Thr Thr Leu Gln Gln Leu Cys Pro Gln Asn Gly Ser Gly Ser Val Leu
        115                 120                 125

Ala Asn Leu Asp Pro Thr Thr Val Asn Thr
    130                 135
```

<210> SEQ ID NO 385
<211> LENGTH: 208
<212> TYPE: PRT
<213> ORGANISM: Pinus radiata

<400> SEQUENCE: 385

```
Met Lys His Ile Pro Gly Leu Thr Leu Gln Phe Gln Ser Val Leu Ile
1               5                   10                  15

Thr Gly Ala Ala Leu Phe Leu Trp Ile Gln Thr Ser Asp Ala Gln Asp
            20                  25                  30

Cys Asn Gly Leu Ser His His Tyr Tyr Gln Lys Ser Cys Pro Asn Ala
        35                  40                  45

Gln Ala Ile Ile Lys Ser Val Val Ser Asp Ala Val Lys Lys Glu Ala
    50                  55                  60

Arg Met Ala Ala Ser Leu Leu Arg Leu His Phe His Asp Cys Phe Val
65                  70                  75                  80

Gln Gly Cys Asp Ala Ser Ile Leu Leu Asp Asp Thr Ala Ser Phe Thr
                85                  90                  95

Gly Glu Lys Thr Ala Leu Pro Asn Arg Asn Ser Val Arg Gly Phe Glu
            100                 105                 110

Val Val Asp Lys Ile Lys Ser Lys Leu Glu Glu Ala Cys Pro Gly Val
        115                 120                 125

Val Ser Cys Ala Asp Ile Leu Ala Val Ala Ala Arg Asp Ser Val Gly
    130                 135                 140

Phe Ser Val Gly Pro Tyr Trp Glu Val Leu Leu Gly Arg Arg Asp Ser
145                 150                 155                 160

Lys Thr Ala Ser Lys Ser Gly Ala Asn Asn Asp Ile Pro Ala Pro Asn
                165                 170                 175

Ser Thr His Gln Thr Leu Glu Thr Lys Phe Asn Leu Lys Gly Leu Asn
            180                 185                 190
```

Val Leu Asp Leu Val Ala Leu Ser Arg Ser His Asn Asn Arg Val Ser
195 200 205

<210> SEQ ID NO 386
<211> LENGTH: 202
<212> TYPE: PRT
<213> ORGANISM: Pinus radiata

<400> SEQUENCE: 386

Met Ala Thr Leu Gly Ile Pro Leu Gly Ser Leu Ser Leu Leu Leu Leu
1 5 10 15

Phe Phe Cys Cys Ala Gln Arg Ser Val Gly Leu Lys Glu Asn Tyr Tyr
20 25 30

Ala Thr Ser Cys Pro Arg Ala Glu His Ile Val Lys Glu Gln Val Tyr
35 40 45

Asn Leu Tyr Gln Glu His Gly Asn Thr Ala Val Ser Trp Ile Arg Leu
50 55 60

Ile Phe His Asp Cys Ile Val Gln Ser Cys Asp Ala Ser Ile Leu Leu
65 70 75 80

Asp Ser Ser Gly Asp Val Gln Thr Glu Lys Gln Ser Asp Arg Asn Phe
85 90 95

Gly Met Arg Asn Phe Lys Tyr Val Asp Thr Ile Lys Glu Ala Ile Glu
100 105 110

Val Glu Cys Pro Gly Val Val Ser Cys Ala Asp Ile Ile Val Leu Ala
115 120 125

Ala Lys Glu Ala Ala Ala Met Leu Gly Gly Pro Arg Ile Ala Val Lys
130 135 140

Thr Gly Arg Arg Asp Ser Arg Lys Ser Ser Ala Ala Val Val Asp Lys
145 150 155 160

Tyr Val Pro Leu His Asn Gly Ser Ile Ser Ser Leu Leu Ser Ala Phe
165 170 175

Ala Ser Val Gly Ile Asp Ala Glu Gly Ala Val Ala Leu Leu Gly Leu
180 185 190

Ile Leu Ile His Ser Val Leu His Tyr Thr
195 200

<210> SEQ ID NO 387
<211> LENGTH: 287
<212> TYPE: PRT
<213> ORGANISM: Pinus radiata

<400> SEQUENCE: 387

Met Lys Ser Phe Pro Cys Ile Ala Val Ile Val Phe Ile Ile Cys Ser
1 5 10 15

Ile Thr Asp Thr Val Asn Gly Lys Leu Ser Ser Thr Phe Tyr Asp Lys
20 25 30

Ser Cys Pro Lys Ala Leu Ser Ile Val Gln Ala Gly Val Lys Gln Ala
35 40 45

Val Ala Lys Glu Lys Arg Met Gly Ala Ser Leu Leu Arg Leu His Phe
50 55 60

His Asp Cys Phe Val Asn Gly Cys Asp Gly Ser Val Leu Leu Asp Asn
65 70 75 80

Ser Thr Thr Phe Thr Ser Glu Lys Tyr Ala Leu Pro Asn Asn Asn Ser
85 90 95

Ala Arg Gly Phe Glu Val Ile Asp Ser Ile Lys Ser Gln Leu Glu Asn
100 105 110

Ala Cys Thr Gly Val Val Ser Cys Ala Asp Ile Leu Thr Ile Ala Ala

```
        115                 120                 125

Arg Asp Ser Val Val Gln Leu Gly Gly Pro Ser Trp Lys Val Met Leu
    130                 135                 140

Gly Arg Arg Asp Ser Thr Thr Ala Ser Ile Ser Gly Ala Asn Asn Asn
145                 150                 155                 160

Ile Pro Pro Pro Thr Ser Asn Leu Thr Lys Leu Ile Ser Leu Phe Gln
                165                 170                 175

Ala Gln Gly Leu Ser Thr Lys Glu Met Val Ala Leu Ser Gly Gly His
            180                 185                 190

Thr Ile Gly Gln Ala Gln Cys Lys Asn Phe Arg Ala His Ile Tyr Asn
        195                 200                 205

Asp Thr Asn Ile Asp Thr Thr Tyr Ala Thr Ser Leu Arg Ser Lys Cys
    210                 215                 220

Pro Ser Thr Thr Gly Ser Gly Asp Ser Asn Leu Ser Pro Leu Asp Tyr
225                 230                 235                 240

Thr Thr Pro Thr Val Phe Asp Lys Asn Tyr Tyr Tyr Asn Leu Lys Ser
                245                 250                 255

Lys Arg Gly Leu Leu His Ser Asp Gln Glu Leu Phe Asn Gly Gly Ser
            260                 265                 270

Thr Asp Ser His Val Thr Lys Tyr Ala Ser Asn Gln Asn Thr Phe
        275                 280                 285


<210> SEQ ID NO 388
<211> LENGTH: 161
<212> TYPE: PRT
<213> ORGANISM: Pinus radiata

<400> SEQUENCE: 388

Ala Asn Ser Asn Leu Pro Ser Pro Ala Ser Ser Leu Ser Thr Leu Met
1               5                   10                  15

Thr Ala Phe Gln Lys Gln Gly Leu Ser Thr Lys Asp Leu Val Ala Leu
            20                  25                  30

Ser Gly Ala His Thr Ile Gly Gln Ala Arg Cys Thr Thr Phe Arg Thr
        35                  40                  45

Arg Ile Tyr Asn Asp Thr Asn Ile Asn Ala Ala Phe Ala Thr Ser Ala
    50                  55                  60

Lys Ala Asn Cys Pro Ser Thr Gly Gly Asp Asn Thr Leu Ser Pro Leu
65                  70                  75                  80

Asp Val Leu Thr Pro Thr Thr Phe Asp Asn Lys Tyr Tyr Thr Asn Leu
                85                  90                  95

Lys Ser Gln Lys Gly Leu Phe His Ser Asp Gln Glu Leu Phe Asn Gly
            100                 105                 110

Gly Ser Thr Asp Ser Arg Val Ser Ile Tyr Ser Thr Ser Gln Ala Ile
        115                 120                 125

Phe Phe Thr Asp Phe Ala Ala Ala Met Val Asn Met Gly Asn Ile Ser
    130                 135                 140

Pro Leu Thr Gly Thr Asn Gly Glu Ile Arg Thr Asn Cys Arg Lys Val
145                 150                 155                 160

Asn


<210> SEQ ID NO 389
<211> LENGTH: 318
<212> TYPE: PRT
<213> ORGANISM: Pinus radiata

<400> SEQUENCE: 389
```

Met Arg Thr Leu Val Cys Ile Gly Leu Met Ala Val Phe Val Ala Phe
1 5 10 15

Ile His Ile Asn Ala Val Asn Gly Gln Leu Ser Ser Thr Phe Tyr Ala
20 25 30

Lys Ser Cys Pro Arg Leu Pro Ser Ile Val Lys Ser Val Val Lys Gln
35 40 45

Ala Val Ala Lys Glu Lys Arg Met Gly Ala Ser Leu Val Arg Leu His
50 55 60

Phe His Asp Cys Phe Val Asn Gly Cys Asp Gly Ser Ile Leu Leu Asp
65 70 75 80

Asp Asn Ala Thr Phe Thr Gly Glu Lys Thr Ala Gly Pro Asn Ala Asn
85 90 95

Ser Ala Arg Gly Phe Glu Val Ile Asp Ser Ile Lys Thr Gln Val Glu
100 105 110

Ala Ala Cys Ser Gly Val Val Ser Cys Ala Asp Ile Leu Thr Ile Ala
115 120 125

Ala Arg Asp Ser Ile Val Glu Leu Gln Gly Pro Thr Trp Thr Val Met
130 135 140

Leu Gly Arg Arg Asp Ser Thr Thr Ala Ser Leu Ser Ala Ala Asn Asn
145 150 155 160

Asn Ile Pro Ser Pro Ala Ser Ser Leu Ser Thr Leu Ile Ser Ser Phe
165 170 175

Gln Ala His Gly Leu Ser Thr Lys Asp Leu Val Ala Leu Ser Gly Ala
180 185 190

His Thr Ile Gly Gln Ser Arg Cys Ala Phe Phe Arg Thr Arg Ile Tyr
195 200 205

Asn Glu Thr Asn Ile Asn Ala Ala Phe Ala Thr Ser Val Lys Ala Asn
210 215 220

Cys Pro Ser Ala Gly Gly Asp Ser Asn Leu Ser Pro Leu Asp Ala Val
225 230 235 240

Thr Ser Ile Thr Phe Asp Asn Lys Tyr Tyr Ser Asn Leu Lys Ile Gln
245 250 255

Lys Gly Leu Leu His Ser Asp Gln Gln Leu Phe Asn Gly Gly Ser Thr
260 265 270

Asp Ser Gln Val Thr Ala Tyr Ser Ser Asn Gln Asn Ser Phe Phe Ile
275 280 285

Asp Phe Thr Ala Ala Met Val Lys Met Gly Asn Ile Ser Pro Leu Thr
290 295 300

Gly Thr Asn Gly Gln Ile Arg Lys Asn Cys Arg Lys Ser Asn
305 310 315

<210> SEQ ID NO 390
<211> LENGTH: 95
<212> TYPE: PRT
<213> ORGANISM: Pinus radiata

<400> SEQUENCE: 390

Lys Leu Pro Lys Ser Gly Gly Asp Asn Asn Leu Ser Pro Leu Asp Leu
1 5 10 15

Leu Thr Pro Thr Thr Phe Asp Asn Lys Tyr Tyr Thr Asn Leu Lys Ser
20 25 30

Gln Lys Gly Leu Leu His Ser Asp Gln Gln Leu Phe Asn Gly Gly Ser
35 40 45

Ala Asp Ser Gln Val Thr Thr Tyr Ser Thr Thr Gln Ser Thr Phe Phe
50 55 60

Thr Asp Phe Ala Ala Ser Met Leu Asn Met Gly Asn Ile Ser Pro Leu
65 70 75 80

Thr Gly Thr Ser Gly Gln Ile Arg Lys Asn Cys Arg Lys Pro Asn
85 90 95

<210> SEQ ID NO 391
<211> LENGTH: 201
<212> TYPE: PRT
<213> ORGANISM: Pinus radiata

<400> SEQUENCE: 391

Met Thr Ser Phe Thr Ala Met Ala Ser Val Val Cys Ile Ala Leu Leu
1 5 10 15

Phe Phe Ser Thr Val Ala Phe Ala Gln Leu Asn Ser Thr Tyr Tyr Asp
20 25 30

Thr Ser Cys Pro Lys Leu Leu Ala Thr Val Lys Ala Ala Val Lys Thr
35 40 45

Ala Val Ala Asn Glu Lys Arg Met Gly Ala Ser Leu Leu Arg Leu His
50 55 60

Phe His Asp Cys Phe Val Asn Gly Cys Asp Gly Ser Val Leu Leu Asp
65 70 75 80

Asp Ser Ser Ser Leu Thr Gly Glu Lys Thr Ala Leu Pro Asn Asn Asn
85 90 95

Ser Leu Arg Gly Phe Asp Val Ile Asp Thr Ile Lys Ser Gln Val Glu
100 105 110

Ala Val Cys Ser Gly Ile Val Ser Cys Ala Asp Ile Leu Ala Ile Thr
115 120 125

Ala Arg Asp Ser Val Val Glu Leu Gly Gly Pro Thr Trp Thr Val Leu
130 135 140

Leu Gly Arg Arg Asp Ser Ala Thr Ala Ser Leu Ser Ala Ala Asn Thr
145 150 155 160

Asn Ile Pro Ala Pro Thr Ser Asn Leu Ser Gly Leu Ile Ser Ser Phe
165 170 175

Gln Ala Gln Gly Leu Ser Thr Lys Asp Met Ile Val Leu Ser Gly Ala
180 185 190

His Thr Ile Gly Gln Ala Arg Cys Thr
195 200

<210> SEQ ID NO 392
<211> LENGTH: 120
<212> TYPE: PRT
<213> ORGANISM: Pinus radiata

<400> SEQUENCE: 392

Leu Ile Ser Ser Phe Thr Ala His Gly Leu Ser Thr Lys Asp Leu Gly
1 5 10 15

Ala Leu Ser Gly Ala His Thr Ile Gly Gln Ala Arg Cys Thr Thr Phe
20 25 30

Arg Ala Arg Val Tyr Asn Glu Ser Asn Ile Asp Thr Ser Phe Ala Thr
35 40 45

Ser Val Lys Ala Asn Trp Pro Ser Ala Gly Gly Asp Asn Thr Leu Ser
50 55 60

Pro Leu Asp Leu Ala Thr Pro Thr Thr Phe Asp Asn Lys Tyr Tyr Thr
65 70 75 80

Asp Leu Arg Ser Gln Lys Gly Leu Leu His Ser Asp Gln Gln Met Phe
85 90 95

Ser Gly Gly Ser Thr Asn Ser Gln Val Thr Thr Tyr Ser Ser Asn Gln

```
            100                 105                 110

Lys His Leu Leu Tyr Arg Leu Tyr
        115                 120


<210> SEQ ID NO 393
<211> LENGTH: 120
<212> TYPE: PRT
<213> ORGANISM: Pinus radiata

<400> SEQUENCE: 393

Lys Arg Ile Asn Phe His Leu Lys Glu Asp Ile Thr Gln Ala Ala Gly
1               5                   10                  15

Leu Leu Arg Val His Phe His Asp Cys Phe Val Gln Gly Cys Asp Gly
            20                  25                  30

Ser Val Leu Leu Asp Gly Ser Ala Ser Gly Pro Ser Glu Gln Asp Ala
        35                  40                  45

Pro Pro Asn Leu Thr Leu Arg Ala Lys Ala Phe Glu Ile Ile Asn Asp
    50                  55                  60

Ile Lys Lys His Val Glu Lys Ala Cys Ser Gly Val Val Ser Cys Ala
65                  70                  75                  80

Asp Leu Thr Ala Leu Ala Ala Arg Glu Ser Val Arg Ala Val Gly Gly
                85                  90                  95

Pro Glu Tyr Arg Val Pro Leu Gly Arg Arg Asp Ser Leu Lys Phe Ala
            100                 105                 110

Thr Arg Lys Val Thr Leu Ala Asn
        115                 120


<210> SEQ ID NO 394
<211> LENGTH: 266
<212> TYPE: PRT
<213> ORGANISM: Pinus radiata

<400> SEQUENCE: 394

Met Ala Ser Phe Thr Ala Met Arg Ser Leu Ala Phe Ile Ala Leu Leu
1               5                   10                  15

Met Cys Ser Thr Val Ala Tyr Ala Gln Leu Ser Ala Thr Phe Tyr Asn
            20                  25                  30

Thr Ser Cys Pro Lys Leu Leu Ser Thr Val Gln Ala Ala Val Lys Gln
        35                  40                  45

Ala Val Ala Asn Glu Lys Arg Met Gly Ala Ser Leu Leu Arg Leu His
    50                  55                  60

Phe His Asp Cys Phe Val Asn Gly Cys Asp Gly Ser Val Leu Leu Asp
65                  70                  75                  80

Asp Ser Ser Thr Leu Thr Gly Glu Lys Thr Ala Val Pro Asn Asn Asn
                85                  90                  95

Ser Ala Arg Gly Phe Asp Val Ile Asp Thr Ile Lys Ser Gln Val Glu
            100                 105                 110

Ala Val Cys Ser Gly Val Val Ser Cys Ala Asp Ile Leu Ala Ile Ala
        115                 120                 125

Ala Arg Asp Ser Val Val Gln Leu Gly Gly Pro Thr Trp Thr Val Gln
    130                 135                 140

Leu Gly Arg Arg Asp Ser Arg Thr Ala Ser Leu Ser Gly Ala Asn Asn
145                 150                 155                 160

Asn Ile Pro Ala Pro Thr Ser Asn Leu Ser Ala Leu Ile Ser Leu Phe
                165                 170                 175

Gln Ala Gln Gly Leu Ser Thr Lys Asp Met Val Val Leu Ser Gly Ala
            180                 185                 190
```

```
His Thr Ile Gly Gln Ala Arg Cys Thr Ser Phe Arg Ala Arg Ile Tyr
        195                 200                 205

Asn Glu Ser Asn Ile Asn Ala Ala Tyr Ala Thr Ser Leu Lys Thr Asn
    210                 215                 220

Cys Pro Thr Thr Gly Ser Asp Asn Asn Leu Ser Pro Leu Asp Arg Val
225                 230                 235                 240

Thr Pro Thr Thr Phe Asp Ile Asn Tyr Tyr Ser Asn Leu Arg Ser Gln
                245                 250                 255

Lys Gly Leu Leu His Ser Asp Gln Gln Leu
            260                 265


<210> SEQ ID NO 395
<211> LENGTH: 323
<212> TYPE: PRT
<213> ORGANISM: Pinus radiata

<400> SEQUENCE: 395

Met Ala Tyr Leu Arg Lys Ser Phe Ala Cys Ile Ala Val Met Val Phe
1               5                   10                  15

Ile Val Cys Ser Ile Thr Asp Thr Val Asn Gly Gln Leu Ser Ser Thr
            20                  25                  30

Phe Tyr Asp Lys Ser Cys Pro Thr Ala Leu Ser Val Val Lys Ala Ala
        35                  40                  45

Val Lys Gln Ala Val Ala Asn Glu Lys Arg Met Gly Ala Ser Leu Leu
    50                  55                  60

Arg Leu His Phe His Asp Cys Phe Val Asn Gly Cys Asp Gly Ser Val
65                  70                  75                  80

Leu Leu Asp Asp Ser Ser Thr Ile Thr Gly Glu Lys Thr Ala Asn Pro
                85                  90                  95

Asn Ala Asn Ser Ala Arg Gly Phe Asp Val Ile Asp Thr Ile Lys Ser
            100                 105                 110

Asn Val Glu Lys Ala Cys Ser Gly Val Val Ser Cys Ala Asp Ile Leu
        115                 120                 125

Ala Ile Ala Ala Arg Asp Ser Val Val Glu Leu Gly Gly Pro Ser Trp
    130                 135                 140

Thr Val Met Leu Gly Arg Arg Asp Ser Thr Thr Ala Ser Lys Ser Gly
145                 150                 155                 160

Ala Asn Ser Asn Ile Pro Pro Pro Thr Ser Ser Leu Ser Asn Leu Ile
                165                 170                 175

Ser Leu Phe Gln Ala Gln Gly Leu Ser Ala Lys Glu Met Val Ala Leu
            180                 185                 190

Ser Gly Gly His Thr Ile Gly Gln Ala Gln Cys Lys Asn Phe Arg Ala
        195                 200                 205

His Ile Tyr Asn Glu Thr Asn Ile Asp Ser Ala Tyr Ala Thr Ser Leu
    210                 215                 220

Arg Ser Lys Cys Pro Ser Thr Thr Gly Ser Gly Asp Ser Asn Leu Ser
225                 230                 235                 240

Pro Leu Asp Tyr Met Thr Pro Thr Val Phe Asp Lys Asn Tyr Tyr Ser
                245                 250                 255

Asp Leu Lys Ser Gln Lys Gly Leu Leu His Ser Asp Gln Glu Leu Phe
            260                 265                 270

Asn Gly Gly Ser Thr Asp Ser Gln Val Thr Thr Tyr Ala Ser Asn Gln
        275                 280                 285

Asn Thr Phe Phe Ser Asp Phe Ala Ala Ala Met Val Lys Met Gly Asn
    290                 295                 300
```

Ile Lys Pro Leu Thr Gly Thr Ser Gly Gln Ile Pro Lys Asn Cys Arg
305 310 315 320

Lys Pro Asn

<210> SEQ ID NO 396
<211> LENGTH: 223
<212> TYPE: PRT
<213> ORGANISM: Pinus radiata

<400> SEQUENCE: 396

Gln Ile Lys Ser Ala Leu Glu Lys Glu Cys Pro Lys Thr Val Ser Cys
1 5 10 15

Ala Asp Ile Leu Ala Ile Ala Ser Arg Asp Ser Val Val Leu Ser Gly
20 25 30

Gly Leu Gly Trp Glu Val Leu Leu Gly Arg Arg Asp Ser Lys Ser Ala
35 40 45

Ser Leu Ser Gly Ser Asn Asn Asn Ile Pro Ala Pro Asn Ser Thr Leu
50 55 60

Gln Thr Leu Thr Thr Lys Phe Lys Leu Gln Gly Leu Asp Glu Val Asp
65 70 75 80

Leu Val Ser Leu Ser Gly Ser His Thr Ile Gly Leu Ser Arg Cys Thr
85 90 95

Ser Phe Arg Gln Arg Leu Tyr Asn Gln Ser Gly Asn Gly Leu Pro Asp
100 105 110

Phe Thr Leu Asn Arg Gly Tyr Tyr Ala Arg Leu Lys Ser Gly Cys Pro
115 120 125

Lys Ser Gly Gly Asp Asn Asn Leu Phe Pro Leu Asp Phe Val Thr Pro
130 135 140

Thr Lys Phe Asp Asn Tyr Tyr Phe Lys Ser Leu Leu Ser Gly Gln Gly
145 150 155 160

Leu Leu Asn Thr Asp Glu Glu Leu Phe Ala Lys Gly Ser Gly Lys Thr
165 170 175

Lys Glu Leu Val Lys Leu Tyr Ala Ala Asn Glu Glu Leu Phe Leu Lys
180 185 190

Gln Phe Ala Leu Ser Met Val Lys Met Gly Asn Ile Lys Pro Leu Thr
195 200 205

Gly Thr Val Gly Glu Ile Arg Val Asn Cys Arg Lys Val Asn Ser
210 215 220

<210> SEQ ID NO 397
<211> LENGTH: 351
<212> TYPE: PRT
<213> ORGANISM: Pinus radiata

<400> SEQUENCE: 397

Met Gly Lys Phe Ile Thr Ala Leu Ala Ser Val Ile Leu Cys Val Phe
1 5 10 15

Val Ile Tyr Gly Gly Ala Val Asn Ala Leu Pro Ser Pro Val Ala Gly
20 25 30

Leu Ser Trp Thr Phe Tyr Ser Ser Ser Cys Pro Ser Leu Glu Ser Ile
35 40 45

Val Trp Glu Arg Met Glu Ala Tyr Leu Ser Ala Asp Ile Thr Gln Ala
50 55 60

Ala Gly Leu Leu Arg Leu His Phe His Asp Cys Phe Val Gln Gly Cys
65 70 75 80

Asp Gly Ser Val Leu Leu Asn Ala Thr Ser Gly Glu Gln Thr Ala Pro

```
                85                  90                  95

Pro Asn Leu Ser Leu Arg Ala Gln Ala Leu Lys Ile Ile Asn Asp Ile
            100                 105                 110

Lys Glu Asn Val Glu Ala Ala Cys Ser Gly Ile Val Ser Cys Ala Asp
        115                 120                 125

Ile Val Thr Leu Ala Ala Arg Asp Ser Val Val Met Ala Gly Gly Pro
    130                 135                 140

Phe Tyr Pro Leu Pro Leu Gly Arg Arg Asp Ser Leu Thr Phe Ala Asn
145                 150                 155                 160

Arg Ser Thr Val Leu Ala Asn Leu Pro Ser Pro Thr Ser Asn Val Thr
                165                 170                 175

Gly Leu Ile Ser Val Leu Gly Pro Lys Gly Leu Asn Phe Thr Asp Leu
            180                 185                 190

Val Ala Leu Ser Gly Gly His Thr Ile Gly Arg Ser Asn Cys Ser Ser
        195                 200                 205

Phe Asp Asn Arg Leu Tyr Asn Ser Thr Thr Gly Thr Gln Met Arg Asp
    210                 215                 220

Pro Thr Met Asp Gln Ser Phe Ala Lys Asn Leu Tyr Leu Thr Cys Pro
225                 230                 235                 240

Thr Ser Thr Thr Val Asn Thr Thr Lys Leu Asp Ile Arg Thr Pro Asn
                245                 250                 255

Val Phe Asp Asn Lys Tyr Tyr Val Asp Leu Leu Asn Arg Gln Thr Leu
            260                 265                 270

Phe Thr Ser Asp Gln Thr Leu Tyr Thr Asp Thr Arg Thr Arg Asp Ile
        275                 280                 285

Val Ile Asn Phe Ala Val Asn Gln Ser Leu Phe Phe Glu Gln Phe Val
    290                 295                 300

Leu Ser Met Leu Lys Met Gly Gln Leu Asp Val Leu Thr Gly Ser Glu
305                 310                 315                 320

Gly Glu Ile Arg Lys Asn Cys Trp Ala Ala Asn Pro Ser Thr Phe Ser
                325                 330                 335

Ile Met Asp Pro Glu Ala Ser Gln Glu Ser Thr Ser Tyr Ser Met
            340                 345                 350


<210> SEQ ID NO 398
<211> LENGTH: 103
<212> TYPE: PRT
<213> ORGANISM: Pinus radiata

<400> SEQUENCE: 398

Leu Asn Phe Ala Leu Ile Phe Cys Val Ser Ser Phe Ser Ser Gln Tyr
1               5                   10                  15

Asp Asp Glu Asp Ser Ser Val His Trp Val Asn Gly Cys Val Cys Ser
            20                  25                  30

Leu His Thr Tyr Lys Arg Leu Asn Gly Gln Leu Ser Ser Thr Phe Tyr
        35                  40                  45

Ala Lys Ser Cys Pro Arg Leu Pro Ser Ile Val Lys Ser Val Val Lys
    50                  55                  60

Gln Ala Val Ala Lys Glu Lys Arg Met Gly Ala Ser Leu Val Arg Leu
65                  70                  75                  80

His Phe His Asp Cys Phe Val Asn Gly Cys Asp Gly Ser Ile Leu Leu
                85                  90                  95

Asp Asp Asn Ala Thr Phe Thr
            100
```

<210> SEQ ID NO 399
<211> LENGTH: 157
<212> TYPE: PRT
<213> ORGANISM: Pinus radiata

<400> SEQUENCE: 399

Ile Asp Ala Ile Lys Thr Ala Leu Glu Ser Ser Cys Asn Ala Thr Val
1               5                   10                  15

Ser Cys Ala Asp Ile Leu Ala Ile Ala Ala Arg Asp Ser Val Tyr Leu
            20                  25                  30

Ser Gly Gly Pro Tyr Trp Gln Val Gln Met Gly Arg Arg Asp Gly Thr
        35                  40                  45

Thr Ala Ser Lys Ser Ala Ala Asn Ala Asp Ile Pro Ser Pro Ile Glu
    50                  55                  60

Ser Leu Gly Ser Leu Ile Ser Gln Phe Gln Gly Val Gly Leu Ser Val
65                  70                  75                  80

His Asp Leu Val Val Leu Ser Gly Ala His Thr Ile Gly Arg Ala His
                85                  90                  95

Cys Gly Thr Phe Ser Ser Arg Leu Phe Asn Phe Ser Gly Ser Asn Ser
            100                 105                 110

Ala Asp Pro Thr Ile His Gln Ser Leu Leu Gln Asp Leu His Ser Leu
        115                 120                 125

Cys Pro Asp Gly Asn Ser Asp Pro Asn Thr Leu Ala Pro Leu Asp Pro
    130                 135                 140

Val Thr Lys Asp Lys Leu His Asn Val Tyr Phe Arg Asn
145                 150                 155

<210> SEQ ID NO 400
<211> LENGTH: 117
<212> TYPE: PRT
<213> ORGANISM: Pinus radiata

<400> SEQUENCE: 400

Leu Ser Val Thr Asp Val Val Ala Leu Ser Gly Gly His Thr Ile Gly
1               5                   10                  15

Arg Ala Arg Cys Thr Val Phe Ser Gly Arg Leu Tyr Asn Phe Ser Gly
            20                  25                  30

Thr Gly Ser Pro Asp Pro Thr Leu Asn Ser Ser Tyr Leu Ser Thr Leu
        35                  40                  45

Gln Ser Thr Cys Pro Gln Asn Gly Ser Ala Asn Thr Leu Thr Ser Leu
    50                  55                  60

Asp Pro Gly Thr Pro Asn Thr Phe Asp Asn Asn Tyr Phe Ala Asn Leu
65                  70                  75                  80

Gln Ile Glu Met Gly Leu Leu Gln Ser Ile Lys Asn Phe Phe Pro His
                85                  90                  95

Arg Glu Gln Ala Pro Ser Leu Leu Ser Met Ile Met Pro Val Val Asn
            100                 105                 110

Pro Ile Ser Ser Ser
        115

<210> SEQ ID NO 401
<211> LENGTH: 143
<212> TYPE: PRT
<213> ORGANISM: Pinus radiata

<400> SEQUENCE: 401

Met Ala Ala Leu Met Lys Ser Ser Ala Cys Ile Ala Val Ile Val Phe
1               5                   10                  15

```
Ile Val Cys Ser Ile Asn Asn Thr Val His Gly Gln Leu Ser Ser Thr
            20                  25                  30

Phe Tyr Asp Lys Ser Cys Pro Thr Val Leu Ser Val Val Lys Ala Gly
        35                  40                  45

Val Lys Gln Ala Val Ala Lys Glu Gln Arg Met Gly Ala Ser Leu Leu
    50                  55                  60

Arg Leu His Phe His Asp Cys Phe Val Asn Gly Cys Asp Gly Ser Val
65                  70                  75                  80

Leu Leu Asp Asp Ser Ser Lys Ile Thr Gly Glu Lys Thr Ala Ile Pro
                85                  90                  95

Asn Ala Asn Ser Ala Arg Gly Phe Asp Val Ile Asp Thr Ile Lys Ser
            100                 105                 110

Gln Val Glu Lys Ser Cys Ser Ala Val Val Ser Cys Ser Asp Ile Leu
        115                 120                 125

Ala Ile Ala Ala Arg Asp Ser Val Val Glu Leu Gly Gly Pro Ser
    130                 135                 140


<210> SEQ ID NO 402
<211> LENGTH: 1474
<212> TYPE: DNA
<213> ORGANISM: Pinus radiata

<400> SEQUENCE: 402

gaattcggca cgagaaaacg tccatagctt ccttgccaac tgcaagcaat acagtacaag     60

agccagacga tcgaatcctg tgaagtggtt ctgaagtgat gggaagcttg gaatctgaaa    120

aaactgttac aggatatgca gctcgggact ccagtggcca cttgtcccct tacacttaca    180

atctcagaaa gaaaggacct gaggatgtaa ttgtaaaggt catttactgc ggaatctgcc    240

actctgattt agttcaaatg cgtaatgaaa tggacatgtc tcattaccca atggtccctg    300

ggcatgaagt ggtggggatt gtaacagaga ttggcagcga ggtgaagaaa ttcaaagtgg    360

gagagcatgt aggggttggt tgcattgttg ggtcctgtcg cagttgcggt aattgcaatc    420

agagcatgga acaatactgc agcaagagga tttggaccta caatgatgtg aaccatgacg    480

gcacacctac tcagggcgga tttgcaagca gtatggtggt tgatcagatg tttgtggttc    540

gaatcccgga gaatcttcct ctggaacaag cggcccctct gttatgtgca ggggttacag    600

ttttcagccc aatgaagcat ttcgccatga cagagcccgg gaagaaatgt gggattttgg    660

gtttaggagg cgtggggcac atgggtgtca agattgccaa agcctttgga ctccacgtga    720

cggttatcag ttcgtctgat aaaaagaaag aagaagccat ggaagtcctc ggcgccgatg    780

cttatcttgt tagcaaggat actgaaaaga tgatggaagc agcagagagc ctagattaca    840

taatggacac cattccagtt gctcatcctc tggaaccata tcttgccctt ctgaagacaa    900

atggaaagct agtgatgctg ggcgttgttc cagagccgtt gcacttcgtg actcctctct    960

taatacttgg gagaaggagc atagctggaa gtttcattgg cagcatggag gaaacacagg   1020

aaactctaga tttctgtgca gagaagaagg tatcatcgat gattgaggtt gtgggcctgg   1080

actacatcaa cacggccatg gaaaggttgg agaagaacga tgtccgttac agatttgtgg   1140

tggatgttgc tagaagcaag ttggataatt agtctgcaat caatcaatca gatcaatgcc   1200

tgcatgcaag atgaatagat ctggactagt agcttaacat gaaagggaaa ttaaattttt   1260

atttaggaac tcgatactgg tttttgttac tttagtttag cttttgtgag gttgaaacaa   1320

ttcagatgtt tttttaactt gtatatgtaa agatcaattt ctcgtgacag taaataataa   1380

tccaatgtct tctgccaaat taatatatgt attcgtattt ttatatgaaa aaaaaaaaaa   1440
```

aaaaaaaaaa aaaaaaaaaa aaaaaaaaaa aaaa 1474

<210> SEQ ID NO 403
<211> LENGTH: 414
<212> TYPE: DNA
<213> ORGANISM: Eucalyptus grandis

<400> SEQUENCE: 403
cacgctcgac gaattcggta ccccgggttc gaaatcgata agcttggatc caaagcaaca 60
cattgaactc tctctctctc tctctctctc tctctctctc tcccccaccc cccctttccca 120 accccaccca catacagaca agtagatacg cgcacacaga agaagaaaag atgggggttt 180
caatgcagtc aatcgcacta gcgacggttc tggccgtcct aacgacatgg gcgtggaggg 240
cggtgaactg ggtgtggctg aggccgaaga ggctcgagag gcttctgaga cagcaaggtc 300
tctccggcaa gtcctacacc ttcctggtcg gcgacctcaa ggagaacctg cggatgctca 360
aggaagccaa gtccaagccc atcgccgtct ccgatgacat caagcctcgt ctct 414

<210> SEQ ID NO 404
<211> LENGTH: 2013
<212> TYPE: DNA
<213> ORGANISM: Eucalyptus grandis

<400> SEQUENCE: 404
agataagttg cgcttaaatc ctctccaaaa gagctaatcc atggatattt tctatttcta 60
ttcccaactc cagtctcttg ttcaaactca actccagcaa tctcccatga ccctcctcct 120
ctccgtcgtc cctcttctcc tcttcctcgg gctcgtggct cggctccggc gcaagccgcc 180
cttcccaccg ggcccgaggg gcctcccggt catcgggaac atgctcatga tgggcgagct 240
cacccaccgc ggcctcgcga gtctggcgaa gaagtatggc gggatcttcc acctccgcat 300
gggcttcctg cacatggttg ccgtgtcgtc ccccgacgtg gcccgccagg tcctccaggt 360
ccacgacggg atcttctcga accggcctgc caccatcgcg atcagctacc tcacgtatga 420
ccgggccgac atggccttcg cgcactacgg cccgttctgg cggcagatgc ggaagctgtg 480
cgtgatgaag ctcttcagcc ggaagcgggc tgagtcgtgg gagtcggtcc gcgatgaggt 540
ggacacgatg gtgcgcaccg tcgcgggcag cgaggggacc gccgtgaaca tcggcgagct 600
cgtgttcgag ctcacgcggg acatcatcta ccgcgcggcc ttcggcacga gctcgaccga 660
gggccaggac gagttcatca gcatactgca ggagttctcg aaattatttg gcgccttcaa 720
catagccgat tttatcccgt acctgagctg gatcgatccg caagggctca ccgccaggct 780
tgtcaaggcg cgccagtcgc tggacgggtt catcgaccac attatagatg atcacatgga 840
caagaagaga aacaagacga gttccggtgg aggcgatcaa gatgtcgata ccgacatggt 900
cgacgatctg ctggccttct acagcgacga agcgaaggtg aacgagtccg acgatttgca 960
gaactcgatc aggctaacga gagacaacat caaggccatc atcatggacg tgatgttcgg 1020
cgggacggag actgtggcgt cggctatcga gtgggccatg gcggagctca tgcgaagccc 1080
cgaggacctg aagaaggtcc agcaagaact cgcggatgtc gtgggcctag accggagagt 1140
cgaggagagc gacttcgaga agctgaccta tctcaagtgc tgcctcaaag agaccctccg 1200
cctccacccg ccgatcccgc tgctcctcca cgagacggca gaggacgccg tgatctccgg 1260
ctaccgcatc cccgcacggt cccgggtcat gatcaatgca tgggccatcg ggcgtgaccc 1320
cggctcgtgg accgaacctg acaagttcaa accgtcccgg ttcctggagt caggcatgcc 1380
cgactacaag gggagcaact tcgagttcat ccctttcggg tcgggccgga ggtcgtgccc 1440
agggatgcag ctcgggctct acgcgctcga catggccgtg gcccacctcc tgcactgctt 1500
cacgtgggaa ctgcccgacg ggatgaagcc gagcgagatg gacatgggcg acgtcttcgg 1560
gctcaccgcg ccgaggtcca cccggctcgt ggcggtgccg actccgaggt tggtgggggc 1620
tctatattga gcaagcaaat ggagggtcgg gttggggggt gcgaggaggg gaacgtattt 1680
ttcagctcct ggagggctgc aagatttgga gtgcataaac ccatccatac aagggcaaaa 1740
gagggtggtg ccaaaatgat ttgcatggat ttttcgattt ttgttttgta ttataaaaaa 1800
ggtcaaataa ccgaagagga caagaaagac aagaaaaaga attgagacgg aacttgaatc 1860
aatgttgttc tgttctctct ttctatttct ttgtggatat tacaagactt atctcatttg 1920
gtgggctttt cttttcttgt gatttctttg atcttgtcat acacaaataa atatggaatg 1980
aagaaacctt tccatcaaaa aaaaaaaaaa aaa 2013

<210> SEQ ID NO 405
<211> LENGTH: 529
<212> TYPE: PRT
<213> ORGANISM: Eucalyptus grandis

<400> SEQUENCE: 405

Met Asp Ile Phe Tyr Phe Tyr Ser Gln Leu Gln Ser Leu Val Gln Thr
1 5 10 15

Gln Leu Gln Gln Ser Pro Met Thr Leu Leu Leu Ser Val Val Pro Leu
20 25 30

Leu Leu Phe Leu Gly Leu Val Ala Arg Leu Arg Arg Lys Pro Pro Phe
35 40 45

Pro Pro Gly Pro Arg Gly Leu Pro Val Ile Gly Asn Met Leu Met Met
50 55 60

Gly Glu Leu Thr His Arg Gly Leu Ala Ser Leu Ala Lys Lys Tyr Gly
65 70 75 80

Gly Ile Phe His Leu Arg Met Gly Phe Leu His Met Val Ala Val Ser
85 90 95

Ser Pro Asp Val Ala Arg Gln Val Leu Gln Val His Asp Gly Ile Phe
100 105 110

Ser Asn Arg Pro Ala Thr Ile Ala Ile Ser Tyr Leu Thr Tyr Asp Arg
115 120 125

Ala Asp Met Ala Phe Ala His Tyr Gly Pro Phe Trp Arg Gln Met Arg
130 135 140

Lys Leu Cys Val Met Lys Leu Phe Ser Arg Lys Arg Ala Glu Ser Trp
145 150 155 160

Glu Ser Val Arg Asp Glu Val Asp Thr Met Val Arg Thr Val Ala Gly
165 170 175

Ser Glu Gly Thr Ala Val Asn Ile Gly Glu Leu Val Phe Glu Leu Thr
180 185 190

Arg Asp Ile Ile Tyr Arg Ala Ala Phe Gly Thr Ser Ser Thr Glu Gly
195 200 205

Gln Asp Glu Phe Ile Ser Ile Leu Gln Glu Phe Ser Lys Leu Phe Gly
210 215 220

Ala Phe Asn Ile Ala Asp Phe Ile Pro Tyr Leu Ser Trp Ile Asp Pro
225 230 235 240

Gln Gly Leu Thr Ala Arg Leu Val Lys Ala Arg Gln Ser Leu Asp Gly
245 250 255

Phe Ile Asp His Ile Ile Asp Asp His Met Asp Lys Lys Arg Asn Lys
260 265 270

Thr Ser Ser Gly Gly Gly Asp Gln Asp Val Asp Thr Asp Met Val Asp

```
        275                 280                 285

Asp Leu Leu Ala Phe Tyr Ser Asp Glu Ala Lys Val Asn Glu Ser Asp
    290                 295                 300

Asp Leu Gln Asn Ser Ile Arg Leu Thr Arg Asp Asn Ile Lys Ala Ile
305                 310                 315                 320

Ile Met Asp Val Met Phe Gly Gly Thr Glu Thr Val Ala Ser Ala Ile
                325                 330                 335

Glu Trp Ala Met Ala Glu Leu Met Arg Ser Pro Glu Asp Leu Lys Lys
            340                 345                 350

Val Gln Gln Glu Leu Ala Asp Val Val Gly Leu Asp Arg Arg Val Glu
        355                 360                 365

Glu Ser Asp Phe Glu Lys Leu Thr Tyr Leu Lys Cys Cys Leu Lys Glu
    370                 375                 380

Thr Leu Arg Leu His Pro Pro Ile Pro Leu Leu Leu His Glu Thr Ala
385                 390                 395                 400

Glu Asp Ala Val Ile Ser Gly Tyr Arg Ile Pro Ala Arg Ser Arg Val
                405                 410                 415

Met Ile Asn Ala Trp Ala Ile Gly Arg Asp Pro Gly Ser Trp Thr Glu
            420                 425                 430

Pro Asp Lys Phe Lys Pro Ser Arg Phe Leu Glu Ser Gly Met Pro Asp
        435                 440                 445

Tyr Lys Gly Ser Asn Phe Glu Phe Ile Pro Phe Gly Ser Gly Arg Arg
    450                 455                 460

Ser Cys Pro Gly Met Gln Leu Gly Leu Tyr Ala Leu Asp Met Ala Val
465                 470                 475                 480

Ala His Leu Leu His Cys Phe Thr Trp Glu Leu Pro Asp Gly Met Lys
                485                 490                 495

Pro Ser Glu Met Asp Met Gly Asp Val Phe Gly Leu Thr Ala Pro Arg
            500                 505                 510

Ser Thr Arg Leu Val Ala Val Pro Thr Pro Arg Leu Val Gly Ala Leu
        515                 520                 525

Tyr

<210> SEQ ID NO 406
<211> LENGTH: 2184
<212> TYPE: DNA
<213> ORGANISM: Pinus radiata

<400> SEQUENCE: 406

gtcgtctgta aattactctg tgagtgttta gtgttttctt ctcttattga tttcagggga     60

caagtaggtg ggggtggggg agcttaagtc aaatctagtg ctttctctgt aagattttcc    120

ctttttttttc ttgctaagag tagccatgat tgaggtacag tcagctcccc ccatggcacg    180

gtccactgag aacgagaata accagcatga tgccgaagaa ggggcggtat tgaatgaggg    240

cggcatggat tttctgtatc ggtcaaagct tccagacata gatattccat accatcttcc    300

attgcactcg tattgcttcg agaaactgga cgagctcaga gagaagccat gtctgataca    360

ggggtcgaac gggaagattt acagctatgg cgaagtggaa ttgatatctc gcaaggtggc    420

ctcgggtttg gccaaattgg gattcaaaaa gggggacgtg gtcatgctgc tgctgcccaa    480

ttgccccgaa tttgtctttg ttttcctagg ggcgtccatg gctggtgcca ttgccaccac    540

ggcgaaccct ttttacactc cctccgatat tgccaaacag cggggcgcat cgggcgctcg    600

gctgattgtc acttacgctg cttgcgtaga aaagctgagg gacctaatgg agaatcatgg    660

ggtccaagtg ataaccatcg acaaccctcc aaagggctgc gaacacattt cacttttgtt    720
```

```
ggacggcgac gagaacgaat actgccctgc agactgtatc gtccagcccg acgacacggt    780

cgcgctgcct tattcatcgg gcacgacggg gctccccaag ggtgtcatgt tgacacacaa    840

ggggctcgtc tctagcgtcg cccaacaagt cgatggagaa aatcccaatc tgtatttgca    900

ttctgaggat gtggtgctct gcgtactgcc tctgtttcat atctactcgc tcaattctgt    960

gctgctctgc tcgctcaggg ccgggtctgc tattctgctc atgcacaagt ttgagatcgg   1020

gagcctgctg gatctggtgc agaggttcaa ggtcacggta gcgcctgtcg tgcctcccat   1080

tgttctcgcc tttgccaaga acgcgctcgt ggaaagctat gatctgtcgt ccattagggt   1140

tgtgctgtcc ggtgccgcgc ctctcggaaa ggagctggag gatgcattga ggctacgact   1200

tcccaaagcc acttttggtc agggatacgg tatgacagag gcaggaccgg tgctatcaat   1260

gtgtctggcc ttcgctaagg agccctttcc gatgaagtcc gggtcgtgtg gaacggttgt   1320

tcggaatgcc cagatgaaga tcattgaccc cgacacgggc acgtgtcttc cctacaacca   1380

acctggagaa atttgcatca gagggcccca gattatgaaa gggtatctga acgatgctga   1440

gtctacagcc agaactatcg atgaagatgg gtggctgcat actggggata ttggttatat   1500

tgatgacgat gaagaagttt tcattgtgga cagagtgaaa gagattatca aatataaggg   1560

ttttcaggta cctccagctg agttagaagc cattctcatc actcatccat ctattgcaga   1620

tgcagcagtt gtacctcaaa aggatgaagt tgcaggagag gttccagtag cctttgtggt   1680

gagatcaaat ggatttgatc ttacagaaga tgaaatcaaa caatttgtgg ctaaacaggt   1740

ggtgttctac aaaaagctgc acaaggtcta tttcatccac gcaattccca agtctccttc   1800

tggaaaaata ctgcgaaagg atttgagggc gaagctctct gcccccacct ccaccgttga   1860

aatcaaagca tgatattctt ttctctaatc gatttgatca cttcaaccag aatttgtggg   1920

catgccatag acgcatgagg gcggccaata cctgtcactc caataatgtc accgctttct   1980

ggactccttt ttcgagatat atttatggat tcctgcttct ctgtaagggt ggcatgatta   2040

ttaagagtaa ttaggataga gagaaagcca ttgaatagtg tgccatattt ctgattcaca   2100

tcgcttcttt catggtctcc tttacagtta gttgtaagtt tctccacctc cattgcgttt   2160

ggttgttacg tggattatgt gttt                                          2184
```

```
<210> SEQ ID NO 407
<211> LENGTH: 575
<212> TYPE: PRT
<213> ORGANISM: Pinus radiata

<400> SEQUENCE: 407

Met Ile Glu Val Gln Ser Ala Pro Pro Met Ala Arg Ser Thr Glu Asn
1               5                   10                  15

Glu Asn Asn Gln His Asp Ala Glu Glu Gly Ala Val Leu Asn Glu Gly
            20                  25                  30

Gly Met Asp Phe Leu Tyr Arg Ser Lys Leu Pro Asp Ile Asp Ile Pro
        35                  40                  45

Tyr His Leu Pro Leu His Ser Tyr Cys Phe Glu Lys Leu Asp Glu Leu
    50                  55                  60

Arg Glu Lys Pro Cys Leu Ile Gln Gly Ser Asn Gly Lys Ile Tyr Ser
65                  70                  75                  80

Tyr Gly Glu Val Glu Leu Ile Ser Arg Lys Val Ala Ser Gly Leu Ala
                85                  90                  95

Lys Leu Gly Phe Lys Lys Gly Asp Val Val Met Leu Leu Leu Pro Asn
            100                 105                 110
```

```
Cys Pro Glu Phe Val Phe Val Phe Leu Gly Ala Ser Met Ala Gly Ala
        115                 120                 125

Ile Ala Thr Thr Ala Asn Pro Phe Tyr Thr Pro Ser Asp Ile Ala Lys
    130                 135                 140

Gln Arg Gly Ala Ser Gly Ala Arg Leu Ile Val Thr Tyr Ala Ala Cys
145                 150                 155                 160

Val Glu Lys Leu Arg Asp Leu Met Glu Asn His Gly Val Gln Val Ile
                165                 170                 175

Thr Ile Asp Asn Pro Pro Lys Gly Cys Glu His Ile Ser Leu Leu Leu
            180                 185                 190

Asp Gly Asp Glu Asn Glu Tyr Cys Pro Ala Asp Cys Ile Val Gln Pro
        195                 200                 205

Asp Asp Thr Val Ala Leu Pro Tyr Ser Ser Gly Thr Thr Gly Leu Pro
    210                 215                 220

Lys Gly Val Met Leu Thr His Lys Gly Leu Val Ser Ser Val Ala Gln
225                 230                 235                 240

Gln Val Asp Gly Glu Asn Pro Asn Leu Tyr Leu His Ser Glu Asp Val
                245                 250                 255

Val Leu Cys Val Leu Pro Leu Phe His Ile Tyr Ser Leu Asn Ser Val
            260                 265                 270

Leu Leu Cys Ser Leu Arg Ala Gly Ser Ala Ile Leu Leu Met His Lys
        275                 280                 285

Phe Glu Ile Gly Ser Leu Leu Asp Leu Val Gln Arg Phe Lys Val Thr
    290                 295                 300

Val Ala Pro Val Val Pro Pro Ile Val Leu Ala Phe Ala Lys Asn Ala
305                 310                 315                 320

Leu Val Glu Ser Tyr Asp Leu Ser Ser Ile Arg Val Val Leu Ser Gly
                325                 330                 335

Ala Ala Pro Leu Gly Lys Glu Leu Glu Asp Ala Leu Arg Leu Arg Leu
            340                 345                 350

Pro Lys Ala Thr Phe Gly Gln Gly Tyr Gly Met Thr Glu Ala Gly Pro
        355                 360                 365

Val Leu Ser Met Cys Leu Ala Phe Ala Lys Glu Pro Phe Pro Met Lys
    370                 375                 380

Ser Gly Ser Cys Gly Thr Val Val Arg Asn Ala Gln Met Lys Ile Ile
385                 390                 395                 400

Asp Pro Asp Thr Gly Thr Cys Leu Pro Tyr Asn Gln Pro Gly Glu Ile
                405                 410                 415

Cys Ile Arg Gly Pro Gln Ile Met Lys Gly Tyr Leu Asn Asp Ala Glu
            420                 425                 430

Ser Thr Ala Arg Thr Ile Asp Glu Asp Gly Trp Leu His Thr Gly Asp
        435                 440                 445

Ile Gly Tyr Ile Asp Asp Asp Glu Glu Val Phe Ile Val Asp Arg Val
    450                 455                 460

Lys Glu Ile Ile Lys Tyr Lys Gly Phe Gln Val Pro Pro Ala Glu Leu
465                 470                 475                 480

Glu Ala Ile Leu Ile Thr His Pro Ser Ile Ala Asp Ala Ala Val Val
                485                 490                 495

Pro Gln Lys Asp Glu Val Ala Gly Glu Val Pro Val Ala Phe Val Val
            500                 505                 510

Arg Ser Asn Gly Phe Asp Leu Thr Glu Asp Glu Ile Lys Gln Phe Val
        515                 520                 525

Ala Lys Gln Val Val Phe Tyr Lys Lys Leu His Lys Val Tyr Phe Ile
    530                 535                 540
```

-continued

```
His Ala Ile Pro Lys Ser Pro Ser Gly Lys Ile Leu Arg Lys Asp Leu
545                 550                 555                 560

Arg Ala Lys Leu Ser Ala Pro Thr Ser Thr Val Glu Ile Lys Ala
            565                 570                 575
```